US010464911B2

(12) United States Patent
Lee et al.

(10) Patent No.: US 10,464,911 B2
(45) Date of Patent: Nov. 5, 2019

(54) 1,3,4-OXADIAZOLE SULFAMIDE DERIVATIVE COMPOUNDS AS HISTONE DEACETYLASE 6 INHIBITOR, AND THE PHARMACEUTICAL COMPOSITION COMPRISING THE SAME

(71) Applicant: Chong Kun Dang Pharmaceutical Corp., Seoul (KR)

(72) Inventors: Jaekwang Lee, Gyeonggi-do (KR); Younghue Han, Gyeonggi-do (KR); Yuntae Kim, Gyeonggi-do (KR); Jaeki Min, Gyeonggi-do (KR); Miseon Bae, Gyeonggi-do (KR); Dohoon Kim, Gyeonggi-do (KR); Seokmin Jin, Gyeonggi-do (KR); Jangbeen Kyung, Gyeonggi-do (KR)

(73) Assignee: Chong Kun Dang Pharmaceutical Corp. (KR)

( * ) Notice: Subject to any disclaimer, the term of this patent is extended or adjusted under 35 U.S.C. 154(b) by 0 days.

(21) Appl. No.: 15/747,850

(22) PCT Filed: Jul. 27, 2016

(86) PCT No.: PCT/KR2016/008218
§ 371 (c)(1),
(2) Date: Jan. 26, 2018

(87) PCT Pub. No.: WO2017/018805
PCT Pub. Date: Feb. 2, 2017

(65) Prior Publication Data
US 2018/0230113 A1 Aug. 16, 2018

(30) Foreign Application Priority Data
Jul. 27, 2015 (KR) ........................ 10-2015-0106177

(51) Int. Cl.
*C07D 271/10* (2006.01)
*C07D 413/14* (2006.01)
*C07D 413/12* (2006.01)
*C07D 471/10* (2006.01)
*C07D 413/04* (2006.01)
*A61P 31/00* (2006.01)
*A61P 25/00* (2006.01)
*A61P 11/00* (2006.01)
*A61P 3/00* (2006.01)
*A61P 9/00* (2006.01)
*A61P 35/00* (2006.01)
*A61P 17/00* (2006.01)
*A61P 5/00* (2006.01)

(52) U.S. Cl.
CPC .............. *C07D 271/10* (2013.01); *A61P 3/00* (2018.01); *A61P 5/00* (2018.01); *A61P 9/00* (2018.01); *A61P 11/00* (2018.01); *A61P 17/00* (2018.01); *A61P 25/00* (2018.01); *A61P 31/00* (2018.01); *A61P 35/00* (2018.01); *C07D 413/04* (2013.01); *C07D 413/12* (2013.01); *C07D 413/14* (2013.01); *C07D 471/10* (2013.01)

(58) Field of Classification Search
CPC ..................................................... C07D 271/10
See application file for complete search history.

(56) References Cited

U.S. PATENT DOCUMENTS

| 4,871,753 | A | 10/1989 | Rorh |
| 8,981,084 | B2 | 3/2015 | Baloglu et al. |
| 9,670,193 | B2 | 6/2017 | Hebach et al. |
| 2005/0288282 | A1 | 12/2005 | Delorme et al. |
| 2006/0058298 | A1 | 3/2006 | Delorme et al. |
| 2007/0293530 | A1 | 12/2007 | Smil et al. |
| 2012/0027874 | A1 | 2/2012 | Charrier et al. |
| 2012/0289495 | A1 | 11/2012 | Baloglu et al. |
| 2013/0059883 | A1 | 3/2013 | Baloglu et al. |

(Continued)

FOREIGN PATENT DOCUMENTS

| CN | 104744446 | 7/2015 |
| JP | 2005513123 | 5/2005 |

(Continued)

OTHER PUBLICATIONS

Bolden et al., Nat. Rev. Drug Discov. 5(9), 769-784 (2006).

(Continued)

*Primary Examiner* — Paul V Ward
(74) *Attorney, Agent, or Firm* — Fish & Richardson P.C.

(57) ABSTRACT

The present invention relates to novel compounds having histone deacetylase 6 (HDAC6) inhibitory activity, stereoisomers thereof or pharmaceutically acceptable salts thereof, the use thereof for the preparation of therapeutic medicaments, pharmaceutical compositions containing the same, a method for treating diseases using the composition, and methods for preparing the novel compounds. The novel compounds, stereoisomers thereof or pharmaceutically acceptable salts thereof according to the present invention have histone deacetylase (HDAC) inhibitory activity and are effective for the prevention or treatment of HDAC6-mediated diseases, including infectious diseases; neoplasms; endocrine, nutritional and metabolic diseases; mental and behavioral disorders; neurological diseases; diseases of the eye and adnexa; cardiovascular diseases; respiratory diseases; digestive diseases; diseases of the skin and subcutaneous tissue; diseases of the musculoskeletal system and connective tissue; or congenital malformations, deformations and chromosomal abnormalities.

8 Claims, No Drawings

(56) References Cited

U.S. PATENT DOCUMENTS

| | | | |
|---|---|---|---|
| 2014/0005133 | A1 | 1/2014 | Trivedi et al. |
| 2014/0142105 | A1 | 5/2014 | Hebach et al. |
| 2014/0329825 | A1 | 11/2014 | Hebach et al. |
| 2017/0015809 | A1 | 1/2017 | Hawkins et al. |
| 2018/0230114 | A1 | 8/2018 | Lee et al. |
| 2018/0251437 | A1 | 9/2018 | Lee et al. |

FOREIGN PATENT DOCUMENTS

| | | |
|---|---|---|
| JP | 2009542752 | 12/2009 |
| JP | 2011008205 | 1/2011 |
| JP | 2011502133 | 1/2011 |
| JP | 2012211149 | 11/2012 |
| JP | 2013517278 | 5/2013 |
| JP | 2013517281 | 5/2013 |
| JP | 2014520794 | 8/2014 |
| JP | 2014524922 | 9/2014 |
| JP | 2014533721 | 12/2014 |
| JP | 2014533734 | 12/2014 |
| KR | 100265385 | 11/2000 |
| KR | 100903743 | 6/2009 |
| KR | 20147017436 | 11/2012 |
| KR | 101262870 | 5/2013 |
| KR | 101320198 | 10/2013 |
| KR | 20130112911 | 10/2013 |
| KR | 20140097459 | 8/2014 |
| KR | 101561860 | 10/2015 |
| RU | 2515611 | 8/2012 |
| WO | WO 2003/028729 | 4/2003 |
| WO | WO 2007011626 | 1/2007 |
| WO | WO 2007/032445 | 3/2007 |
| WO | WO 2007/107758 | 9/2007 |
| WO | WO 2009/010479 | 1/2009 |
| WO | WO 2010/123933 | 10/2010 |
| WO | WO 2010/126002 | 11/2010 |
| WO | WO 2011/088181 | 7/2011 |
| WO | WO 2011/088192 | 7/2011 |
| WO | WO 2011/104680 | 9/2011 |
| WO | WO 2011/133888 | 10/2011 |
| WO | WO 2012/013716 | 2/2012 |
| WO | WO 2013/066833 | 5/2013 |
| WO | WO 2013/066835 | 5/2013 |
| WO | WO 2013/066839 | 5/2013 |
| WO | WO 2013/080120 | 6/2013 |
| WO | WO 2015/033301 | 3/2015 |
| WO | WO 2015/087151 | 6/2015 |
| WO | WO 2016082930 | 6/2016 |
| WO | WO 2017/018803 | 2/2017 |
| WO | WO 2017/018804 | 2/2017 |
| WO | WO 2017/018805 | 2/2017 |
| WO | WO 2017/023133 | 2/2017 |
| WO | WO 2017/065473 | 4/2017 |

OTHER PUBLICATIONS

Hassig et al., Curr. Opin. Chem. Biol. 1, 300-308 (1997).
Hu et al., J. Neurol. Sci. 304, 1-8 (2011).
International Search Report of ISA/KR for PCT/KR2016/0008218 (dated Nov. 21, 2016).
Manku, et al., Bioorganic & Medicinal Chemistry Letters 19, 1866-1870 (2009).
Matthias et al., Mol. Cell. Biol. 28, 1688-1701 (2008).
Methot et al., Bioorg. Med. Chem. Lett. 18, 973-978 (2008).
Pal et al., Journal of Advanced Pharmaceutical Technology & Research, 3(2), 92-99 (Apr.-Jun. 2012).
Piekarz et al., Pharmaceuticals 3, 2751-2767 (2010).
Rajak et al., Bioorganic & Medicinal Chemistry letters 21, 5735-5738 (2011).
Santo et al., Blood 119, 2579-2589 (2012).
Vishwakarma et al., International Immunopharmacology 16, 72-78 (2013).
Warrell et al., Natl. Cancer Inst. 90, 1621-1625 (1998).
Wiest et al., J. Org. Chem 78, 5051-5055 (2013).
Witt et al., Cancer Letters 277, 8-21 (2009).
Woster et al., Med. Chem. Commun., online publication (2015).
Yao et al., Mol. Cell 18,601-607 (2005).
AU Office Action for AU App No. 2016299484, dated Dec. 18, 2018 (3 pages).
AU Office Action for AU App No. 2016299485, dated Sep. 13, 2018 (7 pages).
CA Office Action for CA App No. 2987570, dated Oct. 18, 2018 (5 pages).
EP Extended Search Report for EP App No. 16830836.9, dated Dec. 19, 2018 (7 pages).
EP Extended Search Report for EP App No. 16830837.7, dated Dec. 17, 2018 (9 pages).
EP Extended Search Report for EP App No. 16830838.5, dated Nov. 19, 2018 (7 pages).
JP Office Action for App No. JP 2018-503804, dated Dec. 18, 2018 (with English Translation) (4 pages).
JP Office Action for JP App No. 2018-504096, dated Dec. 18, 2018 (with English Translation) (5 pages).
Rossi et al., 4-N-Hydroxy-4-[ 1-( sulfonyl )piperidin-4-yl ]-butyramides as HDAC inhibitors, Bioorganic & Medicinal Chemistry Letters, 21:6767-6769 (2011).
RU Office Action for App. No. RU2018106877, dated Oct. 18, 2018 (with English translation) (16 pages).
RU Office Action for RU App. No. 2018106904, dated Sep. 20, 2018 (with English translation) (14 pages).
U.S. Appl. No. 15/747,952, filed Jan. 26, 2018, Lee et al.
U.S. Appl. No. 15/747,850, filed Jan. 26, 2018, Lee et al.
U.S. Appl. No. 15/748,081, filed Jan. 26, 2018, Lee et al.
U.S. Appl. No. 15/750,067, filed Feb. 2, 2018, Lee et al.
U.S. Appl. No. 15/763,972, filed Mar. 28, 2018, Kim et al.
AU Office Action for AU App No. 2016299484, dated Aug. 28, 2018 (6 pages).
AU Office Action for AU App No. 2016299486, dated Jul. 31, 2018 (5 pages).
Chen, J.J. et al., *Discovery of 2-methylpyridine-based biaryl amides as γ-secretase modulators for the treatment of Alzheimer's disease*, Bioorganic & Medicinal Chemistry letters, 2013, 23(23):6447-6454.
International Preliminary Report on Patentability and Written Opinion for Intl. App. No. PCT/KR2016/008214 dated Jan. 30, 2018 (8 pages).
International Preliminary Report on Patentability and Written Opinion for Intl. App. No. PCT/KR2016/008216 dated Jan. 30, 2018 (9 pages).
International Preliminary Report on Patentability and Written Opinion for Intl. App. No. PCT/KR2016/008218 dated Jan. 30, 2018 (8 pages).
International Preliminary Report on Patentability and Written Opinion for Intl. App. No. PCT/KR2016/008622 dated Feb. 6, 2018 (8 pages).
International Preliminary Report on Patentability and Written Opinion for Intl. App. No. PCT/KR2016/011355 dated Apr. 17, 2018 (6 pages).
International Search Report for Int. App. No. PCT /KR2016/ 011355, dated Jan. 26, 2017 (5 pages).
International Search Report of ISA/KR for PCT/KR2016/008214, dated Nov. 24, 2016 (5 pages).
International Search Report of ISA/KR for PCT/KR2016/008216, dated Nov. 21, 2016 (4 pages).
International Search Report of ISA/KR for PCT/KR2016/008622, dated Feb. 17, 2017 (5 pages).
Japan Office Action for JP App No. 2018-505725 dated Sep. 12, 2018 (3 pages).
Korea Office Action for KR Application No. 10-2016-0095332, dated Sep. 5, 2017 (15 pages).
Korea Office Action for KR Application No. 10-2016-0095334, dated Sep. 5, 2017 (17 pages).
Korea Office Action for KR Application No. 10-2016-0099508, dated Sep. 5, 2017 (20 pages).
Korea Office Action for KR Application No. 10-2016-0131245, dated Sep. 5, 2017 (7 pages).

(56) References Cited

OTHER PUBLICATIONS

Piekarz et al., *Clinical Toxicities of Histone Deacetylase Inhibitors*, Pharmaceuticals 3, 2751-2767 (2010).
STN Express; Chemical Abstract compound RN: 904653-20-9 (Aug. 25, 2006).
Taiwan Office Action for TW App No. 105132939 dated Nov. 2, 2017 (with English translation) (8 pages).
STN Express; Chemical Abstract compound RN: 1798074-73-3 (Jul. 9, 2015).
STN Express; Chemical Abstract compound RN: 1790675-44-3 (Jun. 29, 2015).
STN Express; Chemical Abstract compound RN: 1708354-35-1 (May 20, 2015).
STN Express; Chemical Abstract compound RN: 1355844-43-7 (Feb. 8, 2012).
Cancer [online], [retrieved on Jul. 6, 2007]. Retrieved from the internet, URL http://www.nlm.nih.gov/mededlineplus/cancer.html (10 pages).
Golub et al., Molecular Classification of Cancer: Class Discovery and Class Prediction by Gene Expression Monitoring, Science 286:531-537 (1999).
Lala et al., Role of nitric oxide in tumor progression: Lessons from experimental tumors, Cancer and Metastasis Reviews 17(1):91-106 (1998).
CAS Registry No. 904645-39-2 Database Registry [Online] retrieved from STN, searched on Nov. 14, 2018.
CAS Registry No. 904652-59-1 Database Registry [Online] retrieved from STN, searched on Nov. 14, 2018.
AU Examination Report No. 1 for App No. AU201603891, dated Nov. 16, 2019 (7 pages).
CA Office Action for App No. CA 2993929, dated Dec. 4, 2018 (4 pages.
CAS Registry No. 1384673-31-7 [Entered STN: Jul. 27, 2012] (Year: 2012).
CAS Registry No. 1436149-02-8 [Entered STN: Jun. 9, 2013] (Year: 2013).
CAS Registry No. 904635-69-4 (Aug. 25, 2006).
CAS Registry No. 904652-71-7 (Aug. 25, 2006).
CAS Registry No. 904653-13-0 (Aug. 25, 2006).
EP Suppl Search Report for App No. EP 16833369, dated Apr. 1, 2019 (6 pages).
CA Office Action for CA App No. 2993918, dated Dec. 4, 2018 (5 pages).
CAS Registry No. 904529-79-9 (Aug. 25, 2006).
CAS Registry No. 904541-56-6 (Aug. 25, 2006).
CAS Registry No. 904541-91-9 (Aug. 25, 2006).
CAS Registry No. 904548-90-9 (Aug. 25, 2006).
CAS Registry No. 904549-01-5 (Aug. 25, 2006).
CAS Registry No. 904549-10-3 (Aug. 25, 2006).
CAS Registry No. 904556-59-8 (Aug. 25, 2006).
CAS Registry No. 904568-68-9 (Aug. 25, 2006).
CAS Registry No. 904568-84-9 (Aug. 25, 2006).
CAS Registry No. 904569-62-6 (Aug. 25, 2006).
CAS Registry No. 904635-15-0 (Aug. 25, 2006).
CAS Registry No. 904635-23-0 (Aug. 25, 2006).
CAS Registry No. 904635-49-0 (Aug. 25, 2006).
CAS Registry No. 904635-57-0 (Aug. 25, 2006).
CAS Registry No. 904635-61-6 Aug. 25, 2006).
CAS Registry No. 904635-67-2 (Aug. 25, 2006).
CAS Registry No. 904644-90-2 (Aug. 25, 2006).
CAS Registry No. 904644-93-5 (Aug. 25, 2006).
CAS Registry No. 904645-01-8 (Aug. 25, 2006).
CAS Registry No. 904645-03-0 (Aug. 25, 2006).
CAS Registry No. 904645-27-8 (Aug. 25, 2006).
CAS Registry No. 904645-29-0 (Aug. 25, 2006).
CAS Registry No. 904645-35-2 (Aug. 25, 2006).
CAS Registry No. 904645-35-8 (Aug. 25, 2006).
CAS Registry No. 904645-37-0 (Aug. 25, 2006).
CAS Registry No. 904645-47-2 (Aug. 25, 2006).
CAS Registry No. 904652-55-1 (Aug. 25, 2006).
CAS Registry No. 904652-68-2 (Aug. 25, 2006).
CAS Registry No. 904653-05-0 (Aug. 25, 2006).
CAS Registry No. 904653-11-8 (Aug. 25, 2006).
CAS Registry No. 904653-15-2 (Aug. 25, 2006).
CAS Registry No. 904653-17-4 (Aug. 25, 2006).
CAS Registry No. 904653-21-0 (Aug. 25, 2006).
CAS Registry No. 904653-22-1 (Aug. 25, 2006).
JP Office Action for App No. JP 2018-504720, dated Jan. 8, 2019 (English Translation) (4 pages).
NZ Office Action for App No. NZ739211, dated Jun. 14, 2019 (3 pages).
RU Office Action for RU App. No. 2018106914, dated Nov. 15, 2018 (with English translation) (14 pages).
CAS Registry No. 904548-10-3 (Aug. 25, 2006).
AU Examination Report No. 1 for App No. AU201603891, dated Nov. 16, 2018 (7 pages).
IN Office Action for App No. 201727037873, dated May 21, 2019 (7 pages).
Gamal El-Din. et, al, European Journal of Medicinal Chemistry, 90:45-52, (Jan. 27, 2015).
IN Office Action for App No. 201817006324, dated Jun. 27, 2019 (6 pages).
Othman et al., *1,3,4-Oxadiazole, 1,3,4-thiadiazole and 1,2,4-triazole derivatives as potential antibacterial agents*, Arabian Journal of Chemistry (2014) https://doi.org/10.1016/j.arabjc.2014.09.003 (16 pages).

1,3,4-OXADIAZOLE SULFAMIDE DERIVATIVE COMPOUNDS AS HISTONE DEACETYLASE 6 INHIBITOR, AND THE PHARMACEUTICAL COMPOSITION COMPRISING THE SAME

TECHNICAL FIELD

The present invention relates to 1,3,4-oxadiazole sulfamide derivative compounds having histone deacetylase 6 (HDAC6) inhibitory activity, stereoisomers thereof, or pharmaceutically acceptable salts thereof; uses thereof for the preparation of therapeutic medicaments; methods of treating diseases using the same; pharmaceutical compositions comprising the same; and methods for preparing the same.

BACKGROUND ART

Post-translational modifications such as acetylation are very crucial regulatory modules at the heart of biological processes in the cells and are tightly regulated by a multitude of enzymes. Histones are the chief protein components of chromatin and act as spools around which DNA strands. Also, the balance of histone acetylation and deacetylation is a critical role in the regulation of gene expression.

Histone deacetylases (HDACs) are enzymes that remove acetyl groups from lysine residues on histone proteins of chromatin, and are known to be associated with gene silencing and induce cell cycle arrest, angiogenic inhibition, immune regulation, cell death, etc. (Hassig et al., Curr. Opin. Chem. Biol. 1997, 1, 300-308). In addition, it was reported that the inhibition of enzymatic function of HDACs induces the apoptosis of cancer cells in vivo by reducing the activity of cancer cell survival-associated factors and activating cancer cell apoptosis-associated factors (Warrell et al, J. Natl. Cancer Inst. 1998, 90, 1621-1625).

In humans, 18 HDACs have been identified and are subdivided into four classes based on their homology to yeast HDACs. Among them, 11 HDACs use zinc as a cofactor and can be divided into three groups: Class I (HDAC1, 2, 3 and 8), Class II (IIa: HDAC4, 5, 7 and 9; IIb: HDAC6 and 10), Class IV (HDAC 11). Additionally, 7 HDACs of Class III (SIRT 1-7) require $NAD^+$ instead of zinc as a cofactor (Bolden et al., Nat. Rev. Drug Discov. 2006, 5(9), 769-784).

Various HDAC inhibitors are in preclinical or clinical development, but to date, only non-selective HDAC inhibitors have been identified as anticancer agents, and only vorinostat (SAHA) and romidepsin (FK228) have been approved for the treatment of cutaneous T-cell lymphoma. However, non-selective HDAC inhibitors are known to cause side effects such as fatigue and nausea, generally at high doses (Piekarz et al., Pharmaceuticals 2010, 3, 2751-2767). Such side effects have been reported to be due to the inhibition of class I HDACs. Due to such side effects, the use of non-selective HDAC inhibitors in the development of drugs other than anticancer drugs has been limited (Witt et al., Cancer Letters, 2009, 277, 8-21).

Meanwhile, it was reported that the selective inhibition of class II HDACs would not show toxicity shown in the inhibition of class I HDACs. Also, when selective HDAC inhibitors are developed, side effects such as toxicity, which are caused by the non-selective HDAC inhibition, can be overcome. Thus, selective HDAC inhibitors have potential to be developed as therapeutic agents effective for the treatment of various diseases (Matthias et al., Mol. Cell. Biol. 2008, 28, 1688-1701).

It is known that HDAC6, a member of Class IIb HDACs, is present mainly in the cytoplasm and is involved in the deacetylation of a number of non-histone substrates (HSP90, cortactin, etc.), including tubulin, (Yao et al., Mol. Cell 2005, 18, 601-607). HDAC6 has two catalytic domains, and the zinc finger domain of C-terminal can bind to ubiquitinated proteins. It is known that HDAC6 has a number of non-histone proteins as substrates, and thus plays an important role in various diseases, including cancer, inflammatory diseases, autoimmune diseases, neurological diseases and neurodegenerative disorders (Santo et al., Blood 2012 119: 2579-258; Vishwakarma et al., International Immunopharmacology 2013, 16, 72-78; Hu et al., J. Neurol. Sci. 2011, 304, 1-8).

The common structural characteristic of various HDAC inhibitors is a structure consisting of a cap group, a linker and a zinc-binding group (ZBG), as shown in the following Vorinostat structure. Many researchers have conducted studies on enzyme inhibitory activity and selectivity by structurally modifying the cap group and the linker. Among these groups, the zinc-binding group is known to play a more important role in enzyme inhibitory activity and selectivity (Wiest et al., J. Org. Chem. 2013 78: 5051-5065; Methot et al., Bioorg. Med. Chem. Lett. 2008, 18, 973-978).

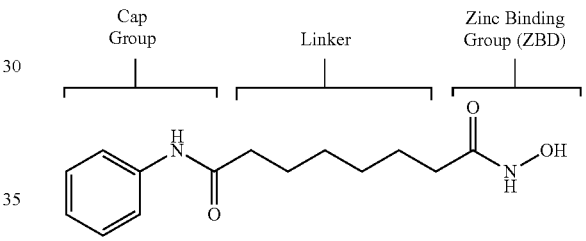

The zinc-binding group is generally a hydroxamic acid or benzamide derivative. Herein, the hydroxamic acid derivative exhibits a potent HDAC inhibitory effect, but has problems of low bioavailability and severe off-target activity. In addition, the benzamide derivative has a problem in that it can produce toxic metabolites in vivo, because it contains aniline (Woster et al., Med. Chem. Commun. 2015, online publication).

Accordingly, there is a need for the development of selective HDAC 6 inhibitors for treatment of diseases such as cancer, inflammatory diseases, autoimmune diseases, neurological diseases and neurodegenerative disorders, which have a zinc-binding group with improved bioavailability and, at the same time, cause no side effects, unlike non-selective inhibitors that cause side effects.

DISCLOSURE OF INVENTION

Technical Problem

It is an object of the present invention to provide 1,3,4-oxadiazole sulfamide derivative compounds having selective HDAC6 inhibitory activity, stereoisomers thereof, or pharmaceutically acceptable salts thereof.

Another object of the present invention is to provide pharmaceutical compositions containing 1,3,4-oxadiazole sulfamide derivative compounds having selective HDAC6 inhibitory activity, stereoisomers thereof, or pharmaceutically acceptable salts thereof.

Still another object of the present invention is to provide methods for preparing the novel compounds.

Still another object of the present invention is to provide pharmaceutical compositions for prevention or treatment of HDAC6 activity-associated diseases, including infectious diseases; neoplasms; endocrine, nutritional and metabolic diseases; mental and behavioral disorders; neurological diseases; diseases of the eye and adnexa; cardiovascular diseases; respiratory diseases; digestive diseases; diseases of the skin and subcutaneous tissue; diseases of the musculoskeletal system and connective tissue; or congenital malformations, deformations and chromosomal abnormalities, which contain the above compound.

Still another object of the present invention is to provide the use of the compounds for the preparation of therapeutic medicaments against HDAC6 activity-associated diseases.

Yet another object of the present invention is to provide methods for treating HDAC6 activity-associated diseases, which comprise administering a therapeutically effective amount of the pharmaceutical compositions containing the compounds.

Solution to Problem

The present inventors have discovered 1,3,4-oxadiazole sulfamide derivative compounds, which have histone deacetylase 6 (HDAC6) inhibitory activity, and have found that these compounds can be used for the inhibition or treatment of histone deacetylase 6 (HDAC6) activity-associated diseases, thereby completing the present invention.

1,3,4-oxadiazole Sulfamide Derivative Compounds

To achieve the above objects, the present invention provides an 1,3,4-oxadiazole sulfamide derivative compound represented by the following formula I, a stereoisomer thereof, or a pharmaceutically acceptable salt thereof:

[Formula I]

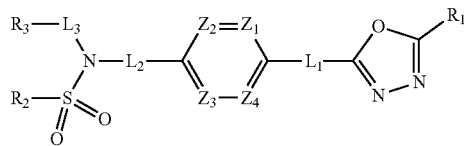

wherein $L_1$, $L_2$ or $L_3$ are each independently —($C_0$-$C_2$ alkyl)-;

$Z_1$ to $Z_4$ are each independently N or $CR^Z$, wherein $R^Z$ is —H or —X;

$R_1$ is —$CX_2H$ or —$CX_3$;

$R_2$ is

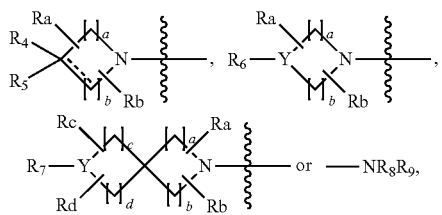

wherein Y is —N—, —O— or —S(=O)$_2$—,
a to d are each independently an integer of 1, 2 or 3,
Ra to Rd are each independently —H or —($C_1$-$C_4$ alkyl),
the dotted line is a single bond or a double bond, $R_4$ and $R_5$ are each independently —H, —X, —($C_1$-$C_4$ alkyl), aryl or —NReRf, provided that the dotted line is a double bond, $R_5$ is null, Re and Rf are each independently —H or —($C_1$-$C_4$ alkyl), when Y is —N—, $R_6$ and $R_7$ are each independently —H, —($C_1$-$C_4$ alkyl), —($C_1$-$C_4$ alkyl)-O—($C_1$-$C_4$ alkyl), —C(=O)—($C_1$-$C_4$ alkyl), —C(=O)—O($C_1$-$C_4$ alkyl), —C(=O)—$CF_3$, —($C_1$-$C_4$ alkyl)-C(=O)—O($C_1$-$C_4$ alkyl), —S(=O)$_2$—($C_1$-$C_4$ alkyl), —($C_3$-$C_7$ cycloalkyl), —($C_2$-$C_6$ heterocycloalkyl), -aryl, —($C_1$-$C_4$ alkyl)-aryl, -heteroaryl or amine protecting group, wherein at least one H of the —($C_1$-$C_4$ alkyl) may be substituted with —X or —OH, at least one H of the -aryl, —($C_1$-$C_4$ alkyl)-aryl or -heteroaryl may be substituted with —X, —OH or —$CF_3$, and the —($C_2$-$C_6$ heterocycloalkyl) may contain an N, O or S atom in the ring, and when Y is —O— or —S(=O)$_2$—, $R_6$ and $R_7$ are null, $R_8$ and $R_9$ are each independently —H, —($C_1$-$C_4$ alkyl), —($C_3$-$C_7$ cycloalkyl), —($C_2$-$C_6$ heterocycloalkyl), —($C_1$-$C_4$ alkyl($C_2$-$C_6$ heterocycloalkyl), -aryl, -heteroaryl or —($C_1$-$C_4$ alkyl)-aryl, wherein at least one H of the —($C_3$-$C_7$ cycloalkyl), —($C_2$-$C_6$ heterocycloalkyl), —($C_1$-$C_4$ alkyl)-($C_2$-$C_6$ heterocycloalkyl), -aryl, -heteroaryl or —($C_1$-$C_4$ alkyl)-aryl may be substituted with —($C_1$-$C_4$ alkyl), —C(=O)—($C_1$-$C_4$ alkyl), —S(=O)$_2$—($C_1$-$C_4$ alkyl) or —($C_2$-$C_6$ heterocycloalkyl); and $R_3$ is —H, —($C_1$-$C_4$ alkyl), —($C_1$-$C_4$ alkyl)-O($C_1$-$C_4$ alkyl), —($C_1$-$C_4$ alkyl)-C(=O)—O($C_1$-$C_4$ alkyl), —($C_3$-$C_7$ cycloalkyl), -aryl, -heteroaryl or

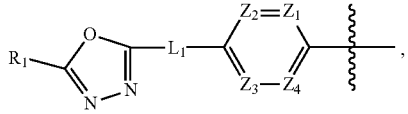

wherein at least one H of the —($C_3$-$C_7$ cycloalkyl), -aryl or -heteroaryl may be substituted with —X, —OH, —($C_1$-$C_4$ alkyl), —$CF_3$, —($C_1$-$C_4$ alkyl)-($C_2$-$C_6$ heterocycloalkyl)-($C_1$-$C_4$ alkyl), —C(=O)—($C_1$-$C_4$ alkyl), —C(=O)—O($C_1$-$C_4$ alkyl), —O($C_1$-$C_4$ alkyl), —$OCF_3$, —S(=O)$_2$—($C_1$-$C_4$ alkyl), -aryl, -heteroaryl or —$NR_{11}R_{12}$, $R_{11}$ and $R_{12}$ are each independently —H or —($C_1$-$C_4$ alkyl), $R_1$, $L_1$, $Z_1$, $Z_2$, $Z_3$ and $Z_4$ are as defined above; and X is F, Cl, Br or I.

According to preferable embodiment of the present invention, $L_1$ or $L_3$ are each independently —($C_0$ alkyl)-;

$L_2$ is —($C_1$ alkyl)-;

$Z_1$ to $Z_4$ are each independently N or $CR^Z$, wherein $R^Z$ is —H or —X;

$R_1$ is —$CX_2H$ or —$CX_3$;

$R_2$ is

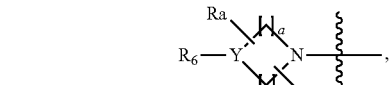

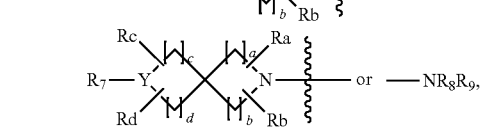

wherein Y is —N—, —O— or —S(=O)$_2$—, a to d are each independently an integer of 1 or 2, R$_a$ to R$_d$ are each independently —H or —(C$_1$-C$_4$ alkyl), when Y is —N—, R$_6$ and R$_7$ are each independently —H, —(C$_1$-C$_4$ alkyl), —C(=O)—(C$_1$-C$_4$ alkyl), —S(=O)$_2$—(C$_1$-C$_4$ alkyl), —(C$_3$-C$_7$ cycloalkyl) or —(C$_2$-C$_6$ heterocycloalkyl), wherein at least one H of —(C$_1$-C$_4$ alkyl) may be substituted with —X or —OH, and —(C$_2$-C$_6$ heterocycloalkyl) may contain an N, O or S atom, and when Y is —O— or —S(=O)$_2$—, R$_6$ and R$_7$ are null, R$_8$ and R$_9$ are each independently —H, —(C$_1$-C$_4$ alkyl) or —(C$_1$-C$_4$ alkyl)-(C$_2$-C$_6$ heterocycloalkyl), wherein at least one H of the —(C$_1$-C$_4$ alkyl)-(C$_2$-C$_6$ heterocycloalkyl) may be substituted with —(C$_1$-C$_4$ alkyl), —C(=O)—(C$_1$-C$_4$ alkyl), —S(=O)$_2$—(C$_1$-C$_4$ alkyl) or —(C$_2$-C$_6$ heterocycloalkyl);

R$_3$ is -aryl or -heteroaryl, wherein at least one H of the -aryl or -heteroaryl may be substituted with —X; and X is F, Cl, Br or I.

According to more preferable embodiment of the present invention,

L$_1$ or L$_3$ are each independently —(C$_0$ alkyl)-;

L$_2$ is —(C$_1$ alkyl)-;

Z$_1$ to Z$_4$ are each independently N or CR$^Z$, wherein R$^Z$ is —H or —X;

R$_1$ is —CF$_2$H or —CF$_3$;

R$_2$ is

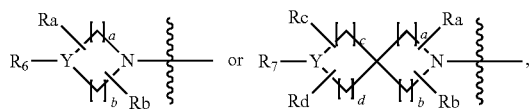

wherein Y is —N— or —S(=O)$_2$—, a to d are each independently an integer of 1 or 2, R$_a$ to R$_d$ are each independently —H or —(C$_1$-C$_4$ alkyl), when Y is —N—, R$_6$ and R$_7$ are each independently —H, —(C$_1$-C$_4$ alkyl), —C(=O)—(C$_1$-C$_4$ alkyl), —S(=O)$_2$—(C$_1$-C$_4$ alkyl), —(C$_3$-C$_7$ cycloalkyl) or —(C$_2$-C$_6$ heterocycloalkyl), wherein at least one H of the —(C$_1$-C$_4$ alkyl) may be substituted with —X or —OH, and the —(C$_2$-C$_6$ heterocycloalkyl) may contain an N, O or S atom, and when Y is —S(=O)$_2$—, R$_6$ and R$_7$ are null;

R$_3$ is -aryl or -heteroaryl, wherein at least one H of the -aryl or -heteroaryl may be substituted with —X; and X is F, Cl, Br or I.

According to particularly preferable embodiment of the present invention,

L$_1$ or L$_3$ are each independently —(C$_0$ alkyl)-;

L$_2$ is —(C$_1$ alkyl)-;

Z$_1$ to Z$_4$ are each independently N or CR$^Z$, wherein R$^Z$ is —H or —X;

R$_1$ is —CF$_2$H or —CF$_3$;

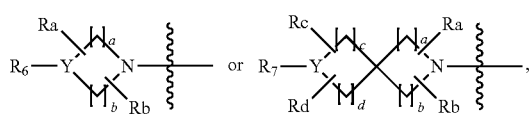

wherein Y is —N— or —S(=O)$_2$—, a and b are 2, c and d are 1,

R$_a$ to R$_d$ are each independently —H or —(C$_1$-C$_4$ alkyl), when Y is —N—, R$_6$ and R$_7$ are each independently —H, —(C$_1$-C$_4$ alkyl), —C(=O)—(C$_1$-C$_4$ alkyl), —S(=O)$_2$—(C$_1$-C$_4$ alkyl), —(C$_3$-C$_7$ cycloalkyl) or —(C$_2$-C$_6$ heterocycloalkyl), wherein at least one H of the —(C$_1$-C$_4$ alkyl) may be substituted with —X or —OH, and the —(C$_2$-C$_6$ heterocycloalkyl) may contain an N, O or S atom, and when Y is —S(=O)$_2$—, R$_6$ and R$_7$ are null;

R$_3$ is -aryl or -heteroaryl, wherein at least one H of the -aryl or -heteroaryl may be substituted with —F; and X is F or Cl.

The specific compounds represented by formula I are shown in Table 1 below:

TABLE 1

| Ex. | Comp. | Structure |
|---|---|---|
| 1 | 11198 | 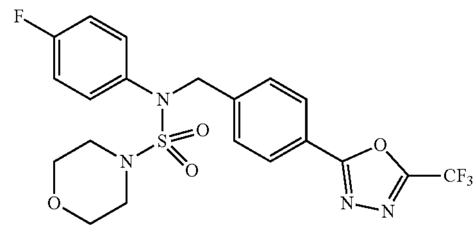 [SMILES: O=S(=O)(N1CCOCC1)N(Cc1ccc(-c2nnc(C(F)(F)F)o2)cc1)c1ccc(F)cc1] |
| 2 | 11199 | 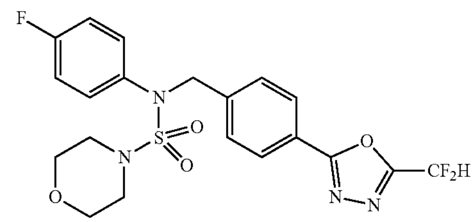 [SMILES: O=S(=O)(N1CCOCC1)N(Cc1ccc(-c2nnc(C(F)F)o2)cc1)c1ccc(F)cc1] |
| 3 | 11293 | 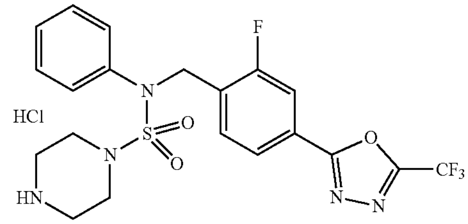 [SMILES: Cl ; O=S(=O)(N1CCNCC1)N(Cc1ccc(-c2nnc(C(F)(F)F)o2)cc1F)c1ccccc1] |
| 4 | 11294 | 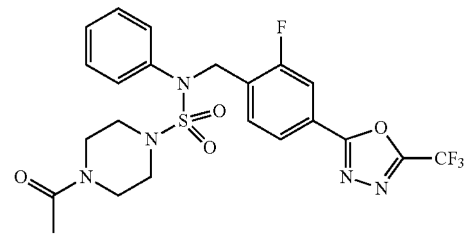 [SMILES: CC(=O)N1CCN(S(=O)(=O)N(Cc2ccc(-c3nnc(C(F)(F)F)o3)cc2F)c2ccccc2)CC1] |
| 5 | 11295 | 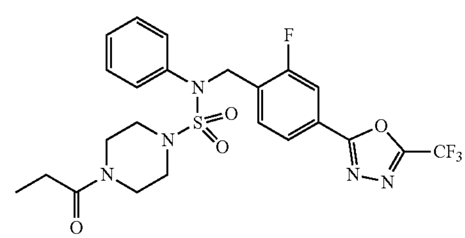 [SMILES: CCC(=O)N1CCN(S(=O)(=O)N(Cc2ccc(-c3nnc(C(F)(F)F)o3)cc2F)c2ccccc2)CC1] |

TABLE 1-continued
| Ex. | Comp. | Structure |
|---|---|---|
| 6 | 11296 | 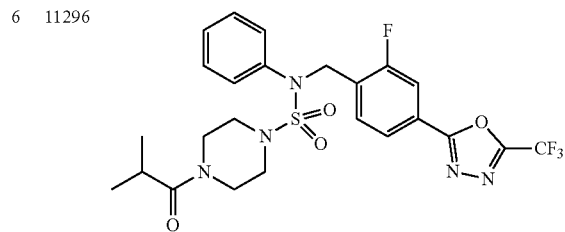 |
| 7 | 11297 | 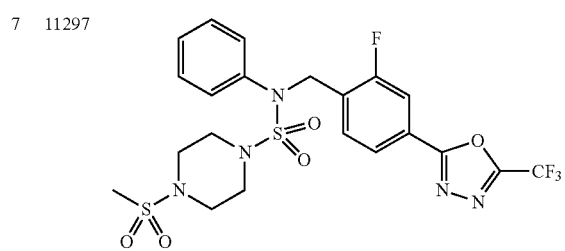 |
| 8 | 11298 | 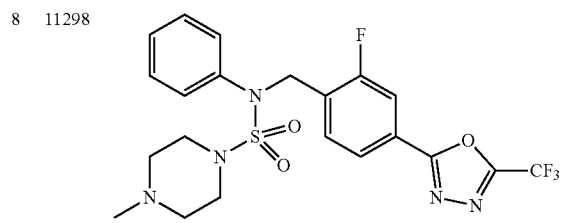 |
| 9 | 11299 | 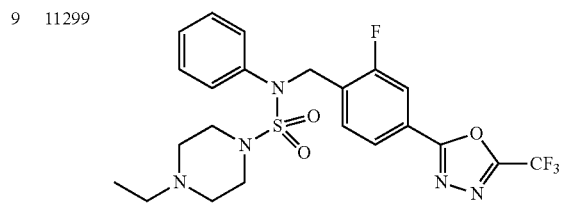 |
| 10 | 11300 | 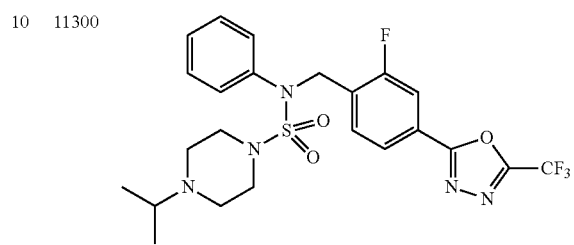 |
| 11 | 11301 | 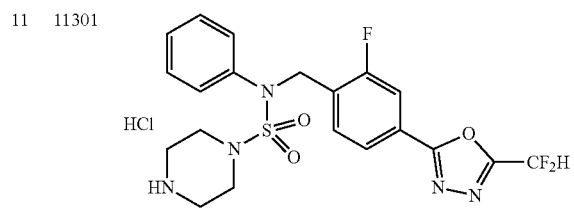 |
TABLE 1-continued
| Ex. | Comp. | Structure |
|---|---|---|
| 12 | 11302 | 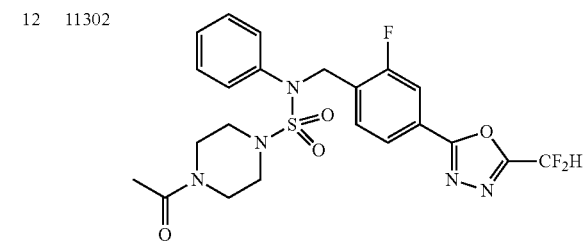 |
| 13 | 11303 | 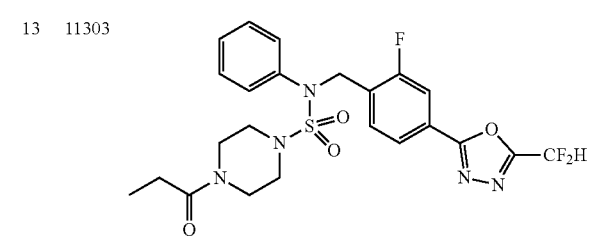 |
| 14 | 11304 | 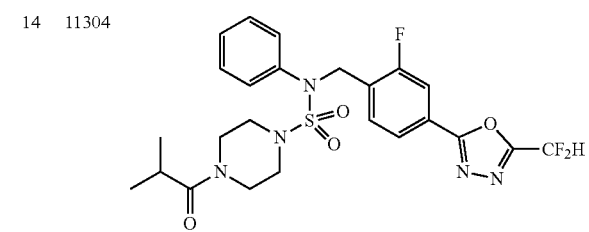 |
| 15 | 11305 | 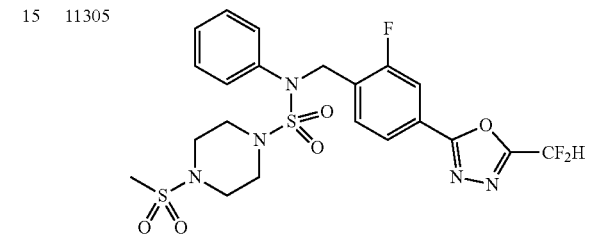 |
| 16 | 11306 | 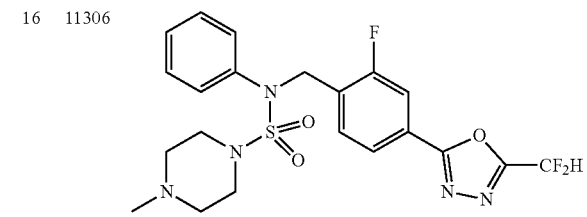 |
| 17 | 11307 | 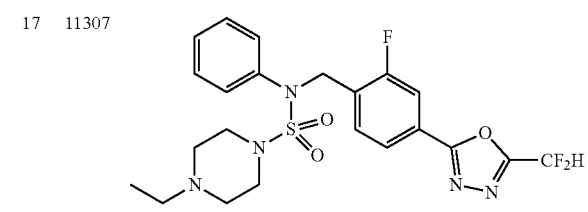 |

TABLE 1-continued
| Ex. | Comp. | Structure |
|---|---|---|
| 18 | 11308 | 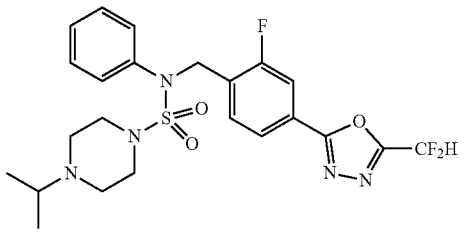 [SMILES: CC(C)N1CCN(S(=O)(=O)N(Cc2ccc(-c3nnc(C(F)F)o3)cc2F)c2ccccc2)CC1] |
| 19 | 11309 | 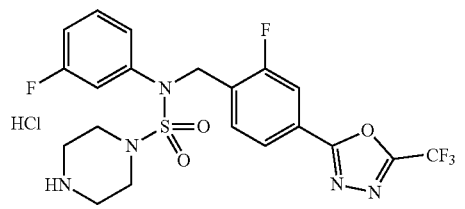 [SMILES: Cl ; O=S(=O)(N1CCNCC1)N(Cc1ccc(-c2nnc(C(F)(F)F)o2)cc1F)c1cccc(F)c1] |
| 20 | 11310 | 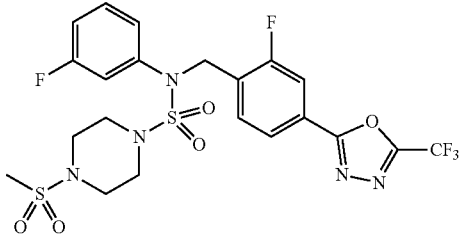 [SMILES: CS(=O)(=O)N1CCN(S(=O)(=O)N(Cc2ccc(-c3nnc(C(F)(F)F)o3)cc2F)c2cccc(F)c2)CC1] |
| 21 | 11311 | 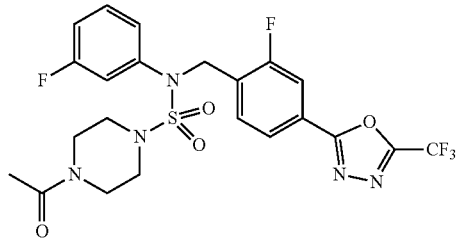 [SMILES: CC(=O)N1CCN(S(=O)(=O)N(Cc2ccc(-c3nnc(C(F)(F)F)o3)cc2F)c2cccc(F)c2)CC1] |
| 22 | 11312 | 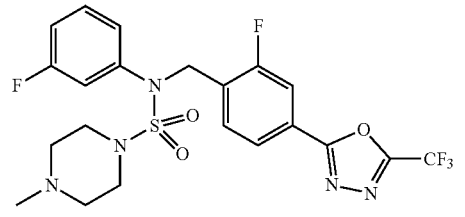 |
| 23 | 11313 | 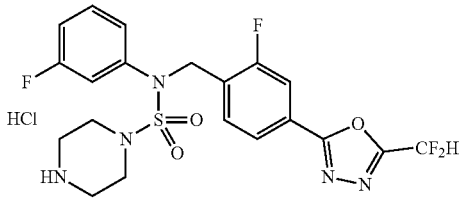 [SMILES: Cl ; O=S(=O)(N1CCNCC1)N(Cc1ccc(-c2nnc(C(F)F)o2)cc1F)c1cccc(F)c1] |
| 24 | 11314 | 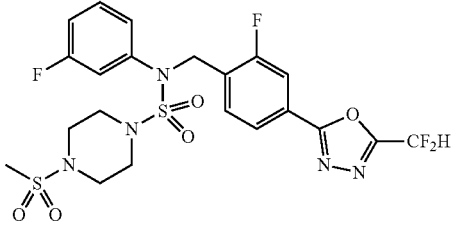 [SMILES: CS(=O)(=O)N1CCN(S(=O)(=O)N(Cc2ccc(-c3nnc(C(F)F)o3)cc2F)c2cccc(F)c2)CC1] |
| 25 | 11315 | 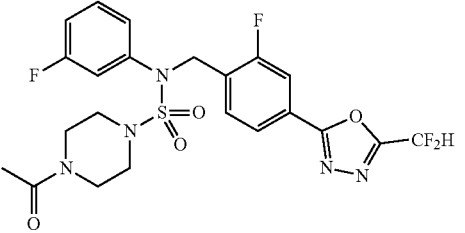 [SMILES: CC(=O)N1CCN(S(=O)(=O)N(Cc2ccc(-c3nnc(C(F)F)o3)cc2F)c2cccc(F)c2)CC1] |
| 26 | 11316 | 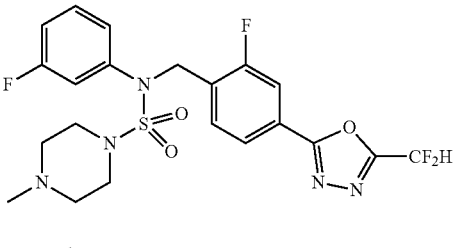 [SMILES: CN1CCN(S(=O)(=O)N(Cc2ccc(-c3nnc(C(F)F)o3)cc2F)c2cccc(F)c2)CC1] |
| 27 | 11317 | 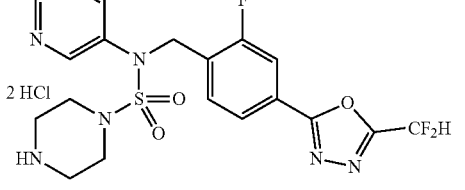 |
| 28 | 11318 | 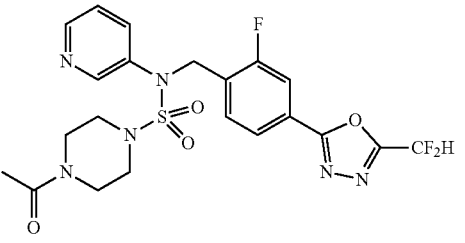 [SMILES: CC(=O)N1CCN(S(=O)(=O)N(Cc2ccc(-c3nnc(C(F)F)o3)cc2F)c2cccnc2)CC1] |
| 29 | 11319 | 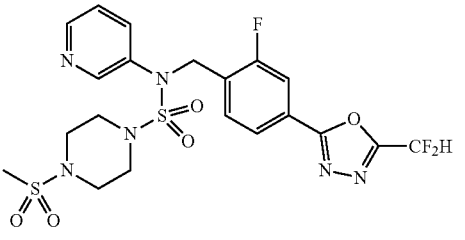 [SMILES: CS(=O)(=O)N1CCN(S(=O)(=O)N(Cc2ccc(-c3nnc(C(F)F)o3)cc2F)c2cccnc2)CC1] |

TABLE 1-continued

| Ex. | Comp. | Structure |
|-----|-------|-----------|
| 30 | 11320 | 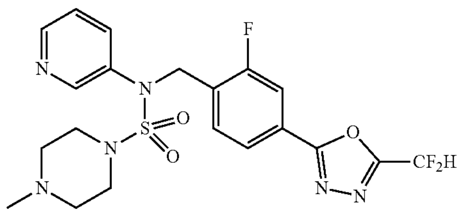 [SMILES: CN1CCN(S(=O)(=O)N(Cc2ccc(-c3nnc(C(F)F)o3)cc2F)c2cccnc2)CC1] |
| 31 | 11321 | 2 HCl |
| 32 | 11322 | 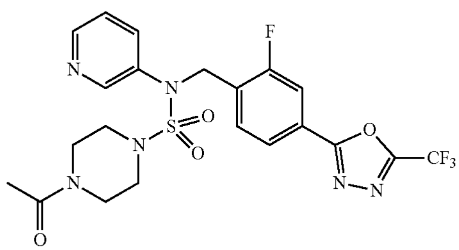 [SMILES: CC(=O)N1CCN(S(=O)(=O)N(Cc2ccc(-c3nnc(C(F)(F)F)o3)cc2F)c2cccnc2)CC1] |
| 33 | 11363 | 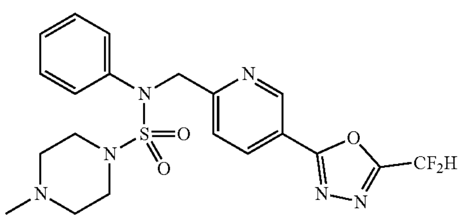 [SMILES: CN1CCN(S(=O)(=O)N(Cc2ccc(-c3nnc(C(F)F)o3)cn2)c2ccccc2)CC1] |
| 34 | 11379 | 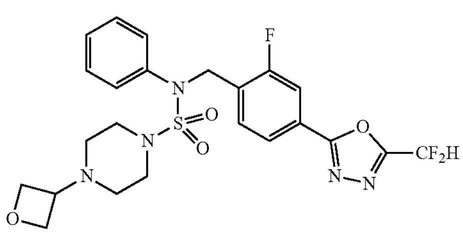 |
| 35 | 11440 | 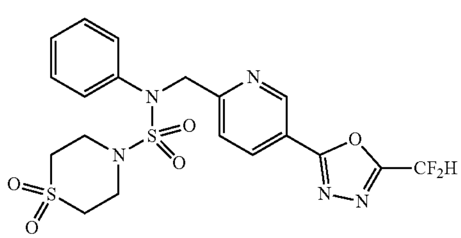 [SMILES: O=S1(=O)CCN(S(=O)(=O)N(Cc2ccc(-c3nnc(C(F)F)o3)cn2)c2ccccc2)CC1] |
| 36 | 11498 | |
| 37 | 11527 | |
| 38 | 11528 | |
| 39 | 11574 | |
| 40 | 11575 | |
| 41 | 11640 | |

TABLE 1-continued

| Ex. | Comp. | Structure |
|---|---|---|
| 42 | 11641 | (structure) |
| 43 | 11642 | (structure) |
| 44 | 11643 | (structure) |
| 45 | 11644 | (structure) |
| 46 | 11651 | (structure) |
| 47 | 11652 | (structure) |
| 48 | 11653 | (structure) |
| 49 | 11654 | (structure) |
| 50 | 11659 | (structure) |
| 51 | 11660 | (structure) |
| 52 | 11661 | (structure) |
| 53 | 11662 | (structure) |

TABLE 1-continued

| Ex. | Comp. | Structure |
|---|---|---|
| 54 | 11670 | (structure) |
| 55 | 11671 | (structure) |
| 56 | 11672 | (structure) |
| 57 | 11673 | (structure) |
| 58 | 11674 | (structure) |
| 59 | 11702 | (structure) |
| 60 | 11704 | (structure) |
| 61 | 11713 | (structure) |
| 62 | 11714 | (structure) |
| 63 | 11787 | (structure) HCl |

TABLE 1-continued

| Ex. | Comp. | Structure |
|---|---|---|
| 64 | 11788 | |
| 65 | 11789 | |
| 66 | 11823 | |
| 67 | 11824 | |
| 68 | 11825 | |
| 69 | 11826 | |
| 70 | 11827 | 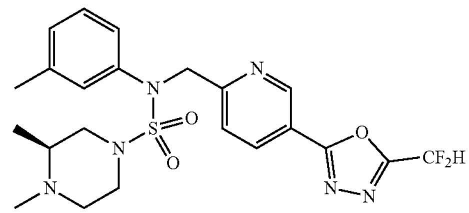 [SMILES: Cc1cccc(N(Cc2ccc(-c3nnc(C(F)F)o3)cn2)S(=O)(=O)N2CCN(C)[C@@H](C)C2)c1] |
| 71 | 11828 | 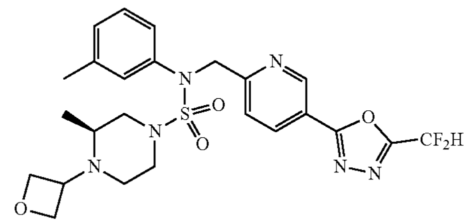 |
| 72 | 11829 | 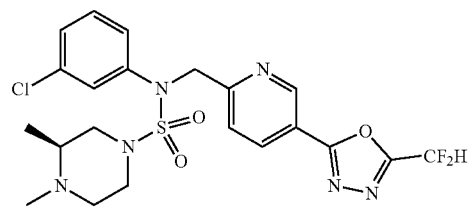 [SMILES: C[C@H]1CN(S(=O)(=O)N(Cc2ccc(-c3nnc(C(F)F)o3)cn2)c2cccc(Cl)c2)CCN1C] |
| 73 | 11830 | 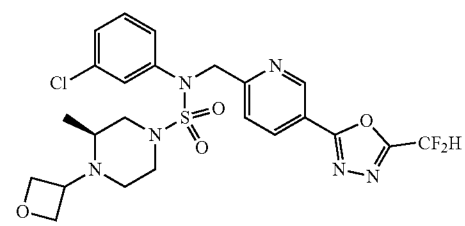 |
| 74 | 11831 | 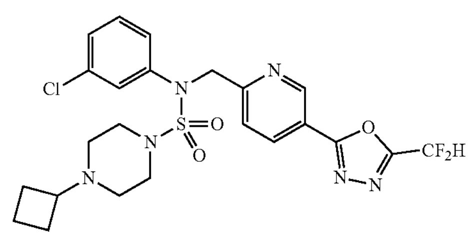 [SMILES: O=S(=O)(N1CCN(C2CCC2)CC1)N(Cc1ccc(-c2nnc(C(F)F)o2)cn1)c1cccc(Cl)c1] |
| 75 | 11832 | 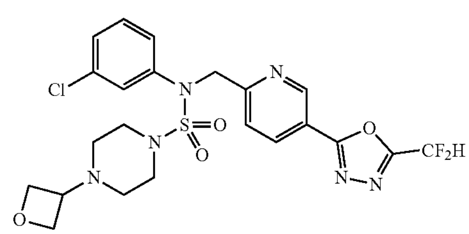 |
| 76 | 11833 | 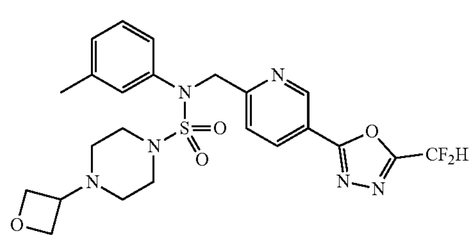 [SMILES: O=S(=O)(N1CCN(C2COC2)CC1)N(Cc1ccc(-c2nnc(C(F)F)o2)cn1)c1cccc(Cl)c1] |

Preferably, the compounds represented by formula I, stereoisomers thereof or pharmaceutically acceptable salts thereof may be selected from the group consisting of compounds 11301, 11302, 11303, 11305, 11306, 11307, 11308, 11313, 11314, 11315, 11316, 11318, 11321, 11363, 11379, 11440, 11498, 11574, 11575, 11641, 11653, 11654, 11659, 11662, 11670, 11671, 11672, 11823, 11824, 11825, 11826, 11827, 11828, 11829, 11830, 11831, 11832 and 11833. More preferably, the compounds represented by formula I, stereoisomers thereof or pharmaceutically acceptable salts thereof may be selected from the group consisting of compounds 11301, 11302, 11303, 11305, 11306, 11313, 11314, 11315, 11316, 11363, 11379, 11440, 11498, 11574, 11641, 11654, 11659, 11670, 11671, 11672, 11825, 11829, 11830, 11831 and 11832.

As used herein, the term "pharmaceutically acceptable salt" means any salt that is generally used in the pharmaceutical field. Examples of the pharmaceutically acceptable salt include, but are not limited to, salts with inorganic ions such as calcium, potassium, sodium or magnesium ions, salts with inorganic acids such as hydrochloric acid, nitric acid, phosphoric acid, bromic acid, iodic acid, perchloric acid or sulfuric acid, salts with organic acids such as acetic acid, trifluoroacetic acid, citric acid, maleic acid, succinic acid, oxalic acid, benzoic acid, tartaric acid, fumaric acid, mandelic acid, propionic acid, lactic acid, glycolic acid, gluconic acid, galacturonic acid, glutamic acid, glutaric acid, glucuronic acid, aspartic acid, ascorbic acid, carbonic acid, vanillic acid, hydroiodic acid or the like, salts with sulfonic acids such as methanesulfonic acid, ethanesulfonic acid, benzenesulfonic acid, p-toluenesulfonic acid or naphthalenesulfonic acid, salts with amino acids such as glycine, arginine or lysine, and salts with amines such as trimethylamine, triethylamine, ammonia, pyridine or picoline.

In the present invention, preferred salts include salts with hydrochloric acid, phosphoric acid, sulfuric acid, trifluoroacetic acid, citric acid, bromic acid, maleic acid, tartaric acid or the like, and preferred examples of such compounds include compounds 11293, 11301, 11306, 11309, 11313, 11317, 11321 and 11787 as disclosed herein.

The compounds represented by formula I may contain one or more asymmetrical carbon atoms, and thus may exist in the form of racemates, racemic mixtures, single enantiomers, diastereomeric mixtures, and individual diastereomers. The compounds of formula I can be separated into such isomers by methods known in the art, for example, column chromatography or HPLC. Alternatively, stereoisomers of the compounds of formula I may be synthesized by stereospecific synthesis using optically pure starting materials and/or reagents of known configuration.

Methods for Preparation of 1,3,4-oxadiazole Sulfamide Derivative Compounds

The present invention provides methods for the preparation of the 1,3,4-oxadiazole sulfamide derivative compounds presented by formula I, stereoisomers thereof, or pharmaceutically acceptable salts thereof.

Preferred methods for the preparation of the 1,3,4-oxadiazole sulfamide derivative compounds presented by formula I, stereoisomers thereof, or pharmaceutically acceptable salts thereof are as shown in reaction schemes 1 to 6 below, and also include modifications obvious to those skilled in the art.

[Reaction Scheme 1]

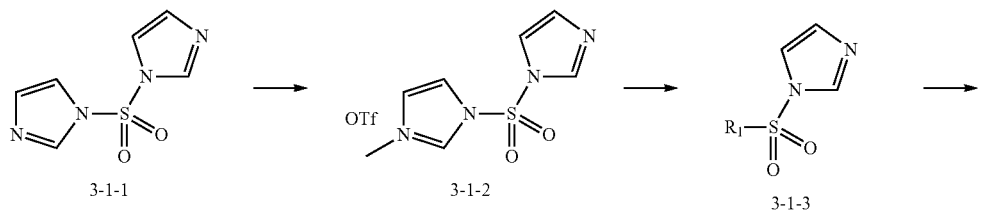

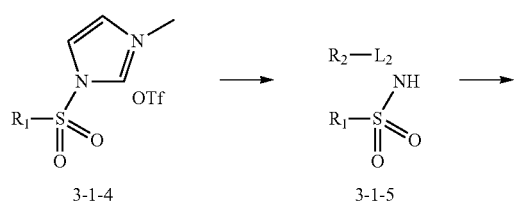

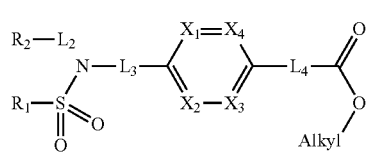

3-1-6

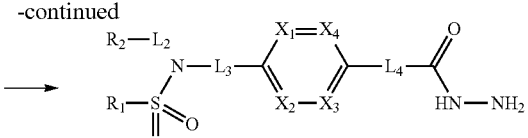

3-1-7

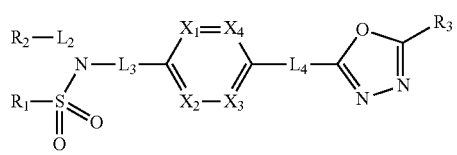

3-1-9

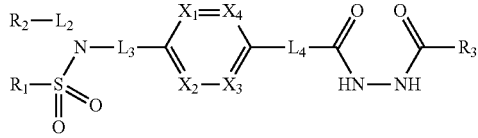

3-1-8

Reaction scheme 1 above shows a general method for synthesis of compounds having a sulfamide structure [Journal of Organic Chemistry, 2003, vol. 68, 115-119]. As shown in reaction scheme 1, a methyl group is introduced into 1,1'-sulfonyldiimidazole to increase reactivity, followed by substitution with an amine. This process is carried out twice, thereby preparing a compound of formula 3-1-5. Then, an alkyl group is introduced into the compound of formula 3-1-5 in the presence of sodium hydride, and the ester moiety is substituted with hydrazine, thereby preparing a compound of formula 3-1-7. Then, the compound of formula 3-1-7 is reacted with trifluoroacetic anhydride or difluoroacetic anhydride to synthesize a compound of formula 3-1-9 or formula 3-1-8, which is then reacted with 1-methoxy-N-triethylamminiosulfonyl-methaneimidate (Burgess reagent), thereby synthesizing compounds 11198, 11199, 11440 and 11498, which have an oxadiazole structure.

[Reaction Scheme 2]

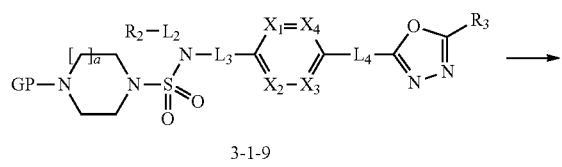

3-1-9

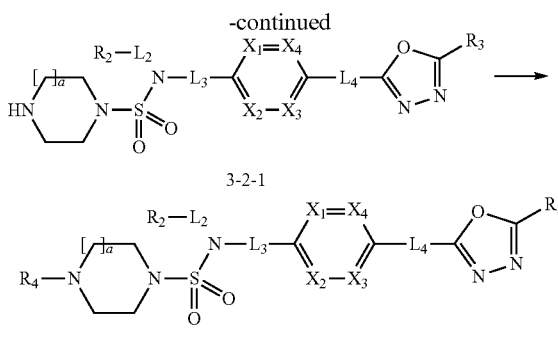

3-2-1

3-2-2

Reaction scheme 2 above shows a process of introducing a substituent into a secondary amine. As shown therein, a protecting group is removed from the compound of formula 3-1-9 synthesized according to reaction scheme 1, thereby synthesizing compounds 11293, 11301, 11309, 11313, 11317 and 11321. Next, a substituent is introduced into the compound of formula 3-2-1 by reaction with acyl chloride or sulfonyl chloride, or an alkyl group is introduced into the compound of formula 3-2-1 by reductive amination, thereby synthesizing compounds 11294, 11295, 11296, 11297, 11298, 11299, 11300, 11302, 11303, 11304, 11305, 11306, 11307, 11308, 11310, 11311, 11312, 11314, 11315, 11316, 11318, 11319, 11320 and 11322.

[Reaction Scheme 3]

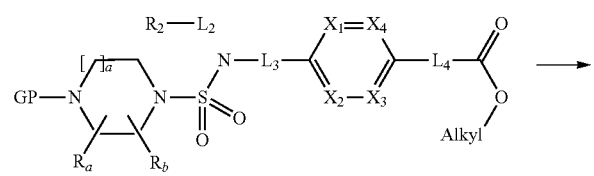

3-1-6

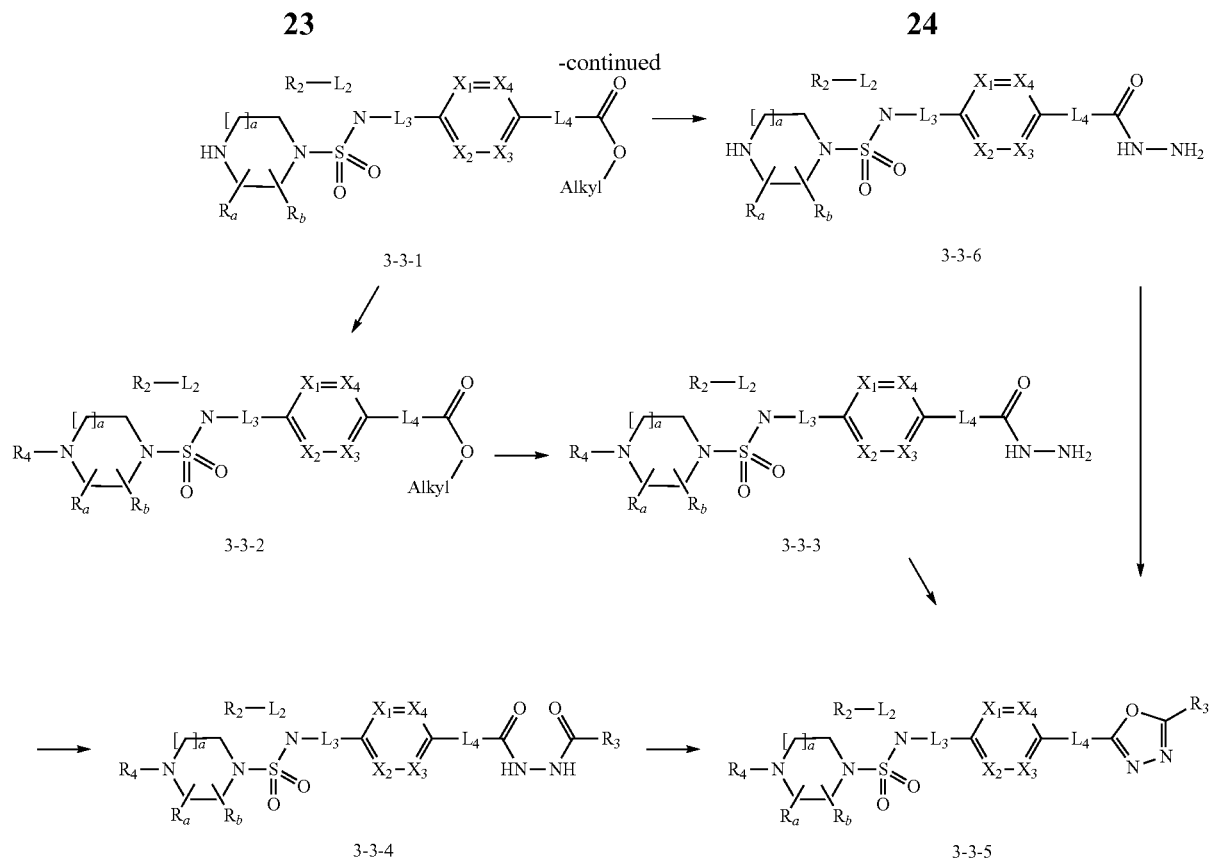

Reaction scheme 3 above shows another process of introducing a substituent into secondary amine. As shown therein, the protecting group of the compound of formula 3-1-6 synthesized according to reaction scheme 1 is removed to synthesize a compound of formula 3-3-1, and an alkyl group is introduced into the compound of formula 3-3-1 by reductive amination, thereby synthesizing a compound of formula 3-3-2. Next, according to the same synthesis method as shown in reaction scheme 1, compounds 11363, 11379, 11527, 11528, 11574, 11575, 11640, 11641, 11642, 11643, 11644, 11651, 11652, 11653, 11654, 11659, 11660, 11661, 11662, 11670, 11671, 11672, 11673, 11674, 11823, 11824, 11825, 11826, 11827, 11828, 11829, 11830, 11831, 11832 and 11833 are synthesized.

[Reaction Scheme 4]

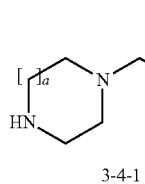

3-4-1

Reaction scheme 4 above shows a reaction for synthesizing a compound which is to be substituted into a sulfamide structure. As shown therein, a protecting group is introduced into a secondary amine which is then reacted with methanesulfonyl chloride to prepare a compound of formula 3-4-3.

[Reaction Scheme 5]

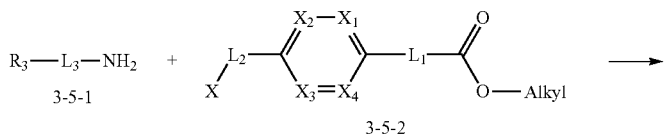

3-5-1  3-5-2

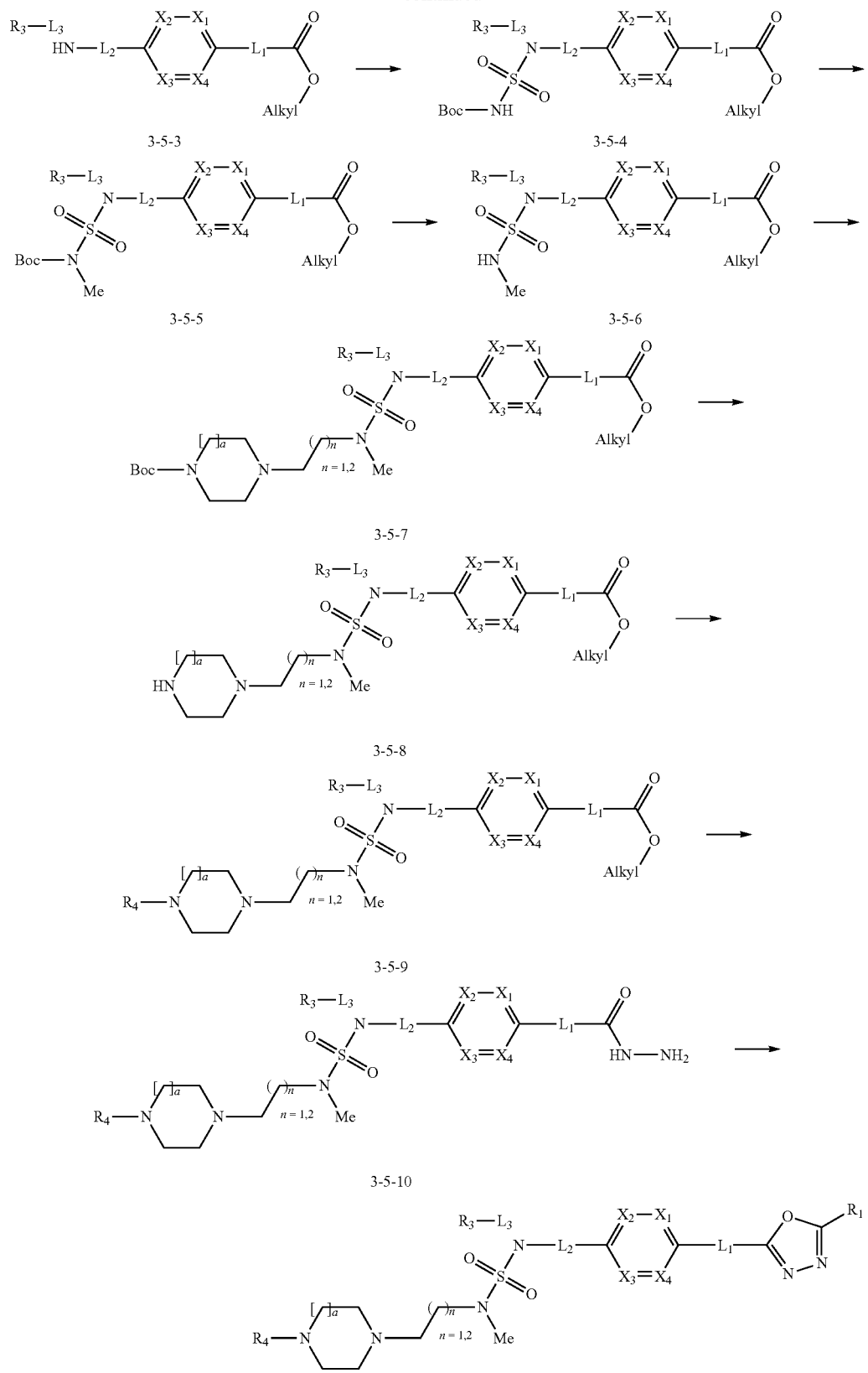

Reaction scheme 5 above shows a general method for synthesizing compounds having a sulfamide structure. As shown therein, a compound of formula 3-5-1 is reacted with a compound of formula 3-5-2 to prepare a compound of formula 3-5-3, and chlorosulfonyl isocyanate and tert-butanol are reacted with each other, and then reacted with the compound of formula 3-5-3, thereby preparing a compound of formula 3-5-4. Next, a methyl group is introduced into the secondary amine to prepare a compound of formula 3-5-5, which is then deprotected, thereby preparing a compound of formula 3-5-6. The compound of formula 3-5-6 is subjected to a substitution reaction with the compound of formula 3-4-3 prepared according to reaction scheme 4, thereby preparing a compound of formula 3-5-7. The compound of formula 3-5-7 is deprotected, thereby preparing a compound of formula 3-5-8. Next, the compound of formula 3-5-8 is subjected to a substitution reaction or a reductive amination reaction to prepare a compound of formula 3-5-9, which is then reacted with hydrazine to prepare a compound of formula 3-5-10. Next, the compound of formula 3-5-10 is reacted with trifluoroacetic anhydride or difluoroacetic anhydride to thereby prepare a compound of formula 3-5-11 which has an oxadiazole structure.

According to reaction scheme 5 above, compounds 11702, 11704, 11713 and 11714 are prepared.

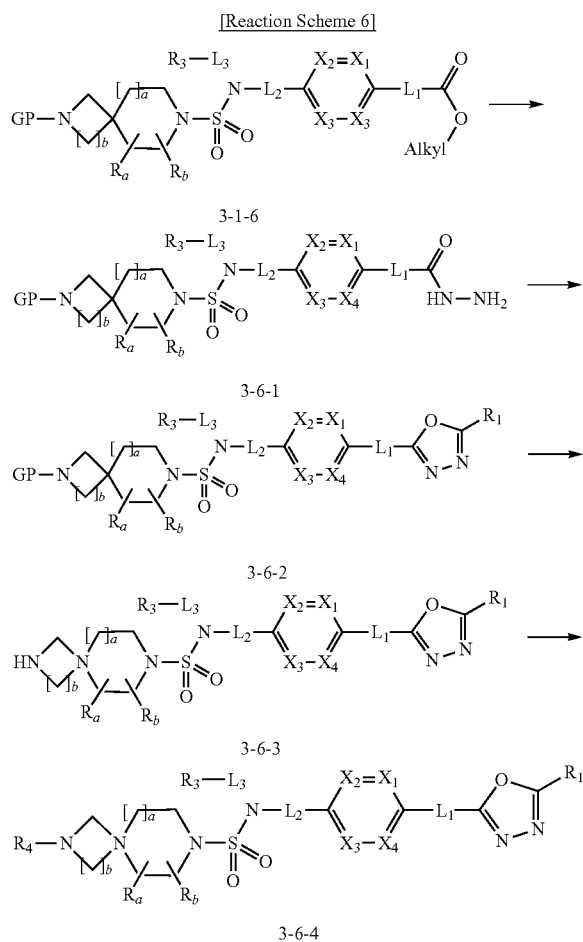

Reaction scheme 6 above shows a process of introducing a substituent into a secondary amine. As shown therein, the compound of formula 3-1-6 synthesized according to reaction scheme 1 is reacted with hydrazine to synthesize a compound of formula 3-6-1. Next, the compound of formula 3-6-1 is reacted with trifluoroacetic anhydride or difluoroacetic anhydride to prepare a compound of formula 3-6-2 having an oxadiazole structure. Next, the compound of formula 3-6-2 is deprotected, thereby synthesizing compound 11787. An alkyl group is introduced into compound 11787 or the compound of formula 3-6-3 by reductive amination, thereby synthesizing compounds 11788 and 11789.

Compositions Comprising 1,3,4-Oxadiazole Sulfamide Derivative Compounds, the Use Thereof and the Method of Treating Diseases The present invention provides a pharmaceutical composition for preventing or treating histone deacetylase 6 (HDAC6) activity-associated diseases, which contains, as an active ingredient, a compound represented by the following formula I, a stereoisomer thereof or a pharmaceutically acceptable salt thereof:

[Formula I]

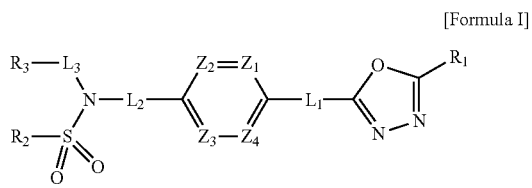

wherein formula I is as defined above.

The pharmaceutical composition according to the present invention exhibits a remarkable effect on the prevention or treatment of histone deacetylase 6 (HDAC6) activity-associated diseases by selectively inhibiting histone deacetylase 6 (HDAC6).

The histone deacetylase 6 (HDAC6) activity-associated diseases include infectious diseases such as prion disease; neoplasms such as benign tumor (e.g. myelodysplastic syndrome) or malignant tumor (e.g. multiple myeloma, lymphoma, leukemia, lung cancer, rectal cancer, colon cancer, prostate cancer, urothelial carcinoma, breast cancer, melanoma, skin cancer, liver cancer, brain cancer, gastric cancer, ovarian cancer, pancreatic cancer, head and neck cancer, oral cancer, or glioma); endocrine, nutritional and metabolic diseases such as Wilson's disease, amyloidosis or diabetes; mental and behavioral disorders such as depression or Rett's syndrome, and the like; neurological diseases such as atrophy of central nervous system (e.g. Huntington's disease, spinal muscular atrophy (SMA), spinocerebellar ataxia (SCA)), neurodegenerative disease (e.g. Alzheimer's disease), movement disorder (e.g. Parkinson's disease), neuropathy (e.g. hereditary neuropathy (Charcot-Marie-Tooth disease), sporadic neuropathy, inflammatory neuropathy, drug-induced neuropathy), motor neuron diseases (amyotrophic lateral sclerosis (ALS)), or demyelinating diseases of the central nervous system (e.g. multiple sclerosis (MS)), and the like; diseases of the eye and adnexa, such as uveitis; cardiovascular diseases such as atrial fibrillation or stroke and the like; respiratory diseases such as asthma; digestive diseases such as alcoholic liver disease, inflammatory bowel disease, Crohn's disease or ulcerative bowel disease, and the like; diseases of the skin and subcutaneous tissue, such as psoriasis; diseases of the musculoskeletal system and connective tissue, such as rheumatoid arthritis, osteoarthritis or systemic lupus erythematosus (SLE), and the like; or congenital malformations, deformations and chromosomal abnormalities, such as autosomal dominant polycystic kidney disease, as well as disorders or diseases associated with the abnormal function of histone deacetylase.

The pharmaceutically acceptable salt is as described above with respect to a pharmaceutically acceptable salt of the compound represented by formula I according to the present invention.

For administration, the pharmaceutical composition according to the present invention may further contain at least one pharmaceutically acceptable carrier in addition to the compound of formula I, an isomer thereof or a pharmaceutically acceptable salt thereof. The pharmaceutically acceptable carrier that is used in the present invention may be at least one of physiological saline, sterile water, Ringer solution, buffered saline, dextrose solution, maltodextrin solution, glycerol, ethanol, and a mixture of two or more thereof. If necessary, the composition may contain other conventional additives such as an antioxidant, a buffer or a bacteriostatic agent. In addition, the composition can be formulated into injectable formulations such as solutions, suspensions, turbid fluid, etc, pills, capsules, granules or tablets using a diluent, a dispersing agent, a surfactant, a binder and a lubricant. Thus, the composition of the present invention may be in the form of patches, liquids, pills, capsules, granules, tablets, suppositories, etc. These formulations can be prepared either by conventional methods that are used for formulation in the art or by the method disclosed in Remington's Pharmaceutical Science (the latest edition), Mack Publishing Company, Easton Pa.

The pharmaceutical composition of the present invention may be administered orally or parenterally (e.g., intravenously, subcutaneously, intraperitoneally or topically) depending on the intended use. The dose of the pharmaceutical composition varies depending on the patient's weight, age, sex, health conditions and diet, the time of administration, the mode of administration, excretion rate, the severity of the disease, and the like. The daily dose of the compound of formula I according to the present invention may be about 1 to 1000 mg/kg, preferably 5 to 100 mg/kg, and may be administered once to several times a day.

The pharmaceutical composition of the present invention may further contain, in addition to the compound represented by formula I, a stereoisomer thereof or a pharmaceutically acceptable salt thereof, one or more active ingredients that exhibit medicinal efficacy identical or similar thereto.

The present invention also provides a method for preventing or treating a histone deacetylase-mediated disease, which comprises administering a therapeutically effective amount of the compound represented by formula I, a stereoisomer thereof or a pharmaceutically acceptable salt thereof.

As used herein, the term "therapeutically effective amount" refers to the amount of the compound represented by formula I, which is effective for the prevention or treatment of histone deacetylase 6 activity-associated diseases.

The present invention also provides a method of selectively inhibiting HDAC6, which comprises administering the compound of formula I, a stereoisomer thereof or a pharmaceutically acceptable salt thereof to mammals including humans.

The method of preventing or treating histone deacetylase 6 activity-associated disease according to the present invention includes inhibiting or averting the disease as well as addressing the disease itself, prior to the onset of symptoms by administering the compound represented by formula I. In the management of diseases, the magnitude of a prophylactic or therapeutic dose of a particular active ingredient will vary with the nature and severity of the disease or condition, and may also vary according to the route by which the active ingredient is administered. The dose and the dose frequency will also vary according to the age, body weight, and response of the individual patient. Suitable dosing regimens can be readily selected by those skilled in the art with due consideration of such factors. In addition, the method of preventing or treating histone deacetylase 6 activity-associated disease according to the present invention may further comprise administering a therapeutically effective amount of an additional active agent helpful for the treatment of the disease together with the compound represented by formula I, in which the additional active agent can exhibit a synergistic effect with the compound of formula I or an assistant effect.

The present invention is also intended to provide the use of the compound represented by formula I, a stereoisomer thereof or a pharmaceutically acceptable salt thereof, for the preparation of a medicament for treating histone deacetylase 6 activity-associated disease. For the preparation of the medicament, the compound represented by formula I may be mixed with a pharmaceutically acceptable adjuvant, diluent, carrier or the like, and combined with other active agents such that the active ingredients can have synergistic effects.

The particulars mentioned in the use, composition and treatment method of the present invention may be appropriately combined unless contradictory to one another.

Advantageous Effects of Invention

The compounds represented by formula I, stereoisomers thereof or pharmaceutically acceptable salts thereof can selectively inhibit HDAC6, and thus exhibit excellent effects on the prevention or treatment of histone deacetylase 6 activity-associated diseases.

MODE FOR THE INVENTION

Hereinafter, preferred examples will be presented to assist in the understanding of the present invention. However, these examples are provided only for a better understanding of the present invention and are not intended to limit the scope of the present invention.

Preparation of 1,3,4-oxadiazole Sulfamide Derivative Compounds

Specific methods for preparing the compounds of formula I are as follows.

Example 1: Compound 11198, N-(4-fluorophenyl)-N-(4-(5-(trifluoromethyl)-1,3,4-oxadiazol-2-yl)benzyl)morpholine-4-sulfonamide

[Step 1] N-(4-fluorophenyl)-N-(4-(hydrazinecarbonyl)benzyl)morpholine-4-sulfonamide

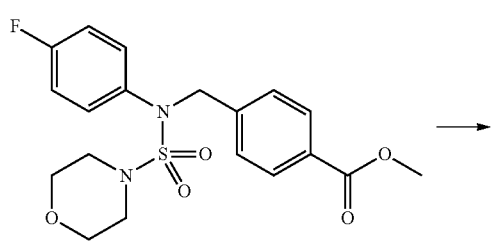

-continued

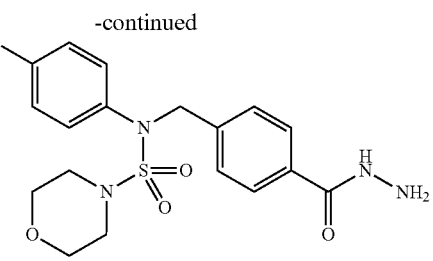

A mixture of methyl 4-((N-(4-fluorophenyl)morpholine-4-sulfonamido)methyl)benzoate (0.150 g, 0.367 mmol) and hydrazine monohydrate (0.347 mL, 7.345 mmol) in ethanol (3 mL) was heated at 120° C. for 2 hr under the microwaves, and cooled down to the room temperature to terminate the reaction. Then, water was added to the reaction mixture, followed by extraction with ethyl acetate. The organic layer was washed with saturated aqueous sodium chloride solution, dried with anhydrous MgSO$_4$, filtered, and concentrated in vacuo. The title compound was used without further purification (0.136 g, 90.5%, colorless oil).

[Step 2] Compound 11198

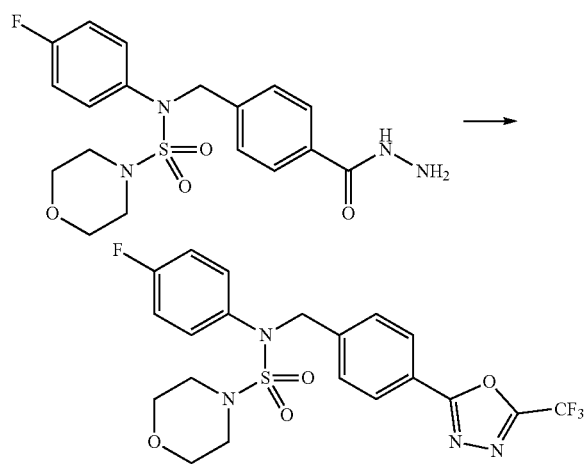

A solution of N-(4-fluorophenyl)-N-(4-(hydrazinecarbonyl)benzyl)morpholine-4-sulfonamide (0.067 g, 0.164 mmol) and triethylamine (0.045 mL, 0.328 mmol) in N,N-dimethylformide (2 mL) was stirred at 0° C., and mixed with trifluoroacetic anhydride (0.028 mL, 0.197 mmol). The reaction mixture was stirred at 80° C. for additional 18 hr, cooled down to the room temperature to terminate the reaction, and concentrated under the reduced pressure to remove the solvent. Then, saturated aqueous sodium bicarbonate solution was added to the concentrate, followed by extraction with ethyl acetate. The organic layer was washed with aqueous saturated sodium chloride solution, dried with anhydrous MgSO$_4$, filtered, and concentrated in vacuo. The residue was chromatographed (Sift, 4 g cartridge; ethyl acetate/hexane=10% to 40%) to give the title compound as yellow solid (0.047 g, 59.0%).
$^1$H NMR (400 MHz, CDCl$_3$) δ 8.04~8.02 (m, 2H), 7.42 (d, 2H, J=8.4 Hz), 7.25~7.22 (m, 2H), 7.02~6.98 (m, 2H), 4.85 (s, 2H), 3.64 (t, 4H, J=4.7 Hz), 3.17 (t, 4H, J=4.8 Hz); LRMS (ES) m/z 487.4 (M$^+$+1).

Example 2: Compound 11199, N-(4-(5-(difluoromethyl)-1,3,4-oxadiazol-2-yl)benzyl)-N-(4-fluorophenyl)morpholine-4-sulfonamide

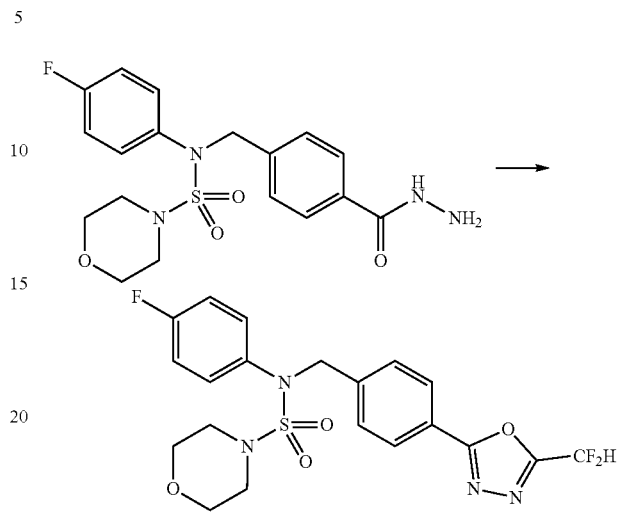

A solution of N-(4-fluorophenyl)-N-(4-(hydrazinecarbonyl)benzyl)morpholine-4-sulfonamide (0.067 g, 0.164 mmol) and triethylamine (0.045 mL, 0.328 mmol) in N,N-dimethylformide (3 mL) was stirred at 0° C., and mixed with 2,2-difluoroacetic anhydride (0.021 mL, 0.197 mmol). The reaction mixture was stirred at 80° C. for additional 18 hr, cooled down to the room temperature to terminate the reaction, and concentrated under the reduced pressure to remove the solvent. Then, saturated aqueous sodium bicarbonate solution was added to the concentrate, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 4 g cartridge; ethyl acetate/hexane=10% to 40%) to give the title compound as yellow solid (0.051 g, 65.8%).
$^1$H NMR (400 MHz, CDCl$_3$) δ 8.04~8.02 (m, 2H), 7.40 (d, 2H, J=8.3 Hz), 7.25~7.21 (m, 2H), 7.02~6.98 (m, 2H), 6.90 (t, 1H, J=51.7 Hz), 4.85 (s, 2H), 3.64 (t, 4H, J=4.7 Hz), 3.17 (t, 4H, J=4.7 Hz); LRMS (ES) m/z 469.3 (M$^+$+1).

Example 3: Compound 11293, N-(2-fluoro-4-(5-(trifluoromethyl)-1,3,4-oxadiazol-2-yl)benzyl)-N-phenylpiperazine-1-sulfonamide Hydrochloride

[Step 1] 1-((1H-imidazol-1-yl)sulfonyl)-3-methyl-1H-imidazol-3-ium trifluoromethanesulfonate

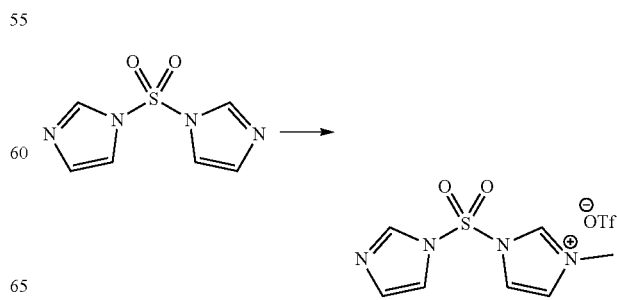

A solution of 1,1'-sulfonylbis(1H-imidazole) (10.000 g, 50.454 mmol) in dichloromethane (120 mL) was mixed at 0° C. with trifluoromethanesulfonate (MeOTf, 5.710 mL, 50.454 mmol), and stirred at the same temperature for 3 hr. The precipitates were collected by filtration, washed by dichloromethane, and dried to give 1-((1H-imidazol-1-yl)sulfonyl)-3-methyl-1H-imidazol-3-ium trifluoromethanesulfonate as white solid (16.720 g, 91.5%).

[Step 2] tert-butyl 4-((1H-imidazol-1-yl)sulfonyl)piperazine-1-carboxylate

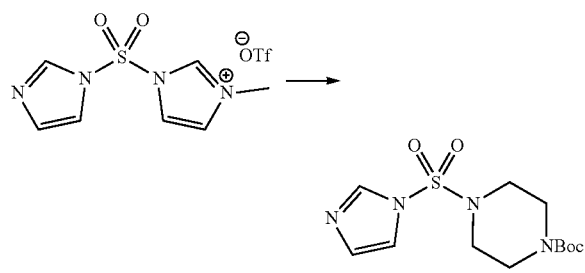

A mixture of tert-butyl piperazine-1-carboxylate (2.500 g, 13.422 mmol) and 1-((1H-imidazol-1-yl)sulfonyl)-3-methyl-1H-imidazol-3-ium trifluoromethanesulfonate (5.835 g, 16.107 mmol) in acetonitrile (50 mL) was stirred at the room temperature for 16 hr. Then, water was added to the reaction mixture, followed by extraction with ethyl acetate. The organic layer was washed with saturated aqueous sodium chloride solution, dried with anhydrous MgSO₄, filtered, and concentrated in vacuo. The residue was chromatographed (SiO₂, 80 g cartridge; ethyl acetate/hexane=20% to 50%) to give tert-butyl 4-((1H-imidazol-1-yl)sulfonyl)piperazine-1-carboxylate as beige solid (2.417 g, 56.9%).

[Step 3] 1-((4-(tert-butoxycarbonyl)piperazin-1-yl)sulfonyl)-3-methyl-1H-imidazol-3-ium Trifluoromethanesulfonate

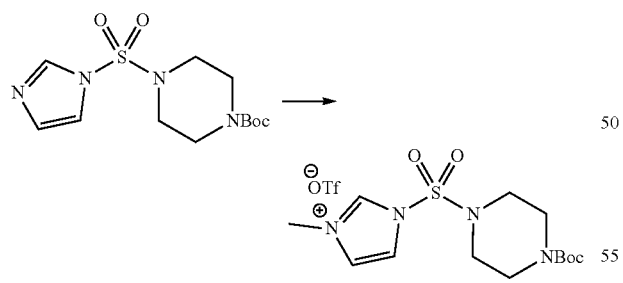

A solution of tert-butyl 4-((1H-imidazol-1-yl)sulfonyl)piperazine-1-carboxylate (2.417 g, 7.640 mmol) in dichloromethane (30 mL) was mixed at 0° C. with MeOTf (0.908 mL, 8.022 mmol), and stirred at the room temperature for 5 hr. The reaction mixture was diluted with hexane (30 mL), and stirred. The resulting precipitates were collected by filtration, washed by hexane, and dried to give 1-((4-(tert-butoxycarbonyl)piperazin-1-yl)sulfonyl)-3-methyl-1H-imidazol-3-ium trifluoromethanesulfonate as white solid (3.510 g, 95.6%).

[Step 4] tert-butyl 4-(N-phenylsulfamoyl)piperazine-1-carboxylate

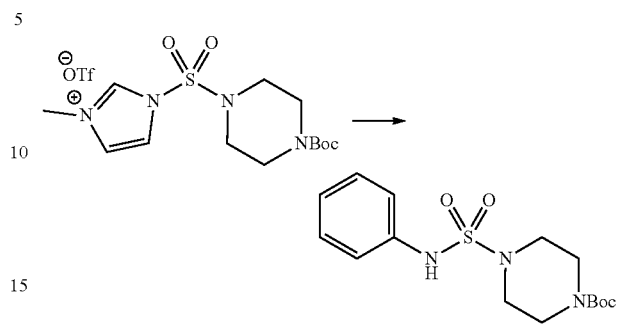

A mixture of 1-((4-(tert-butoxycarbonyl)piperazin-1-yl)sulfonyl)-3-methyl-1H-imidazol-3-ium trifluoromethanesulfonate (3.510 g, 7.305 mmol) and aniline (0.734 mL, 8.036 mmol) in acetonitrile (40 mL), prepared at the ambient temperature, was heated at reflux for 16 hr, and cooled down to the ambient temperature. Then, water was added to the reaction mixture, followed by extraction with ethyl acetate. The organic layer was washed with saturated aqueous sodium chloride solution, dried with anhydrous MgSO₄, filtered, and concentrated in vacuo. The residue was chromatographed (SiO₂, 40 g cartridge; ethyl acetate/hexane=20% to 50%) to give the crude product, which was dissolved in ethyl acetate (20 mL) and hexane (100 mL), and stirred. The resulting precipitates were collected by filtration, washed by hexane, and dried to give tert-butyl 4-(N-phenylsulfamoyl)piperazine-1-carboxylate as white solid (2.440 g, 97.8%).

[Step 5] tert-butyl 4-(N-(2-fluoro-4-(methoxycarbonyl)benzyl)-N-phenylsulfamoyl)piperazine-1-carboxylate

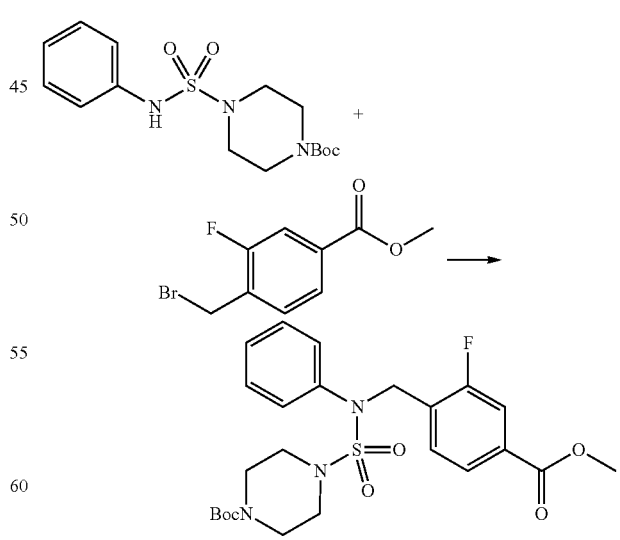

To a solution of tert-butyl 4-(N-phenylsulfamoyl)piperazine-1-carboxylate (2.440 g, 7.146 mmol) in N,N-dimethylformide (50 mL) was added NaH (60.00%, 0.372 g, 9.290 mmol) at 0° C., and the mixture was stirred at the same temperature for 10 min. The reaction mixture was treated with methyl 4-(bromomethyl)-3-fluorobenzoate (1.942 g, 7.861 mmol), and stirred for additional 1 hr at the room temperature. Then, saturated aqueous ammonium chloride solution was added to the reaction mixture, followed by extraction with ethyl acetate. The organic layer was washed with saturated aqueous sodium chloride solution, dried with anhydrous MgSO$_4$, filtered, and concentrated in vacuo. The residue was chromatographed (SiO$_2$, 40 g cartridge; ethyl acetate/hexane=10% to 30%) to give tert-butyl 4-(N-(2-fluoro-4-(methoxycarbonyl)benzyl)-N-phenylsulfamoyl)piperazine-1-carboxylate as white solid (3.070 g, 84.6%).

[Step 6] tert-butyl 4-(N-(2-fluoro-4-(hydrazinecarbonyl)benzyl)-N-phenylsulfamoyl)piperazine-1-carboxylate

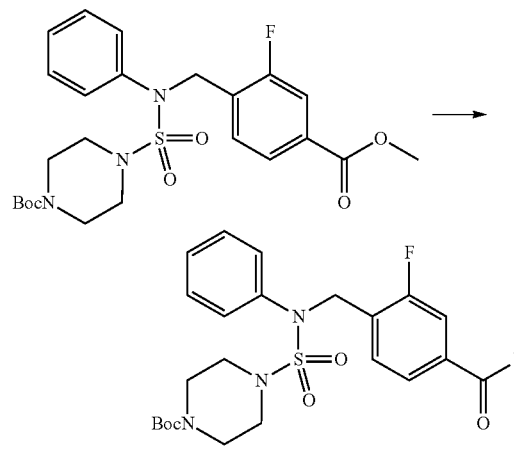

A mixture of tert-butyl 4-(N-(2-fluoro-4-(methoxycarbonyl)benzyl)-N-phenylsulfamoyl)piperazine-1-carboxylate (2.570 g, 5.063 mmol) and Hydrazine monohydrate (4.782 mL, 101.265 mmol) in ethanol (20 mL) was heated at 120° C. for 2 hr under the microwaves, and cooled down to the room temperature to terminate the reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The title compound was used without further purification (2.462 g, 95.8%, white solid).

[Step 7] tert-butyl 4-(N-(2-fluoro-4-(2-(2,2,2-trifluoroacetyl)hydrazine-1-carbonyl)benzyl)-N-phenylsulfamoyl)piperazine-1-carboxylate

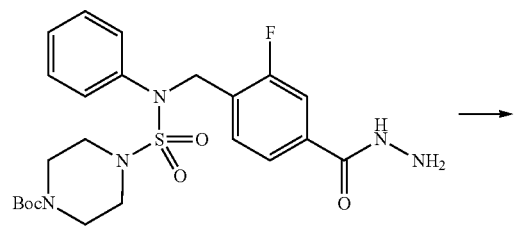

-continued

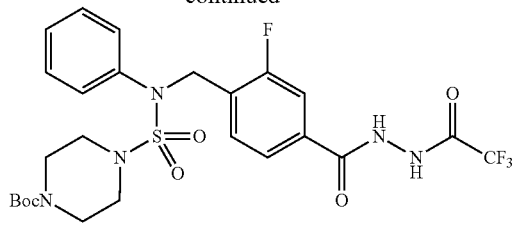

A solution of tert-butyl 4-(N-(2-fluoro-4-(hydrazinecarbonyl)benzyl)-N-phenylsulfamoyl)piperazine-1-carboxylate (1.458 g, 2.872 mmol) and triethylamine (0.796 mL, 5.745 mmol) in N,N-dimethylformide (10 mL) was stirred at 0° C., and mixed with trifluoroacetic anhydride (0.486 mL, 3.447 mmol). The reaction mixture was stirred at 80° C. for additional 18 hr, cooled down to the room temperature to terminate the reaction, and concentrated under the reduced pressure to remove the solvent. Then, water was added to the concentrates, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 24 g cartridge; ethyl acetate/hexane=10% to 70%) to give the title compound as white solid (0.393 g, 23.3%).

[Step 8] tert-butyl 4-(N-(2-fluoro-4-(5-(trifluoromethyl)-1,3,4-oxadiazol-2-yl)benzyl)-N-phenylsulfamoyl)piperazine-1-carboxylate

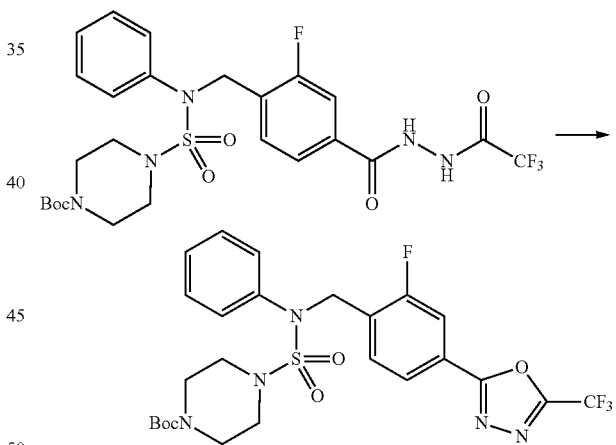

A mixture of tert-butyl 4-(N-(2-fluoro-4-(2-(2,2,2-trifluoroacetyl)hydrazine-1-carbonyl)benzyl)-N-phenylsulfamoyl)piperazine-1-carboxylate (0.614 g, 1.017 mmol) and 1-methoxy-N-triethylammoniosulfonyl-methanimidate (Burgess reagent, 0.364 g, 1.526 mmol) in tetrahydrofuran (4 mL) was heated at 150° C. for 30 min under the microwaves, cooled down to the room temperature to terminate the reaction. The reaction mixture was concentrated under the reduced pressure to remove the solvent. Then, water was added to the concentrate, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 12 g cartridge; ethyl acetate/hexane=0% to 25%) to give the title compound as white solid (0.576 g, 96.7%).

[Step 9] Compound 11293

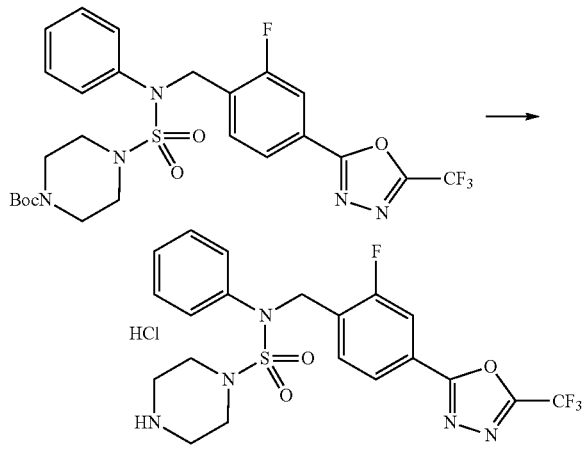

A solution of tert-butyl 4-(N-(2-fluoro-4-(5-(trifluoromethyl)-1,3,4-oxadiazol-2-yl)benzyl)-N-phenylsulfamoyl)piperazine-1-carboxylate (0.969 g, 1.655 mmol) in 1,4-dioxane (10 mL) was mixed at the room temperature with hydrochloric acid (4.00 M solution in 1,4-dioxane, 8.274 mL, 33.096 mmol), and stirred at the same temperature for 2 hr. The reaction mixture was concentrated under the reduced pressure to remove the solvent. The residue was diluted with diethylether (5 mL) and hexane (50 mL), and stirred. The resulting precipitates were collected by filtration, washed by hexane, and dried to give N-(2-fluoro-4-(5-(trifluoromethyl)-1,3,4-oxadiazol-2-yl)benzyl)-N-phenylpiperazine-1-sulfonamide hydrochloride as white solid (0.860 g, 99.6%).

$^1$H NMR (400 MHz, DMSO-$d_6$) δ 8.96 (s, 2H), 7.86 (dd, 1H, J=8.0, 1.6 Hz), 7.83 (d, 1H, J=10.2 Hz), 7.62 (t, 1H, J=7.8 Hz), 7.43 (d, 2H, J=8.1 Hz), 7.37 (t, 2H, J=7.6 Hz), 7.29 (m, 1H), 5.05 (s, 2H), 3.40-3.37 (m, 4H), 3.13-3.11 (m, 4H); LRMS (ES) m/z 486.0 (M$^+$+1).

Example 4: Compound 11294, 4-acetyl-N-(2-fluoro-4-(5-(trifluoromethyl)-1,3,4-oxadiazol-2-yl)benzyl)-N-phenylpiperazine-1-sulfonamide

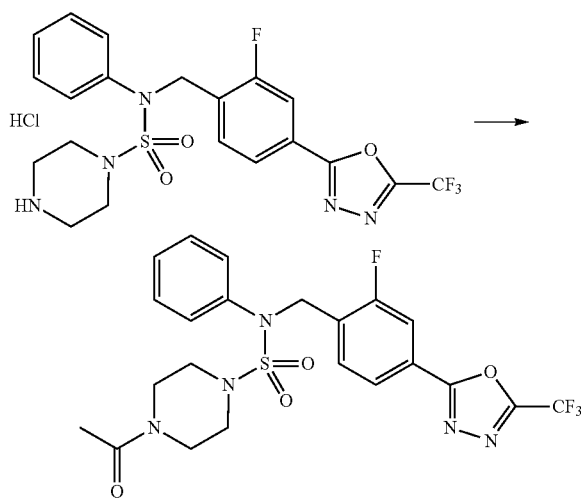

A slurry of N-(2-fluoro-4-(5-(trifluoromethyl)-1,3,4-oxadiazol-2-yl)benzyl)-N-phenylpiperazine-1-sulfonamide hydrochloride (0.030 g, 0.057 mmol) in dichloromethane (3 mL) was mixed at the room temperature with acetyl chloride (0.008 mL, 0.115 mmol) and N,N-diisopropylethylamine (0.030 mL, 0.172 mmol), and stirred at the same temperature for 1 hr. Then, saturated aqueous sodium bicarbonate solution was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 12 g cartridge; ethyl acetate/hexane=30% to 70%) to give 4-acetyl-N-(2-fluoro-4-(5-(trifluoromethyl)-1,3,4-oxadiazol-2-yl)benzyl)-N-phenylpiperazine-1-sulfonamide as bright yellow oil (0.020 g, 66.0%).

$^1$H NMR (400 MHz, DMSO-$d_6$) δ 7.86 (d, 1H, J=8.2 Hz), 7.81 (d, 1H, J=10.0 Hz), 7.63 (t, 1H, J=7.7 Hz), 7.44 (d, 2H, J=7.6 Hz), 7.35 (t, 2H, J=7.6 Hz), 7.26 (t, 1H, J=7.3 Hz), 5.04 (s, 2H), 3.44 (s, 4H), 3.20 (m, 2H), 3.14 (m, 2H), 2.00 (s, 3H); LRMS (ES) m/z 528.3 (M$^+$+1).

Example 5: Compound 11295, N-(2-fluoro-4-(5-(trifluoromethyl)-1,3,4-oxadiazol-2-yl)benzyl)-N-phenyl-4-propionylpiperazine-1-sulfonamide

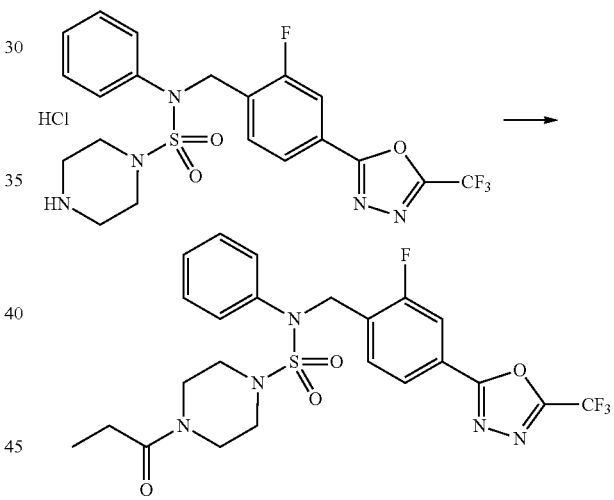

A slurry of N-(2-fluoro-4-(5-(trifluoromethyl)-1,3,4-oxadiazol-2-yl)benzyl)-N-phenylpiperazine-1-sulfonamide hydrochloride (0.030 g, 0.057 mmol) in dichloromethane (3 mL) was mixed at the room temperature with propionyl chloride (0.010 mL, 0.115 mmol) and N,N-diisopropylethylamine (0.030 mL, 0.172 mmol), and stirred at the same temperature for 1 hr. Then, saturated aqueous sodium bicarbonate solution was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 12 g cartridge; ethyl acetate/hexane=30% to 70%) to give N-(2-fluoro-4-(5-(trifluoromethyl)-1,3,4-oxadiazol-2-yl)benzyl)-N-phenyl-4-propionylpiperazine-1-sulfonamide as colorless liquid (0.024 g, 77.1%).

$^1$H NMR (400 MHz, DMSO-$d_6$) δ 7.86 (dd, 1H, J=8.0, 1.6 Hz), 7.83-7.77 (m, 1H), 7.63 (t, 1H, J=7.7 Hz), 7.44 (d, 2H, J=7.3 Hz), 7.34 (t, 2H, J=7.6 Hz), 7.26 (t, 1H, J=7.3 Hz), 5.04 (s, 2H), 3.45 (m, 4H), 3.18 (m, 4H), 2.32 (q, 2H, J=7.4 Hz), 0.98 (t, 3H, J=7.4 Hz); LRMS (ES) m/z 542.3 (M⁺+1).

Example 6: Compound 11296, N-(2-fluoro-4-(5-(trifluoromethyl)-1,3,4-oxadiazol-2-yl)benzyl)-4-isobutyryl-N-phenylpiperazine-1-sulfonamide

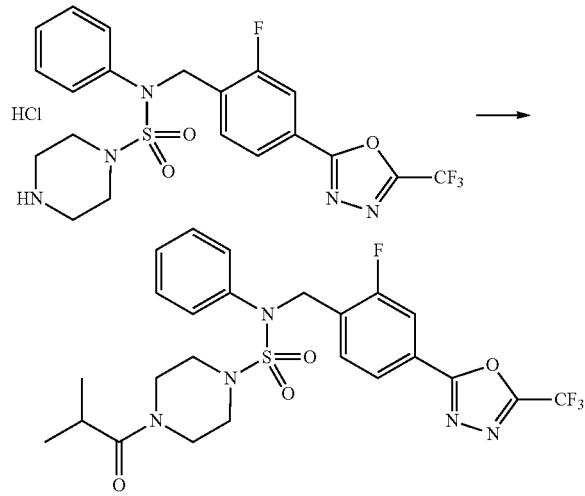

A slurry of N-(2-fluoro-4-(5-(trifluoromethyl)-1,3,4-oxadiazol-2-yl)benzyl)-N-phenylpiperazine-1-sulfonamide hydrochloride (0.030 g, 0.057 mmol) in dichloromethane (3 mL) was mixed at the room temperature with isobutyryl chloride (0.012 mL, 0.115 mmol) and N,N-diisopropylethylamine (0.030 mL, 0.172 mmol), and stirred at the same temperature for 1 hr. Then, saturated aqueous sodium bicarbonate solution was added to the reaction mixture, followed by extraction with dichloromethane. The organic layer was washed with aqueous saturated sodium chloride solution, dried with anhydrous MgSO₄, filtered, and concentrated in vacuo. The residue was chromatographed (SiO₂, 12 g cartridge; ethyl acetate/hexane=20% to 50%) to give N-(2-fluoro-4-(5-(trifluoromethyl)-1,3,4-oxadiazol-2-yl)benzyl)-4-isobutyryl-N-phenylpiperazine-1-sulfonamide as white solid (0.025 g, 78.3%).

¹H NMR (400 MHz, DMSO-d₆) δ 7.86 (dd, 1H, J=8.0, 1.6 Hz), 7.83-7.77 (m, 1H), 7.63 (t, 1H, J=7.6 Hz), 7.44 (d, 2H, J=7.9 Hz), 7.34 (t, 2H, J=7.7 Hz), 7.26 (t, 1H, J=7.3 Hz), 5.05 (s, 2H), 3.49 (m, 4H), 3.16 (s, 4H), 2.84 (dt, 1H, J=13.6, 6.8 Hz), 0.98 (d, 6H, J=6.7 Hz); LRMS (ES) m/z 556.3 (M⁺+1).

Example 7: Compound 11297, N-(2-fluoro-4-(5-(trifluoromethyl)-1,3,4-oxadiazol-2-yl)benzyl)-4-(methylsulfonyl)-N-phenylpiperazine-1-sulfonamide

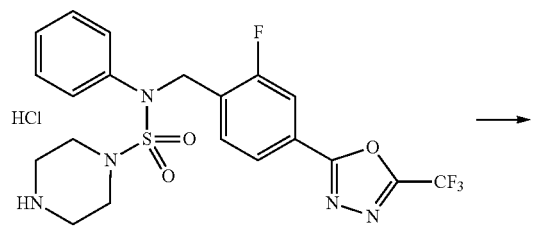

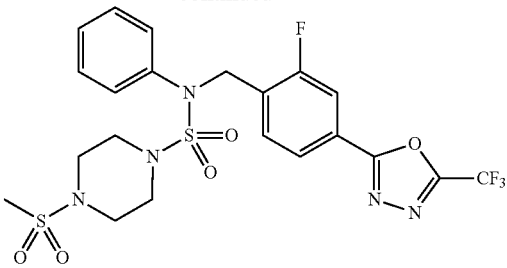

A slurry of N-(2-fluoro-4-(5-(trifluoromethyl)-1,3,4-oxadiazol-2-yl)benzyl)-N-phenylpiperazine-1-sulfonamide hydrochloride (0.030 g, 0.057 mmol) in dichloromethane (3 mL) was mixed at the room temperature with methanesulfonyl chloride (0.009 mL, 0.115 mmol) and N,N-diisopropylethylamine (0.030 mL, 0.172 mmol), and stirred at the same temperature for 1 hr. Then, saturated aqueous sodium bicarbonate solution was added to the reaction mixture, followed by extraction with dichloromethane. The organic layer was washed with aqueous saturated sodium chloride solution, dried with anhydrous MgSO₄, filtered, and concentrated in vacuo. The residue was chromatographed (SiO₂, 12 g cartridge; ethyl acetate/hexane=20% to 50%) to give N-(2-fluoro-4-(5-(trifluoromethyl)-1,3,4-oxadiazol-2-yl)benzyl)-4-(methylsulfonyl)-N-phenylpiperazine-1-sulfonamide as white solid (0.029 g, 89.5%).

¹H NMR (400 MHz, DMSO-d₆) δ 7.86 (dd, 1H, J=8.1, 1.6 Hz), 7.84-7.78 (m, 1H), 7.63 (t, 1H, J=7.6 Hz), 7.45 (d, 2H, J=8.1 Hz), 7.36 (t, 2H, J=7.7 Hz), 7.27 (t, 1H, J=7.3 Hz), 5.05 (s, 2H), 3.31-3.25 (m, 4H), 3.19-3.07 (m, 4H), 2.90 (s, 3H); LRMS (ES) m/z 564.2 (M⁺+1).

Example 8: Compound 11298, N-(2-fluoro-4-(5-(trifluoromethyl)-1,3,4-oxadiazol-2-yl)benzyl)-4-methyl-N-phenylpiperazine-1-sulfonamide

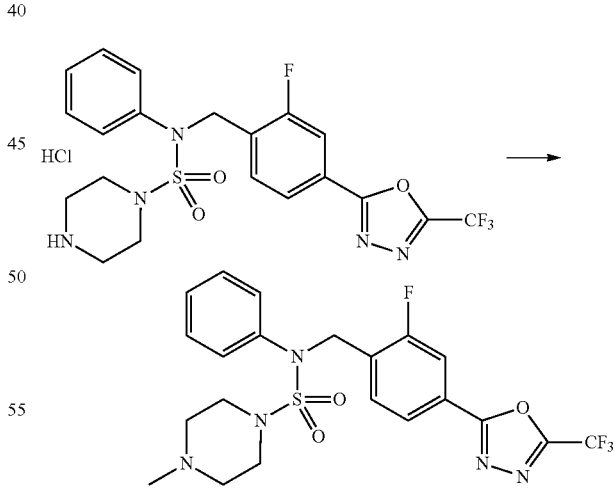

A mixture of N-(2-fluoro-4-(5-(trifluoromethyl)-1,3,4-oxadiazol-2-yl)benzyl)-N-phenylpiperazine-1-sulfonamide hydrochloride (0.050 g, 0.096 mmol) and formaldehyde (37.00% solution in water, 0.071 mL, 0.958 mmol) in dichloromethane (4 mL) was treated at the room temperature with sodium triacetoxyborohydride (0.061 g, 0.287 mmol), and stirred at the same temperature for 16 hr. Then, saturated aqueous sodium bicarbonate solution was added to the reaction mixture, followed by extraction with dichloromethane. The organic layer was washed with aqueous saturated sodium chloride solution, dried with anhydrous MgSO₄, filtered, and concentrated in vacuo. The residue was chromatographed (SiO₂, 4 g cartridge; ethyl acetate/hexane=70% to 100%) to give N-(2-fluoro-4-(5-(trifluoromethyl)-1,3,4-oxadiazol-2-yl)benzyl)-4-methyl-N-phenylpiperazine-1-sulfonamide as light yellow solid (0.031 g, 64.8%).

¹H NMR (400 MHz, DMSO-d₆) δ 7.86 (dd, 1H, J=7.9, 1.6 Hz), 7.81 (d, 1H, J=10.1 Hz), 7.62 (t, 1H, J=7.8 Hz), 7.43 (d, 2H, J=7.5 Hz), 7.35 (t, 2H, J=7.7 Hz), 7.26 (t, 1H, J=7.2 Hz), 5.03 (s, 2H), 3.15 (m, 4H), 2.30 (s, 4H), 2.16 (s, 3H); LRMS (ES) m/z 500.3 (M⁺+1).

Example 9: Compound 11299, 4-ethyl-N-(2-fluoro-4-(5-(trifluoromethyl)-1,3,4-oxadiazol-2-yl)benzyl)-N-phenylpiperazine-1-sulfonamide

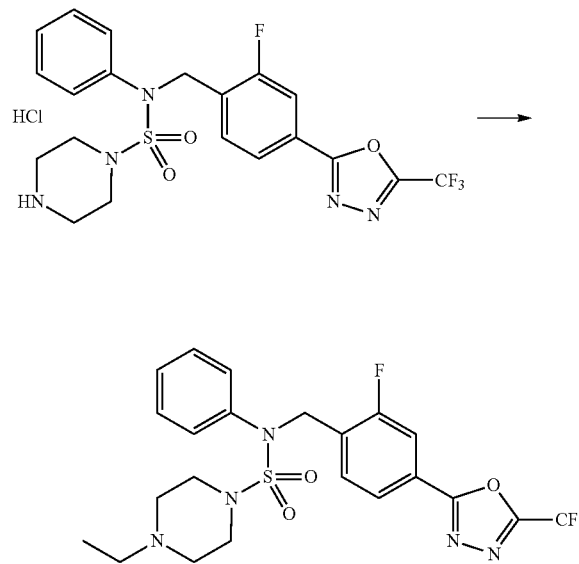

A mixture of N-(2-fluoro-4-(5-(trifluoromethyl)-1,3,4-oxadiazol-2-yl)benzyl)-N-phenylpiperazine-1-sulfonamide hydrochloride (0.050 g, 0.096 mmol) and acetaldehyde (0.027 mL, 0.479 mmol) in dichloromethane (4 mL) was treated at the room temperature with sodium triacetoxyborohydride (0.061 g, 0.287 mmol), and stirred at the same temperature for 16 hr. Then, saturated aqueous sodium bicarbonate solution was added to the reaction mixture, followed by extraction with dichloromethane. The organic layer was washed with aqueous saturated sodium chloride solution, dried with anhydrous MgSO₄, filtered, and concentrated in vacuo. The residue was chromatographed (Sift, 4 g cartridge; ethyl acetate/hexane=70% to 100%) to give 4-ethyl-N-(2-fluoro-4-(5-(trifluoromethyl)-1,3,4-oxadiazol-2-yl)benzyl)-N-phenylpiperazine-1-sulfonamide as brown solid (0.023 g, 46.8%).

¹H NMR (400 MHz, DMSO-d₆) δ 7.86 (dd, 1H, J=8.0, 1.6 Hz), 7.83-7.77 (m, 1H), 7.62 (t, 1H, J=7.6 Hz), 7.43 (d, 2H, J=8.1 Hz), 7.35 (t, 2H, J=7.7 Hz), 7.26 (t, 1H, J=7.3 Hz), 5.03 (s, 2H), 3.15 (m, 4H), 2.48-2.08 (m, 6H), 0.97 (t, 3H, J=7.2 Hz); LRMS (ES) m/z 514.1 (M⁺+1).

Example 10: Compound 11300, N-(2-fluoro-4-(5-(trifluoromethyl)-1,3,4-oxadiazol-2-yl)benzyl)-4-isopropyl-N-phenylpiperazine-1-sulfonamide

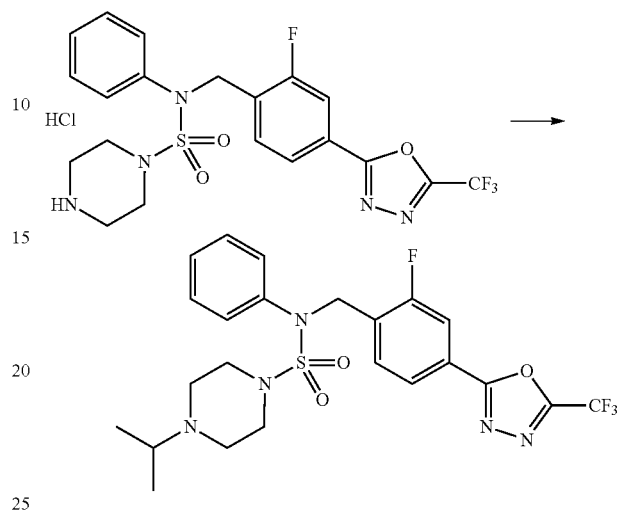

A mixture of N-(2-fluoro-4-(5-(trifluoromethyl)-1,3,4-oxadiazol-2-yl)benzyl)-N-phenylpiperazine-1-sulfonamide hydrochloride (0.050 g, 0.096 mmol) and acetone (0.035 mL, 0.479 mmol) in dichloromethane (4 mL) was treated at the room temperature with sodium triacetoxyborohydride (0.061 g, 0.287 mmol), and stirred at the same temperature for 16 hr. Then, saturated aqueous sodium bicarbonate solution was added to the reaction mixture, followed by extraction with dichloromethane. The organic layer was washed with aqueous saturated sodium chloride solution, dried with anhydrous MgSO₄, filtered, and concentrated in vacuo. The residue was chromatographed (SiO₂, 4 g cartridge; ethyl acetate/hexane=60% to 90%) to give N-(2-fluoro-4-(5-(trifluoromethyl)-1,3,4-oxadiazol-2-yl)benzyl)-4-isopropyl-N-phenylpiperazine-1-sulfonamide as white solid (0.020 g, 39.6%).

¹H NMR (400 MHz, DMSO-d₆) δ 7.86 (dd, 1H, J=8.0, 1.7 Hz), 7.81 (dd, 1H, J=10.0, 1.6 Hz), 7.63 (t, 1H, J=7.7 Hz), 7.48-7.41 (m, 2H), 7.35 (t, 2H, J=7.7 Hz), 7.25 (t, 1H, J=7.3 Hz), 5.03 (s, 2H), 3.12 (m, 4H), 2.69-2.60 (m, 1H), 2.36 (m, 4H), 0.93 (d, 6H, J=6.6 Hz); LRMS (ES) m/z 528.1 (M⁺+1).

Example 11: Compound 11301, N-(4-(5-(difluoromethyl)-1,3,4-oxadiazol-2-yl)-2-fluorobenzyl)-N-phenylpiperazine-1-sulfonamide Hydrochloride

[Step 1] tert-butyl 4-(N-(4-(2-(2,2-difluoroacetyl)hydrazine-1-carbonyl)-2-fluorobenzyl)-N-phenylsulfamoyl)piperazine-1-carboxylate

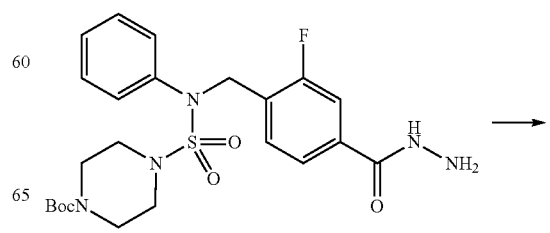

-continued

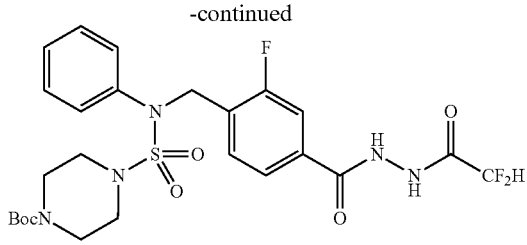

A solution of tert-butyl 4-(N-(2-fluoro-4-(hydrazinecarbonyl)benzyl)-N-phenylsulfamoyl)piperazine-1-carboxylate (1.458 g, 2.872 mmol) and triethylamine (0.796 mL, 5.745 mmol) in N,N-dimethylformide (10 mL) was stirred at 0° C., and mixed with 2,2-difluorocetic anhydride (0.375 mL, 3.447 mmol). The reaction mixture was stirred at 80° C. for additional 18 hr, cooled down to the room temperature to terminate the reaction, and concentrated under the reduced pressure to remove the solvent. Then, water was added to the concentrates, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 24 g cartridge; ethyl acetate/hexane=10% to 70%) to give the title compound as colorless oil (0.078 g, 4.8%).

[Step 2] tert-butyl 4-(N-(4-(5-(difluoromethyl)-1,3,4-oxadiazol-2-yl)-2-fluorobenzyl)-N-phenylsulfamoyl)piperazine-1-carboxylate

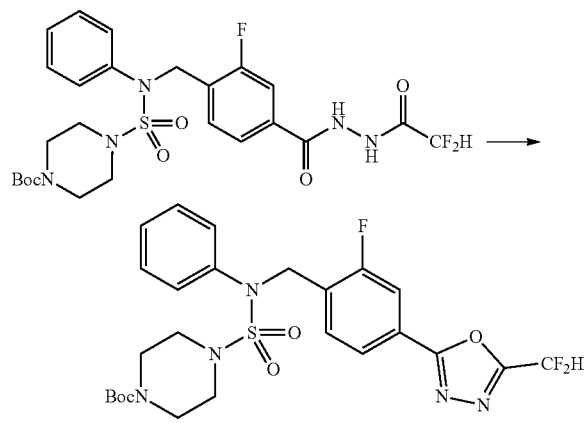

A mixture of tert-butyl 4-(N-(4-(2-(2,2-difluoroacetyl)hydrazine-1-carbonyl)-2-fluorobenzyl)-N-phenylsulfamoyl)piperazine-1-carboxylate (0.671 g, 1.146 mmol) and 1-methoxy-N-triethylammoniosulfonyl-methanimidate (Burgess reagent, 0.410 g, 1.719 mmol) in tetrahydrofuran (4 mL) was heated at 150° C. for 30 min under the microwaves, and cooled down to the room temperature to terminate the reaction. The reaction mixture was concentrated under the reduced pressure to remove the solvent. Then, water was added to the concentrate, followed by extraction with dichloromethane. The organic layer was washed with aqueous saturated sodium chloride solution, dried with anhydrous MgSO$_4$, filtered, and concentrated in vacuo. The residue was chromatographed (Sift, 12 g cartridge; ethyl acetate/hexane=0% to 25%) to give the title compound as white solid (0.382 g, 58.7%).

[Step 3] Compound 11301

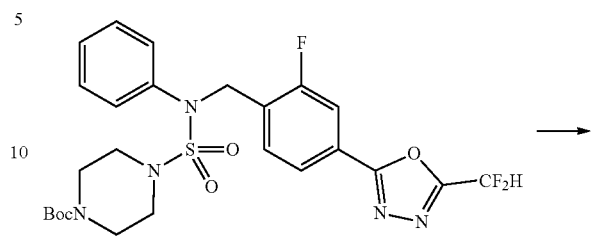

A solution of tert-butyl 4-(N-(4-(5-(difluoromethyl)-1,3,4-oxadiazol-2-yl)-2-fluorobenzyl)-N-phenylsulfamoyl)piperazine-1-carboxylate (0.460 g, 0.810 mmol) in 1,4-dioxane (10 mL) was mixed at the room temperature with hydrochloric acid (4.00 M solution in 1,4-dioxane, 4.052 mL, 16.209 mmol), and stirred at the same temperature for 2 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was diluted with diethylether (5 mL) and hexane (50 mL), and stirred. The resulting precipitates were collected by filtration, washed by hexane, and dried to give N-(4-(5-(difluoromethyl)-1,3,4-oxadiazol-2-yl)-2-fluorobenzyl)-N-phenylpiperazine-1-sulfonamide hydrochloride as white solid (0.400 g, 97.9%).

$^1$H NMR (400 MHz, DMSO-d$_6$) δ 9.04 (s, 2H), 7.84 (m, 1H), 7.78 (m, 1H), 7.67 (s, 0.25H), 7.61 (t, 1H, J=7.8 Hz), 7.54 (s, 0.5H), 7.44-7.38 (m, 2.25H), 7.37 (t, 2H, J=7.6 Hz), 7.30 (t, 1H, J=7.2 Hz), 5.04 (s, 2H), 3.41-3.37 (m, 4H), 3.14-3.09 (m, 4H); LRMS (ES) m/z 468.2 (M$^+$+1).

Example 12: Compound 11302, 4-acetyl-N-(4-(5-(difluoromethyl)-1,3,4-oxadiazol-2-yl)-2-fluorobenzyl)-N-phenylpiperazine-1-sulfonamide

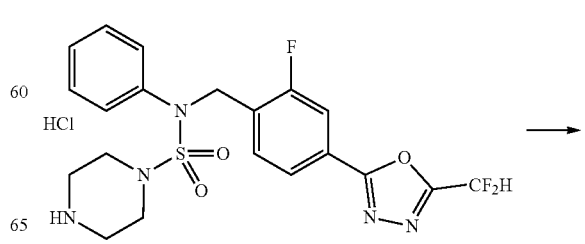

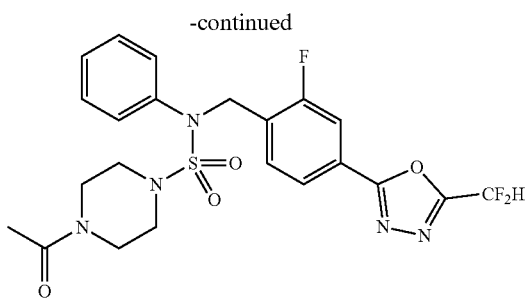

A slurry of N-(4-(5-(difluoromethyl)-1,3,4-oxadiazol-2-yl)-2-fluorobenzyl)-N-phenylpiperazine-1-sulfonamide hydrochloride (0.030 g, 0.060 mmol) in dichloromethane (3 mL) was mixed at the room temperature with acetyl chloride (0.008 mL, 0.119 mmol) and N,N-diisopropylethylamine (0.031 mL, 0.179 mmol), and stirred at the same temperature for 1 hr. Then, saturated aqueous sodium bicarbonate solution was added to the reaction mixture, followed by extraction with dichloromethane. The organic layer was washed with aqueous saturated sodium chloride solution, dried with anhydrous $MgSO_4$, filtered, and concentrated in vacuo. The residue was chromatographed ($SiO_2$, 12 g cartridge; ethyl acetate/hexane=30% to 70%) to give 4-acetyl-N-(4-(5-(difluoromethyl)-1,3,4-oxadiazol-2-yl)-2-fluorobenzyl)-N-phenylpiperazine-1-sulfonamide as light yellow liquid (0.017 g, 56.0%).

$^1$H NMR (400 MHz, DMSO-$d_6$) δ 7.83 (m, 1H), 7.77 (m, 1H), 7.66 (s, 0.25H), 7.61 (t, 1H, J=7.7 Hz), 7.53 (s, 0.5H), 7.44 (d, 2H, J=7.5 Hz), 7.40 (s, 0.25H), 7.35 (t, 2H, J=7.7 Hz), 7.26 (t, 1H, J=7.3 Hz), 5.03 (s, 2H), 3.43 (s, 4H), 3.19 (m, 2H), 3.14 (m, 2H), 2.00 (s, 3H); LRMS (ES) m/z 510.3 ($M^+$+1).

Example 13: Compound 11303, N-(4-(5-(difluoromethyl)-1,3,4-oxadiazol-2-yl)-2-fluorobenzyl)-N-phenyl-4-propionylpiperazine-1-sulfonamide

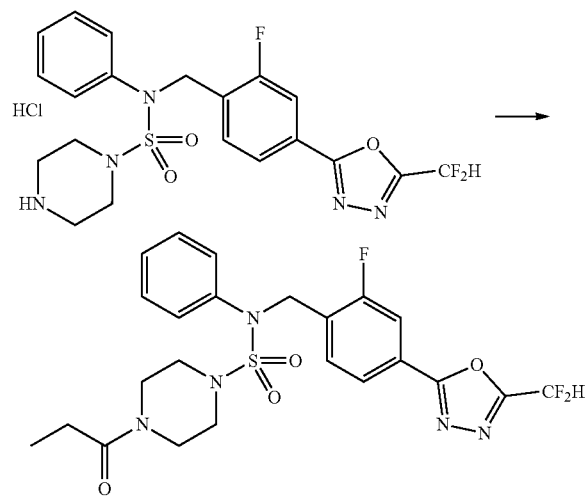

A slurry of N-(4-(5-(difluoromethyl)-1,3,4-oxadiazol-2-yl)-2-fluorobenzyl)-N-phenylpiperazine-1-sulfonamide hydrochloride (0.030 g, 0.060 mmol) in dichloromethane (3 mL) was mixed at the room temperature with propionyl chloride (0.010 mL, 0.119 mmol) and N,N-diisopropylethylamine (0.031 mL, 0.179 mmol), and stirred at the same temperature for 1 hr. Then, saturated aqueous sodium bicarbonate solution was added to the reaction mixture, followed by extraction with dichloromethane. The organic layer was washed with aqueous saturated sodium chloride solution, dried with anhydrous $MgSO_4$, filtered, and concentrated in vacuo. The residue was chromatographed (Sift, 12 g cartridge; ethyl acetate/hexane=30% to 70%) to give N-(4-(5-(difluoromethyl)-1,3,4-oxadiazol-2-yl)-2-fluorobenzyl)-N-phenyl-4-propionylpiperazine-1-sulfonamide as colorless liquid (0.021 g, 67.4%).

$^1$H NMR (400 MHz, DMSO-$d_6$) δ 7.83 (dd, 1H, J=8.0, 1.7 Hz), 7.77 (dd, 1H, J=10.1, 1.5 Hz), 7.66 (s, 0.25H), 7.62 (t, 1H, J=7.8 Hz), 7.53 (s, 0.5H), 7.44 (d, 2H, J=7.4 Hz), 7.41 (s, 0.25H), 7.35 (t, 2H, J=7.7 Hz), 7.26 (t, 1H, J=7.3 Hz), 5.03 (s, 2H), 3.44 (s, 4H), 3.16 (m, 4H), 2.32 (q, 2H, J=7.4 Hz), 0.98 (t, 3H, J=7.4 Hz); LRMS (ES) m/z 524.3 ($M^+$+1).

Example 14: Compound 11304, N-(4-(5-(difluoromethyl)-1,3,4-oxadiazol-2-yl)-2-fluorobenzyl)-4-isobutyryl-N-phenylpiperazine-1-sulfonamide

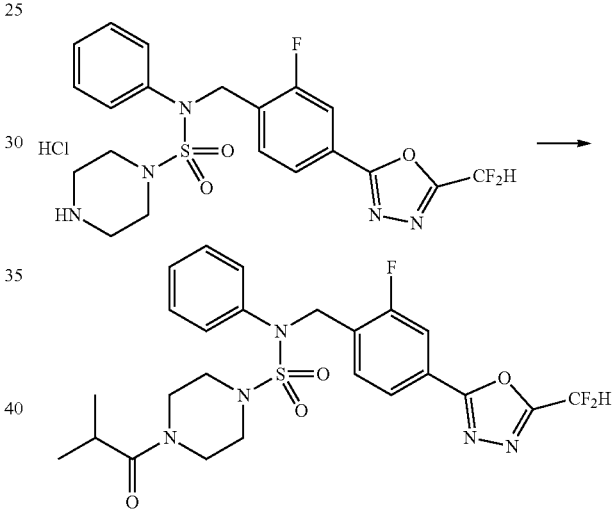

A slurry of N-(4-(5-(difluoromethyl)-1,3,4-oxadiazol-2-yl)-2-fluorobenzyl)-N-phenylpiperazine-1-sulfonamide hydrochloride (0.030 g, 0.060 mmol) in dichloromethane (3 mL) was mixed at the room temperature with isobutyryl chloride (0.012 mL, 0.119 mmol) and N,N-diisopropylethylamine (0.031 mL, 0.179 mmol), and stirred at the same temperature for 1 hr. Then, saturated aqueous sodium bicarbonate solution was added to the reaction mixture, followed by extraction with dichloromethane. The organic layer was washed with aqueous saturated sodium chloride solution, dried with anhydrous $MgSO_4$, filtered, and concentrated in vacuo. The residue was chromatographed (Sift, 12 g cartridge; ethyl acetate/hexane=20% to 50%) to give N-(4-(5-(difluoromethyl)-1,3,4-oxadiazol-2-yl)-2-fluorobenzyl)-4-isobutyryl-N-phenylpiperazine-1-sulfonamide as colorless oil (0.023 g, 71.9%).

$^1$H NMR (400 MHz, DMSO-$d_6$) δ 7.83 (dd, 1H, J=8.0, 1.6 Hz), 7.77 (dd, 1H, J=10.1, 1.6 Hz), 7.66 (s, 0.25H), 7.62 (t, 1H, J=7.8 Hz), 7.53 (s, 0.5H), 7.47-7.42 (m, 2H), 7.41 (s, 0.25H), 7.35 (t, 2H, J=7.6 Hz), 7.26 (t, 1H, J=7.3 Hz), 5.03 (s, 2H), 3.50 (m, 4H), 3.16 (s, 4H), 2.84 (dt, 1H, J=13.6, 6.7 Hz), 0.98 (d, 6H, J=6.7 Hz); LRMS (ES) m/z 538.1 ($M^+$+1).

Example 15: Compound 11305, N-(4-(5-(difluoromethyl)-1,3,4-oxadiazol-2-yl)-2-fluorobenzyl)-4-(methylsulfonyl)-N-phenylpiperazine-1-sulfonamide

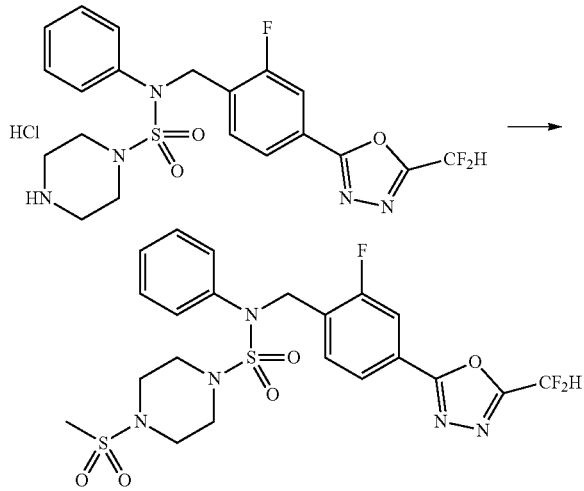

A slurry of N-(4-(5-(difluoromethyl)-1,3,4-oxadiazol-2-yl)-2-fluorobenzyl)-N-phenylpiperazine-1-sulfonamide hydrochloride (0.030 g, 0.060 mmol) in dichloromethane (3 mL) was mixed at the room temperature with methanesulfonyl chloride (0.009 mL, 0.119 mmol) and N,N-diisopropylethylamine (0.031 mL, 0.179 mmol), and stirred at the same temperature for 1 hr. Then, saturated aqueous sodium bicarbonate solution was added to the reaction mixture, followed by extraction with dichloromethane. The organic layer was washed with aqueous saturated sodium chloride solution, dried with anhydrous MgSO₄, filtered, and concentrated in vacuo. The residue was chromatographed (SiO₂, 12 g cartridge; ethyl acetate/hexane=20% to 50%) to give N-(4-(5-(difluoromethyl)-1,3,4-oxadiazol-2-yl)-2-fluorobenzyl)-4-(methylsulfonyl)-N-phenylpiperazine-1-sulfonamide as white solid (0.028 g, 86.2%).

$^1$H NMR (400 MHz, DMSO-$d_6$) δ 7.83 (m, 1H), 7.78 (d, 1H, J=10.1 Hz), 7.66 (s, 0.25H), 7.62 (t, 1H, J=7.8 Hz), 7.53 (s, 0.5H), 7.46 (d, 2H, J=7.4 Hz), 7.41 (s, 0.25H), 7.36 (t, 2H, J=7.7 Hz), 7.28 (t, 1H, J=7.3 Hz), 5.04 (s, 2H), 3.31-3.21 (m, 4H), 3.19-3.06 (m, 4H), 2.90 (s, 3H); LRMS (ES) m/z 546.2 (M⁺+1).

Example 16: Compound 11306 Hydrochloride, N-(4-(5-(difluoromethyl)-1,3,4-oxadiazol-2-yl)-2-fluorobenzyl)-4-methyl-N-phenylpiperazine-1-sulfonamide Hydrochloride

[Step 1] Compound 11306, N-(4-(5-(difluoromethyl)-1,3,4-oxadiazol-2-yl)-2-fluorobenzyl)-4-methyl-N-phenylpiperazine-1-sulfonamide

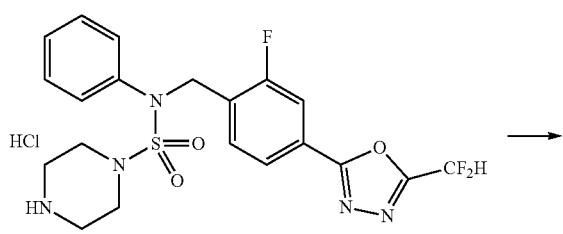

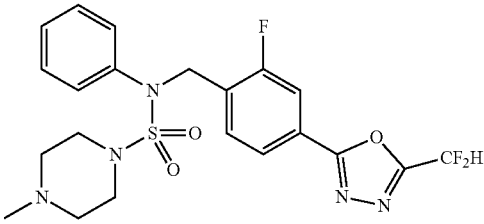

A mixture of N-(4-(5-(difluoromethyl)-1,3,4-oxadiazol-2-yl)-2-fluorobenzyl)-N-phenylpiperazine-1-sulfonamide hydrochloride (0.050 g, 0.099 mmol) and formaldehyde (37.00% solution in water, 0.074 mL, 0.992 mmol) in dichloromethane (4 mL) was treated at the room temperature with sodium triacetoxyborohydride (0.063 g, 0.298 mmol), and stirred at the same temperature for 16 hr. Then, saturated aqueous sodium bicarbonate solution was added to the reaction mixture, followed by extraction with dichloromethane. The organic layer was washed with aqueous saturated sodium chloride solution, dried with anhydrous MgSO₄, filtered, and concentrated in vacuo. The residue was chromatographed (SiO₂, 4 g cartridge; ethyl acetate/hexane=70% to 100%) to give N-(4-(5-(difluoromethyl)-1,3,4-oxadiazol-2-yl)-2-fluorobenzyl)-4-methyl-N-phenylpiperazine-1-sulfonamide as white solid (0.020 g, 41.9%).

$^1$H NMR (400 MHz, DMSO-$d_6$) δ 7.83 (dd, 1H, J=8.1, 1.6 Hz), 7.80-7.74 (m, 1H), 7.66 (s, 0.25H), 7.61 (t, 1H, J=7.7 Hz), 7.53 (s, 0.5H), 7.46-7.42 (m, 2H), 7.41 (s, 0.25H), 7.35 (t, 2H, J=7.6 Hz), 7.26 (t, 1H, J=7.3 Hz), 5.00 (s, 2H), 3.20-3.07 (m, 4H), 2.36-2.20 (m, 4H), 2.15 (s, 3H); LRMS (ES) m/z 482.5 (M⁺+1).

[Step 2] Compound 11306 Hydrochloride

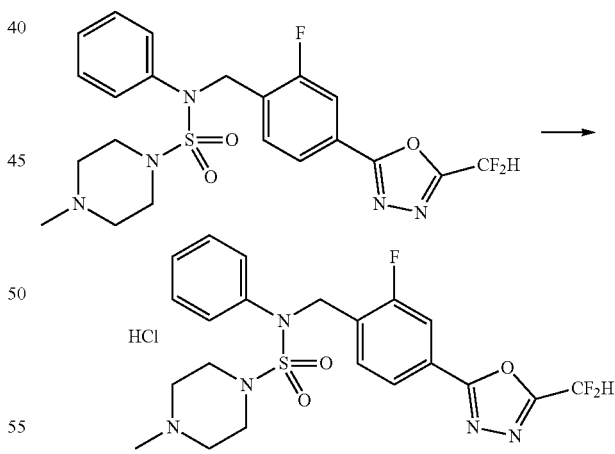

A solution of N-(4-(5-(difluoromethyl)-1,3,4-oxadiazol-2-yl)-2-fluorobenzyl)-4-methyl-N-phenylpiperazine-1-sulfonamide (0.040 g, 0.083 mmol) in ethyl acetate (5 mL) was mixed at the room temperature with hydrochloric acid (1.00 M solution in EtOAc, 0.249 mL, 0.249 mmol), and stirred at the same temperature for 10 min. The reaction mixture was concentrated under the reduced pressure to remove the solvent. The residue was diluted with ethyl acetate (2 mL) and hexane (20 mL) and stirred. The resulting precipitates were collected by filtration, washed by hexane, and dried to give N-(4-(5-(difluoromethyl)-1,3,4-oxadiazol-2-yl)-2-fluorobenzyl)-4-methyl-N-phenylpiperazine-1-sulfonamide hydrochloride as white solid (0.036 g, 83.7%).

Example 17: Compound 11307, N-(4-(5-(difluoromethyl)-1,3,4-oxadiazol-2-yl)-2-fluorobenzyl)-4-ethyl-N-phenylpiperazine-1-sulfonamide

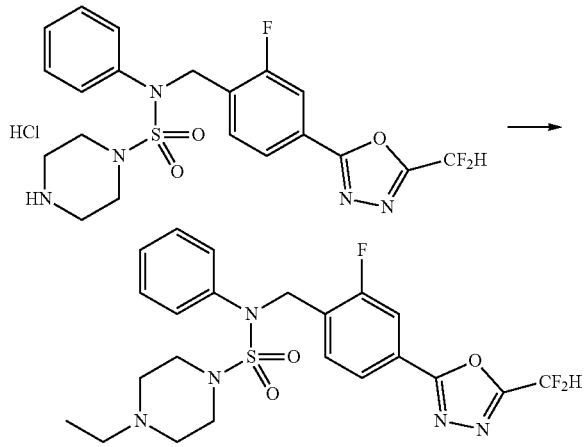

A mixture of N-(4-(5-(difluoromethyl)-1,3,4-oxadiazol-2-yl)-2-fluorobenzyl)-N-phenylpiperazine-1-sulfonamide hydrochloride (0.050 g, 0.099 mmol) and acetaldehyde (0.028 mL, 0.496 mmol) in dichloromethane (4 mL) was treated at the room temperature with sodium triacetoxyborohydride (0.063 g, 0.298 mmol), and stirred at the same temperature for 16 hr. Then, saturated aqueous sodium bicarbonate solution was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 4 g cartridge; ethyl acetate/hexane=70% to 100%) to give N-(4-(5-(difluoromethyl)-1,3,4-oxadiazol-2-yl)-2-fluorobenzyl)-4-ethyl-N-phenylpiperazine-1-sulfonamide as brown liquid (0.025 g, 50.8%).

$^1$H NMR (400 MHz, DMSO-d$_6$) δ 7.83 (d, 1H, J=8.0 Hz), 7.78 (d, 1H, J=10.1 Hz), 7.66 (s, 0.25H), 7.61 (t, 1H, J=7.8 Hz), 7.53 (s, 0.5H), 7.44 (d, 2H, J=8.0 Hz), 7.41 (s, 0.25H), 7.35 (t, 2H, J=7.7 Hz), 7.26 (t, 1H, J=7.3 Hz), 5.03 (s, 2H), 3.15 (m, 4H), 2.33 (m, 6H), 0.97 (t, 3H, J=7.1 Hz); LRMS (ES) m/z 496.1 (M$^+$+1).

Example 18: Compound 11308, N-(4-(5-(difluoromethyl)-1,3,4-oxadiazol-2-yl)-2-fluorobenzyl)-4-isopropyl-N-phenylpiperazine-1-sulfonamide

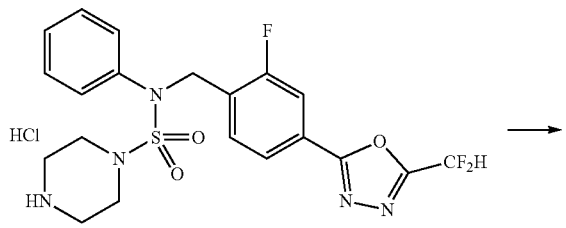

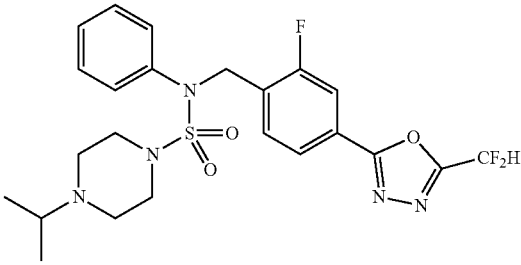

A mixture of N-(4-(5-(difluoromethyl)-1,3,4-oxadiazol-2-yl)-2-fluorobenzyl)-N-phenylpiperazine-1-sulfonamide hydrochloride (0.050 g, 0.099 mmol) and acetone (0.036 mL, 0.496 mmol) in dichloromethane (4 mL) was treated at the room temperature with sodium triacetoxyborohydride (0.063 g, 0.298 mmol), and stirred at the same temperature for 16 hr. Then, saturated aqueous sodium bicarbonate solution was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 4 g cartridge; ethyl acetate/hexane=60% to 90%) to give N-(4-(5-(difluoromethyl)-1,3,4-oxadiazol-2-yl)-2-fluorobenzyl)-4-isopropyl-N-phenylpiperazine-1-sulfonamide as white solid (0.019 g, 37.6%).

$^1$H NMR (400 MHz, DMSO-d$_6$) δ 7.83 (dd, 1H, J=7.9, 1.6 Hz), 7.78 (dd, 1H, J=10.2, 1.6 Hz), 7.66 (s, 0.25H), 7.62 (t, 1H, J=7.7 Hz), 7.54 (s, 0.5H), 7.44 (d, 2H, J=8.0 Hz), 7.41 (s, 0.25H), 7.35 (t, 2H, J=7.7 Hz), 7.26 (t, 1H, J=7.3 Hz), 5.00 (s, 2H), 3.19-3.07 (m, 4H), 2.70-2.60 (m, 1H), 2.43-2.34 (m, 4H), 0.92 (d, 6H, J=6.5 Hz); LRMS (ES) m/z 510.4 (M$^+$+1).

Example 19: Compound 11309, N-(2-fluoro-4-(5-(trifluoromethyl)-1,3,4-oxadiazol-2-yl)benzyl)-N-(3-fluorophenyl)piperazine-1-sulfonamide Hydrochloride

[Step 1] tert-butyl 4-(N-(3-fluorophenyl) sulfamoyl)piperazine-1-carboxylate

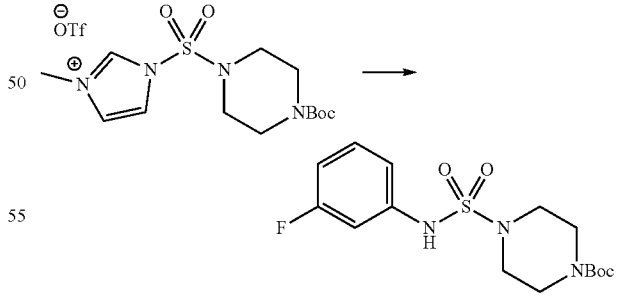

A mixture of 1-((4-(tert-butoxycarbonyl)piperazin-1-yl)sulfonyl)-3-methyl-1H-imidazol-3-ium trifluoromethanesulfonate (3.340 g, 6.952 mmol) and 3-fluoroaniline (0.732 mL, 7.647 mmol) in acetonitrile (30 mL), prepared at the ambient temperature, was heated at reflux for 16 hr, and cooled down to the ambient temperature. Then, water was added to the reaction mixture, followed by extraction with ethyl acetate. The organic layer was washed with saturated aqueous sodium chloride solution, dried with anhydrous MgSO₄, filtered, and concentrated in vacuo. The residue was chromatographed (SiO₂, 40 g cartridge; ethyl acetate/hexane=20% to 50%) to give the crude product, which was dissolved in ethyl acetate (10 mL) and hexane (100 mL), and stirred. The resulting precipitates were collected by filtration, washed by diethylether, and dried to give tert-butyl 4-(N-(3-fluorophenyl)sulfamoyl)piperazine-1-carboxylate as white solid (1.950 g, 78.0%).

[Step 2] tert-butyl 4-(N-(2-fluoro-4-(methoxycarbonyl)benzyl)-N-(3-fluorophenyl)sulfamoyl)piperazine-1-carboxylate

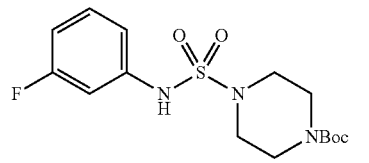

+

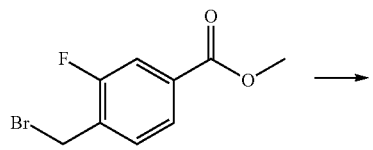

→

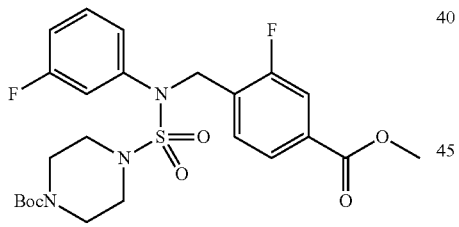

To a solution of tert-butyl 4-(N-(3-fluorophenyl)sulfamoyl)piperazine-1-carboxylate (1.950 g, 5.425 mmol) in N,N-dimethylformide (20 mL) was added sodium hydride (60.00%, 0.282 g, 7.053 mmol) at the room temperature, and the mixture was stirred at the same temperature for 10 min. The reaction mixture was treated with methyl 4-(bromomethyl)-3-fluorobenzoate (1.474 g, 5.968 mmol), and stirred for additional 1 hr at the same temperature. Then, saturated aqueous sodium bicarbonate solution was added to the reaction mixture, followed by extraction with ethyl acetate. The organic layer was washed with aqueous saturated sodium chloride solution, dried with anhydrous MgSO₄, filtered, and concentrated in vacuo. The residue was chromatographed (Sift, 40 g cartridge; ethyl acetate/hexane=10% to 30%) to give tert-butyl 4-(N-(2-fluoro-4-(methoxycarbonyl)benzyl)-N-(3-fluorophenyl)sulfamoyl)piperazine-1-carboxylate as white solid (2.810 g, 98.5%).

[Step 3] tert-butyl 4-(N-(2-fluoro-4-(hydrazinecarbonyl)benzyl)-N-(3-fluorophenyl)sulfamoyl)piperazine-1-carboxylate

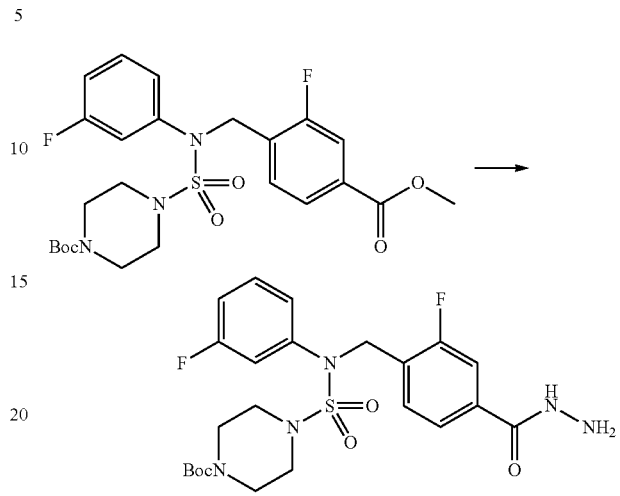

tert-butyl 4-(N-(2-fluoro-4-(methoxycarbonyl)benzyl)-N-(3-fluorophenyl)sulfamoyl)piperazine-1-carboxylate (2.810 g, 5.347 mmol) and hydrazine hydrate (5.197 mL, 106.932 mmol) were mixed at the room temperature in ethanol (70 mL), and then the mixture was stirred at 100° C. for 16 hr. The reaction mixture was cooled down to the room temperature to terminate the reaction, and concentrated under the reduced pressure to remove the solvent. Then, water was added to the concentrate, followed by extraction with ethyl acetate. The organic layer was washed with aqueous saturated sodium chloride solution, dried with anhydrous MgSO₄, filtered, and concentrated in vacuo. The title compound was used without further purification (tert-butyl 4-(N-(2-fluoro-4-(hydrazinecarbonyl)benzyl)-N-(3-fluorophenyl)sulfamoyl)piperazine-1-carboxylate, 2.376 g, 84.6%, white solid).

[Step 4] tert-butyl 4-(N-(2-fluoro-4-(2-(2,2,2-trifluoroacetyl)hydrazine-1-carbonyl)benzyl)-N-(3-fluorophenyl)sulfamoyl)piperazine-1-carboxylate

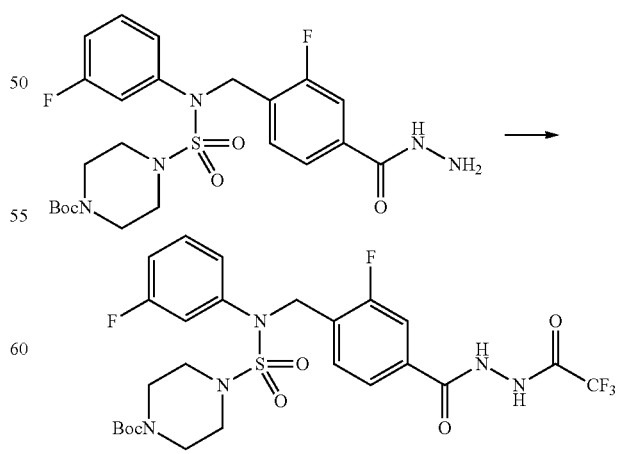

A solution of tert-butyl 4-(N-(2-fluoro-4-(hydrazinecarbonyl)benzyl)-N-(3-fluorophenyl)sulfamoyl)piperazine-1- carboxylate (1.000 g, 1.903 mmol) in 1,4-dioxane (15 mL) was mixed at the room temperature with 2,2,2-trifluoroacetic anhydride (0.265 mL, 1.903 mmol) and triethylamine (0.659 mL, 4.757 mmol). The reaction mixture was heated at reflux for 3 hr, and cooled down to the room temperature to terminate the reaction. Then, saturated aqueous sodium bicarbonate solution was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 40 g cartridge; ethyl acetate/hexane=20% to 50%) to give tert-butyl 4-(N-(2-fluoro-4-(2-(2,2,2-trifluoroacetyl)hydrazine-1-carbonyl)benzyl)-N-(3-fluorophenyl)sulfamoyl)piperazine-1-carboxylate as white solid (0.855 g, 72.3%).

[Step 5] tert-butyl 4-(N-(2-fluoro-4-(5-(trifluoromethyl)-1,3,4-oxadiazol-2-yl)benzyl)-N-(3-fluorophenyl) sulfamoyl)piperazine-1-carboxylate

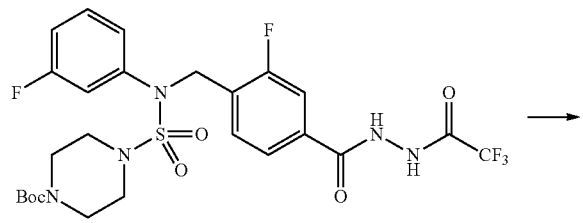

tert-butyl 4-(N-(2-fluoro-4-(2-(2,2,2-trifluoroacetyl)hydrazine-1-carbonyl)benzyl)-N-(3-fluorophenyl)sulfamoyl) piperazine-1-carboxylate (0.855 g, 1.376 mmol) and 1-methoxy-N-triethylammoniosulfonyl-methanimidate (Burgess reagent, 0.492 g, 2.063 mmol) was mixed at the room temperature in tetrahydrofuran (10 mL), and then the mixture was heated at 150° C. under the microwaves for 30 min. The reaction mixture was cooled down to the room temperature to terminate the reaction. Then, saturated aqueous sodium bicarbonate solution was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 40 g cartridge; ethyl acetate/hexane=5% to 30%) to give tert-butyl 4-(N-(2-fluoro-4-(5-(trifluoromethyl)-1,3,4-oxadiazol-2-yl)benzyl)-N-(3-fluorophenyl) sulfamoyl)piperazine-1-carboxylate as white solid (0.525 g, 63.2%).

[Step 6] Compound 11309

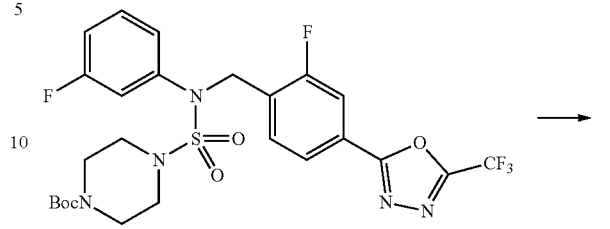

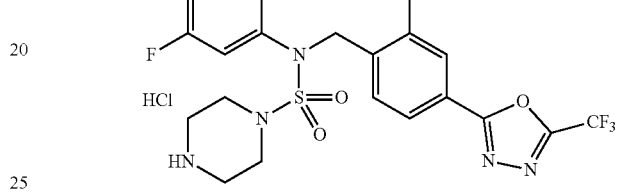

A solution of tert-butyl 4-(N-(2-fluoro-4-(5-(trifluoromethyl)-1,3,4-oxadiazol-2-yl)benzyl)-N-(3-fluorophenyl) sulfamoyl)piperazine-1-carboxylate (0.525 g, 0.870 mmol) in 1,4-dioxane (10 mL) was mixed at the room temperature with hydrochloric acid (4.00 M solution in 1,4-dioxane, 4.349 mL, 17.396 mmol), and stirred at the same temperature for 2 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was diluted with diethylether (5 mL) and hexane (50 mL), and stirred. The resulting precipitates were collected by filtration, washed by hexane, and dried to give N-(2-fluoro-4-(5-(trifluoromethyl)-1,3,4-oxadiazol-2-yl)benzyl)-N-(3-fluorophenyl)piper azine-1-sulfonamide hydrochloride as beige solid (0.460 g, 98.0%).

$^1$H NMR (400 MHz, DMSO-d$_6$) δ 9.17 (s, 2H), 7.88-7.85 (m, 2H), 7.64 (t, 1H, J=7.7 Hz), 7.43-7.38 (m, 2H), 7.29 (d, 1H, J=8.0 Hz), 7.16 (t, 1H, J=8.5 Hz), 5.07 (s, 2H), 3.53-3.38 (m, 4H), 3.22-3.05 (m, 4H); LRMS (ES) m/z 504.2 (M$^+$+1).

Example 20: Compound 11310, N-(2-fluoro-4-(5-(trifluoromethyl)-1,3,4-oxadiazol-2-yl)benzyl)-N-(3-fluorophenyl)-4-(methylsulfonyl)piperazine-1-sulfonamide

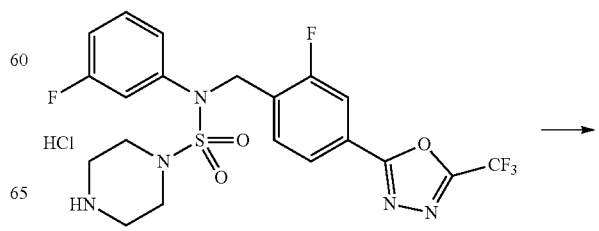

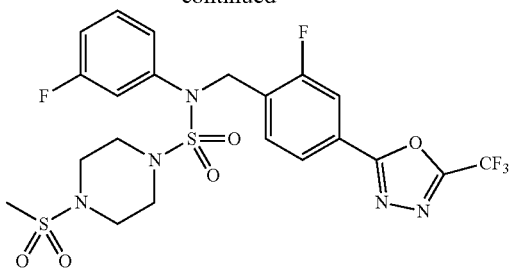

A slurry of N-(2-fluoro-4-(5-(trifluoromethyl)-1,3,4-oxadiazol-2-yl)benzyl)-N-(3-fluorophenyl)piper azine-1-sulfonamide hydrochloride (0.050 g, 0.093 mmol) in dichloromethane (3 mL) was mixed at the room temperature with methanesulfonyl chloride (0.014 mL, 0.185 mmol) and N,N-diisopropylethylamine (0.049 mL, 0.278 mmol), and stirred at the same temperature for 1 hr. Then, saturated aqueous sodium bicarbonate solution was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 12 g cartridge; ethyl acetate/hexane=30% to 70%) to give N-(2-fluoro-4-(5-(trifluoromethyl)-1,3,4-oxadiazol-2-yl)benzyl)-N-(3-fluorophenyl)-4-(methylsulfonyl)piperazine-1-sulfonamide as white solid (0.044 g, 81.7%).

$^1$H NMR (400 MHz, DMSO-d$_6$) δ 7.87 (d, 1H, J=8.1 Hz), 7.83 (d, 1H, J=10.2 Hz), 7.63 (t, 1H, J=7.6 Hz), 7.43-7.37 (m, 2H), 7.32 (d, 1H, J=7.9 Hz), 7.15 (m, 1H), 5.08 (s, 2H), 3.32 (m, 4H), 3.15 (m, 4H), 2.91 (s, 3H); LRMS (ES) m/z 582.2 (M$^+$+1).

Example 21: Compound 11311, 4-acetyl-N-(2-fluoro-4-(5-(trifluoromethyl)-1,3,4-oxadiazol-2-yl)benzyl)-N-(3-fluorophenyl)piperazine-1-sulfonamide

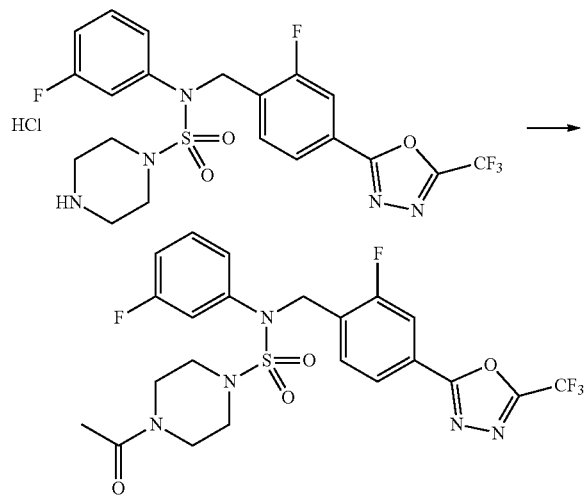

A slurry of N-(2-fluoro-4-(5-(trifluoromethyl)-1,3,4-oxadiazol-2-yl)benzyl)-N-(3-fluorophenyl)piper azine-1-sulfonamide hydrochloride (0.050 g, 0.093 mmol) in dichloromethane (3 mL) was mixed at the room temperature with acetyl chloride (0.013 mL, 0.185 mmol) and N,N-diisopropylethylamine (0.049 mL, 0.278 mmol), and stirred at the same temperature for 1 hr. Then, saturated aqueous sodium bicarbonate solution was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (Sift, 12 g cartridge; ethyl acetate/hexane=40% to 80%) to give 4-acetyl-N-(2-fluoro-4-(5-(trifluoromethyl)-1,3,4-oxadiazol-2-yl)benzyl)-N-(3-fluorophenyl)piperazine-1-sulfonamide as brown liquid (0.035 g, 69.3%).

$^1$H NMR (400 MHz, DMSO-d$_6$) δ 7.87 (dd, 1H, J=8.0, 1.6 Hz), 7.84-7.79 (m, 1H), 7.63 (t, 1H, J=7.7 Hz), 7.44-7.34 (m, 2H), 7.30 (m, 1H), 7.12 (m, 1H), 5.07 (s, 2H), 3.45 (m, 4H), 3.23 (m, 2H), 3.19 (m, 2H), 2.01 (s, 3H); LRMS (ES) m/z 546.1 (M$^+$+1).

Example 22: Compound 11312, N-(2-fluoro-4-(5-(trifluoromethyl)-1,3,4-oxadiazol-2-yl)benzyl)-N-(3-fluorophenyl)-4-methylpiperazine-1-sulfonamide

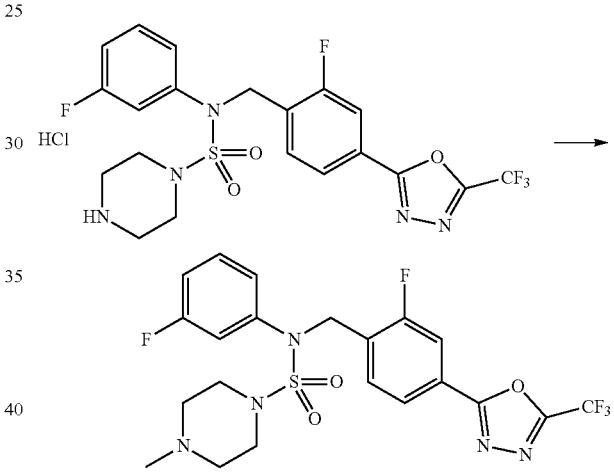

A mixture of N-(2-fluoro-4-(5-(trifluoromethyl)-1,3,4-oxadiazol-2-yl)benzyl)-N-(3-fluorophenyl)piper azine-1-sulfonamide hydrochloride (0.050 g, 0.093 mmol) and formaldehyde (37.00% solution in water, 0.069 mL, 0.926 mmol) in dichloromethane (4 mL) was treated at the room temperature with sodium triacetoxyborohydride (0.059 g, 0.278 mmol), and stirred at the same temperature for 16 hr. Then, saturated aqueous sodium bicarbonate solution was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 4 g cartridge; ethyl acetate/hexane=70% to 100%) to give N-(2-fluoro-4-(5-(trifluoromethyl)-1,3,4-oxadiazol-2-yl)benzyl)-N-(3-fluorophenyl)-4-methylpiperazine-1-sulfonamide as white solid (0.040 g, 83.5%).

$^1$H NMR (400 MHz, DMSO-d$_6$) δ 7.87 (dd, 1H, J=7.9, 1.7 Hz), 7.84 (dd, 1H, J=10.1, 1.6 Hz), 7.64 (t, 1H, J=7.8 Hz), 7.43-7.37 (m, 2H), 7.30 (m, 1H), 7.16 (m, 1H), 5.07 (s, 2H), 3.41 (m, 4H), 3.02 (m, 4H), 2.68 (s, 3H); LRMS (ES) m/z 518.3 (M$^+$+1).

Example 23: Compound 11313, N-(4-(5-(difluoromethyl)-1,3,4-oxadiazol-2-yl)-2-fluorobenzyl)-N-(3-fluorophenyl)piperazine-1-sulfonamide Hydrochloride

[Step 1] tert-butyl 4-(N-(4-(2-(2,2-difluoroacetyl)hydrazine-1-carbonyl)-2-fluorobenzyl)-N-(3-fluorophenyl)sulfamoyl)piperazine-1-carboxylate

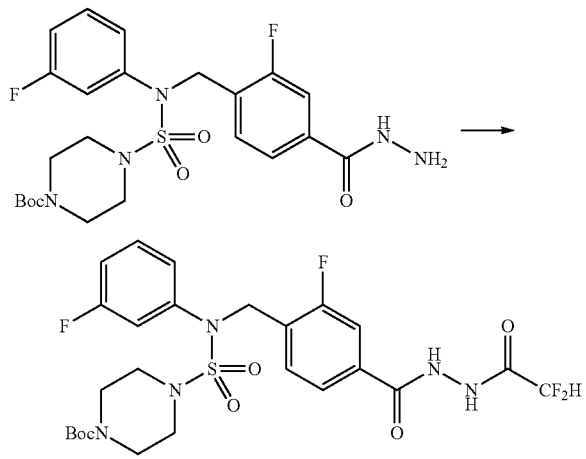

A solution of tert-butyl 4-(N-(2-fluoro-4-(hydrazinecarbonyl)benzyl)-N-(3-fluorophenyl)sulfamoyl)piperazine-1-carboxylate (1.370 g, 2.607 mmol) in 1,4-dioxane (15 mL) was mixed at the room temperature with 2,2-difluoroacetic anhydride (0.324 mL, 2.607 mmol) and triethylamine (0.903 mL, 6.517 mmol). The reaction mixture was heated at reflux for 3 hr, and cooled down to the room temperature to terminate the reaction. Then, saturated aqueous sodium bicarbonate solution was added to the reaction mixture, followed by extraction with ethyl acetate. The organic layer was washed with aqueous saturated sodium chloride solution, dried with anhydrous $MgSO_4$, filtered, and concentrated in vacuo. The residue was chromatographed ($SiO_2$, 40 g cartridge; ethyl acetate/hexane=20% to 50%) to give tert-butyl 4-(N-(4-(2-(2,2-difluoroacetyl)hydrazine-1-carbonyl)-2-fluorobenzyl)-N-(3-fluorophenyl)sulfamoyl)piperazine-1-carboxylate as beige solid (1.230 g, 78.2%).

[Step 2] tert-butyl 4-(N-(4-(5-(difluoromethyl)-1,3,4-oxadiazol-2-yl)-2-fluorobenzyl)-N-(3-fluorophenyl) sulfamoyl)piperazine-1-carboxylate

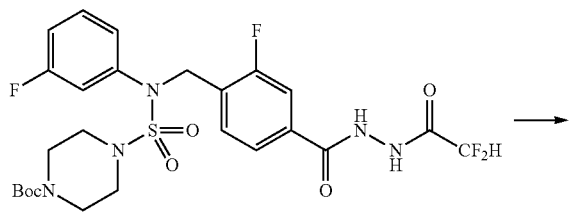

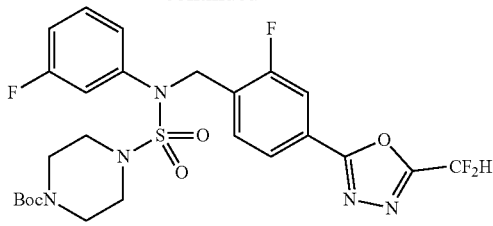

tert-butyl 4-(N-(4-(2-(2,2-difluoroacetyl)hydrazine-1-carbonyl)-2-fluorobenzyl)-N-(3-fluorophenyl)sulfamoyl)piperazine-1-carboxylate (1.230 g, 2.038 mmol) and 1-methoxy-N-triethylammoniosulfonyl-methanimidate (Burgess reagent, 0.728 g, 3.057 mmol) was mixed at the room temperature in tetrahydrofuran (10 mL), and then the mixture was heated at 150° C. under the microwaves for 30 min. The reaction mixture was cooled down to the room temperature to terminate the reaction. Then, saturated aqueous sodium bicarbonate solution was added to the concentrate, followed by extraction with ethyl acetate. The organic layer was washed with aqueous saturated sodium chloride solution, dried with anhydrous $MgSO_4$, filtered, and concentrated in vacuo. The residue was chromatographed ($SiO_2$, 40 g cartridge; ethyl acetate/hexane=5% to 30%) to give tert-butyl 4-(N-(4-(5-(difluoromethyl)-1,3,4-oxadiazol-2-yl)-2-fluorobenzyl)-N-(3-fluorophenyl) sulfamoyl)piperazine-1-carboxylate as white solid (0.941 g, 78.9%).

[Step 3] Compound 11313

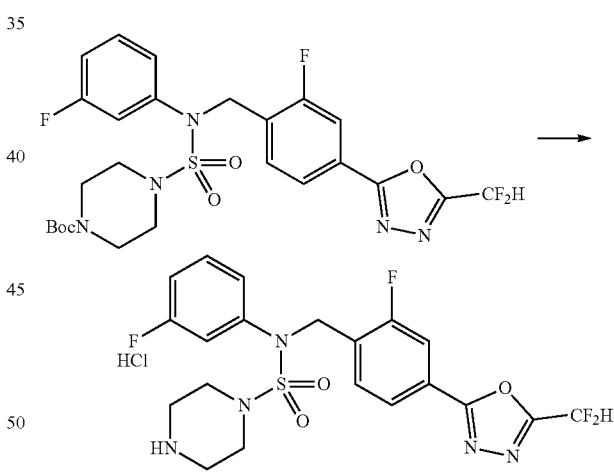

A solution of tert-butyl 4-(N-(4-(5-(difluoromethyl)-1,3,4-oxadiazol-2-yl)-2-fluorobenzyl)-N-(3-fluorophenyl) sulfamoyl)piperazine-1-carboxylate (0.941 g, 1.607 mmol) in 1,4-dioxane (10 mL) was mixed at the room temperature with hydrochloric acid (4.00 M solution in 1,4-dioxane, 8.035 mL, 32.140 mmol), and stirred at the same temperature for 2 hr. Then, water was added to the reaction mixture, followed by extraction with ethyl acetate. The organic layer was washed with aqueous saturated sodium chloride solution, dried with anhydrous $MgSO_4$, filtered, and concentrated in vacuo. The residue was diluted with diethylether (5 mL) and hexane (50 mL), and stirred. The resulting precipitates were collected by filtration, washed by hexane, and dried to give N-(4-(5-(difluoromethyl)-1,3,4-oxadiazol-2- yl)-2-fluorobenzyl)-N-(3-fluorophenyl)piperazine-1-sulfonamide hydrochloride as white solid (0.785 g, 93.6%).

$^1$H NMR (400 MHz, DMSO-$d_6$) δ 9.02 (s, 2H), 7.85 (dd, 1H, J=7.9, 1.8 Hz), 7.81 (d, 1H, J=10.2 Hz), 7.67 (s, 0.25H), 7.62 (t, 1H, J=7.8 Hz), 7.54 (s, 0.5H), 7.46 7.36 (m, 2.25H), 7.29 (d, 1H, J=7.1 Hz), 7.17 (t, 1H, J=8.4 Hz), 5.07 (s, 2H), 3.44-3.37 (m, 4H), 3.14-3.12 (m, 4H); LRMS (ES) m/z 486.2 (M$^+$+1).

Example 24: Compound 11314, N-(4-(5-(difluoromethyl)-1,3,4-oxadiazol-2-yl)-2-fluorobenzyl)-N-(3-fluorophenyl)-4-(methylsulfonyl)piperazine-1-sulfonamide

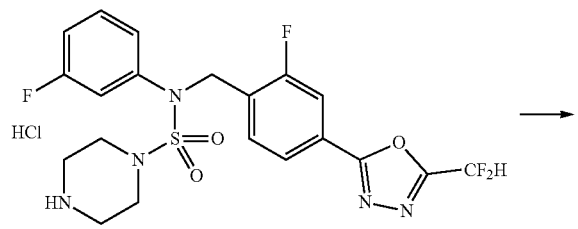

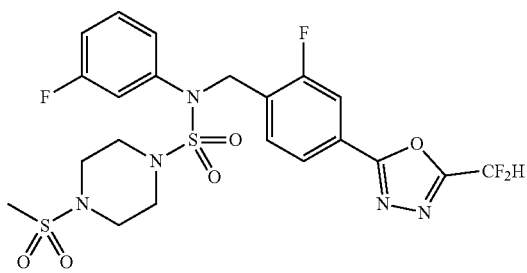

A slurry of N-(4-(5-(difluoromethyl)-1,3,4-oxadiazol-2-yl)-2-fluorobenzyl)-N-(3-fluorophenyl)piperazine-1-sulfonamide hydrochloride (0.050 g, 0.096 mmol) in dichloromethane (3 mL) was mixed at the room temperature with methanesulfonyl chloride (0.015 mL, 0.192 mmol) and N,N-diisopropylethylamine (0.050 mL, 0.287 mmol), and stirred at the same temperature for 1 hr. Then, saturated aqueous sodium bicarbonate solution was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 12 g cartridge; ethyl acetate/hexane=20% to 50%) to give N-(4-(5-(difluoromethyl)-1,3,4-oxadiazol-2-yl)-2-fluorobenzyl)-N-(3-fluorophenyl)-4-(methylsulfonyl)piperazine-1-sulfonamide as white solid (0.047 g, 87.1%).

$^1$H NMR (400 MHz, DMSO-$d_6$) δ 7.84 (dd, 1H, J=8.0, 1.7 Hz), 7.80 (dd, 1H, J=10.2, 1.5 Hz), 7.66 (s, 0.25H), 7.62 (t, 1H, J=7.7 Hz), 7.54 (s, 0.5H), 7.46-7.36 (m, 2.25H), 7.32 (d, 1H, J=8.9 Hz), 7.19-7.10 (m, 1H), 5.07 (s, 2H), 3.31 (m, 4H), 3.20-3.11 (m, 4H), 2.91 (s, 3H); LRMS (ES) m/z 564.3 (M$^+$+1).

Example 25: Compound 11315, 4-acetyl-N-(4-(5-(difluoromethyl)-1,3,4-oxadiazol-2-yl)-2-fluorobenzyl)-N-(3-fluorophenyl)piperazine-1-sulfonamide

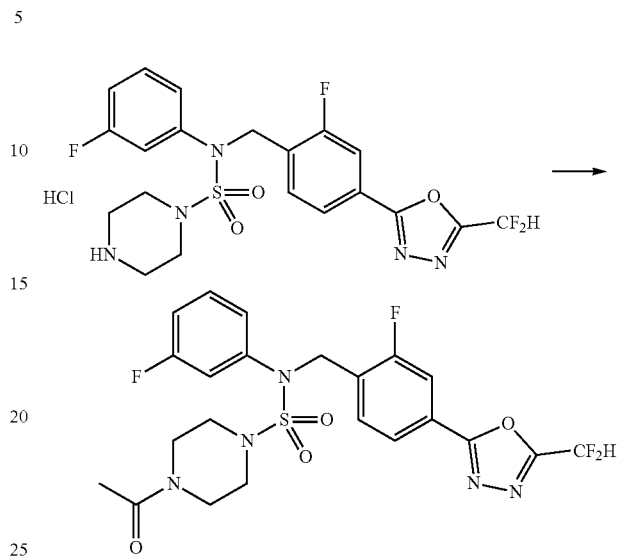

A slurry of N-(4-(5-(difluoromethyl)-1,3,4-oxadiazol-2-yl)-2-fluorobenzyl)-N-(3-fluorophenyl)piperazine-1-sulfonamide hydrochloride (0.050 g, 0.096 mmol) in dichloromethane (3 mL) was mixed at the room temperature with acetyl chloride (0.014 mL, 0.192 mmol) and N,N-diisopropylethylamine (0.050 mL, 0.287 mmol), and stirred at the same temperature for 1 hr. Then, saturated aqueous sodium bicarbonate solution was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 12 g cartridge; ethyl acetate/hexane=40% to 80%) to give 4-acetyl-N-(4-(5-(difluoromethyl)-1,3,4-oxadiazol-2-yl)-2-fluorobenzyl)-N-(3-fluorophenyl)piperazine-1-sulfonamide as yellow liquid (0.036 g, 71.2%).

$^1$H NMR (400 MHz, DMSO-$d_6$) δ 7.84 (dd, 1H, J=8.0, 1.5 Hz), 7.81-7.75 (m, 1H), 7.66 (s, 0.25H), 7.62 (t, 1H, J=7.8 Hz), 7.53 (s, 0.5H), 7.43-7.37 (m, 2H), 7.36 (s, 0.25H), 7.30 (d, 1H, J=8.0 Hz), 7.12 (t, 1H, J=7.3 Hz), 5.07 (s, 2H), 3.44 (m, 4H), 3.23 (m, 4H), 3.17 (m, 2H), 2.01 (s, 3H); LRMS (ES) m/z 528.2 (M$^+$+1).

Example 26: Compound 11316, N-(4-(5-(difluoromethyl)-1,3,4-oxadiazol-2-yl)-2-fluorobenzyl)-N-(3-fluorophenyl)-4-methylpiperazine-1-sulfonamide

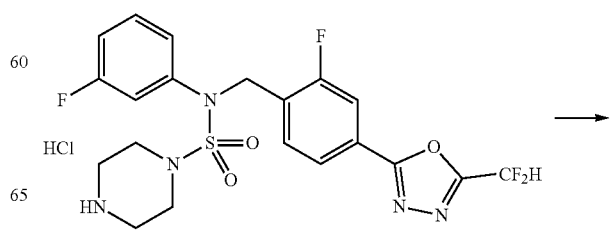

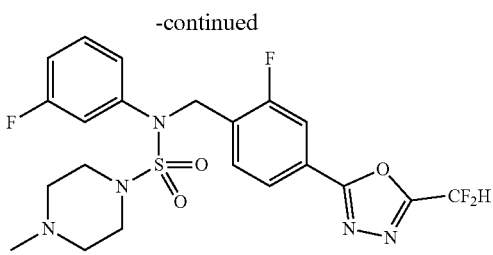

A mixture of N-(4-(5-(difluoromethyl)-1,3,4-oxadiazol-2-yl)-2-fluorobenzyl)-N-(3-fluorophenyl)piperazine-1-sulfonamide hydrochloride (0.050 g, 0.096 mmol) and formaldehyde (37.00% solution in water, 0.071 mL, 0.958 mmol) in dichloromethane (4 mL) was treated at the room temperature with sodium triacetoxyborohydride (0.061 g, 0.287 mmol), and stirred at the same temperature for 16 hr. Then, saturated aqueous sodium bicarbonate solution was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 4 g cartridge; ethyl acetate/hexane=70% to 100%) to give N-(4-(5-(difluoromethyl)-1,3,4-oxadiazol-2-yl)-2-fluorobenzyl)-N-(3-fluorophenyl)-4-methylpiperazine-1-sulfonamide as light yellow liquid (0.038 g, 79.4%).

$^1$H NMR (400 MHz, DMSO-d$_6$) δ 7.84 (d, 1H, J=8.0 Hz), 7.80 (d, 1H, J=10.1 Hz), 7.66 (s, 0.25H), 7.62 (t, 1H, J=7.7 Hz), 7.54 (s, 0.5H), 7.45-7.35 (m, 2.25H), 7.30 (d, 1H, J=8.2 Hz), 7.12 (t, 1H, J=7.1 Hz), 5.06 (s, 2H), 3.17 (s, 4H), 2.36 (m, 4H), 2.17 (s, 3H); LRMS (ES) m/z 500.2 (M$^+$+1).

Example 27: Compound 11317, N-(4-(5-(difluoromethyl)-1,3,4-oxadiazol-2-yl)-2-fluorobenzyl)-N-(pyridin-3-yl)piperazine-1-sulfonamide Dihydrochloride

[Step 1] tert-butyl 4-(N-(pyridin-3-yl)sulfamoyl)piperazine-1-carboxylate

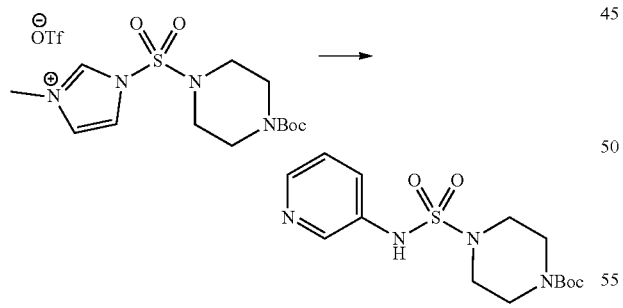

A mixture of 1-((4-(tert-butoxycarbonyl)piperazin-1-yl)sulfonyl)-3-methyl-1H-imidazol-3-ium trifluoromethanesulfonate (3.340 g, 6.952 mmol) and pyridin-3-amine (0.720 g, 7.647 mmol) in acetonitrile (30 mL), prepared at the ambient temperature, was heated at reflux for 16 hr, and cooled down to the ambient temperature. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 40 g cartridge; ethyl acetate/hexane=50% to 80%) to give the crude product, which was dissolved in ethyl acetate (10 mL) and hexane (100 mL), and stirred. The resulting precipitates were collected by filtration, washed by hexane, and dried to give tert-butyl 4-(N-(pyridin-3-yl)sulfamoyl)piperazine-1-carboxylate as white solid (1.745 g, 73.3%).

[Step 2] tert-butyl 4-(N-(2-fluoro-4-(methoxycarbonyl)benzyl)-N-(pyridin-3-yl)sulfamoyl)piperazine-1-carboxylate

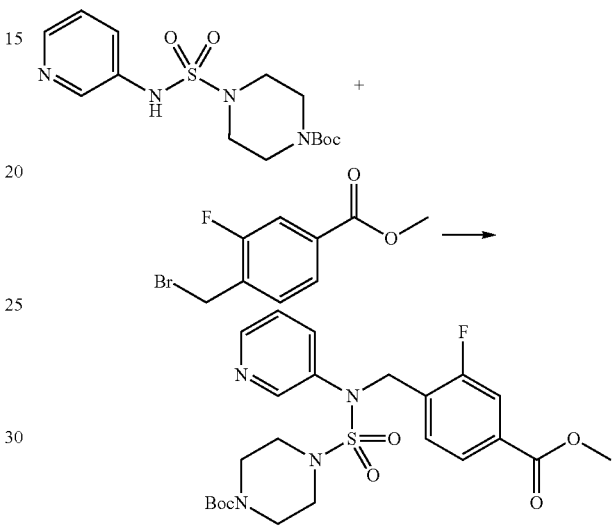

To a solution of tert-butyl 4-(N-(pyridin-3-yl)sulfamoyl)piperazine-1-carboxylate (1.745 g, 5.096 mmol) in N,N-dimethylformide (20 mL) was added sodium hydride (60.00%, 0.265 g, 6.625 mmol) at the room temperature, and the mixture was stirred at the same temperature for 10 min. The reaction mixture was treated with methyl 4-(bromomethyl)-3-fluorobenzoate (1.385 g, 5.606 mmol), and stirred for additional 1 hr at the same temperature. Then, saturated aqueous sodium bicarbonate solution was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 40 g cartridge; ethyl acetate/hexane=20% to 50%) to give tert-butyl 4-(N-(2-fluoro-4-(methoxycarbonyl)benzyl)-N-(pyridin-3-yl)sulfamoyl)piperazine-1-carboxylate as beige solid (1.220 g, 47.1%).

[Step 3] tert-butyl 4-(N-(2-fluoro-4-(hydrazinecarbonyl)benzyl)-N-(pyridin-3-yl)sulfamoyl)piperazine-1-carboxylate

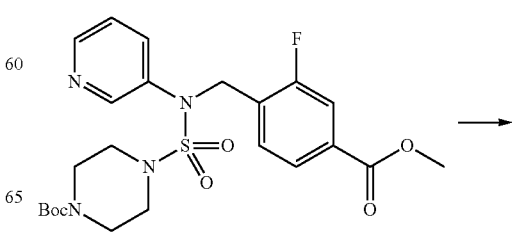

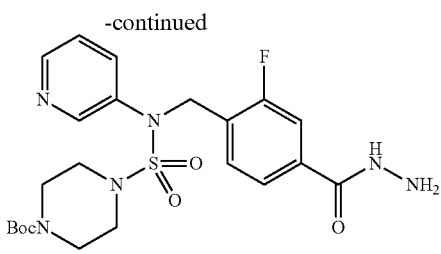

tert-butyl 4-(N-(2-fluoro-4-(methoxycarbonyl)benzyl)-N-(pyridin-3-yl)sulfamoyl)piperazine-1-carboxylate (1.220 g, 2.399 mmol) and hydrazine hydrate (2.332 mL, 47.978 mmol) were mixed at the room temperature in ethanol (50 mL), and then the mixture was stirred at 100° C. for 16 hr. The reaction mixture was cooled down to the room temperature to terminate the reaction, and concentrated under the reduced pressure to remove the solvent. Then, water was added to the concentrate, followed by extraction with ethyl acetate. The organic layer was washed with aqueous saturated sodium chloride solution, dried with anhydrous MgSO$_4$, filtered, and concentrated in vacuo. The title compound was used without further purification (tert-butyl 4-(N-(2-fluoro-4-(hydrazinecarbonyl)benzyl)-N-(pyridin-3-yl)sulfamoyl)piperazine-1-carboxylate, 0.702 g, 57.5%, white solid).

[Step 4] tert-butyl 4-(N-(4-(5-(difluoromethyl)-1,3,4-oxadiazol-2-yl)-2-fluorobenzyl)-N-(pyridin-3-yl)sulfamoyl)piperazine-1-carboxylate

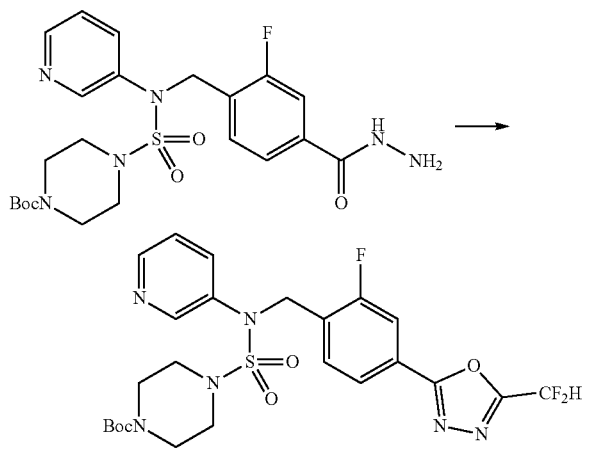

A solution of tert-butyl 4-(N-(2-fluoro-4-(hydrazinecarbonyl)benzyl)-N-(pyridin-3-yl)sulfamoyl)piperazine-1-carboxylate (0.350 g, 0.688 mmol) in 1,4-dioxane (15 mL) was mixed at the room temperature with 2,2-difluoroacetic anhydride (0.086 mL, 0.688 mmol) and triethylamine (0.238 mL, 1.721 mmol). The reaction mixture was heated at reflux for 3 hr, and cooled down to the room temperature to terminate the reaction. Then, saturated aqueous sodium bicarbonate solution was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 40 g cartridge; ethyl acetate/hexane=10% to 40%) to give tert-butyl 4-(N-(4-(5-(difluoromethyl)-1,3,4-oxadiazol-2-yl)-2-fluorobenzyl)-N-(pyridin-3-yl)sulfamoyl)piperazine-1-carboxylate as white solid (0.233 g, 59.5%).

[Step 5] Compound 11317

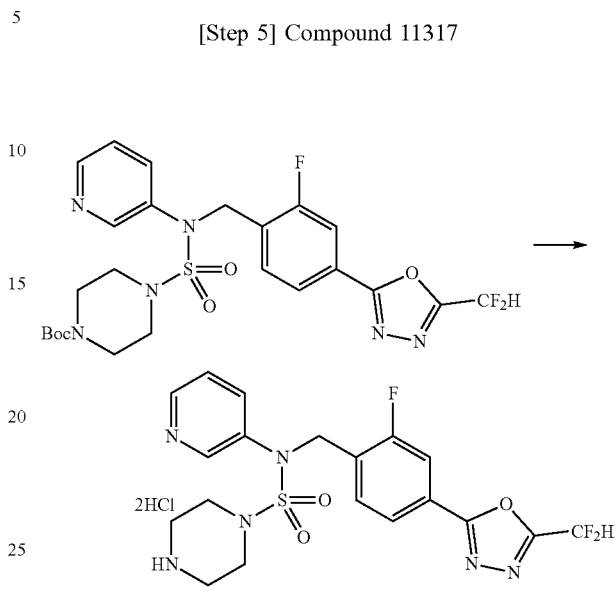

A solution of tert-butyl 4-(N-(4-(5-(difluoromethyl)-1,3,4-oxadiazol-2-yl)-2-fluorobenzyl)-N-(pyridin-3-yl)sulfamoyl)piperazine-1-carboxylate (0.233 g, 0.410 mmol) in 1,4-dioxane (5 mL) was mixed at the room temperature with hydrochloric acid (4.00 M solution in 1,4-dioxane, 2.049 mL, 8.196 mmol), and stirred at the same temperature for 2 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was diluted with hexane (30 mL) and stirred. The resulting precipitates were collected by filtration, washed by hexane, and dried to give N-(4-(5-(difluoromethyl)-1,3,4-oxadiazol-2-yl)-2-fluorobenzyl)-N-(pyridin-3-yl)piperazine-1-sulfonamide dihydrochloride as bright yellow solid (0.210 g, 94.8%).

$^1$H NMR (400 MHz, DMSO-d$_6$) δ 9.61 (s, 2H), 8.81 (m, 1H), 8.60 (m, 1H), 8.20 (d, 1H, J=8.0 Hz), 7.86-7.79 (m, 1.25H), 7.75-7.37 (m, 3.75H), 5.11 (2, 2H), 3.49 (m, 4H), 3.14 (m, 4H); LRMS (ES) m/z 469.3 (M$^+$+1).

Example 28: Compound 11318, 4-acetyl-N-(4-(5-(difluoromethyl)-1,3,4-oxadiazol-2-yl)-2-fluorobenzyl)-N-(pyridin-3-yl)piperazine-1-sulfonamide

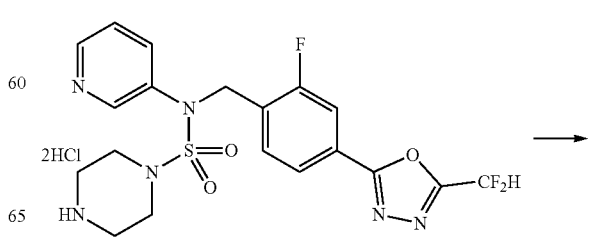

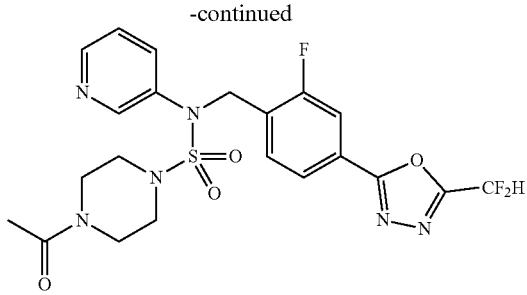

A slurry of N-(4-(5-(difluoromethyl)-1,3,4-oxadiazol-2-yl)-2-fluorobenzyl)-N-(pyridin-3-yl)piperazine-1-sulfonamide dihydrochloride (0.050 g, 0.092 mmol) in dichloromethane (3 mL) was mixed at the room temperature with acetyl chloride (0.013 mL, 0.185 mmol) and N,N-diisopropylethylamine (0.065 mL, 0.369 mmol), and stirred at the same temperature for 1 hr. Then, saturated aqueous sodium bicarbonate solution was added to the reaction mixture, followed by extraction with dichloromethane. The organic layer was washed with aqueous saturated sodium chloride solution, dried with anhydrous $MgSO_4$, filtered, and concentrated in vacuo. The residue was chromatographed ($SiO_2$, 12 g cartridge; ethyl acetate/hexane=60% to 90%) to give 4-acetyl-N-(4-(5-(difluoromethyl)-1,3,4-oxadiazol-2-yl)-2-fluorobenzyl)-N-(pyridin-3-yl)piperazine-1-sulfonamide as brown liquid (0.018 g, 38.2%).

$^1$H NMR (400 MHz, DMSO-$d_6$) δ 8.60 (m, 1H), 8.45 (dd, 1H, J=4.7, 1.4 Hz), 7.97-7.89 (m, 1H), 7.85 (dd, 1H, J=8.0, 1.6 Hz), 7.79 (dd, 1H, J=10.1, 1.5 Hz), 7.65 (d, 1H, J=8.9 Hz), 7.52 (s, 0.25H), 7.53 (s, 0.5H), 7.43 (s, 0.25H), 7.41 (t, 1H, J=4.1 Hz), 5.08 (s, 2H), 3.46 (s, 4H), 3.28-3.16 (m, 4H), 2.02 (s, 3H); LRMS (ES) m/z 511.2 (M$^+$+1).

Example 29: Compound 11319, N-(4-(5-(difluoromethyl)-1,3,4-oxadiazol-2-yl)-2-fluorobenzyl)-4-(methylsulfonyl)-N-(pyridin-3-yl)piperazine-1-sulfonamide

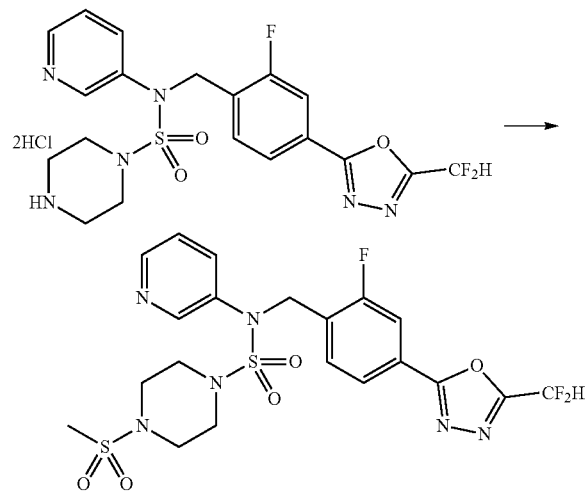

A slurry of N-(4-(5-(difluoromethyl)-1,3,4-oxadiazol-2-yl)-2-fluorobenzyl)-N-(pyridin-3-yl)piperazine-1-sulfonamide dihydrochloride (0.050 g, 0.092 mmol) in dichloromethane (3 mL) was mixed at the room temperature with methanesulfonyl chloride (0.014 mL, 0.185 mmol) and N,N-diisopropylethylamine (0.065 mL, 0.369 mmol), and stirred at the same temperature for 1 hr. Then, saturated aqueous sodium bicarbonate solution was added to the reaction mixture, followed by extraction with dichloromethane. The organic layer was washed with aqueous saturated sodium chloride solution, dried with anhydrous $MgSO_4$, filtered, and concentrated in vacuo. The residue was chromatographed (Sift, 12 g cartridge; ethyl acetate/hexane=30% to 70%) to give N-(4-(5-(difluoromethyl)-1,3,4-oxadiazol-2-yl)-2-fluorobenzyl)-4-(methylsulfonyl)-N-(pyridin-3-yl)piperazine-1-sulfonamide as beige solid (0.041 g, 81.2%).

$^1$H NMR (400 MHz, DMSO-$d_6$) δ 8.61 (s, 1H), 8.46 (d, 1H, J=4.5 Hz), 7.95 (d, 1H, J=8.7 Hz), 7.85 (d, 1H, J=8.2 Hz), 7.79 (d, 1H, J=9.8 Hz), 7.69-7.60 (m, 1.25H), 7.53 (s, 0.5H), 7.42 (m, 1.25H), 5.08 (s, 2H), 3.34 (m, 4H), 3.16 (s, 4H), 2.91 (s, 3H); LRMS (ES) m/z 547.0 (M$^+$+1).

Example 30: Compound 11320, N-(4-(5-(difluoromethyl)-1,3,4-oxadiazol-2-yl)-2-fluorobenzyl)-4-methyl-N-(pyridin-3-yl)piperazine-1-sulfonamide

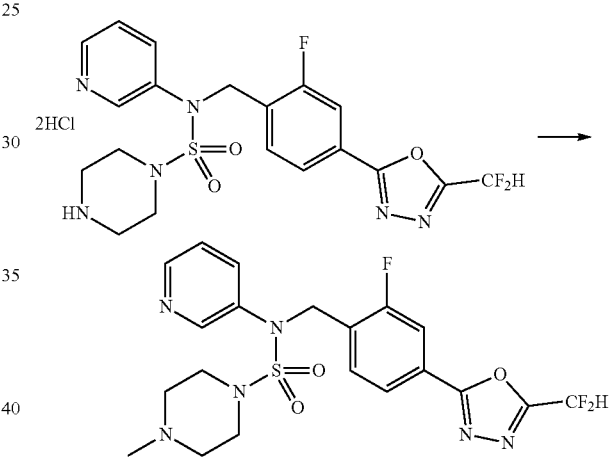

A mixture of N-(4-(5-(difluoromethyl)-1,3,4-oxadiazol-2-yl)-2-fluorobenzyl)-N-(pyridin-3-yl)piperazine-1-sulfonamide dihydrochloride (0.050 g, 0.092 mmol) and formaldehyde (37.00% solution in water, 0.069 mL, 0.924 mmol) in dichloromethane (4 mL) was treated at the room temperature with sodium triacetoxyborohydride (0.059 g, 0.277 mmol), and stirred at the same temperature for 16 hr. Then, saturated aqueous sodium bicarbonate solution was added to the reaction mixture, followed by extraction with dichloromethane. The organic layer was washed with aqueous saturated sodium chloride solution, dried with anhydrous $MgSO_4$, filtered, and concentrated in vacuo. The residue was chromatographed ($SiO_2$, 12 g cartridge; methanol/dichloromethane=0% to 10%) to give N-(4-(5-(difluoromethyl)-1,3,4-oxadiazol-2-yl)-2-fluorobenzyl)-4-methyl-N-(pyridin-3-yl)piperazine-1-sulfonamide as colorless liquid (0.011 g, 24.7%).

$^1$H NMR (400 MHz, DMSO-$d_6$) δ 8.59 (d, 1H, J=2.6 Hz), 8.44 (dd, 1H, J=4.7, 1.5 Hz), 7.96-7.89 (m, 1H), 7.85 (dd, 1H, J=8.0, 1.6 Hz), 7.79 (dd, 1H, J=10.1, 1.6 Hz), 7.66 (s, 0.25H), 7.63 (t, 1H, J=7.8 Hz), 7.54 (s, 0.5H), 7.43 (s, 0.25H), 7.41 (t, 1H, J=4.1 Hz), 5.07 (s, 2H), 3.26-3.13 (m, 4H), 2.36-2.22 (m, 4H), 2.17 (s, 3H); LRMS (ES) m/z 483.3 (M$^+$+1).

Example 31: Compound 11321, N-(2-fluoro-4-(5-(trifluoromethyl)-1,3,4-oxadiazol-2-yl)benzyl)-N-(pyridin-3-yl)piperazine-1-sulfonamide Dihydrochloride

[Step 1] tert-butyl 4-(N-(2-fluoro-4-(5-(trifluoromethyl)-1,3,4-oxadiazol-2-yl)benzyl)-N-(pyridin-3-yl)sulfamoyl)piperazine-1-carboxylate

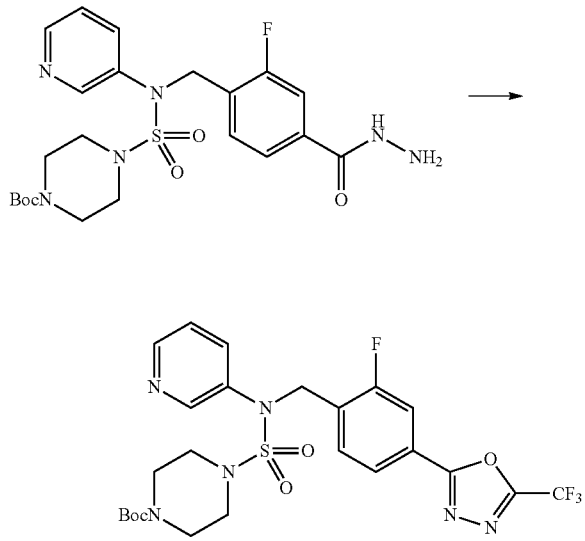

A solution of tert-butyl 4-(N-(2-fluoro-4-(hydrazinecarbonyl)benzyl)-N-(pyridin-3-yl)sulfamoyl)piperazine-1-carboxylate (0.350 g, 0.688 mmol) in 1,4-dioxane (15 mL) was mixed at the room temperature with 2,2,2-trifluoroacetic anhydride (0.096 mL, 0.688 mmol) and triethylamine (0.238 mL, 1.721 mmol). The reaction mixture was heated at reflux for 3 hr, and cooled down to the room temperature to terminate the reaction. Then, saturated aqueous sodium bicarbonate solution was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 40 g cartridge; ethyl acetate/hexane=10% to 40%) to give tert-butyl 4-(N-(2-fluoro-4-(5-(trifluoromethyl)-1,3,4-oxadiazol-2-yl)benzyl)-N-(pyridin-3-yl) sulfamoyl)piperazine-1-carboxylate as white solid (0.097 g, 24.0%).

[Step 2] Compound 11321

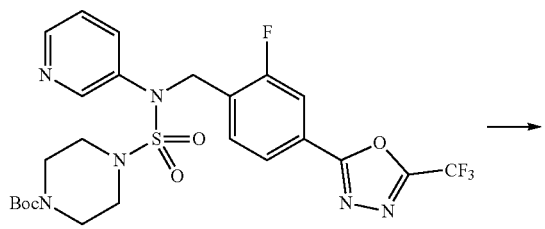

-continued

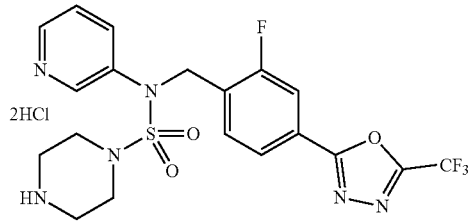

A solution of tert-butyl 4-(N-(2-fluoro-4-(5-(trifluoromethyl)-1,3,4-oxadiazol-2-yl)benzyl)-N-(pyridin-3-yl)sulfamoyl)piperazine-1-carboxylate (0.097 g, 0.165 mmol) in 1,4-dioxane (5 mL) was mixed at the room temperature with hydrochloric acid (4.00 M solution in 1,4-dioxane, 0.827 mL, 3.307 mmol), and stirred at the same temperature for 2 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was diluted with hexane (30 mL) and stirred. The resulting precipitates were collected by filtration, washed by hexane, and dried to give N-(2-fluoro-4-(5-(trifluoromethyl)-1,3,4-oxadiazol-2-yl)benzyl)-N-(pyridin-3-yl)piperazine-1-sulfonamide dihydrochloride as white solid (0.082 g, 88.6%).
$^1$H NMR (400 MHz, DMSO-d$_6$) δ 9.57 (s, 2H), 8.76 (d, 1H, J=2.3 Hz), 8.57 (d, 1H, J=4.1 Hz), 8.16 (d, 1H, J=8.3 Hz), 7.91-7.80 (m, 2H), 7.68 (t, 1H, J=7.7 Hz), 7.60 (dd, 1H, J=8.3, 4.9 Hz), 5.13 (s, 2H), 3.53-3.45 (m, 4H), 3.14 (s, 4H); LRMS (ES) m/z 487.3 (M$^+$+1).

Example 32: Compound 11322, 4-acetyl-N-(2-fluoro-4-(5-(trifluoromethyl)-1,3,4-oxadiazol-2-yl)benzyl)-N-(pyridin-3-yl)piperazine-1-sulfonamide

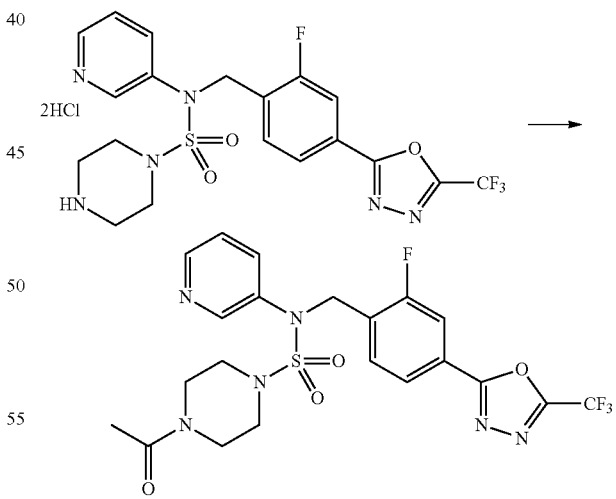

A slurry of N-(2-fluoro-4-(5-(trifluoromethyl)-1,3,4-oxadiazol-2-yl)benzyl)-N-(pyridin-3-yl)piperazine-1-sulfonamide dihydrochloride (0.070 g, 0.125 mmol) in dichloromethane (3 mL) was mixed at the room temperature with acetyl chloride (0.018 mL, 0.250 mmol) and N,N-diisopropylethylamine (0.087 mL, 0.501 mmol), and stirred at the same temperature for 1 hr. Then, saturated aqueous sodium bicarbonate solution was added to the reaction mixture, followed by extraction with dichloromethane. The organic layer was washed with aqueous saturated sodium chloride solution, dried with anhydrous MgSO₄, filtered, and concentrated in vacuo. The residue was chromatographed (SiO₂, 12 g cartridge; methanol/dichloromethane=0% to 5%) to give 4-acetyl-N-(2-fluoro-4-(5-(trifluoromethyl)-1,3,4-oxadiazol-2-yl)benzyl)-N-(pyridin-3-yl)piperazine-1-sulfonamide as yellow liquid (0.046 g, 69.6%).

¹H NMR (400 MHz, DMSO-d₆) δ 8.60 (d, 1H, J=2.2 Hz), 8.44 (dd, 1H, J=4.7, 1.4 Hz), 7.93 (m, 1H), 7.87 (dd, 1H, J=8.0, 1.7 Hz), 7.82 (dd, 1H, J=10.1, 1.7 Hz), 7.65 (t, 1H, J=7.8 Hz), 7.41 (m, 1H), 5.09 (s, 2H), 3.48-3.45 (m, 4H), 3.25 (m, 2H), 3.20 (m, 2H), 2.02 (s, 3H); LRMS (ES) m/z 529.3 (M⁺+1).

Example 33: Compound 11363, N-((5-(5-(difluoromethyl)-1,3,4-oxadiazol-2-yl)pyridin-2-yl)methyl)-4-methyl-N-phenylpiperazine-1-sulfonamide

[Step 1] tert-butyl 4-(N-((5-(methoxycarbonyl)pyridin-2-yl)methyl)-N-phenylsulfamoyl)piperazine-1-carboxylate

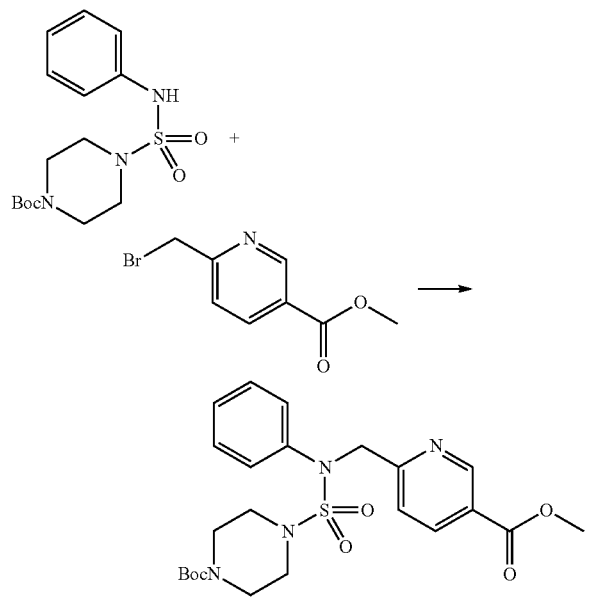

To a solution of tert-butyl 4-(N-phenylsulfamoyl)piperazine-1-carboxylate (0.600 g, 1.757 mmol) in N,N-dimethylformide (10 mL) was slowly added sodium hydride (60.00%, 0.091 g, 2.285 mmol) at the room temperature, and the mixture was stirred for 5 min at the same temperature. The reaction mixture was treated with methyl 6-(bromomethyl)nicotinate (0.485 g, 2.109 mmol), and stirred at the same temperature for additional 16 hr. Then, saturated aqueous sodium bicarbonate solution was added to the reaction mixture, followed by extraction with ethyl acetate. The organic layer was washed with aqueous saturated sodium chloride solution, dried with anhydrous MgSO₄, filtered, and concentrated in vacuo. The residue was chromatographed (Sift, 40 g cartridge; ethyl acetate/hexane=10% to 50%) to give the crude product, which was dissolved in hexane (100 mL), and stirred. The resulting precipitates were collected by filtration, washed by hexane, and dried to give tert-butyl 4-(N-((5-(methoxycarbonyl)pyridin-2-yl)methyl)-N-phenylsulfamoyl)piperazine-1-carboxylate as white solid (0.585 g, 67.9%).

[Step 2] methyl 6-((N-phenylpiperazine-1-sulfonamido)methyl)nicotinate Dihydrochloride

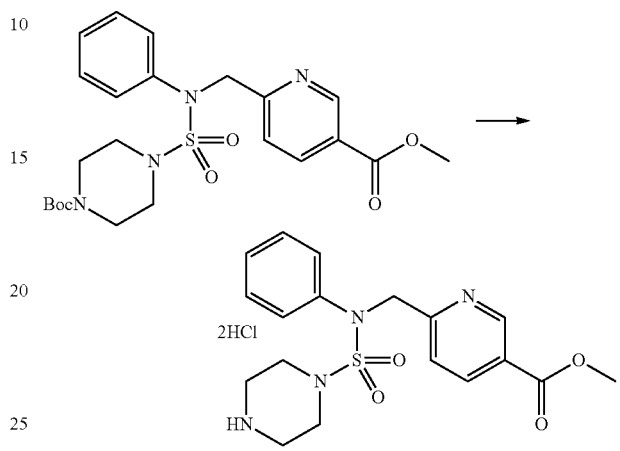

A solution of tert-butyl 4-(N-((5-(methoxycarbonyl)pyridin-2-yl)methyl)-N-phenylsulfamoyl)piperazine-1-carboxylate (0.585 g, 1.192 mmol) in 1,4-dioxane (5 mL) was mixed at the room temperature with hydrochloric acid (4.00 M solution in 1,4-dioxane, 4.472 mL, 17.887 mmol), and stirred at the same temperature for 2 hr. The reaction mixture and concentrated under the reduced pressure to remove the solvent. The residue was diluted with ethyl acetate (10 mL) and hexane (20 mL), and stirred. The resulting precipitates were collected by filtration, washed by hexane, and dried to give methyl 6-((N-phenylpiperazine-1-sulfonamido)methyl) nicotinate dihydrochloride as beige solid (0.550 g, 99.5%).

[Step 3] methyl 6-(((4-methyl-N-phenylpiperazine)-1-sulfonamido)methyl)nicotinate

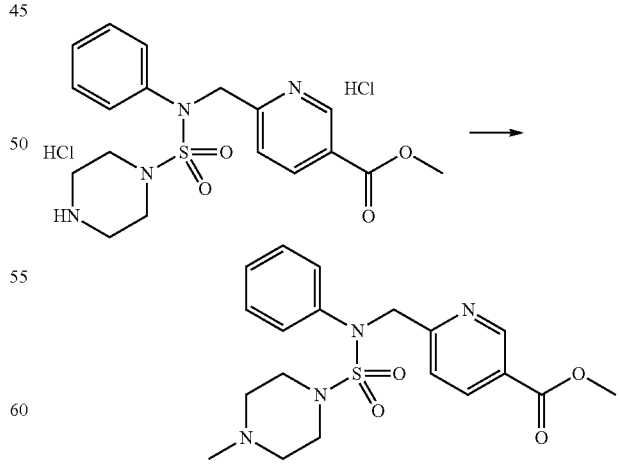

A mixture of methyl 6-((N-phenylpiperazine-1-sulfonamido)methyl)nicotinate Dihydrochloride (0.550 g, 1.187 mmol) and formaldehyde (37.00% solution in water, 0.884 mL, 11.870 mmol) in dichloromethane (15 mL) was treated at the room temperature with sodium triacetoxyborohydride (0.755 g, 3.561 mmol), and stirred at the same temperature for 16 hr. Then, saturated aqueous sodium bicarbonate solution was added to the reaction mixture, followed by extraction with dichloromethane. The organic layer was washed with aqueous saturated sodium chloride solution, dried with anhydrous MgSO₄, filtered, and concentrated in vacuo. The residue was chromatographed (SiO₂, 40 g cartridge; methanol/dichloromethane=0% to 10%) to give the crude product, which was dissolved in dichloromethane (3 mL) and hexane (50 mL), and stirred. The resulting precipitates were collected by filtration, washed by hexane, and dried to give methyl 6-(((4-methyl-N-phenylpiperazine)-1-sulfonamido)methyl)nicotinate as white solid (0.420 g, 87.5%).

[Step 4] N-((5-(hydrazinecarbonyl)pyridin-2-yl)methyl)-4-methyl-N-phenylpiperazine-1-sulfonamide

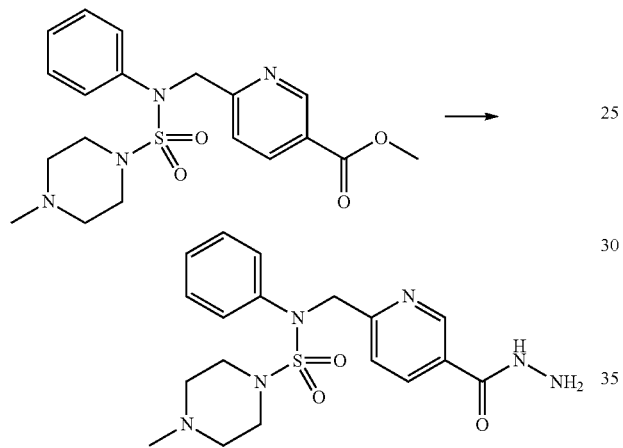

A slurry of methyl 6-(((4-methyl-N-phenylpiperazine)-1-sulfonamido)methyl)nicotinate (0.420 g, 1.038 mmol) in ethanol (10 mL) was mixed at the room temperature with hydrazine monohydrate (1.009 mL, 20.767 mmol), and stirred at 110° C. for 16 hr. The reaction mixture was cooled down to the room temperature to terminate the reaction, and concentrated under the reduced pressure to remove the solvent. The residue was diluted with dichloromethane (10 mL) and diethylether (70 mL), and stirred. The resulting precipitates were collected by filtration, washed by diethylether, and dried to give N-((5-(hydrazinecarbonyl)pyridin-2-yl)methyl)-4-methyl-N-phenylpiperazine-1-sulfonamide as white solid (0.299 g, 71.2%).

[Step 5] N-((5-(2-(2,2-difluoroacetyl)hydrazine-1-carbonyl)pyridin-2-yl)methyl)-4-methyl-N-phenylpiperazine-1-sulfonamide

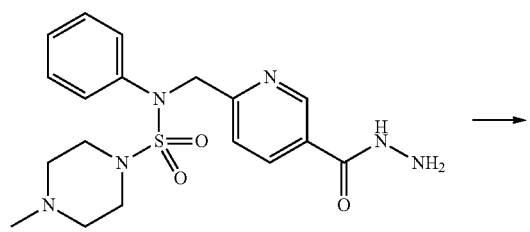

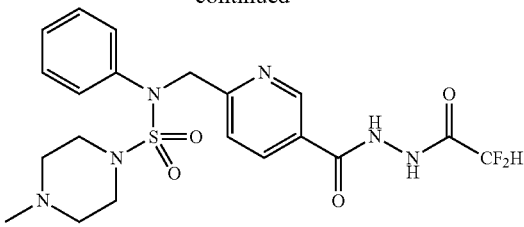

A solution of N-((5-(hydrazinecarbonyl)pyridin-2-yl)methyl)-4-methyl-N-phenylpiperazine-1-sulfonamide (0.299 g, 0.739 mmol) in tetrahydrofuran (20 mL) was mixed at 70° C. with 2,2-difluoroacetic anhydride (0.088 mL, 0.813 mmol), and stirred at the same temperature for 1 hr. The reaction mixture was cooled down to the room temperature to terminate the reaction. Then, saturated aqueous sodium bicarbonate solution was added to the reaction mixture, followed by extraction with ethyl acetate. The organic layer was washed with aqueous saturated sodium chloride solution, dried with anhydrous MgSO₄, filtered, and concentrated in vacuo. The residue was chromatographed (SiO₂, 12 g cartridge; methanol/dichloromethane=0% to 10%) to give the crude product, which was dissolved in dichloromethane (5 mL) and hexane (100 mL), and stirred. The resulting precipitates were collected by filtration, washed by hexane, and dried to give N-((5-(2-(2,2-difluoroacetyl)hydrazine-1-carbonyl)pyridin-2-yl)methyl)-4-methyl-N-phenylpiperazine-1-sulfonamide as bright yellow solid (0.256 g, 71.8%).

[Step 6] Compound 11363

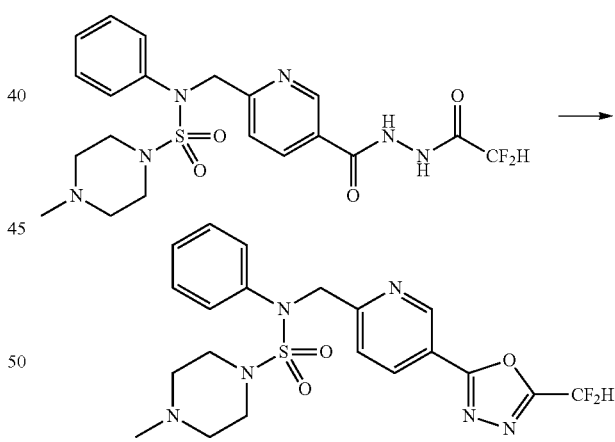

N-((5-(2-(2,2-difluoroacetyl)hydrazine-1-carbonyl)pyridin-2-yl)methyl)-4-methyl-N-phenylpiperazine-1-sulfonamide (0.256 g, 0.531 mmol) and 1-methoxy-N-triethylammoniosulfonyl-methanimidate (Burgess reagent, 0.632 g, 2.653 mmol) was mixed at the room temperature in tetrahydrofuran (10 mL), and then the mixture was heated at 150° C. under the microwaves for 30 min. The reaction mixture was cooled down to the room temperature to terminate the reaction. Then, saturated aqueous sodium bicarbonate solution was added to the reaction mixture, followed by extraction with ethyl acetate. The organic layer was washed with aqueous saturated sodium chloride solution, dried with anhydrous MgSO₄, filtered, and concentrated in vacuo. The residue was chromatographed (SiO$_2$, 12 g cartridge; methanol/dichloromethane=0% to 10%) to give the crude product, which was dissolved in hexane (20 mL), and stirred. The resulting precipitates were collected by filtration, washed by hexane, and dried to give N-((5-(5-(difluoromethyl)-1,3,4-oxadiazol-2-yl)pyridin-2-yl)methyl)-4-methyl-N-phenylpiperazine-1-sulfonamide as beige solid (0.082 g, 33.3%).

$^1$H NMR (400 MHz, DMSO-d$_6$) δ 9.10 (d, 1H, J=2.2 Hz), 8.40 (dd, 1H, J=8.3, 2.3 Hz), 7.70-7.68 (m, 1.25H), 7.56 (s, 0.5H), 7.51 (dd, 2H, J=8.3, 1.0 Hz), 7.43 (s, 0.25H), 7.38-7.34 (m, 2H), 7.24 (m, 1H), 5.11 (s, 2H), 3.17 (t, 4H, J=5.0 Hz), 2.28 (t, 4H, J=4.7 Hz), 2.15 (s, 3H); LRMS (ES) m/z 465.4 (M$^+$+1).

Example 34: Compound 11379, N-(4-(5-(difluoromethyl)-1,3,4-oxadiazol-2-yl)-2-fluorobenzyl)-4-(oxetan-3-yl)-N-phenylpiperazine-1-sulfonamide

[Step 1] methyl 3-fluoro-4-((N-phenylpiperazine-1-sulfonamido)methyl)benzoate Hydrochloride

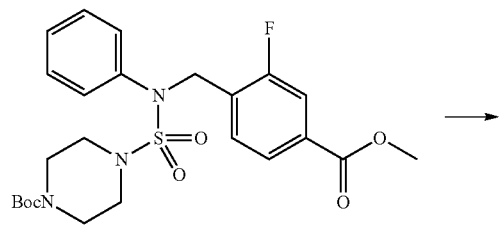

A slurry of tert-butyl 4-(N-(2-fluoro-4-(methoxycarbonyl)benzyl)-N-phenylsulfamoyl)piperazine-1-carboxylate (2.640 g, 5.201 mmol) in ethyl acetate (20 mL) was mixed at the room temperature with hydrochloric acid (4.00 M solution in 1,4-dioxane, 13.003 mL, 52.012 mmol), and stirred at the same temperature for 1 hr. The reaction mixture was concentrated under the reduced pressure to remove the solvent. The residue was diluted with ethyl acetate (20 mL) and hexane (20 mL), and stirred. The resulting precipitates were collected by filtration, washed by hexane, and dried to give methyl 3-fluoro-4-((N-phenylpiperazine-1-sulfonamido)methyl)benzoate hydrochloride as beige solid (2.280 g, 98.7%).

[Step 2] methyl 3-fluoro-4-4-(4-(oxetan-3-yl)-N-phenylpiperazine)-1-sulfonamido)methyl)benzoate

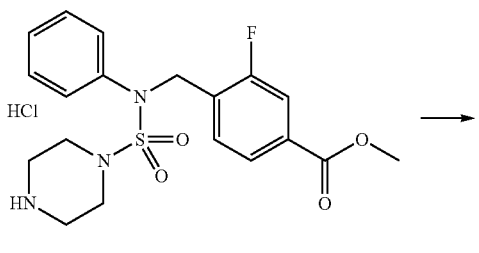

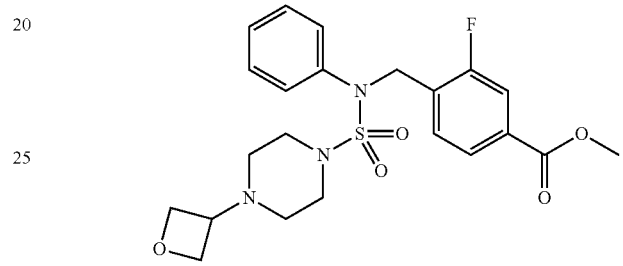

methyl 3-fluoro-4-((N-phenylpiperazine-1-sulfonamido)methyl)benzoate hydrochloride (0.440 g, 0.991 mmol), oxetan-3-one (0.214 g, 2.974 mmol) and sodium triacetoxyborohydride (0.630 g, 2.974 mmol) were mixed at the room temperature in dichloromethane (10 mL), and then the mixture was stirred at the same temperature for 16 hr. Then, saturated aqueous sodium bicarbonate solution was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (Sift, 12 g cartridge; methanol/dichloromethane=0% to 10%) to give the crude product, which was dissolved in dichloromethane (3 mL) and hexane (50 mL), and stirred. The resulting precipitates were collected by filtration, washed by hexane, and dried to give methyl 3-fluoro-4-4-(4-(oxetan-3-yl)-N-phenylpiperazine)-1-sulfonamido)methyl)benzoate as beige solid (0.286 g, 62.3%).

[Step 3] N-(2-fluoro-4-(hydrazinecarbonyl)benzyl)-4-(oxetan-3-yl)-N-phenylpiperazine-1-sulfonamide

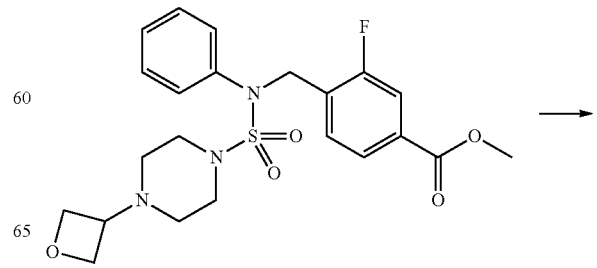

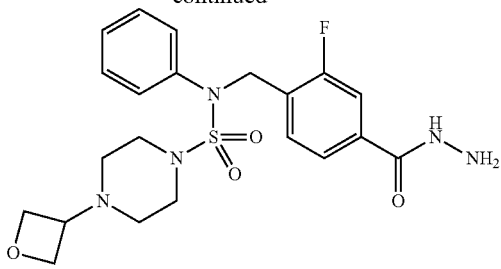

methyl 3-fluoro-4-4-(4-(oxetan-3-yl)-N-phenylpiperazine)-1-sulfonamido)methyl)benzoate (0.286 g, 0.617 mmol) and hydrazine monohydrate (0.300 mL, 6.170 mmol) were mixed at the room temperature in ethanol (10 mL), and then the mixture was stirred at 100° C. for 16 hr. The reaction mixture was cooled down to the room temperature to terminate the reaction, and concentrated under the reduced pressure to remove the solvent. The residue was diluted with dichloromethane (5 mL) and hexane (30 mL), and stirred. The resulting precipitates were collected by filtration, washed by hexane, and dried to give N-(2-fluoro-4-(hydrazinecarbonyl)benzyl)-4-(oxetan-3-yl)-N-phenylpiperazine-1-sulfonamide as white solid (0.241 g, 84.3%).

[Step 4] N-(4-(2-(2,2-difluoroacetyl)hydrazine-1-carbonyl)-2-fluorobenzyl)-4-(oxetan-3-yl)-N-phenylpiperazine-1-sulfonamide

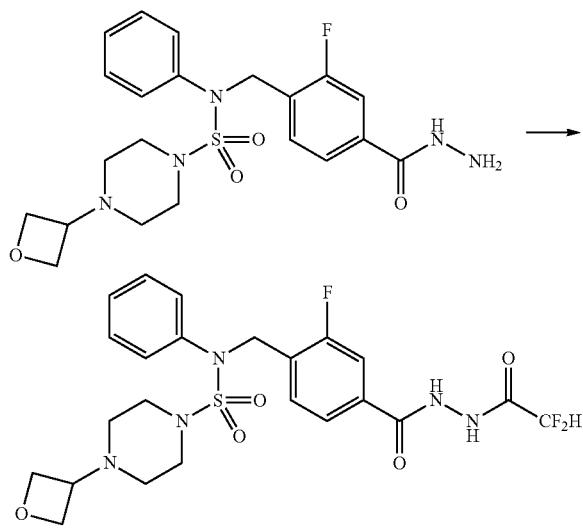

A solution of N-(2-fluoro-4-(hydrazinecarbonyl)benzyl)-4-(oxetan-3-yl)-N-phenylpiperazine-1-sulfonamide (0.241 g, 0.520 mmol) in tetrahydrofuran (10 mL) was mixed at 70° C. with 2,2-difluoroacetic anhydride (0.068 mL, 0.624 mmol) and N,N-diisopropylethylamine (0.136 mL, 0.780 mmol), and stirred at the same temperature for 1 hr. The reaction mixture was cooled down to the room temperature to terminate the reaction, and concentrated under the reduced pressure to remove the solvent. The crude product was used without further purification (N-(4-(2-(2,2-difluoroacetyl)hydrazine-1-carbonyl)-2-fluorobenzyl)-4-(oxetan-3-yl)-N-phenylpiperazine-1-sulfonamide, 0.270 g, 95.9%, brown solid).

[Step 5] Compound 11379

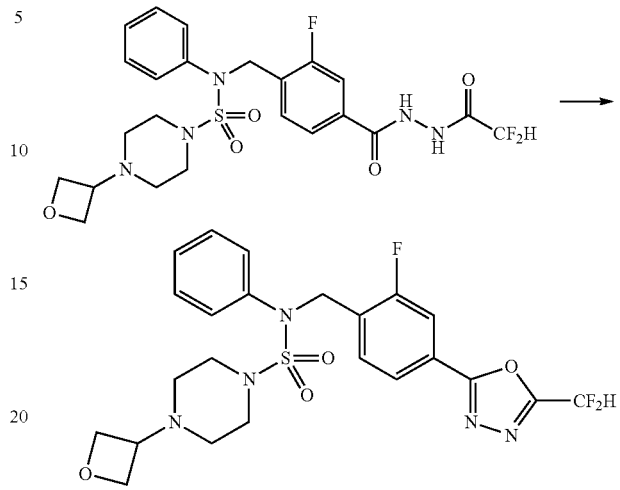

N-(4-(2-(2,2-difluoroacetyl)hydrazine-1-carbonyl)-2-fluorobenzyl)-4-(oxetan-3-yl)-N-phenylpiperazine-1-sulfonamide (0.270 g, 0.499 mmol) and 1-methoxy-N-triethylammoniosulfonyl-methanimidate (Burgess reagent, 0.238 g, 0.997 mmol) was mixed at the room temperature in tetrahydrofuran (10 mL), and then the mixture was heated at 150° C. under the microwaves for 30 min. The reaction mixture was cooled down to the room temperature to terminate the reaction. Then, saturated aqueous sodium bicarbonate solution was added to the reaction mixture, followed by extraction with ethyl acetate. The organic layer was washed with aqueous saturated sodium chloride solution, dried with anhydrous $MgSO_4$, filtered, and concentrated in vacuo. The residue was chromatographed ($SiO_2$, 12 g cartridge; ethyl acetate/hexane=60% to 90%) to give N-(4-(5-(difluoromethyl)-1,3,4-oxadiazol-2-yl)-2-fluorobenzyl)-4-(oxetan-3-yl)-N-phenylpiperazine-1-sulfonamide as white solid (0.042 g, 16.1%).

$^1$H NMR (400 MHz, DMSO-$d_6$) δ 7.83 (dd, 1H, J=7.9, 1.7 Hz), 7.78 (dd, 1H, J=10.2, 1.7 Hz), 7.69-7.57 (m, 1.25H), 7.54 (s, 0.5H), 7.48-7.40 (m, 2.25H), 7.40-7.31 (m, 2H), 7.31-7.22 (m, 1H), 5.03 (s, 2H), 4.52 (t, 2H, J=6.6 Hz), 4.40 (t, 2H, J=6.1 Hz), 3.41 (p, 1H, J=6.2 Hz), 3.20-3.17 (m, 4H), 2.25 (t, 4H, J=4.9 Hz); LRMS (ES) m/z 524.4 (M$^+$+1).

Example 35: Compound 11440, N-((5-(5-(difluoromethyl)-1,3,4-oxadiazol-2-yl)pyridin-2-yl)methyl)-N-phenylthiomorpholine-4-sulfonamide 1,1-dioxide

[Step 1] 4-((1H-imidazol-1-yl)sulfonyl)thiomorpholine 1,1-dioxide

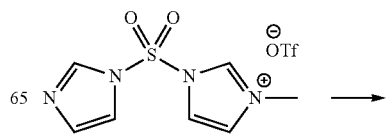

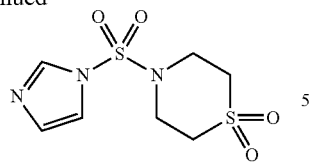

A mixture of 1-((1H-imidazol-1-yl)sulfonyl)-3-methyl-1H-imidazol-3-ium trifluoromethanesulfonate (4.400 g, 12.145 mmol) and thiomorpholine 1,1-dioxide (1.970 g, 14.574 mmol) in acetonitrile (50 mL) was stirred at the room temperature for 16 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 40 g cartridge; ethyl acetate/hexane=40% to 70%) to give the crude product, which was dissolved in dichloromethane (10 mL) and hexane (200 mL), and stirred. The resulting precipitates were collected by filtration, washed by hexane, and dried to give 4-((1H-imidazol-1-yl)sulfonyl)thiomorpholine 1,1-dioxide as white solid (1.635 g, 50.7%).

[Step 2] 1-((1,1-dioxidothiomorpholino)sulfonyl)-3-methyl-1H-imidazol-3-ium trifluoromethanesulfonate

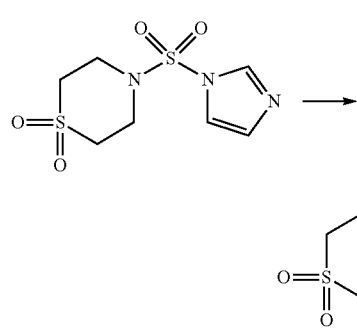

A solution of 4-((1H-imidazol-1-yl)sulfonyl)thiomorpholine 1,1-dioxide (1.635 g, 6.163 mmol) in dichloromethane (20 mL) was mixed at 0° C. with methyl trifluoromethanesulfonate (0.744 mL, 6.779 mmol), and stirred at the room temperature for 5 hr. The reaction mixture was diluted with hexane (40 mL) and stirred. The resulting precipitates were collected by filtration, washed by hexane, and dried to give 1-((1,1-dioxidothiomorpholino)sulfonyl)-3-methyl-1H-imidazol-3-ium trifluoromethanesulfonate as white solid (2.600 g, 98.2%).

[Step 3] N-phenylthiomorpholine-4-sulfonamide 1,1-dioxide

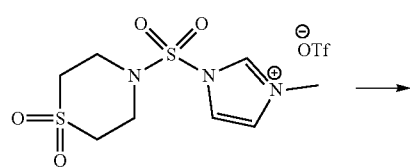

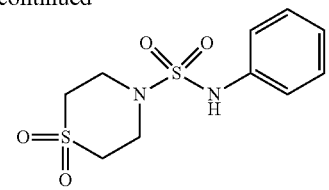

A solution of 1-((1,1-dioxidothiomorpholino)sulfonyl)-3-methyl-1H-imidazol-3-ium trifluoromethanesulfonate (1.300 g, 3.027 mmol) in acetonitrile (10 mL) was mixed at the room temperature with aniline (0.415 mL, 4.541 mmol). The reaction mixture was heated at reflux for 16 hr, and cooled down to the room temperature to terminate the reaction. Then, saturated aqueous ammonium chloride solution was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (Sift, 12 g cartridge; ethyl acetate/hexane=30% to 70%) to give N-phenylthiomorpholine-4-sulfonamide 1,1-dioxide as brown solid (0.220 g, 25.0%).

[Step 4] methyl 6-(((1,1-dioxido-N-phenylthiomorpholine)-4-sulfonamido)methyl)nicotinate

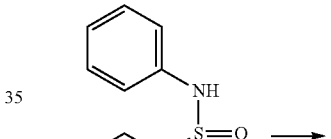

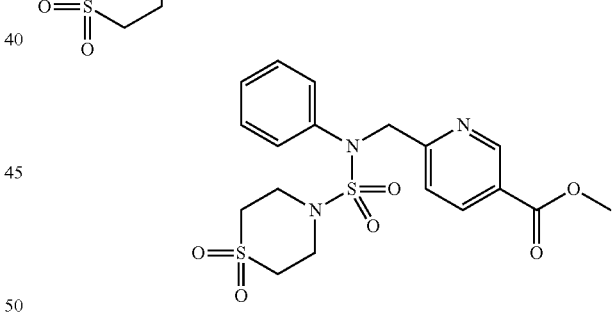

To a solution of N-phenylthiomorpholine-4-sulfonamide 1,1-dioxide (0.220 g, 0.758 mmol) in N,N-dimethylformide (10 mL) was added sodium hydride (60.00%, 0.036 g, 0.909 mmol) at the room temperature, and the mixture was stirred at the same temperature for 5 min. The reaction mixture was treated with methyl 6-(bromomethyl)nicotinate (0.227 g, 0.985 mmol), and stirred for additional 3 hr at the same temperature. Then, saturated aqueous sodium bicarbonate solution was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 12 g cartridge; ethyl acetate/hexane=40% to 70%) to give the crude product, which was dissolved in dichloromethane (5 mL) and hexane (50 mL), and stirred. The resulting precipitates were collected by filtration, washed by hexane, and dried to give methyl 6-(((1,1-dioxido-N-phenylthiomorpholine)-4-sulfonamido)methyl)nicotinate as beige solid (0.250 g, 75.1%).

[Step 5] N-((5-(hydrazinecarbonyl)pyridin-2-yl)methyl)-N-phenylthiomorpholine-4-sulfonamide 1,1-dioxide

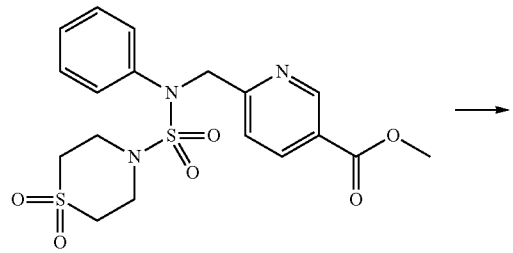

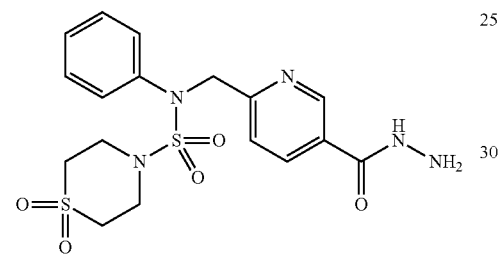

methyl 6-(((1,1-dioxido-N-phenylthiomorpholine)-4-sulfonamido)methyl)nicotinate (0.250 g, 0.569 mmol) and hydrazine monohydrate (0.036 mL, 0.739 mmol) were mixed at the room temperature in ethanol (10 mL), and then the mixture was stirred at 100° C. for 16 hr. The reaction mixture was cooled down to the room temperature to terminate the reaction, and concentrated under the reduced pressure to remove the solvent. The residue was diluted with ethyl acetate (10 mL) and hexane (20 mL), and stirred. The resulting precipitates were collected by filtration, washed by hexane, and dried to give N-((5-(hydrazinecarbonyl)pyridin-2-yl)methyl)-N-phenylthiomorpholine-4-sulfonamide 1,1-dioxide as white solid (0.212 g, 84.8%).

[Step 6] N-((5-(2-(2,2-difluoroacetyl)hydrazine-1-carbonyl)pyridin-2-yl)methyl)-N-phenylthiomorpholine-4-sulfonamide 1,1-dioxide

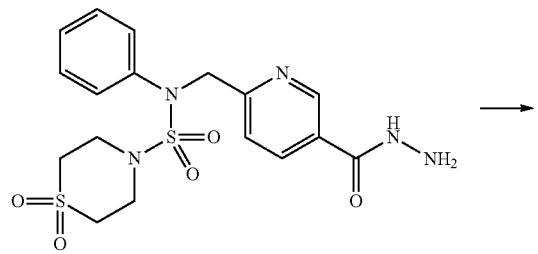

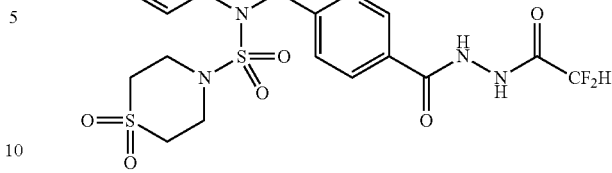

A solution of N-((5-(hydrazinecarbonyl)pyridin-2-yl)methyl)-N-phenylthiomorpholine-4-sulfonamide 1,1-dioxide (0.212 g, 0.482 mmol) in tetrahydrofuran (10 mL) was mixed at 70° C. with 2,2-difluoroacetic anhydride (0.063 mL, 0.579 mmol) and N,N-diisopropylethylamine (0.126 mL, 0.724 mmol), and stirred at the same temperature for 1 hr. The reaction mixture was cooled down to the room temperature to terminate the reaction. Then, saturated aqueous sodium bicarbonate solution was added to the reaction mixture, followed by extraction with ethyl acetate. The organic layer was washed with aqueous saturated sodium chloride solution, dried with anhydrous MgSO$_4$, filtered, and concentrated in vacuo. The crude product was used without further purification (N-((5-(2-(2,2-difluoroacetyl)hydrazine-1-carbonyl)pyridin-2-yl)methyl)-N-phenylthio morpholine-4-sulfonamide 1,1-dioxide, 0.220 g, 88.1%, yellow liquid).

[Step 7] Compound 11440

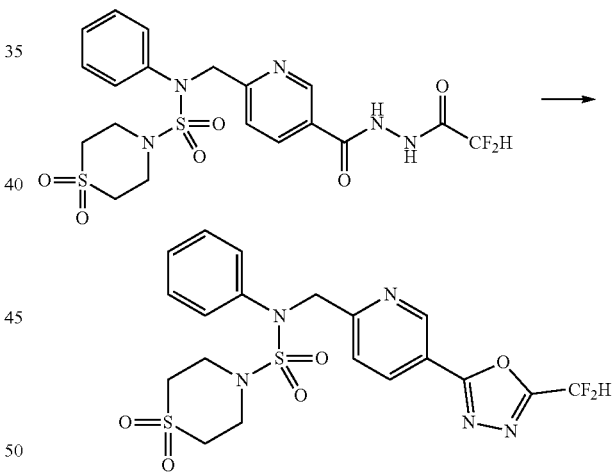

N-((5-(2-(2,2-difluoroacetyl)hydrazine-1-carbonyl)pyridin-2-yl)methyl)-N-phenylthiomorpholine-4-sulfonamide 1,1-dioxide (0.220 g, 0.425 mmol) and 1-methoxy-N-triethylammoniosulfonyl-methanimidate (Burgess reagent, 0.203 g, 0.850 mmol) was mixed at the room temperature in tetrahydrofuran (10 mL), and then the mixture was heated at 150° C. under the microwaves for 30 min. The reaction mixture was cooled down to the room temperature to terminate the reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 12 g cartridge; ethyl acetate/hexane=40% to 70%) to give N-((5-(5-(difluoromethyl)-1,3,4-oxadiazol-2-yl)pyridin-2-yl)methyl)-N-phenylthiomorpholine-4-sulfonamide 1,1-dioxide as beige solid (0.043 g, 20.3%).

¹H NMR (400 MHz, DMSO-d₆) δ 9.13 (d, 1H, J=2.2 Hz), 8.39 (dd, 1H, J=8.3, 2.3 Hz), 7.72-7.63 (m, 1.25H), 7.59-7.47 (m, 2.5H), 7.46-7.34 (m, 2.25H), 7.29 (t, 1H, J=7.3 Hz), 5.11 (s, 2H), 3.69-3.68 (m, 4H), 3.22-3.20 (m, 4H); LRMS (ES) m/z 500.3 (M⁺+1).

Example 36: Compound 11498, N-(3-chloro-4-fluorophenyl)-N-((5-(5-(difluoromethyl)-1,3,4-oxadiazol-2-yl)pyridin-2-yl) methyl)thiomorpholine-4-sulfonamide 1,1-dioxide

[Step 1] N-(3-chloro-4-fluorophenyl)thiomorpholine-4-sulfonamide 1,1-dioxide

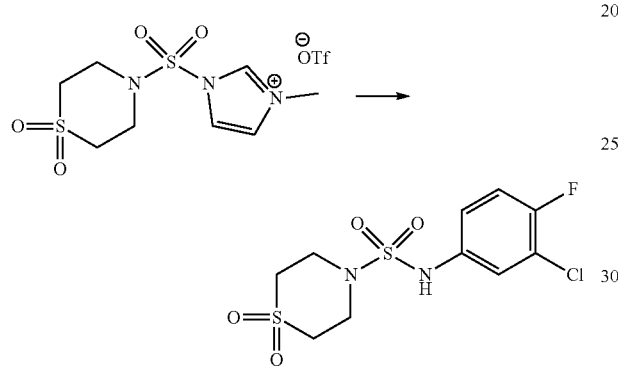

A mixture of 1-(((1,1-dioxidothiomorpholino)sulfonyl)-3-methyl-1H-imidazol-3-ium trifluoromethanesulfonate (1.460 g, 3.400 mmol) and 3-chloro-4-fluoroaniline (0.594 g, 4.080 mmol) in acetonitrile (20 mL), prepared at the ambient temperature, was heated at reflux for 16 hr, and cooled down to the room temperature to terminate the reaction. Then, water was added to the reaction mixture, followed by extraction with ethyl acetate. The organic layer was washed with aqueous saturated sodium chloride solution, dried with anhydrous MgSO₄, filtered, and concentrated in vacuo. The residue was chromatographed (SiO₂, 40 g cartridge; ethyl acetate/hexane=20% to 50%) to give N-(3-chloro-4-fluorophenyl)thiomorpholine-4-sulfonamide 1,1-dioxide as beige solid (0.709 g, 60.8%).

[Step 2] methyl 6-(((N-(3-chloro-4-fluorophenyl)-1,1-dioxidothiomorpholine)-4-sulfonamido)methyl) nicotinate

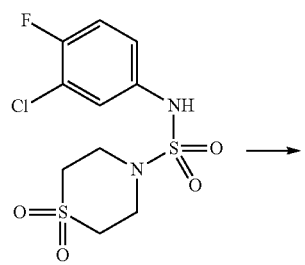

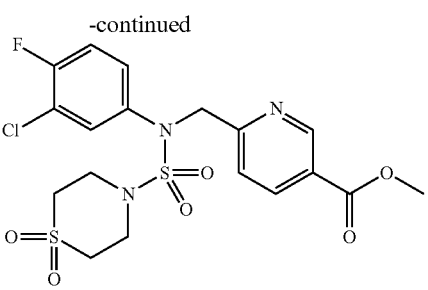

To a solution of N-(3-chloro-4-fluorophenyl)thiomorpholine-4-sulfonamide 1,1-dioxide (0.400 g, 1.167 mmol) in N,N-dimethylformide (10 mL) was added sodium hydride (60.00%, 0.061 g, 1.517 mmol) at the room temperature, and the mixture was stirred at the same temperature for 5 min. The reaction mixture was treated with methyl 6-(bromomethyl)nicotinate (0.322 g, 1.400 mmol), and stirred for additional 3 hr at the same temperature. Then, saturated aqueous ammonium chloride solution was added to the reaction mixture, followed by extraction with ethyl acetate. The organic layer was washed with aqueous saturated sodium chloride solution, dried with anhydrous MgSO₄, filtered, and concentrated in vacuo. The residue was chromatographed (SiO₂, 12 g cartridge; ethyl acetate/hexane=30% to 60%) to give methyl 6-(((N-(3-chloro-4-fluorophenyl)-1,1-dioxidothiomorpholine)-4-sulfonamido)methyl)nicotinate as beige solid (0.348 g, 60.6%).

[Step 3] N-(3-chloro-4-fluorophenyl)-N-((5-(hydrazinecarbonyl)pyridin-2-yl)methyl)thiomorpholine-4-sulfonamide 1,1-dioxide

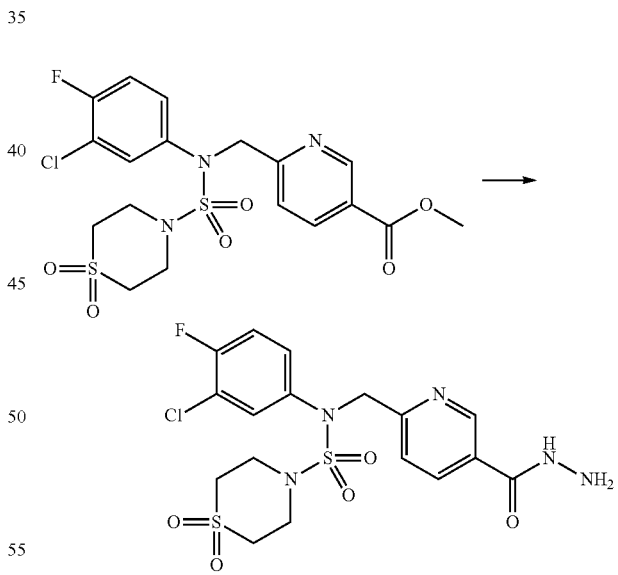

A slurry of methyl 6-(((N-(3-chloro-4-fluorophenyl)-1,1-dioxidothiomorpholine)-4-sulfonamido)methyl)nicotinate (0.250 g, 0.508 mmol) in ethanol (10 mL) was mixed at the room temperature with hydrazine monohydrate (0.494 mL, 10.164 mmol), and stirred at 100° C. for 16 hr. The reaction mixture was cooled down to the room temperature to terminate the reaction, and concentrated under the reduced pressure to remove the solvent. The residue was diluted with ethyl acetate (5 mL) and hexane (20 mL), and stirred. The resulting precipitates were collected by filtration, washed by hexane, and dried to give N-(3-chloro-4-fluorophenyl)-N-((5-(hydrazinecarbonyl)pyridin-2-yl)methyl)thiomorpholine-4-sulfonamide 1,1-dioxide as light yellow solid (0.207 g, 82.8%).

[Step 4] N-(3-chloro-4-fluorophenyl)-N-((5-(2-(2,2-difluoroacetyl)hydrazine-1-carbonyl)pyridin-2-yl)methyl)thiomorpholine-4-sulfonamide 1,1-dioxide

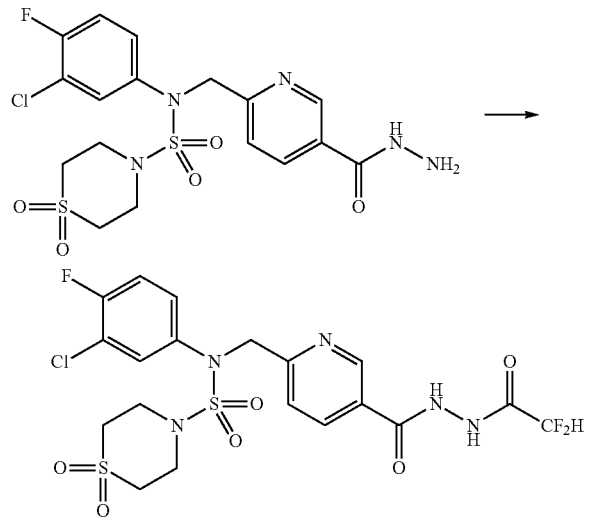

A solution of N-(3-chloro-4-fluorophenyl)-N-((5-(hydrazinecarbonyl)pyridin-2-yl)methyl)thiomorpholine-4-sulfonamide 1,1-dioxide (0.207 g, 0.421 mmol) in tetrahydrofuran (10 mL) was mixed at 70° C. with 2,2-difluoroacetic anhydride (0.115 mL, 0.926 mmol) and N,N-diisopropylethylamine (0.220 mL, 1.262 mmol). The reaction mixture was stirred at the same temperature for 1 hr, and cooled down to the room temperature to terminate the reaction. Then, saturated aqueous sodium bicarbonate solution was added to the reaction mixture, followed by extraction with ethyl acetate. The organic layer was washed with aqueous saturated sodium chloride solution, dried with anhydrous MgSO₄, filtered, and concentrated in vacuo. The residue was chromatographed (SiO₂, 12 g cartridge; ethyl acetate/hexane=60% to 90%) to give N-(3-chloro-4-fluorophenyl)-N-((5-(2-(2,2-difluoroacetyl)hydrazine-1-carbonyl)pyridin-2-yl)methyl)thiomorpholine-4-sulfonamide 1,1-dioxide as light yellow solid (0.148 g, 61.7%).

[Step 5] Compound 11498

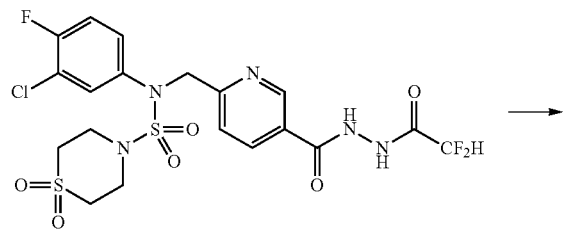

-continued

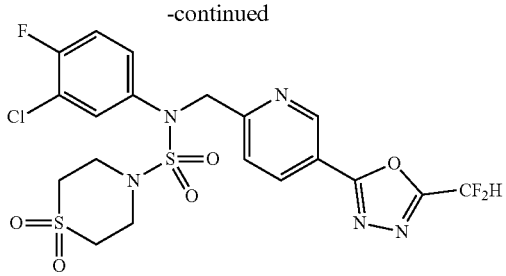

N-(3-chloro-4-fluorophenyl)-N-((5-(2-(2,2-difluoroacetyl)hydrazine-1-carbonyl)pyri din-2-yl)methyl)thiomorpholine-4-sulfonamide 1,1-dioxide (0.148 g, 0.260 mmol) and 1-methoxy-N-triethylammoniosulfonyl-methanimidate (Burgess reagent, 0.093 g, 0.390 mmol) was mixed at the room temperature in tetrahydrofuran (5 mL), and then the mixture was heated at 150° C. under the microwaves for 30 min. The reaction mixture was cooled down to the room temperature to terminate the reaction. Then, water was added to the reaction mixture, followed by extraction with ethyl acetate. The organic layer was washed with aqueous saturated sodium chloride solution, dried with anhydrous MgSO₄, filtered, and concentrated in vacuo. The residue was chromatographed (SiO₂, 12 g cartridge; ethyl acetate/hexane=30% to 60%) to give N-(3-chloro-4-fluorophenyl)-N-((5-(5-(difluoromethyl)-1,3,4-oxadiazol-2-yl)pyridin-2-yl) methyl)thiomorpholine-4-sulfonamide 1,1-dioxide as brown solid (0.051 g, 35.6%).

$^1$H NMR (400 MHz, DMSO-d₆) δ 9.14 (dd, 1H, J=2.2, 0.8 Hz), 8.40 (dd, 1H, J=8.2, 2.3 Hz), 7.86 (dd, 1H, J=6.6, 2.7 Hz), 7.71-7.64 (m, 1.25H), 7.62-7.51 (m, 1.5H), 7.47-7.37 (m, 1.25H), 5.11 (s, 2H), 3.79-3.71 (m, 4H), 3.26 (m, 4H); LRMS (ES) m/z 552.5 (M⁺+1).

Example 37: Compound 11527, N-(2-fluoro-4-(5-(trifluoromethyl)-1,3,4-oxadiazol-2-yl)benzyl)-4-(oxetan-3-yl)-N-phenylpiperazine-1-sulfonamide

[Step 1] N-(2-fluoro-4-(2-(2,2,2-trifluoroacetyl)hydrazine-1-carbonyl)benzyl)-4-(oxetan-3-yl)-N-phenylpiperazine-1-sulfonamide

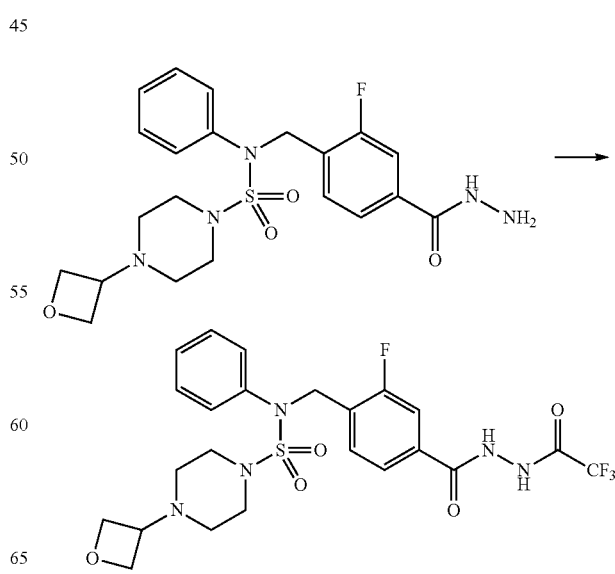

A solution of N-(2-fluoro-4-(hydrazinecarbonyl)benzyl)-4-(oxetan-3-yl)-N-phenylpiperazine-1-sulfonamide (0.500 g, 1.079 mmol) in tetrahydrofuran (20 mL) was mixed at 70° C. with trifluoroacetic anhydride (0.168 mL, 1.187 mmol) and N,N-diisopropylethylamine (0.225 mL, 1.294 mmol), and stirred at the same temperature for 30 min. The reaction mixture was cooled down to the room temperature to terminate the reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 40 g cartridge; ethyl acetate/hexane=70% to 100%) to give the crude product, which was dissolved in ethyl acetate (5 mL) and hexane (30 mL), and stirred. The resulting precipitates were collected by filtration, washed by hexane, and dried to give N-(2-fluoro-4-(2-(2,2,2-trifluoroacetyl)hydrazine-1-carbonyl)benzyl)-4-(oxetan-3-yl)-N-phenylpiperazine-1-sulfonamide as white solid (0.589 g, 97.6%).

[Step 2] Compound 11527

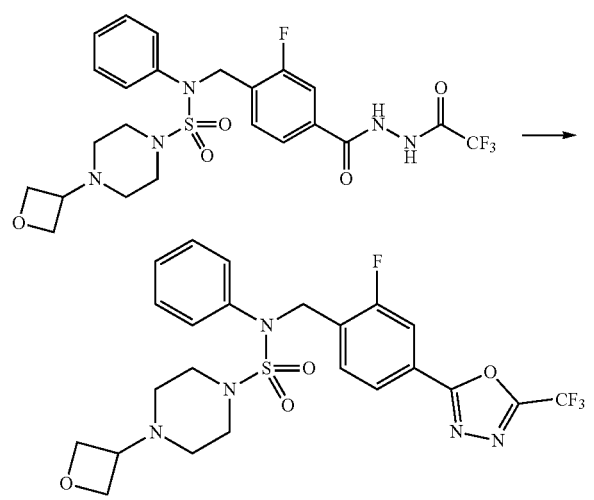

A slurry of N-(2-fluoro-4-(2-(2,2,2-trifluoroacetyl)hydrazine-1-carbonyl)benzyl)-4-(oxetan-3-yl)-N-phenylpiperazine-1-sulfonamide (0.569 g, 1.017 mmol) in dichloromethane (10 mL) was mixed at the room temperature with methanesulfonyl chloride (0.157 mL, 2.034 mmol) and N,N-diisopropylethylamine (0.354 mL, 2.034 mmol), and stirred at the same temperature for 3 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 40 g cartridge; ethyl acetate/hexane=40% to 70%) to give the crude product, which was dissolved in ethyl acetate (5 mL) and hexane (30 mL), and stirred. The resulting precipitates were collected by filtration, washed by hexane, and dried to give N-(2-fluoro-4-(5-(trifluoromethyl)-1,3,4-oxadiazol-2-yl)benzyl)-4-(oxetan-3-yl)-N-phenylpiperazine-1-sulfonamide as white solid (0.186 g, 33.8%).

$^1$H NMR (400 MHz, DMSO-d$_6$) δ 7.86 (dd, 1H, J=8.0, 1.7 Hz), 7.84-7.77 (m, 1H), 7.63 (t, 1H, J=7.7 Hz), 7.48-7.41 (m, 2H), 7.36 (t, 2H, J=7.6 Hz), 7.28 (t, 1H, J=7.2 Hz), 5.05 (s, 2H), 4.53 (s, 2H), 4.39 (s, 2H), 3.40 (m, 1H), 3.19 (s, 4H), 2.26 (s, 4H); LRMS (ES) m/z 542.5 (M$^+$+1).

Example 38: Compound 11528, 4-(oxetan-3-yl)-N-phenyl-N-((5-(5-(trifluoromethyl)-1,3,4-oxadiazol-2-yl)pyridin-2-yl) methyl)piperazine-1-sulfonamide

[Step 1] methyl 6-((N-phenylpiperazine-1-sulfonamido)methyl)nicotinate Dihydrochloride

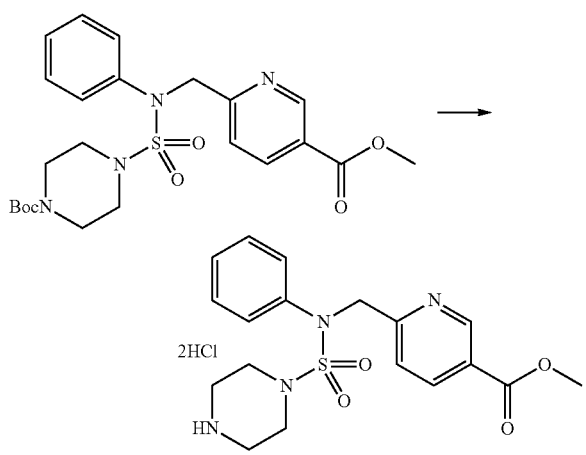

A suspension of tert-butyl 4-(N-((5-(methoxycarbonyl)pyridin-2-yl)methyl)-N-phenylsulfamoyl)piperazine-1-carboxylate (0.760 g, 1.549 mmol) in 1,4-dioxane (10 mL) was mixed at the room temperature with hydrogen chloride (4.00 M solution in 1,4-dioxane, 5.809 mL, 23.238 mmol), and stirred at the same temperature for 6 hr. The reaction mixture was concentrated under the reduced pressure to remove the solvent. The residue was diluted with ethyl acetate (20 mL) and hexane (20 mL), and stirred. The resulting precipitates were collected by filtration, washed by hexane, and dried to give methyl 6-((N-phenylpiperazine-1-sulfonamido)methyl)nicotinate dihydrochloride as brown solid (0.710 g, 98.9%).

[Step 2] methyl 6-(((4-(oxetan-3-yl)-N-phenylpiperazine)-1-sulfonamido)methyl)nicotinate

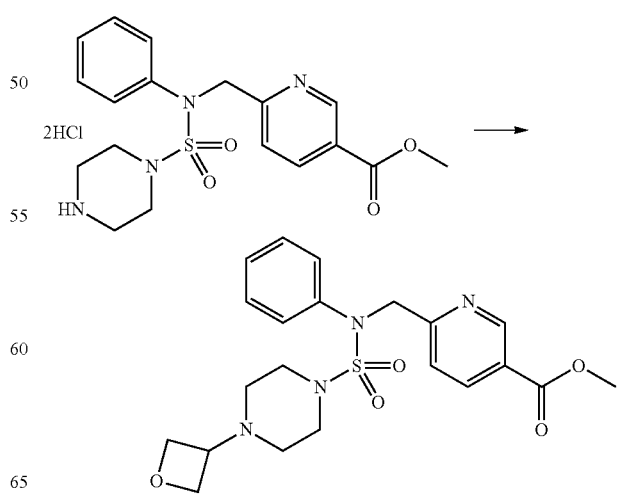

A mixture of methyl 6-((N-phenylpiperazine-1-sulfonamido)methyl)nicotinate dihydrochloride (0.710 g, 1.532 mmol), oxetan-3-one (0.269 mL, 4.597 mmol) and N,N-diisopropylethylamine (0.667 mL, 3.831 mmol) in dichloromethane (20 mL) was treated at the room temperature with sodium triacetoxyborohydride (0.649 g, 3.065 mmol), and stirred at the same temperature for 6 hr. Then, saturated aqueous sodium bicarbonate solution was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 40 g cartridge; methanol/dichloromethane=0% to 10%) to give methyl 6-(((4-(oxetan-3-yl)-N-phenylpiperazine)-1-sulfonamido)methyl)nicotinate as beige solid (0.621 g, 90.8%).

[Step 3] N-((5-(hydrazinecarbonyl)pyridin-2-yl)methyl)-4-(oxetan-3-yl)-N-phenylpiperazine-1-sulfonamide

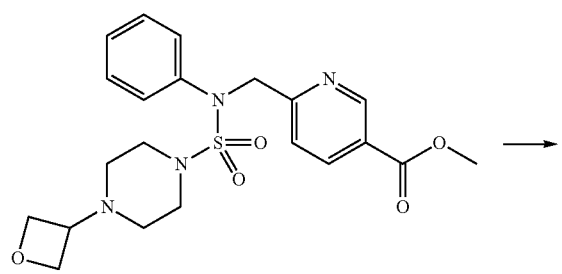

A slurry of methyl 6-(((4-(oxetan-3-yl)-N-phenylpiperazine)-1-sulfonamido)methyl)nicotinate (0.621 g, 1.391 mmol) in ethanol (10 mL) was mixed at the room temperature with hydrazine monohydrate (1.352 mL, 27.815 mmol), and heated at reflux for 16 hr. The reaction mixture was cooled down to the room temperature to terminate the reaction, and concentrated under the reduced pressure to remove the solvent. The residue was chromatographed (SiO$_2$, 80 g cartridge; methanol/dichloromethane=0% to 5%) to give N-((5-(hydrazinecarbonyl)pyridin-2-yl)methyl)-4-(oxetan-3-yl)-N-phenylpiperazine-1-sulfonamide as beige solid (0.420 g, 67.6%).

[Step 4] 4-(oxetan-3-yl)-N-phenyl-N-((5-(2-(2,2,2-trifluoroacetyl)hydrazine-1-carbonyl)pyridin-2-yl)methyl)piperazine-1-sulfonamide

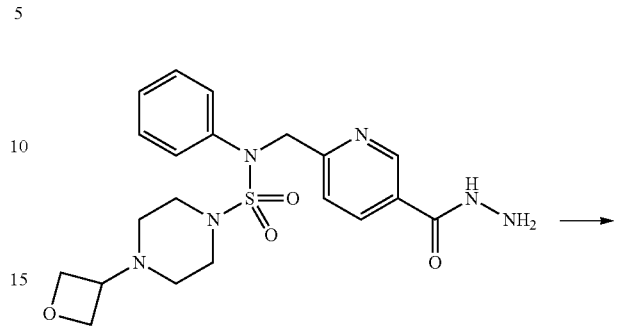

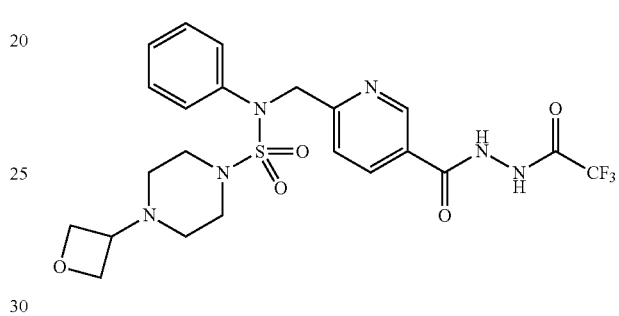

A solution of N-((5-(hydrazinecarbonyl)pyridin-2-yl)methyl)-4-(oxetan-3-yl)-N-phenylpiperazine-1-sulfonamide (0.200 g, 0.448 mmol) in tetrahydrofuran (10 mL) was mixed at 70° C. with trifluoroacetic anhydride (0.070 mL, 0.493 mmol) and N,N-diisopropylethylamine (0.094 mL, 0.537 mmol), and stirred at the same temperature for 30 min. The reaction mixture was cooled down to the room temperature to terminate the reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (Sift, 12 g cartridge; ethyl acetate/hexane=80% to 100%) to give the crude product, which was dissolved in ethyl acetate (3 mL) and hexane (30 mL), and stirred. The resulting precipitates were collected by filtration, washed by hexane, and dried to give 4-(oxetan-3-yl)-N-phenyl-N-((5-(2-(2,2,2-trifluoroacetyl)hydrazine-1-carbonyl)pyridin-2-yl)methyl)piperazine-1-sulfonamide as white solid (0.202 g, 83.1%).

[Step 5] Compound 11528

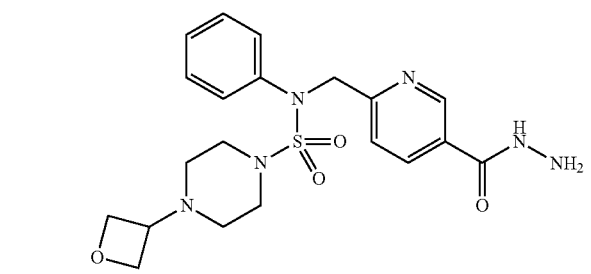

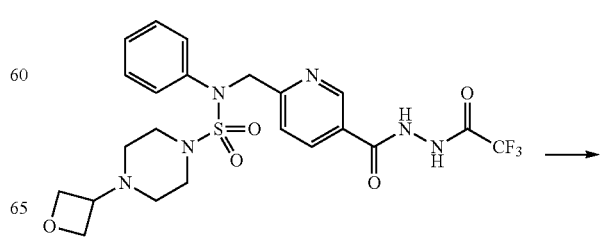

-continued

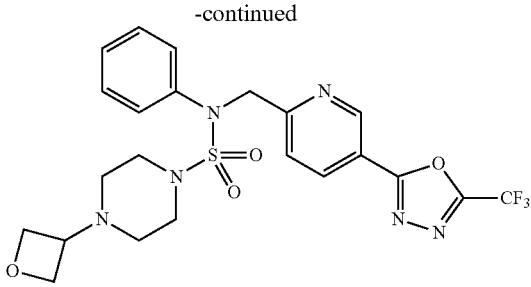

A slurry of 4-(oxetan-3-yl)-N-phenyl-N-((5-(2-(2,2,2-trifluoroacetyl)hydrazine-1-carbonyl)pyridin-2-yl)methyl)piperazine-1-sulfonamide (0.202 g, 0.372 mmol) in dichloromethane (10 mL) was mixed at the room temperature with methanesulfonyl chloride (0.058 mL, 0.745 mmol) and N,N-diisopropylethylamine (0.130 mL, 0.745 mmol), and stirred at the same temperature for 3 hr. Then, water was added to the reaction mixture, followed by extraction with dichloromethane. The organic layer was washed with aqueous saturated sodium chloride solution, dried with anhydrous MgSO₄, filtered, and concentrated in vacuo. The residue was chromatographed (SiO₂, 12 g cartridge; ethyl acetate/hexane=50% to 80%) to give the crude product, which was dissolved in ethyl acetate (3 mL) and hexane (15 mL), and stirred. The resulting precipitates were collected by filtration, washed by hexane, and dried to give 4-(oxetan-3-yl)-N-phenyl-N-((5-(5-(trifluoromethyl)-1,3,4-oxadiazol-2-yl)pyridin-2-yl) methyl)piperazine-1-sulfonamide as beige solid (0.092 g, 47.1%).

$^1$H NMR (400 MHz, DMSO-d₆) δ 9.13 (d, 1H, J=2.1 Hz), 8.43 (dd, 1H, J=8.2, 2.3 Hz), 7.70 (d, 1H, J=8.2 Hz), 7.56-7.48 (m, 2H), 7.37 (t, 2H, J=7.7 Hz), 7.26 (t, 1H, J=7.4 Hz), 5.13 (s, 2H), 4.54 (s, 2H), 4.43 (s, 2H), 3.37 (m, 1H), 3.23 (s, 4H), 2.34-2.28 (s, 4H); LRMS (ES) m/z 525.4 (M⁺+1).

Example 39: Compound 11574, N-((5-(5-(difluoromethyl)-1,3,4-oxadiazol-2-yl)pyridin-2-yl) methyl)-4-(oxetan-3-yl)-N-phenylpiperazine-1-sulfonamide

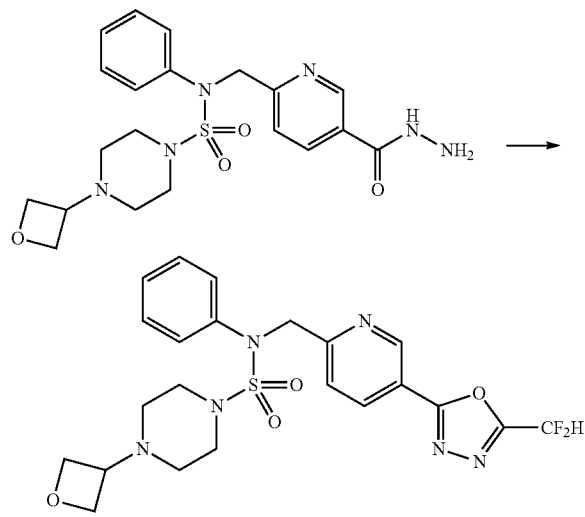

A solution of N-((5-(hydrazinecarbonyl)pyridin-2-yl) methyl)-4-(oxetan-3-yl)-N-phenylpiperazine-1-sulfonamide (0.600 g, 1.344 mmol) in tetrahydrofuran (15 mL), prepared at the ambient temperature, was mixed at reflux with 2,2-difluoroacetic anhydride (0.501 mL, 4.031 mmol) and N,N-diisopropylethylamine (0.936 mL, 5.375 mmol). The reaction mixture was heated at reflux for the additional 1 hr, and cooled down to the room temperature to terminate the reaction. Then, saturated aqueous sodium bicarbonate solution was added to the reaction mixture, followed by extraction with ethyl acetate. The organic layer was washed with aqueous saturated sodium chloride solution, dried with anhydrous MgSO₄, filtered, and concentrated in vacuo. The residue was chromatographed (SiO₂, 40 g cartridge; ethyl acetate/hexane=70% to 100%) to give the crude product, which was dissolved in ethyl acetate (5 mL) and hexane (30 mL), and stirred. The resulting precipitates were collected by filtration, washed by hexane, and dried to give N-((5-(5-(difluoromethyl)-1,3,4-oxadiazol-2-yl)pyridin-2-yl) methyl)-4-(oxetan-3-yl)-N-phenylpiperazine-1-sulfonamide as white solid (0.480 g, 70.5%).

$^1$H NMR (400 MHz, DMSO-d₆) δ 9.10 (s, 1H), 8.43-8.36 (m, 1H), 7.70-7.68 (m, 1.25H), 7.59-7.43 (m, 2.75H), 7.36 (t, 2H, J=7.7 Hz), 7.25 (t, 1H, J=7.3 Hz), 5.12 (s, 2H), 4.52 (t, 2H, J=6.6 Hz), 4.40 (t, 2H, J=6.1 Hz), 3.40 (t, 1H, J=6.4 Hz), 3.21 (s, 4H), 2.25 (s, 4H); LRMS (ES) m/z 507.2 (M⁺+1).

Example 40: Compound 11575, N-(4-(5-(difluoromethyl)-1,3,4-oxadiazol-2-yl)benzyl)-4-(oxetan-3-yl)-N-phenylpiperazine-1-sulfonamide

[Step 1] methyl 4-((N-phenylpiperazine-1-sulfonamido)methyl)benzoate Hydrochloride

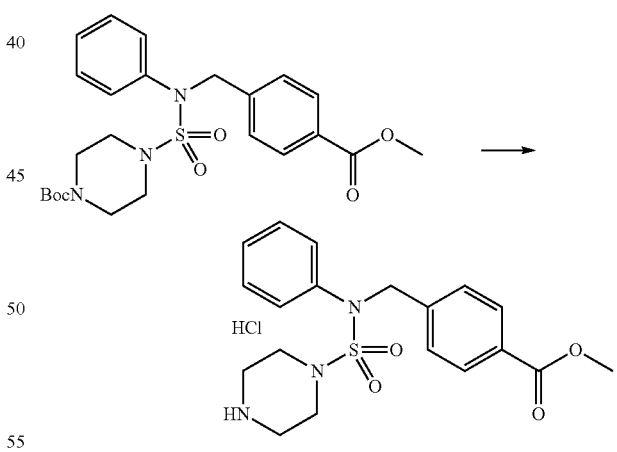

A suspension of tert-butyl 4-(N-(4-(methoxycarbonyl) benzyl)-N-phenylsulfamoyl)piperazine-1-carboxylate (3.060 g, 6.250 mmol) in 1,4-dioxane (30 mL) was mixed at the room temperature with hydrochloric acid (4.00 M solution in 1,4-dioxane, 15.625 mL, 62.501 mmol), and stirred at the same temperature for 6 hr. The reaction mixture was diluted with ethyl acetate (20 mL) and hexane (100 mL), and stirred. The resulting precipitates were collected by filtration, washed by hexane, and dried to give methyl 4-((N-phenylpiperazine-1-sulfonamido)methyl)benzoate hydrochloride as white solid (2.560 g, 96.2%).

[Step 2] methyl 4-(((4-(oxetan-3-yl)-N-phenylpiperazine)-1-sulfonamido)methyl)benzoate

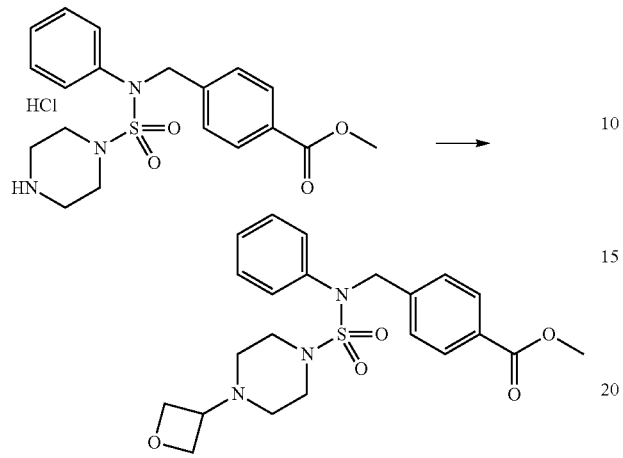

A mixture of methyl 4-((N-phenylpiperazine-1-sulfonamido)methyl)benzoate hydrochloride (2.560 g, 6.010 mmol), oxetan-3-one (0.704 mL, 12.021 mmol) and N,N-diisopropylethylamine (1.570 mL, 9.016 mmol) in dichloromethane (50 mL) was stirred at the room temperature for 30 min, and treated with sodium triacetoxyborohydride (2.548 g, 12.021 mmol). The reaction mixture was stirred at the same temperature for additional 6 hr. Then, saturated aqueous sodium bicarbonate solution was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 40 g cartridge; methanol/dichloromethane=0% to 10%) to give methyl 4-4-(4-(oxetan-3-yl)-N-phenylpiperazine)-1-sulfonamido)methyl)benzoate as white solid (2.450 g, 91.5%).

[Step 3] N-(4-(hydrazinecarbonyl)benzyl)-4-(oxetan-3-yl)-N-phenylpiperazine-1-sulfonamide

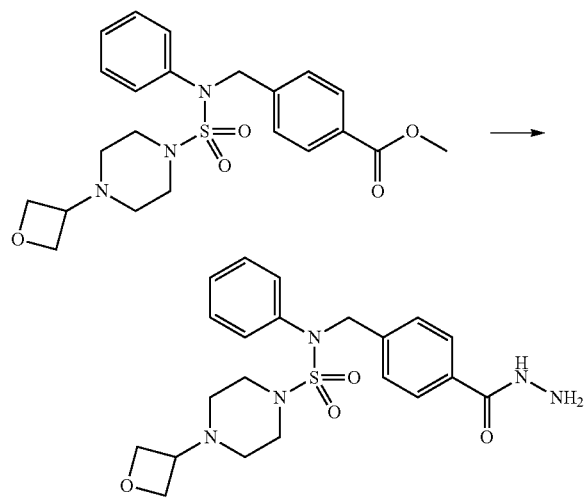

A mixture of methyl 4-(((4-(oxetan-3-yl)-N-phenylpiperazine)-1-sulfonamido)methyl)benzoate (1.850 g, 4.152 mmol) and potassium carbonate (11.477 g, 83.047 mmol) in water (5 mL)/methanol (50 mL) was treated at the room temperature with hydrazine monohydrate (6.054 mL, 124.571 mmol), and stirred at the same temperature for 3 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was diluted with ethyl acetate (50 mL), and stirred. The resulting precipitates were collected by filtration, washed by ethyl acetate, and dried to give N-(4-(hydrazinecarbonyl)benzyl)-4-(oxetan-3-yl)-N-phenylpiperazine-1-sulfonamide as white solid (1.120 g, 60.5%).

[Step 4] Compound 11575

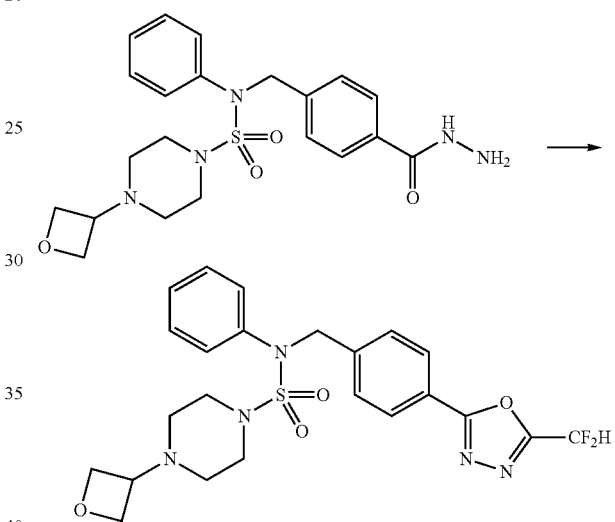

A stirred solution of N-(4-(hydrazinecarbonyl)benzyl)-4-(oxetan-3-yl)-N-phenylpiperazine-1-sulfonamide (0.500 g, 1.122 mmol) in tetrahydrofuran (15 mL), prepared at the ambient temperature, was mixed at reflux with 2,2-difluoroacetic anhydride (0.419 mL, 3.367 mmol) and N,N-diisopropylethylamine (0.586 mL, 3.367 mmol). The reaction mixture was heated at reflux for the additional 1 hr, and cooled down to the room temperature to terminate the reaction. Then, saturated aqueous sodium bicarbonate solution was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (Sift, 40 g cartridge; ethyl acetate/hexane=70% to 100%) to give the crude product, which was dissolved in ethyl acetate (5 mL) and hexane (30 mL), and stirred. The resulting precipitates were collected by filtration, washed by hexane, and dried to give N-(4-(5-(difluoromethyl)-1,3,4-oxadiazol-2-yl)benzyl)-4-(oxetan-3-yl)-N-phenylpiperazine-1-sulfonamide as white solid (0.397 g, 70.0%).

$^1$H NMR (400 MHz, DMSO-d$_6$) δ 7.97 (d, 2H, J=8.0 Hz), 7.66 (s, 0.25H), 7.52 7.50 (m, 2.5H), 7.45-7.36 (m, 2.25H), 7.34 (t, 2H, J=7.6 Hz), 7.24 (m, 1H), 5.03 (s, 2H), 4.52 (t, 2H, J=6.5 Hz), 4.40 (t, 2H, J=6.1 Hz), 3.41 (m, 1H), 3.20 (s, 4H), 2.26 (s, 4H); LRMS (ES) m/z 506.3 (M$^+$+1).

Example 41: Compound 11640, (3S,5R)—N-(4-(5-(difluoromethyl)-1,3,4-oxadiazol-2-yl)benzyl)-4-ethyl-3,5-dimethyl-N-phenylpiperazine-1-sulfonamide

[Step 1] tert-butyl (2S,6R)-4-((1H-imidazol-1-yl)sulfonyl)-2,6-dimethylpiperazine-1-carboxylate

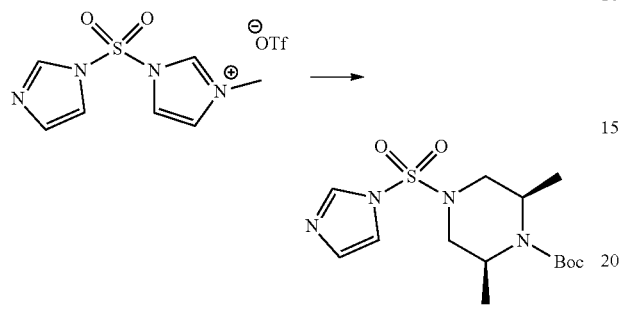

A solution of 1-((1H-imidazol-1-yl)sulfonyl)-3-methyl-1H-imidazol-3-ium trifluoromethanesulfonate (4.000 g, 11.041 mmol) and tert-butyl (2S,6R)-2,6-dimethylpiperazine-1-carboxylate (2.603 g, 12.145 mmol) in acetonitrile (100 mL) was stirred at the room temperature for 16 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 80 g cartridge; ethyl acetate/hexane=0% to 40%) to give tert-butyl (2S,6R)-4-((1H-imidazol-1-yl)sulfonyl)-2,6-dimethylpiperazine-1-carboxylate as yellow solid (2.800 g, 73.6%).

[Step 2] 1-4-(3S,5R)-4-(tert-butoxycarbonyl)-3,5-dimethylpiperazin-1-yl)sulfonyl)-3-methyl-1H-imidazol-3-ium trifluoromethanesulfonate

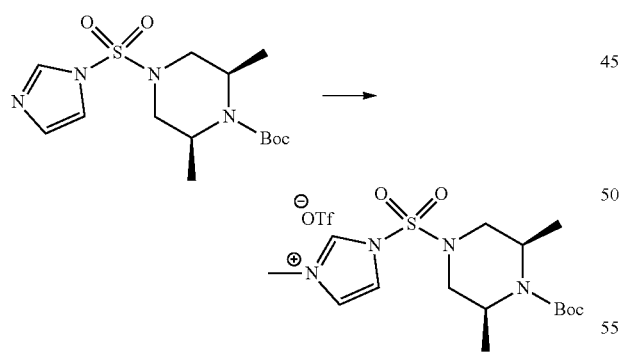

A solution of tert-butyl (2S,6R)-4-((1H-imidazol-1-yl)sulfonyl)-2,6-dimethylpiperazine-1-carboxylate (2.800 g, 8.129 mmol) and methyl trifluoromethanesulfonate (0.892 mL, 8.129 mmol) in dichloromethane (80 mL) was stirred at 0° C. for 3 hr, and concentrated under the reduced pressure to remove the solvent. The title compound was used without further purification (1-(((3S,5R)-4-(tert-butoxycarbonyl)-3,5-dimethylpiperazin-1-yl)sulfonyl)-3-methyl-1H-imidazol-3-ium trifluoromethanesulfonate, 4.000 g, 96.8%, white solid).

[Step 3] tert-butyl (2S,6R)-2,6-dimethyl-4-(N-phenylsulfamoyl)piperazine-1-carboxylate

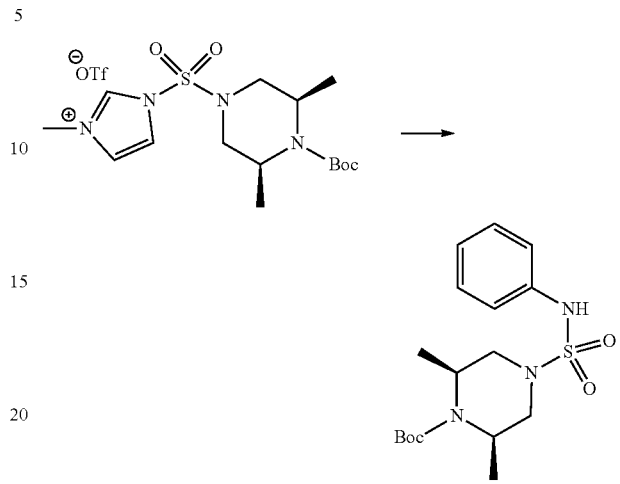

A mixture of 1-(((3S,5R)-4-(tert-butoxycarbonyl)-3,5-dimethylpiperazin-1-yl)sulfonyl)-3-methyl-1H-imidazol-3-ium trifluoromethanesulfonate (4.000 g, 7.866 mmol) and aniline (0.790 mL, 8.652 mmol) in acetonitrile (100 mL), prepared at the ambient temperature, was heated at reflux for 16 hr, and cooled down to the ambient temperature. Then, water was added to the reaction mixture, followed by extraction with ethyl acetate. The organic layer was washed with aqueous saturated ammonium chloride solution, dried with anhydrous MgSO$_4$, filtered, and concentrated in vacuo. The residue was chromatographed (SiO$_2$, 40 g cartridge; ethyl acetate/hexane=0% to 30%) to give tert-butyl (2S,6R)-2,6-dimethyl-4-(N-phenylsulfamoyl)piperazine-1-carboxylate as white solid (1.800 g, 61.9%).

[Step 4] tert-butyl (2S,6R)-4-(N-(4-(methoxycarbonyl)benzyl)-N-phenylsulfamoyl)-2,6-dimethylpiperazine-1-carboxylate

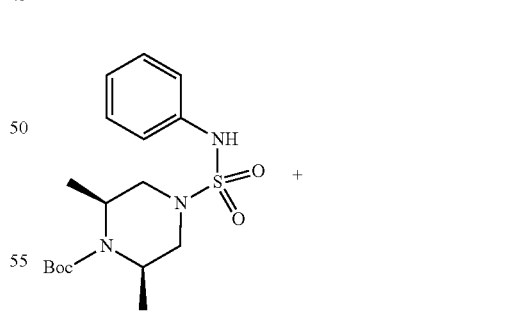
+
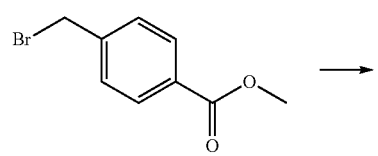

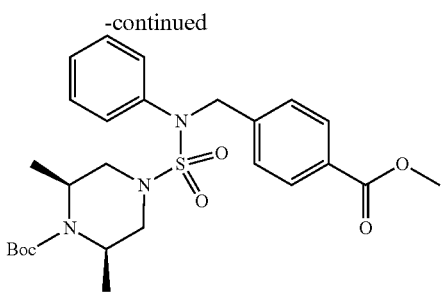

A solution of tert-butyl (2S,6R)-2,6-dimethyl-4-(N-phenylsulfamoyl)piperazine-1-carboxylate (1.700 g, 4.601 mmol) and potassium carbonate (0.954 g, 6.902 mmol) in N,N-dimethylformide (5 mL) was stirred at the room temperature for 30 min, and mixed with methyl 4-(bromomethyl)benzoate (1.159 g, 5.061 mmol) and potassium iodide (0.382 g, 2.301 mmol). The reaction mixture was stirred at the same temperature for additional 12 hr. Then, water was added to the reaction mixture, followed by extraction with ethyl acetate. The organic layer was washed with aqueous saturated ammonium chloride solution, dried with anhydrous MgSO₄, filtered, and concentrated in vacuo. The residue was chromatographed (SiO₂, 24 g cartridge; ethyl acetate/hexane=0% to 40%) to give tert-butyl (2S,6R)-4-(N-(4-(methoxycarbonyl)benzyl)-N-phenylsulfamoyl)-2,6-dimethylpiperazine-1-carboxylate as white solid (2.100 g, 88.2%).

[Step 5] methyl 4-((((3S,5R)-3,5-dimethyl-N-phenylpiperazine)-1-sulfonamido)methyl)benzoate Hydrochloride

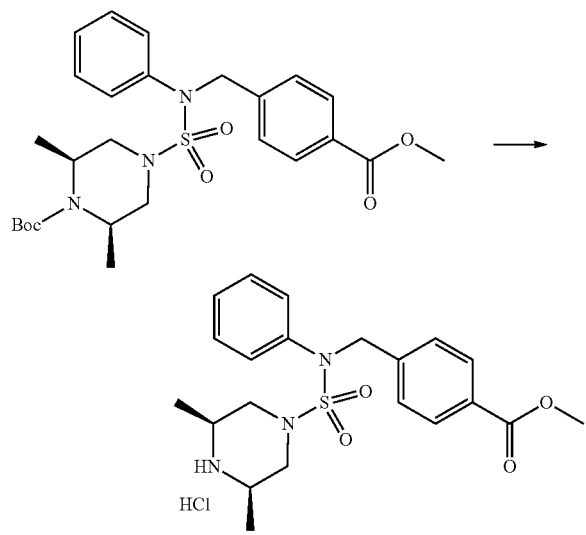

A solution of tert-butyl (2S,6R)-4-(N-(4-(methoxycarbonyl)benzyl)-N-phenylsulfamoyl)-2,6-dimethylpiperazine-1-carboxylate (1.500 g, 2.898 mmol) and hydrogen chloride (4.00 M solution in 1,4-dioxane, 1.449 mL, 5.796 mmol) in dichloromethane (50 mL) was stirred at the room temperature for 5 hr, and concentrated under the reduced pressure to remove the solvent. The crude product was used without further purification (methyl 4-((((3S,5R)-3,5-dimethyl-N-phenylpiperazine)-1-sulfonamido)methyl)benzoate hydrochloride, 1.300 g, 98.8%, white solid).

[Step 6] methyl 4-((((3S,5R)-4-ethyl-3,5-dimethyl-N-phenylpiperazine)-1-sulfonamido)methyl)benzoate

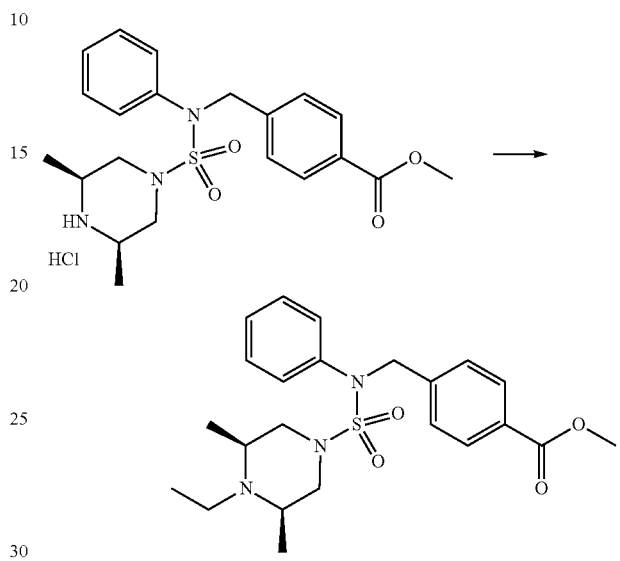

A solution of methyl 4-((((3S,5R)-3,5-dimethyl-N-phenylpiperazine)-1-sulfonamido)methyl)benzoate hydrochloride (0.200 g, 0.441 mmol), acetaldehyde (0.039 g, 0.881 mmol) and acetic acid (0.028 mL, 0.485 mmol) in dichloromethane (12 mL) was stirred at the room temperature for 30 min, and mixed with sodium triacetoxyborohydride (0.187 g, 0.881 mmol). The reaction mixture was stirred at the same temperature for additional 12 hr. Then, water wad added to the reaction mixture, followed by extraction with dichloromethane. The organic layer was washed with aqueous saturated sodium bicarbonate solution, dried with anhydrous MgSO₄, filtered, and concentrated in vacuo. The residue was chromatographed (SiO₂, 4 g cartridge; methanol/dichloromethane=0% to 5%) to give methyl 4-((((3S,5R)-4-ethyl-3,5-dimethyl-N-phenylpiperazine)-1-sulfonamido)methyl)benzoate as yellow oil (0.130 g, 66.2%).

[Step 7] (3S,5R)-4-ethyl-N-(4-(hydrazinecarbonyl)benzyl)-3,5-dimethyl-N-phenylpiperazine-1-sulfonamide

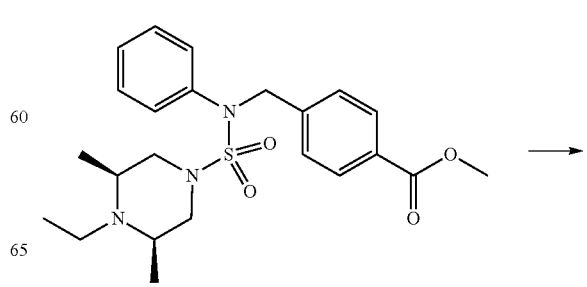

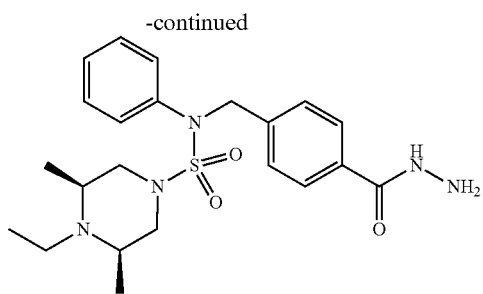

A solution of methyl 4-((((3S,5R)-4-ethyl-3,5-dimethyl-N-phenylpiperazine)-1-sulfonamido)methyl)benzoate (0.130 g, 0.292 mmol) and hydrazine monohydrate (0.142 mL, 2.918 mmol) in ethanol (10 mL) was stirred at 90° C. for 12 hr, and cooled down to the room temperature to terminate the reaction. The reaction mixture was concentrated under the reduced pressure to remove the solvent. The residue was diluted with water (10 mL) and sodium bicarbonate (5 mL) and stirred. The resulting precipitates were collected by filtration and dried to give (3S,5R)-4-ethyl-N-(4-(hydrazinecarbonyl)benzyl)-3,5-dimethyl-N-phenylpiperazine-1-sulfonamide as white solid (0.100 g, 76.9%).

[Step 8] Compound 11640

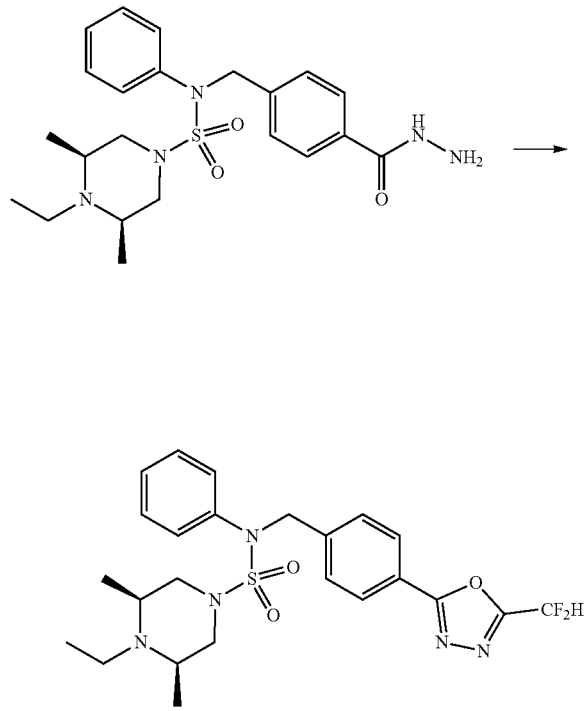

A solution of (3S,5R)-4-ethyl-N-(4-(hydrazinecarbonyl) benzyl)-3,5-dimethyl-N-phenylpiperazine-1-sulfonamide (0.050 g, 0.112 mmol), triethylamine (0.078 mL, 0.561 mmol) and 2,2-difluoroacetic anhydride (0.042 mL, 0.337 mmol) in tetrahydrofuran (5 mL) was stirred at 70° C. for 5 hr, and cooled down to the room temperature to terminate the reaction. Then, water was added to the reaction mixture, followed by extraction with dichloromethane. The organic layer was washed with aqueous saturated ammonium chloride solution, dried with anhydrous MgSO$_4$, filtered, and concentrated in vacuo. The residue was chromatographed (SiO$_2$, 4 g cartridge; ethyl acetate/hexane=0% to 80%) to give (3S,5R)—N-(4-(5-(difluoromethyl)-1,3,4-oxadiazol-2-yl)benzyl)-4-ethyl-3,5-dimethyl-N-phenylpiperazine-1-sulfonamide as white solid (0.035 g, 61.7%).

$^1$H NMR (400 MHz, CDCl$_3$) δ 8.02-8.01 (m, 2H), 7.44-7.42 (m, 2H), 7.34-7.24 (m, 5H), 7.04 (s, 0.3H), 6.91 (s, 0.5H), 6.78 (s, 0.3H), 4.90 (s, 2H), 3.55-3.53 (m, 2H), 3.04-3.01 (m, 2H), 2.97-2.49 (m, 4H), 1.16-1.00 (m, 6H), 0.98-0.82 (m, 3H); LRMS (ES) m/z 506.4 (M$^+$+1).

Example 42: Compound 11641, (3S,5R)-4-acetyl-N-(4-(5-(difluoromethyl)-1,3,4-oxadiazol-2-yl)benzyl)-3,5-dimethyl-N-phenylpiperazine-1-sulfonamide

[Step 1] methyl 4-((((3S,5R)-4-acetyl-3,5-dimethyl-N-phenylpiperazine)-1-sulfonamido)methyl)benzoate

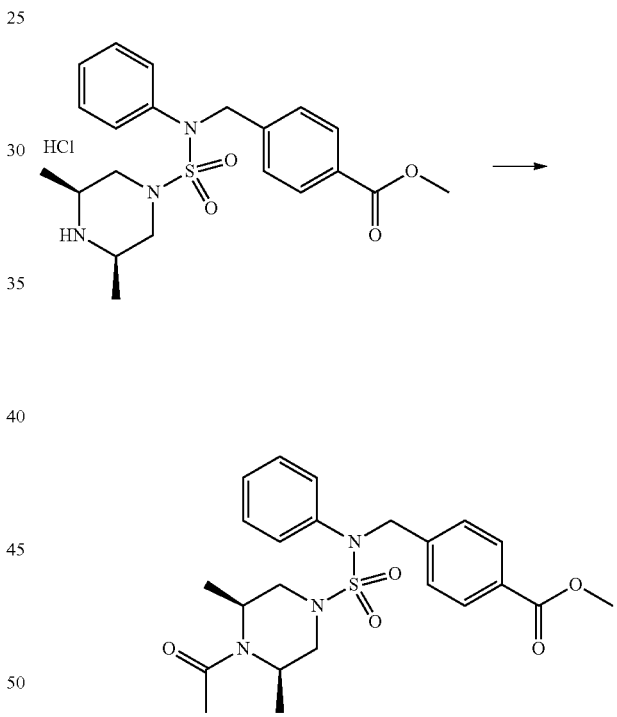

A solution of methyl 4-((((3S,5R)-3,5-dimethyl-N-phenylpiperazine)-1-sulfonamido)methyl)benzoate hydrochloride (0.200 g, 0.441 mmol), triethylamine (0.092 mL, 0.661 mmol) and acetic anhydride (0.083 mL, 0.881 mmol) in dichloromethane (10 mL) was stirred at the room temperature for 12 hr. Then, water was added to the reaction mixture, followed by extraction with dichloromethane. The organic layer was washed with aqueous saturated ammonium chloride solution, dried with anhydrous MgSO$_4$, filtered, and concentrated in vacuo. The residue was chromatographed (Sift, 4 g cartridge; methanol/dichloromethane=0% to 5%) to give methyl 4-((((3S,5R)-4-acetyl-3,5-dimethyl-N-phenylpiperazine)-1-sulfonamido)methyl)benzoate as yellow oil (0.140 g, 69.1%).

[Step 2] (3S,5R)-4-acetyl-N-(4-(hydrazinecarbonyl)benzyl)-3,5-dimethyl-N-phenylpiperazine-1-sulfonamide

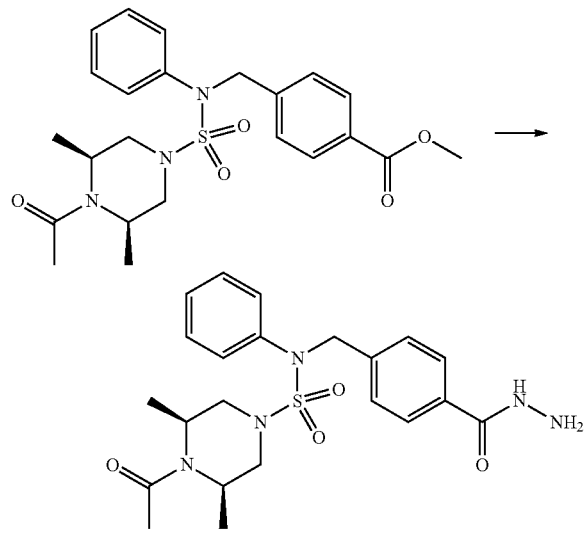

A solution of methyl 4-((((3S,5R)-4-acetyl-3,5-dimethyl-N-phenylpiperazine)-1-sulfonamido)methyl)benzoate (0.140 g, 0.305 mmol) and hydrazine monohydrate (0.148 mL, 3.046 mmol) in ethanol (10 mL) was stirred at 90° C. for 12 hr, and cooled down to the room temperature to terminate the reaction. The reaction mixture was and concentrated under the reduced pressure to remove the solvent. The residue was diluted with water (10 mL) and sodium bicarbonate (5 mL), and stirred. The resulting precipitates were collected by filtration, washed by water, and dried to give (3S,5R)-4-acetyl-N-(4-(hydrazinecarbonyl)benzyl)-3,5-dimethyl-N-phenylpiperazine-1-sulfonamide as white solid (0.098 g, 70.0%).

[Step 3] Compound 11641

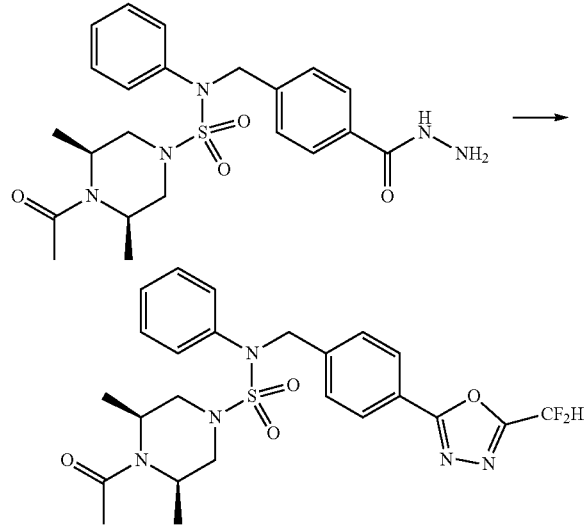

A solution of (3S,5R)-4-acetyl-N-(4-(hydrazinecarbonyl)benzyl)-3,5-dimethyl-N-phenylpiperazine-1-sulfonamide (0.050 g, 0.109 mmol), triethylamine (0.076 mL, 0.544 mmol) and 2,2-difluoroacetic anhydride (0.041 mL, 0.326 mmol) in tetrahydrofuran (10 mL) was stirred at 70° C. for 5 hr, and cooled down to the room temperature to terminate the reaction. Then, water was added to the reaction mixture, followed by extraction with dichloromethane. The organic layer was washed with aqueous saturated ammonium chloride solution, dried with anhydrous MgSO$_4$, filtered, and concentrated in vacuo. The residue was chromatographed (SiO$_2$, 4 g cartridge; ethyl acetate/hexane=0% to 80%) to give (3S,5R)-4-acetyl-N-(4-(5-(difluoromethyl)-1,3,4-oxadiazol-2-yl)benzyl)-3,5-dimethyl-N-phenylpiperazine-1-sulfonamide as white solid (0.039 g, 69.0%).

$^1$H NMR (400 MHz, CDCl$_3$) δ 8.05-8.03 (m, 2H), 7.45-7.43 (m, 2H), 7.36-7.16 (m, 5H), 7.04 (s, 0.2H), 6.91 (s, 0.4H), 6.79 (s, 0.2H), 4.94 (s, 2H), 3.97 (brs, 2H), 3.53-3.45 (m, 2H), 2.70-2.66 (m, 2H), 2.06 (s, 3H), 1.31-1.22 (m, 6H); LRMS (ES) m/z 520.3 (M$^+$+1).

Example 43: Compound 11642, (3S,5R)—N-(4-(5-(difluoromethyl)-1,3,4-oxadiazol-2-yl)benzyl)-3,5-dimethyl-N-phenyl-4-propylpiperazine-1-sulfonamide

[Step 1] methyl 4-((((3S,5R)-3,5-dimethyl-N-phenyl-4-propylpiperazine)-1-sulfonamido)methyl)benzoate

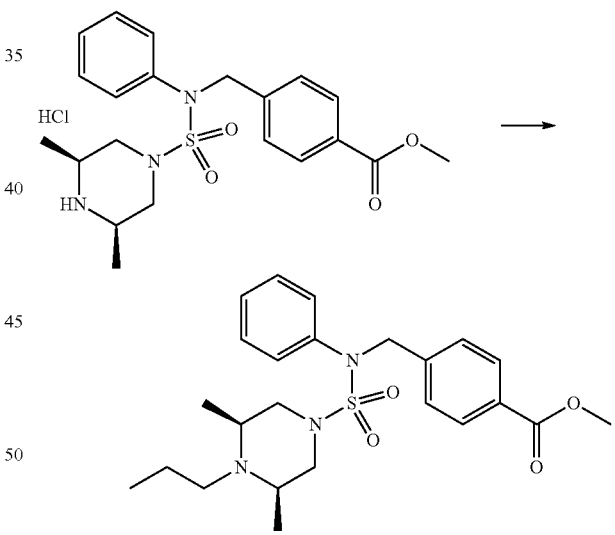

A solution of methyl 4-((((3S,5R)-3,5-dimethyl-N-phenylpiperazine)-1-sulfonamido)methyl)benzoate hydrochloride (0.200 g, 0.441 mmol), propionaldehyde (0.051 g, 0.881 mmol) and acetic acid (0.028 mL, 0.485 mmol) in dichloromethane (10 mL) was stirred at the room temperature for 30 min, and mixed with sodium triacetoxyborohydride (0.187 g, 0.881 mmol). The reaction mixture was stirred at the same temperature for additional 12 hr. Then, water was added to the reaction mixture, followed by extraction with dichloromethane. The organic layer was washed with aqueous saturated sodium bicarbonate solution, dried with anhydrous MgSO$_4$, filtered, and concentrated in vacuo. The residue was chromatographed (SiO$_2$, 4 g cartridge; methanol/dichloromethane=0% to 5%) to give methyl 4-((((3S,5R)-3,5-dimethyl-N-phenyl-4-propylpiperazine)-1-sulfonamido)methyl)benzoate as yellow oil (0.150 g, 74.1%).

[Step 2] (3S,5R)—N-(4-(hydrazinecarbonyl)benzyl)-3,5-dimethyl-N-phenyl-4-propylpiperazine-1-sulfonamide

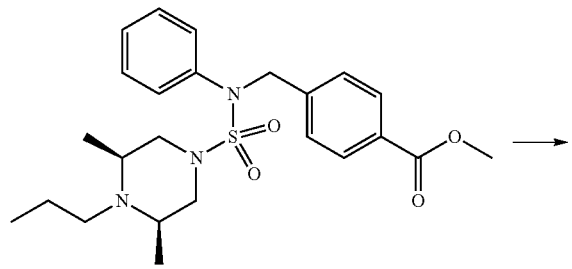

A solution of methyl 4-((((3S,5R)-3,5-dimethyl-N-phenyl-4-propylpiperazine)-1-sulfonamido)methyl)benzoate (0.150 g, 0.326 mmol) and hydrazine monohydrate (0.016 mL, 0.573 mmol) was stirred at 90° C. for 12 hr, and cooled down to the room temperature to terminate the reaction. The reaction mixture was concentrated under the reduced pressure to remove the solvent. The residue was diluted with water (10 mL) and sodium bicarbonate (5 mL) and stirred. The resulting precipitates were collected by filtration, washed by hexane, and dried to give (3S,5R)—N-(4-(hydrazinecarbonyl)benzyl)-3,5-dimethyl-N-phenyl-4-propylpiperazine-1-sulfonamide as white solid (0.110 g, 73.3%).

[Step 3] Compound 11642

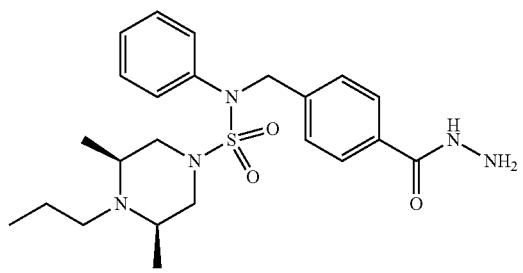

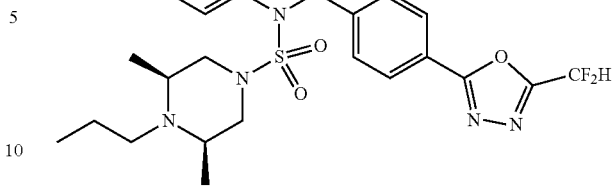

A solution of (3S,5R)—N-(4-(hydrazinecarbonyl)benzyl)-3,5-dimethyl-N-phenyl-4-propylpiperazine-1-sulfonamide (0.050 g, 0.109 mmol), triethylamine (0.076 mL, 0.544 mmol) and 2,2-difluoroacetic anhydride (0.041 mL, 0.326 mmol) in tetrahydrofuran (10 mL) was stirred at 70° C. for 5 hr, and cooled down to the room temperature to terminate the reaction. Then, water was added to the reaction mixture, followed by extraction with dichloromethane. The organic layer was washed with aqueous saturated ammonium chloride solution, dried with anhydrous MgSO₄, filtered, and concentrated in vacuo. The residue was chromatographed (Sift, 4 g cartridge; methanol/dichloromethane=0% to 5%) to give (3S,5R)—N-(4-(5-(difluoromethyl)-1,3,4-oxadiazol-2-yl)benzyl)-3,5-dimethyl-N-phenyl-4-propylpiperazine-1-sulfonamide as white solid (0.034 g, 60.1%).

$^1$H NMR (400 MHz, CDCl$_3$) δ 8.04-8.01 (m, 2H), 7.43-7.41 (m, 2H), 7.37-7.27 (m, 5H), 7.04 (s, 0.3H), 6.91 (s, 0.5H), 6.78 (s, 0.3H), 4.88 (s, 2H), 3.65 (brs, 4H), 3.29-3.21 (m, 4H), 1.64-1.60 (m, 2H), 1.45-1.40 (m, 6H), 1.29-1.26 (m, 3H); LRMS (ES) m/z 520.3 (M$^+$+1).

Example 44: Compound 11643, (3S,5R)—N-(4-(5-(difluoromethyl)-1,3,4-oxadiazol-2-yl)benzyl)-3,4,5-trimethyl-N-phenylpiperazine-1-sulfonamide

[Step 1] methyl 4-((((3S,5R)-3,4,5-trimethyl-N-phenylpiperazine)-1-sulfonamido)methyl)benzoate

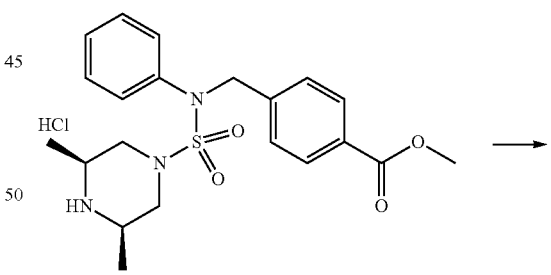

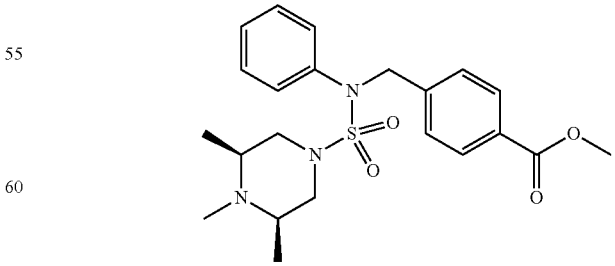

A mixture of methyl 4-((((3S,5R)-3,5-dimethyl-N-phenylpiperazine)-1-sulfonamido)methyl)benzoate hydrochloride (0.200 g, 0.441 mmol), N,N-diisopropylethylamine

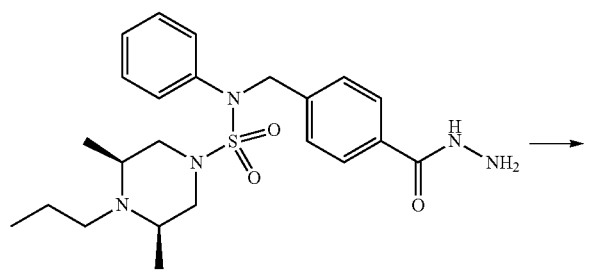

(0.077 mL, 0.441 mmol), paraformaldehyde (0.066 g, 2.203 mmol) and sodium triacetoxyborohydride (0.187 g, 0.881 mmol) in dichloromethane (10 mL), prepared at the ambient temperature, was heated at reflux for 12 hr, and cooled down to the ambient temperature to terminate the reaction. Then, water was added to the reaction mixture, followed by extraction with dichloromethane. The organic layer was washed with aqueous saturated sodium bicarbonate solution, dried with anhydrous MgSO$_4$, filtered, and concentrated in vacuo. The residue was chromatographed (Sift, 4 g cartridge; methanol/dichloromethane=0% to 5%) to give methyl 4-((((3S,5R)-3,4,5-trimethyl-N-phenylpiperazine)-1-sulfonamido)methyl)benzoate as white solid (0.160 g, 84.2%).

[Step 2] (3S,5R)—N-(4-(hydrazinecarbonyl)benzyl)-3,4,5-trimethyl-N-phenylpiperazine-1-sulfonamide

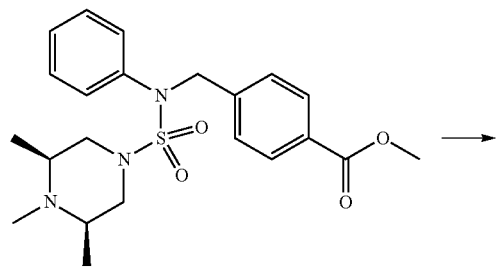

A solution of methyl 4-((((3S,5R)-3,4,5-trimethyl-N-phenylpiperazine)-1-sulfonamido)methyl)benzoate (0.160 g, 0.371 mmol) and hydrazine monohydrate (0.180 mL, 3.708 mmol) in ethanol (10 mL) was stirred at 90° C. for 12 hr, and cooled down to the room temperature to terminate the reaction. The reaction mixture was concentrated under the reduced pressure to remove the solvent. The residue was diluted with water (10 mL) and sodium bicarbonate (5 mL), and stirred. The resulting precipitates were collected by filtration, washed by hexane, and dried to give (3S,5R)—N-(4-(hydrazinecarbonyl)benzyl)-3,4,5-trimethyl-N-phenylpiperazine-1-sulfonamide as white solid (0.130 g, 81.2%).

[Step 3] Compound 11643

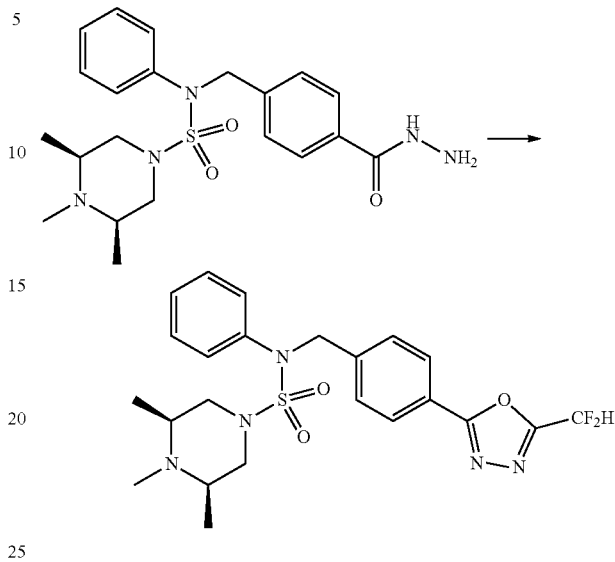

A solution of (3S,5R)—N-(4-(hydrazinecarbonyl)benzyl)-3,4,5-trimethyl-N-phenylpiperazine-1-sulfonamide (0.050 g, 0.116 mmol), triethylamine (0.081 mL, 0.579 mmol) and 2,2-difluoroacetic anhydride (0.043 mL, 0.348 mmol) in tetrahydrofuran (5 mL) was stirred at 70° C. for 5 hr, and cooled down to the room temperature to terminate the reaction. Then, water was added to the reaction mixture, followed by extraction with dichloromethane. The organic layer was washed with aqueous saturated ammonium chloride solution, dried with anhydrous MgSO$_4$, filtered, and concentrated in vacuo. The residue was chromatographed (SiO$_2$, 4 g cartridge; ethyl acetate/hexane=0% to 80%) to give (3S,5R)—N-(4-(5-(difluoromethyl)-1,3,4-oxadiazol-2-yl)benzyl)-3,4,5-trimethyl-N-phenylpiperazine-1-sulfonamide as white solid (0.036 g, 63.2%).

$^1$H NMR (400 MHz, CDCl$_3$) δ 8.04-8.01 (m, 2H), 7.44-7.42 (m, 2H), 7.35-7.25 (m, 5H), 7.04 (s, 0.3H), 6.91 (s, 0.5H), 6.78 (s, 0.3H), 4.90 (s, 2H), 3.56-3.53 (m, 2H), 2.50 (brs, 2H), 2.41-2.37 (m, 5H), 1.29-1.26 (brs, 6H); LRMS (ES) m/z 492.1 (M$^+$+1).

Example 45: Compound 11644, (3S,5R)-4-(2,2-difluoroacetyl)-N-(4-(5-(difluoromethyl)-1,3,4-oxadiazol-2-yl)benzyl)-3,5-dimethyl-N-phenylpiperazine-1-sulfonamide

[Step 1] (3S,5R)—N-(4-(hydrazinecarbonyl)benzyl)-3,5-dimethyl-N-phenylpiperazine-1-sulfonamide

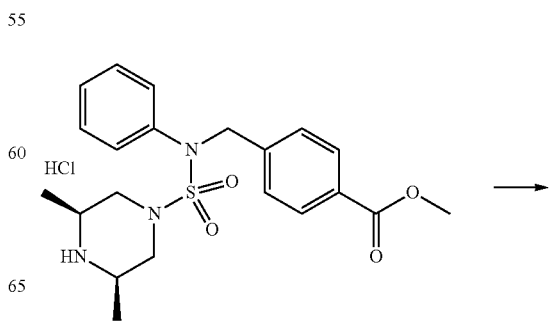

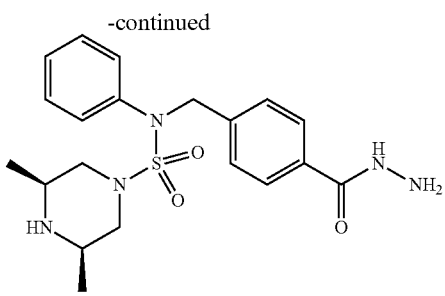

A solution of methyl 4-((((3S,5R)-3,5-dimethyl-N-phenylpiperazine)-1-sulfonamido)methyl)benzoate hydrochloride (0.150 g, 0.359 mmol) and hydrazine monohydrate (0.175 mL, 3.593 mmol) in ethanol (10 mL) was stirred at 90° C. for 12 hr, and cooled down to the room temperature to terminate the reaction. The reaction mixture was concentrated under the reduced pressure to remove the solvent. The residue was diluted with water (10 mL) and sodium bicarbonate (5 mL) and stirred. The resulting precipitates were collected by filtration and dried to give (3S,5R)—N-(4-(hydrazinecarbonyl)benzyl)-3,5-dimethyl-N-phenylpiperazine-1-sulfonamide as white solid (0.110 g, 73.3%).

[Step 2] Compound 11644

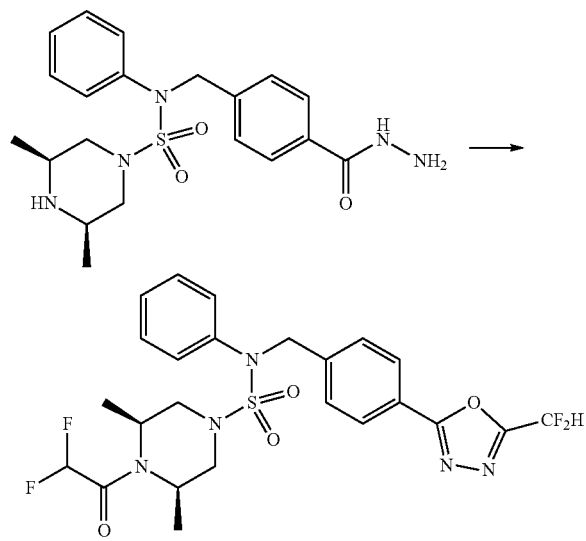

A solution of (3S,5R)—N-(4-(hydrazinecarbonyl)benzyl)-3,5-dimethyl-N-phenylpiperazine-1-sulfonamide (0.050 g, 0.120 mmol), triethylamine (0.083 mL, 0.599 mmol) and 2,2-difluoroacetic anhydride (0.045 mL, 0.359 mmol) in tetrahydrofuran (10 mL) was stirred at 70° C. for 5 hr, and cooled down to the room temperature to terminate the reaction. Then, water was added to the reaction mixture, followed by extraction with dichloromethane. The organic layer was washed with aqueous saturated ammonium chloride solution, dried with anhydrous MgSO$_4$, filtered, and concentrated in vacuo. The residue was chromatographed (SiO$_2$, 4 g cartridge; ethyl acetate/hexane=0% to 50%) to give (3S,5R)-4-(2,2-difluoroacetyl)-N-(4-(5-(difluoromethyl)-1,3,4-oxadiazol-2-yl)benzyl)-3,5-dimethyl-N-phenylpiperazine-1-sulfonamide as white solid (0.031 g, 46.6%).

$^1$H NMR (400 MHz, CDCl$_3$) δ 8.05-8.01 (m, 2H), 7.44-7.42 (m, 2H), 7.36-7.05 (m, 5H), 6.92 (s, 0.3H), 6.92 (s, 0.5H), 6.79 (s, 0.3H), 6.23 (s, 0.3H), 6.09 (s, 0.5H), 5.96 (s, 0.3H), 4.93 (s, 2H), 4.55 (brs, 1H), 4.24-4.22 (m, 1H), 3.56 (d, 2H, J=12.4 Hz), 2.76-2.72 (m, 2H), 1.42-1.37 (m, 6H); LRMS (ES) m/z 555.9 (M$^+$+1).

Example 46: Compound 11651, N-(3-chloro-4-fluorophenyl)-N-(4-(5-(difluoromethyl)-1,3,4-oxadiazol-2-yl)benzyl)-4-iso propylpiperazine-1-sulfonamide

[Step 1] tert-butyl 4-(N-(3-chloro-4-fluorophenyl)sulfamoyl)piperazine-1-carboxylate

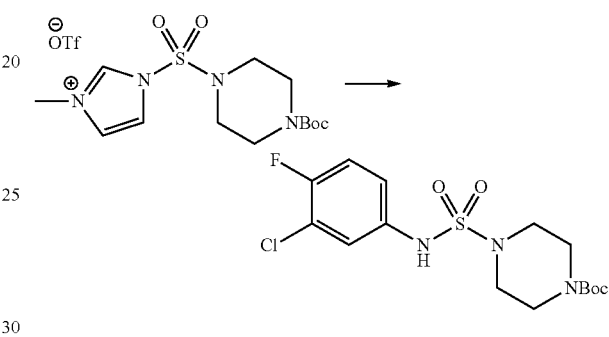

1-((4-(tert-butoxycarbonyl)piperazin-1-yl)sulfonyl)-3-methyl-1H-imidazol-3-ium trifluoromethanesulfonate (1.500 g, 3.122 mmol) and 3-chloro-4-fluoroaniline (0.682 g, 4.683 mmol) were mixed at the room temperature in acetonitrile (100 mL), and then the mixture was stirred at 80° C. for 18 hr. The reaction mixture was cooled down to the room temperature to terminate the reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (Sift, 12 g cartridge; ethyl acetate/hexane=0% to 30%) to give tert-butyl 4-(N-(3-chloro-4-fluorophenyl)sulfamoyl)piperazine-1-carboxylate as purple solid (0.710 g, 57.7%).

[Step 2] tert-butyl 4-(N-(3-chloro-4-fluorophenyl)-N-(4-(methoxycarbonyl)benzyl)sulfamoyl)piperazine-1-carboxylate

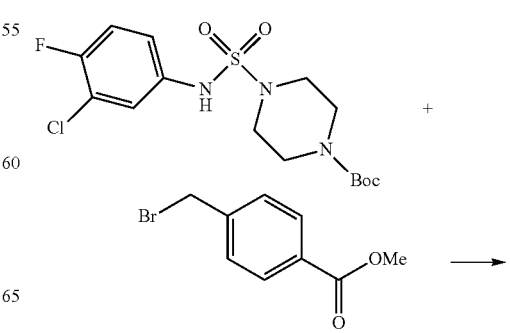

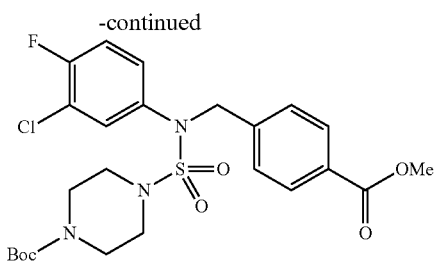

A solution of tert-butyl 4-(N-(3-chloro-4-fluorophenyl)sulfamoyl)piperazine-1-carboxylate (0.710 g, 1.803 mmol) and sodium hydride (60.00%, 0.216 g, 5.408 mmol) in N,N-dimethylformamide (80 mL) was mixed at the room temperature with methyl 4-(bromomethyl)benzoate (0.619 g, 2.704 mmol), and stirred at 50° C. for 18 hr. The reaction mixture was cooled down to the room temperature to terminate the reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 12 g cartridge; ethyl acetate/hexane=0% to 80%) to give tert-butyl 4-(N-(3-chloro-4-fluorophenyl)-N-(4-(methoxycarbonyl)benzyl)sulfamoyl)piperazine-1-carboxylate as white solid (0.616 g, 63.0%).

[Step 3] methyl 4-((N-(3-chloro-4-fluorophenyl)piperazine-1-sulfonamido)methyl)benzoate Hydrochloride

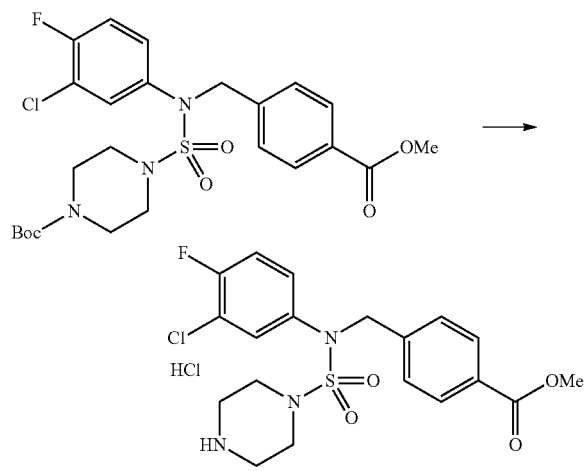

A solution of tert-butyl 4-(N-(3-chloro-4-fluorophenyl)-N-(4-(methoxycarbonyl)benzyl)sulfamoyl)piperazine-1-carboxylate (0.616 g, 1.136 mmol) in dichloromethane (15 mL) was mixed at the room temperature with hydrochloric acid (4.00 M solution in dioxane, 1.136 mL, 4.546 mmol). The reaction mixture was stirred at the same temperature for 18 hr. Then, water was added to the reaction mixture, followed by extraction with ethyl acetate. The organic layer was washed with saturated aqueous sodium chloride solution, dried with anhydrous MgSO$_4$, filtered, and concentrated in vacuo. The precipitates were collected by filtration, washed by dichloromethane, and dried to give methyl 4-((N-(3-chloro-4-fluorophenyl)piperazine-1-sulfonamido)methyl)benzoate hydrochloride as white solid (0.330 g, 60.7%).

[Step 4] methyl 4-(((N-(3-chloro-4-fluorophenyl)-4-isopropylpiperazine)-1-sulfonamido)methyl)benzoate

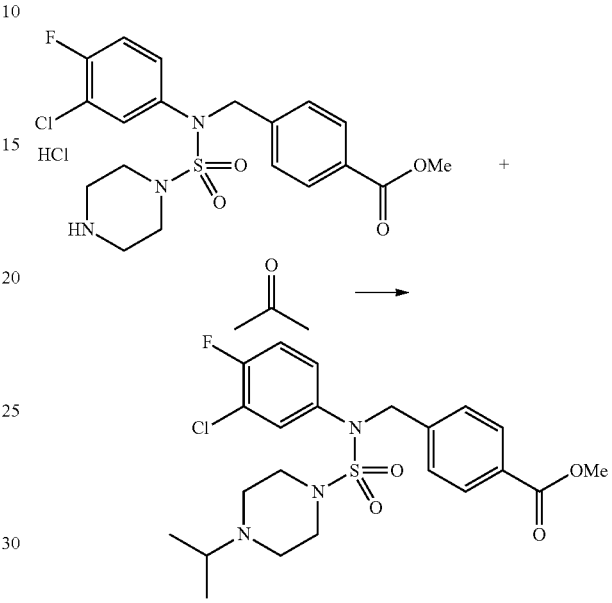

A solution of methyl 4-((N-(3-chloro-4-fluorophenyl)piperazine-1-sulfonamido)methyl)benzoate hydrochloride (0.100 g, 0.209 mmol) and propan-2-one (0.023 mL, 0.314 mmol) in dichloromethane (10 mL) was mixed at the room temperature with sodium triacetoxyborohydride (0.133 g, 0.627 mmol). The reaction mixture was stirred at the same temperature for 18 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 4 g cartridge; methanol/dichloromethane=0% to 15%) to give methyl 4-(((N-(3-chloro-4-fluorophenyl)-4-isopropylpiperazine)-1-sulfonamido)methyl)benzoate as white solid (0.042 g, 41.5%).

[Step 5] N-(3-chloro-4-fluorophenyl)-N-(4-(hydrazinecarbonyl)benzyl)-4-isopropylpiperazine-1-sulfonamide

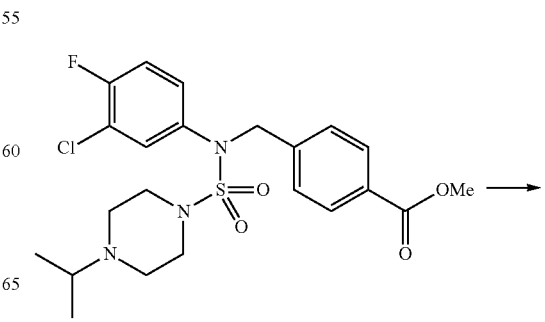

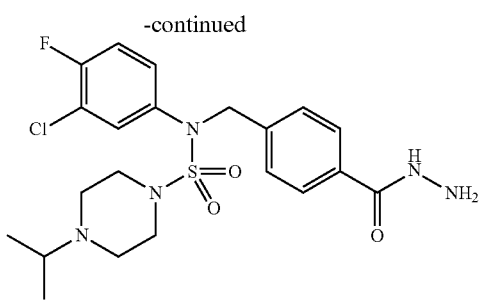

methyl 4-(((N-(3-chloro-4-fluorophenyl)-4-isopropylpiperazine)-1-sulfonamido)methyl)benzoate (0.042 g, 0.087 mmol) and hydrazine monohydrate (0.084 mL, 1.736 mmol) were mixed at the room temperature in ethanol (8 mL)/water (2 mL), and then the mixture was stirred at 80° C. for 18 hr. The reaction mixture was cooled down to the room temperature to terminate the reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The title compound was used without further purification (N-(3-chloro-4-fluorophenyl)-N-(4-(hydrazinecarbonyl)benzyl)-4-isopropylpiperazine-1-sulfonamide, 0.038 g, 90.5%, colorless oil).

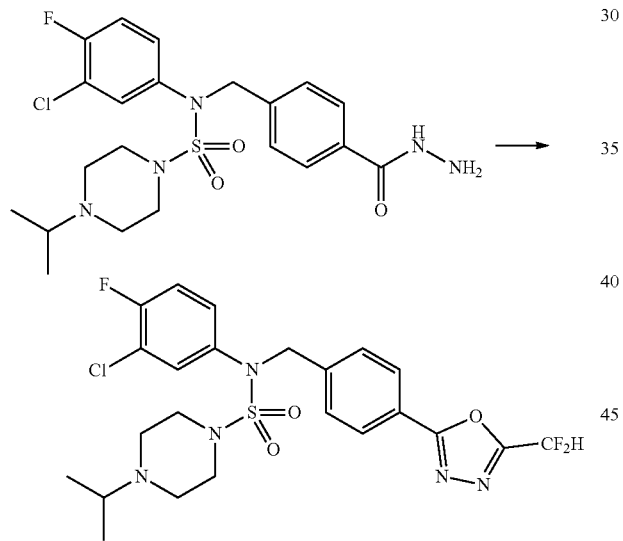

A solution of N-(3-chloro-4-fluorophenyl)-N-(4-(hydrazinecarbonyl)benzyl)-4-isopropylpiperazine-1-sulfonamide (0.042 g, 0.087 mmol) and triethylamine (0.024 mL, 0.174 mmol) in tetrahydrofuran (10 mL) was mixed at the room temperature with 2,2-difluoroacetic anhydride (0.032 mL, 0.260 mmol), and stirred at 80° C. for 2 hr. The reaction mixture was cooled down to the room temperature to terminate the reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$ plate, 20×20×1 mm; methanol/dichloromethane=10%) to give N-(3-chloro-4-fluorophenyl)-N-(4-(5-(difluoromethyl)-1,3,4-oxadiazol-2-yl)benzyl)-4-isopropylpiperazine-1-sulfonamide as white solid (0.009 g, 19.1%).

$^1$H NMR (400 MHz, CDCl$_3$) δ 8.04-8.02 (m, 2H), 7.42 (d, 2H, J=8.4 Hz), 7.25~7.22 (m, 2H), 7.02~6.98 (m, 2H), 4.85 (s, 2H), 3.64 (t, 4H, J=4.7 Hz), 3.17 (t, 4H, J=4.8 Hz); LRMS (ES) m/z 544.0 (M$^+$+1).

Example 47: Compound 11652, N-(3-chloro-4-fluorophenyl)-4-cyclobutyl-N-(4-(5-(difluoromethyl)-1,3,4-oxadiazol-2-yl) benzyl)piperazine-1-sulfonamide

[Step 1] methyl 4-(((N-(3-chloro-4-fluorophenyl)-4-cyclobutylpiperazine)-1-sulfonamido)methyl)benzoate

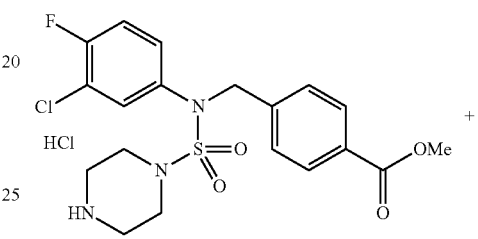

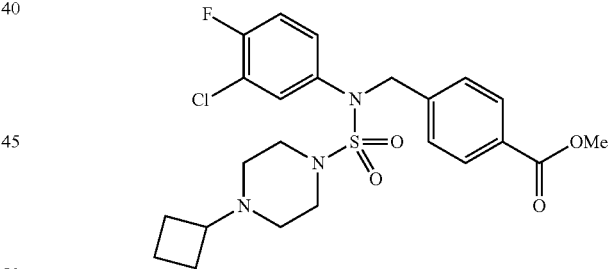

A solution of methyl 4-((N-(3-chloro-4-fluorophenyl)piperazine-1-sulfonamido)methyl)benzoate hydrochloride (0.100 g, 0.209 mmol) and cyclobutanone (0.023 mL, 0.314 mmol) in dichloromethane (10 mL) was mixed at the room temperature with sodium triacetoxyborohydride (0.133 g, 0.627 mmol). The reaction mixture was stirred at the same temperature for 18 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 4 g cartridge; methanol/dichloromethane=0% to 30%) to give methyl 4-(((N-(3-chloro-4-fluorophenyl)-4-cyclobutylpiperazine)-1-sulfonamido)methyl)benzoate as white solid (0.098 g, 94.5%).

111

[Step 2] N-(3-chloro-4-fluorophenyl)-4-cyclobutyl-N-(4-(hydrazinecarbonyl)benzyl)piperazine-1-sulfonamide

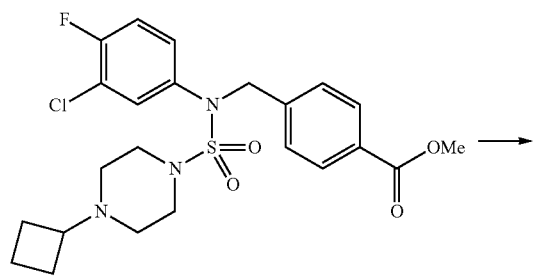

methyl 4-(((N-(3-chloro-4-fluorophenyl)-4-cyclobutylpiperazine)-1-sulfonamido)methyl)benzoate (0.098 g, 0.198 mmol) and hydrazine monohydrate (0.192 mL, 3.952 mmol) were mixed at the room temperature in ethanol (8 mL)/water (2 mL), and then the mixture was stirred at 80° C. for 18 hr. The reaction mixture was cooled down to the room temperature to terminate the reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The title compound was used without further purification (N-(3-chloro-4-fluorophenyl)-4-cyclobutyl-N-(4-(hydrazinecarbonyl)benzyl)piperazine-1-sulfonamide, 0.087 g, 88.8%, colorless oil).

[Step 3] Compound 11652

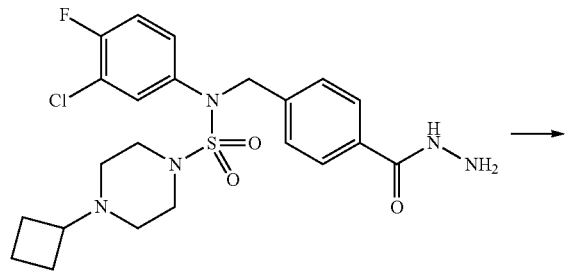

112

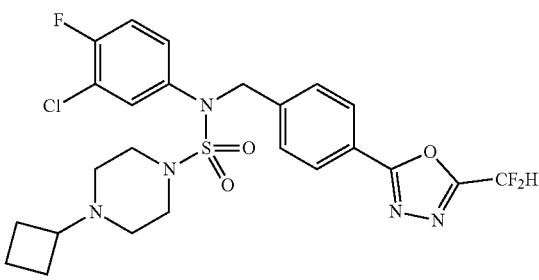

A solution of N-(3-chloro-4-fluorophenyl)-4-cyclobutyl-N-(4-(hydrazinecarbonyl)benzyl)piperazine-1-sulfonamide (0.098 g, 0.198 mmol) and triethylamine (0.055 mL, 0.395 mmol) in tetrahydrofuran (10 mL) was mixed at the room temperature with 2,2-difluoroacetic anhydride (0.074 mL, 0.593 mmol), and stirred at 80° C. for 2 hr. The reaction mixture was cooled down to the room temperature to terminate the reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$ plate, 20×20×1 mm; methanol/dichloromethane=10%) to give N-(3-chloro-4-fluorophenyl)-4-cyclobutyl-N-(4-(5-(difluoromethyl)-1,3,4-oxadiazol-2-yl)benzyl)piperazine-1-sulfonamide as white solid (0.007 g, 6.4%).

$^1$H NMR (400 MHz, CDCl$_3$) δ 8.05~8.00 (m, 2H), 7.40~7.35 (m, 2H), 7.15~7.04 (m, 2H), 7.03 (s, 0.25H), 6.90 (s, 0.5H), 6.77 (s, 0.25H), 4.82 (s, 2H), 4.67~4.60 (m, 4H), 3.60~3.45 (m, 1H), 3.40~3.20 (m, 4H), 2.45~2.23 (m, 4H); LRMS (ES) m/z 556.0 (M$^+$+1).

Example 48: Compound 11653, N-(3-chloro-4-fluorophenyl)-N-(4-(5-(difluoromethyl)-1,3,4-oxadiazol-2-yl)benzyl)-4-(oxetan-3-yl)piperazine-1-sulfonamide

[Step 1] methyl 4-(((N-(3-chloro-4-fluorophenyl)-4-(oxetan-3-yl)piperazine)-1-sulfonamido)methyl)benzoate

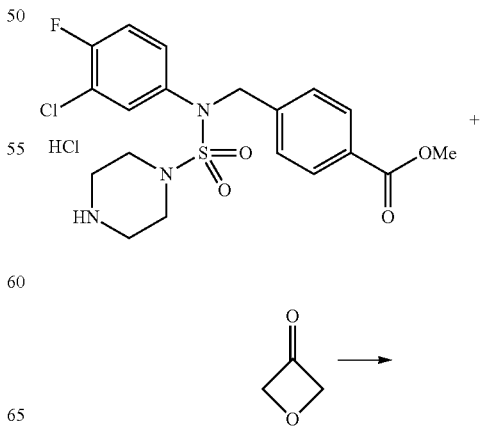

-continued

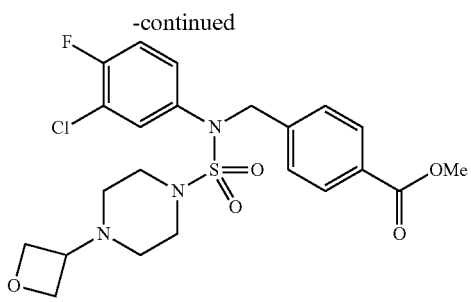

A solution of methyl 4-((N-(3-chloro-4-fluorophenyl)piperazine-1-sulfonamido)methyl)benzoate hydrochloride (0.100 g, 0.209 mmol) and oxetan-3-one (0.020 mL, 0.314 mmol) in dichloromethane (10 mL) was mixed at the room temperature with sodium triacetoxyborohydride (0.133 g, 0.627 mmol). The reaction mixture was stirred at the same temperature for 18 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 4 g cartridge; methanol/dichloromethane=0% to 15%) to give methyl 4-(((N-(3-chloro-4-fluorophenyl)-4-(oxetan-3-yl)piperazine)-1-sulfonamido)methyl)benzoate as white solid (0.079 g, 75.9%).

[Step 2] N-(3-chloro-4-fluorophenyl)-N-(4-(hydrazinecarbonyl)benzyl)-4-(oxetan-3-yl)piperazine-1-sulfonamide

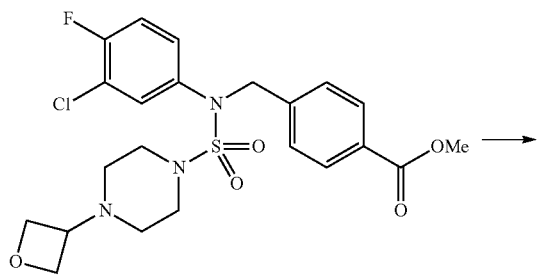

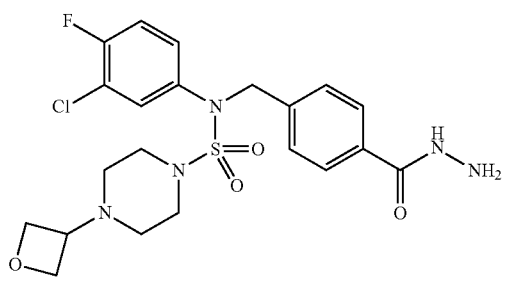

methyl 4-(((N-(3-chloro-4-fluorophenyl)-4-(oxetan-3-yl)piperazine)-1-sulfonamido)methyl)benzoate (0.079 g, 0.159 mmol) and hydrazine monohydrate (0.154 mL, 3.173 mmol) were mixed at the room temperature in ethanol (8 mL)/water (2 mL), and then the mixture was stirred at 80° C. for 18 hr. The reaction mixture was cooled down to the room temperature to terminate the reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The title compound was used without further purification (N-(3-chloro-4-fluorophenyl)-N-(4-(hydrazinecarbonyl)benzyl)-4-(oxetan-3-yl)piperazine-1-sulfonamide, 0.068 g, 86.1%, colorless oil).

[Step 3] Compound 11653

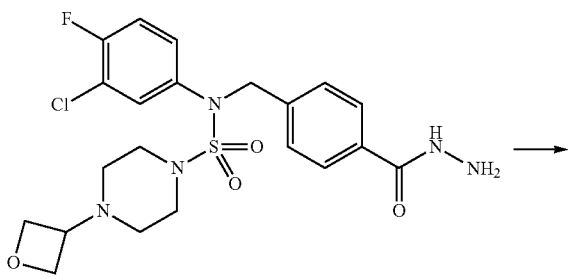

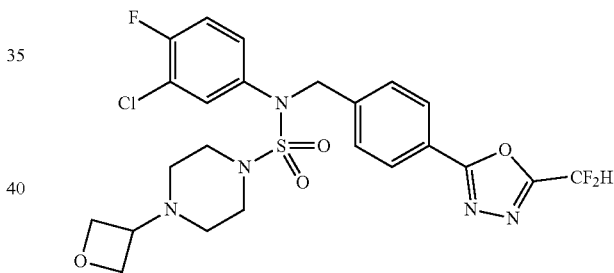

A solution of N-(3-chloro-4-fluorophenyl)-N-(4-(hydrazinecarbonyl)benzyl)-4-(oxetan-3-yl)piperazine-1-sulfonamide (0.076 g, 0.153 mmol) and triethylamine (0.043 mL, 0.305 mmol) in tetrahydrofuran (10 mL) was mixed at the room temperature with 2,2-difluoroacetic anhydride (0.057 mL, 0.458 mmol), and stirred at 80° C. for 2 hr. The reaction mixture was cooled down to the room temperature to terminate the reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$ plate, 20×20×1 mm; methanol/dichloromethane=10%) to give N-(3-chloro-4-fluorophenyl)-N-(4-(5-(difluoromethyl)-1,3,4-oxadiazol-2-yl)benzyl)-4-(oxetan-3-yl)piperazine-1-sulfonamide as white solid (0.008 g, 9.4%).

$^1$H NMR (400 MHz, CDCl$_3$) δ 8.05~8.02 (m, 2H), 7.40~7.35 (m, 3H), 7.16~7.12 (m, 1H), 7.07~7.03 (m, 1H), 7.03 (s, 0.25H), 6.90 (s, 0.5H), 6.77 (s, 0.25H), 4.82 (s, 2H), 3.43~3.22 (m, 4H), 2.78~2.82 (m, 1H), 2.62~2.21 (m, 4H), 2.20~1.81 (m, 4H), 1.80~1.61 (m, 2H); LRMS (ES) m/z 558.0 (M$^+$+1).

Example 49: Compound 11654, N-(3-chloro-4-fluorophenyl)-N-(4-(5-(difluoromethyl)-1,3,4-oxadiazol-2-yl)benzyl)-4-methylpiperazine-1-sulfonamide

[Step 1] methyl 4-(((N-(3-chloro-4-fluorophenyl)-4-methylpiperazine)-1-sulfonamido)methyl)benzoate

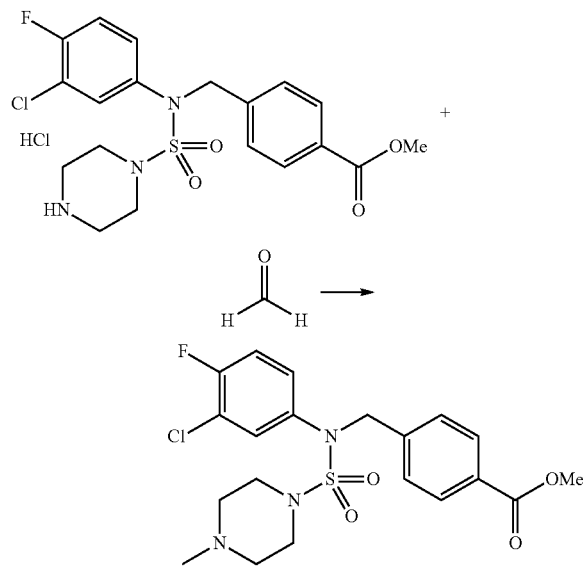

A solution of methyl 4-((N-(3-chloro-4-fluorophenyl)piperazine-1-sulfonamido)methyl)benzoate hydrochloride (0.060 g, 0.125 mmol) and paraformaldehyde (0.006 g, 0.188 mmol) in dichloromethane (10 mL) was mixed at the room temperature with sodium triacetoxyborohydride (0.080 g, 0.376 mmol). The reaction mixture was stirred at the same temperature for 18 hr. Then, water was added to the reaction mixture, followed by extraction with ethyl acetate. The organic layer was washed with aqueous saturated sodium chloride solution, dried with anhydrous MgSO₄, filtered, and concentrated in vacuo. The residue was chromatographed (SiO₂, 4 g cartridge; methanol/dichloromethane=0% to 15%) to give methyl 4-(((N-(3-chloro-4-fluorophenyl)-4-methylpiperazine)-1-sulfonamido)methyl)benzoate as white solid (0.038 g, 66.4%).

[Step 2] N-(3-chloro-4-fluorophenyl)-N-(4-(hydrazinecarbonyl)benzyl)-4-methylpiperazine-1-sulfonamide

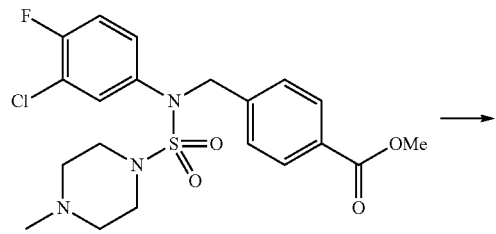

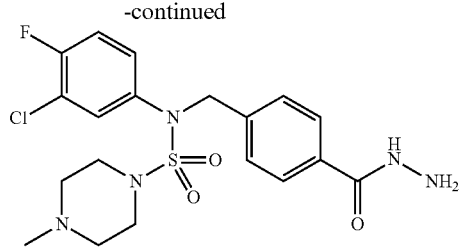

methyl 4-(((N-(3-chloro-4-fluorophenyl)-4-methylpiperazine)-1-sulfonamido)methyl)benzoate (0.038 g, 0.083 mmol) and hydrazine monohydrate (0.081 mL, 1.667 mmol) were mixed at the room temperature in ethanol (8 mL)/water (2 mL), and then the mixture was stirred at 80° C. for 18 hr. The reaction mixture was cooled down to the room temperature to terminate the reaction. Then, water was added to the reaction mixture, followed by extraction with ethyl acetate. The organic layer was washed with aqueous saturated sodium chloride solution, dried with anhydrous MgSO₄, filtered, and concentrated in vacuo. The title compound was used without further purification (N-(3-chloro-4-fluorophenyl)-N-(4-(hydrazinecarbonyl)benzyl)-4-methylpiperazine-1-sulfonamide, 0.033 g, 86.8%, colorless oil).

[Step 3] Compound 11654

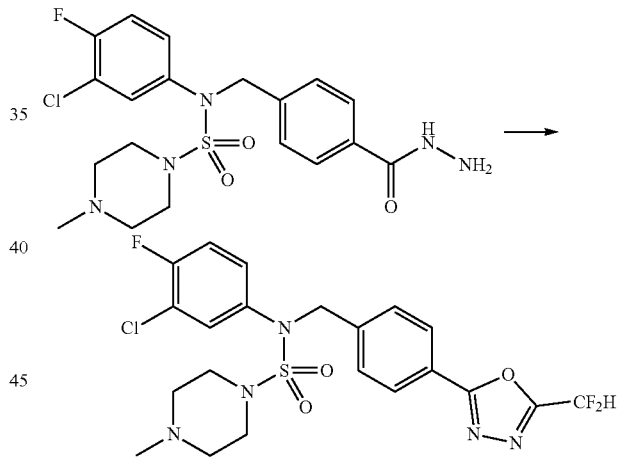

A solution of N-(3-chloro-4-fluorophenyl)-N-(4-(hydrazinecarbonyl)benzyl)-4-methylpiperazine-1-sulfonamide (0.038 g, 0.083 mmol) and triethylamine (0.023 mL, 0.167 mmol) in tetrahydrofuran (10 mL) was mixed at the room temperature with 2,2-difluoroacetic anhydride (0.031 mL, 0.250 mmol), and stirred at 80° C. for 2 hr. The reaction mixture was cooled down to the room temperature to terminate the reaction. Then, water was added to the reaction mixture, followed by extraction with ethyl acetate. The organic layer was washed with aqueous saturated sodium chloride solution, dried with anhydrous MgSO₄, filtered, and concentrated in vacuo. The residue was chromatographed (SiO₂ plate, 20×20×1 mm; methanol/dichloromethane=10%) to give N-(3-chloro-4-fluorophenyl)-N-(4-(5-(difluoromethyl)-1,3,4-oxadiazol-2-yl)benzyl)-4-methylpiperazine-1-sulfonamide as white solid (0.008 g, 18.6%).

$^1$H NMR (400 MHz, CDCl₃) δ 8.05~8.03 (m, 2H), 7.40~7.36 (m, 3H), 7.20~7.08 (m, 2H), 7.03 (s, 0.25H), 6.90

(s, 0.5H), 6.77 (s, 0.25H), 4.83 (s, 2H), 3.80~3.57 (m, 4H), 3.18~2.80 (m, 4H), 2.64 (s, 3H); LRMS (ES) m/z 516.0 (M++1).

Example 50: Compound 11659, (3S,5R)-4-acetyl-N-((5-(5-(difluoromethyl)-1,3,4-oxadiazol-2-yl)pyridin-2-yl)methyl)-3,5-dimethyl-N-phenylpiperazine-1-sulfonamide

[Step 1] tert-butyl (2S,6R)-4-(N-((5-(methoxycarbonyl)pyridin-2-yl)methyl)-N-phenylsulfamoyl)-2,6-dimethylpiperazine-1-carboxylate

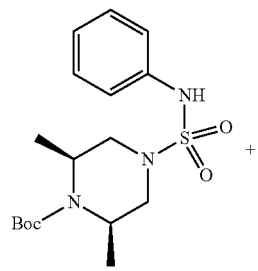

+

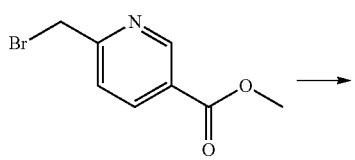

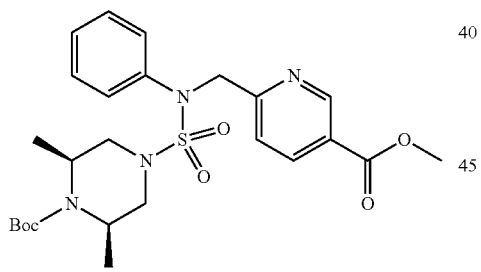

A solution of tert-butyl (2S,6R)-2,6-dimethyl-4-(N-phenylsulfamoyl)piperazine-1-carboxylate (1.110 g, 3.004 mmol) and potassium carbonate (0.623 g, 4.506 mmol) in N,N-dimethylformide (20 mL) was stirred at the room temperature for 30 min, and mixed with methyl 6-(bromomethyl)nicotinate (0.760 g, 3.305 mmol) and potassium iodide (0.249 g, 1.502 mmol). The reaction mixture was stirred at the same temperature for additional 12 hr. Then, water was added to the reaction mixture, followed by extraction with ethyl acetate. The organic layer was washed with aqueous saturated ammonium chloride solution, dried with anhydrous MgSO4, filtered, and concentrated in vacuo. The residue was chromatographed (Sift, 24 g cartridge; ethyl acetate/hexane=0% to 50%) to give tert-butyl (2S,6R)-4-(N-((5-(methoxycarbonyl)pyridin-2-yl)methyl)-N-phenylsulfamoyl)-2,6-dimethylpiperazine-1-carboxylate as yellow solid (1.440 g, 92.4%).

[Step 2] methyl 6-((((3S,5R)-3,5-dimethyl-N-phenylpiperazine)-1-sulfonamido)methyl)nicotinate Hydrochloride

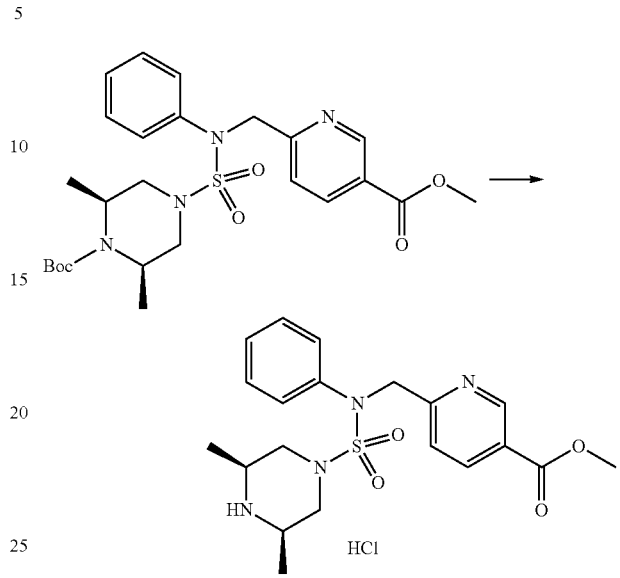

A solution of tert-butyl (2S,6R)-4-(N-((5-(methoxycarbonyl)pyridin-2-yl)methyl)-N-phenylsulfamoyl)-2,6-dimethylpiperazine-1-carboxylate (1.440 g, 2.777 mmol) and hydrogen chloride (4.00 M solution in 1,4-dioxane, 1.388 mL, 5.553 mmol) in (80 mL) was stirred at the room temperature for 5 hr, and concentrated under the reduced pressure. The crude product was used without further purification (methyl 6-((((3S,5R)-3,5-dimethyl-N-phenylpiperazine)-1-sulfonamido)methyl)nicotinate hydrochloride, 0.900 g, 71.2%, white solid).

[Step 3] methyl 6-((((3S,5R)-4-acetyl-3,5-dimethyl-N-phenylpiperazine)-1-sulfonamido)methyl)nicotinate

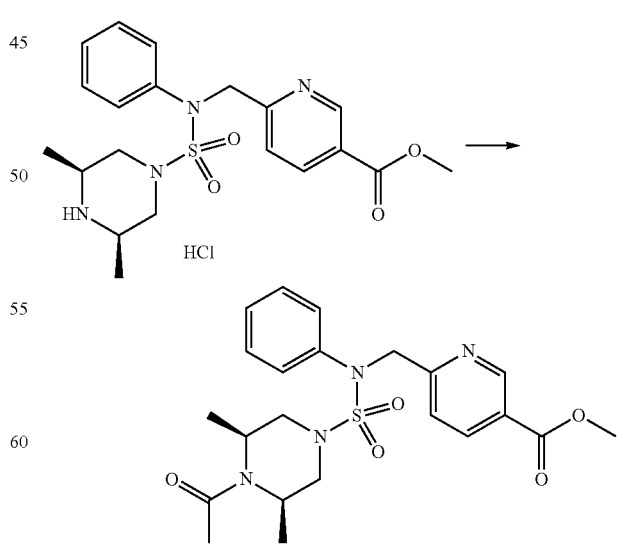

A solution of methyl 6-((((3S,5R)-3,5-dimethyl-N-phenylpiperazine)-1-sulfonamido)methyl)nicotinate hydrochloride (0.200 g, 0.440 mmol), triethyl amine (0.032 g, 0.319 mmol) and acetic anhydride (0.062 mL, 0.659 mmol) in dichloromethane (10 mL) was stirred at the room temperature for 12 hr. Then, water was added to the reaction mixture, followed by extraction with dichloromethane. The organic layer was washed with aqueous saturated ammonium chloride solution, dried with anhydrous MgSO$_4$, filtered, and concentrated in vacuo. The residue was chromatographed (SiO$_2$, 4 g cartridge; methanol/dichloromethane=0% to 5%) to give methyl 6-((((3S,5R)-4-acetyl-3,5-dimethyl-N-phenylpiperazine)-1-sulfonamido)methyl)nicotinate as colorless oil (0.130 g, 64.2%).

[Step 4] (3S,5R)-4-acetyl-N-((5-(hydrazinecarbonyl)pyridin-2-yl)methyl)-3,5-dimethyl-N-phen ylpiperazine-1-sulfonamide

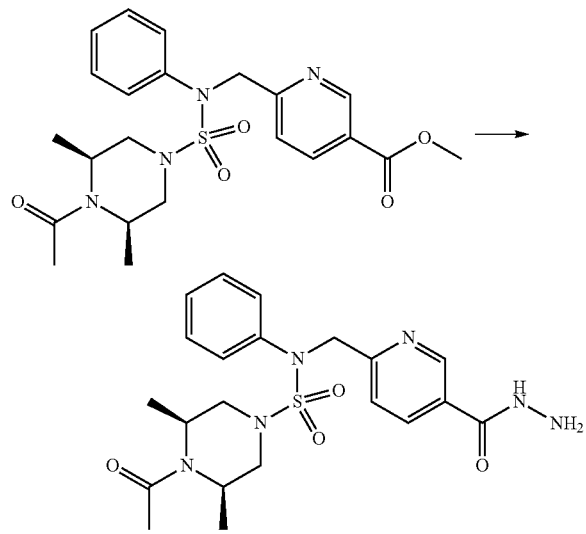

A solution of methyl 6-((((3S,5R)-4-acetyl-3,5-dimethyl-N-phenylpiperazine)-1-sulfonamido)methyl)nicotinate (0.130 g, 0.282 mmol) and hydrazine monohydrate (0.137 mL, 2.823 mmol) in ethanol (10 mL) was stirred at 90° C. for 12 hr. The reaction mixture was cooled down to the room temperature to terminate the reaction, and concentrated under the reduced pressure to remove the solvent. The residue was diluted with water (5 mL) and sodium bicarbonate (10 mL) and stirred. The resulting precipitates were collected by filtration, washed by water, and dried to give (3S,5R)-4-acetyl-N-((5-(hydrazinecarbonyl)pyridin-2-yl) methyl)-3,5-dimethyl-N-phen ylpiperazine-1-sulfonamide as white solid (0.085 g, 65.4%).

[Step 5] Compound 11659

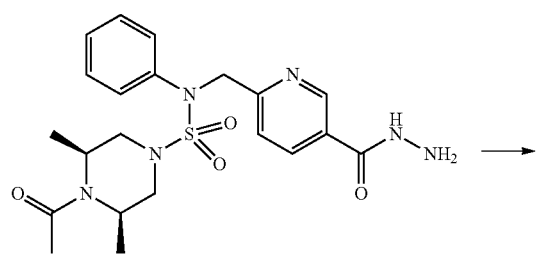

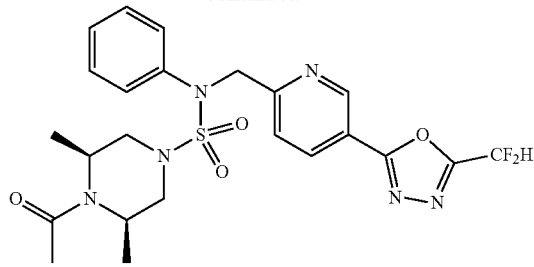

A solution of (3S,5R)-4-acetyl-N-((5-(hydrazinecarbonyl)pyridin-2-yl)methyl)-3,5-dimethyl-N-phen ylpiperazine-1-sulfonamide (0.085 g, 0.185 mmol), triethyl amine (0.129 mL, 0.923 mmol) and difluoroacetic anhydride (0.069 mL, 0.554 mmol) in tetrahydrofuran (10 mL) was stirred at 70° C. for 12 hr, and cooled down to the room temperature to terminate the reaction. Then, water was added to the reaction mixture, followed by extraction with dichloromethane. The organic layer was washed with aqueous saturated ammonium chloride solution, dried with anhydrous MgSO$_4$, filtered, and concentrated in vacuo. The residue was chromatographed (SiO$_2$, 4 g cartridge; ethyl acetate/hexane=0% to 60%) to give (3S,5R)-4-acetyl-N-((5-(5-(difluoromethyl)-1,3,4-oxadiazol-2-yl)pyridin-2-yl) methyl)-3,5-dimethyl-N-phenylpiperazine-1-sulfonamide as white solid (0.015 g, 15.6%).

$^1$H NMR (400 MHz, CDCl$_3$) δ 9.20 (s, 1H), 8.37-8.35 (m, 1H), 7.69 (d, 1H, J=8.2 Hz), 7.46-7.44 (m, 2H), 7.35-7.31 (m, 2H), 7.28-7.23 (m, 2H), 7.06 (s, 0.3H), 6.93 (s, 0.5H), 6.81 (s, 0.3H), 5.15 (s, 2H), 4.63 (brs, 1H), 3.95 (brs, 1H), 3.53 (d, 2H, J=12.1 Hz), 2.79-2.76 (m, 2H), 2.08 (s, 3H), 1.28 (s, 6H); LRMS (ES) m/z 521.2 (M$^+$+1).

Example 51: Compound 11660, (3S,5R)-4-acetyl-N-(4-(5-(difluoromethyl)-1,3,4-oxadiazol-2-yl)benzyl)-3,5-dimethyl-N-(pyridin-3-yl)piperazine-1-sulfonamide

[Step 1] tert-butyl (2S,6R)-2,6-dimethyl-4-(N-(pyridin-3-yl)sulfamoyl)piperazine-1-carboxylate

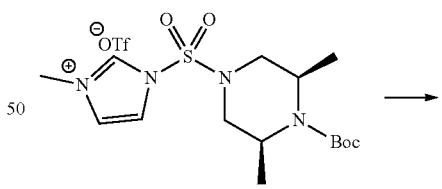

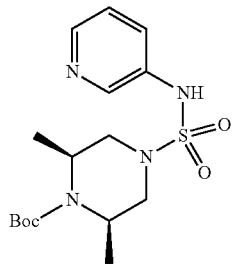

A solution of 1-4-(3S,5R)-4-(tert-butoxycarbonyl)-3,5-dimethylpiperazin-1-yl) sulfonyl)-3-methyl-1H-imidazol-3-ium trifluoromethanesulfonate (2.000 g, 3.933 mmol) and pyridin-3-amine (0.407 g, 4.326 mmol) in acetonitrile (5 mL) was stirred at the room temperature for 16 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 24 g cartridge; ethyl acetate/hexane=0% to 20%) to give tert-butyl (2S,6R)-2,6-dimethyl-4-(N-(pyridin-3-yl)sulfamoyl)piperazine-1-carboxylate as yellow solid (1.100 g, 75.5%).

[Step 2] tert-butyl (2S,6R)-4-(N-(4-(methoxycarbonyl)benzyl)-N-(pyridin-3-yl)sulfamoyl)-2,6-dimethylpiperazine-1-carboxylate

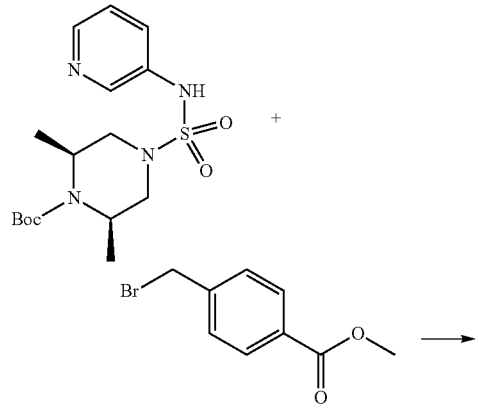

A solution of tert-butyl (2S,6R)-2,6-dimethyl-4-(N-(pyridin-3-yl)sulfamoyl)piperazine-1-carboxylate (0.510 g, 1.377 mmol) and potassium carbonate (0.285 g, 2.065 mmol) in N,N-dimethylformide (20 mL) was stirred at the room temperature for 30 min, and mixed with methyl 4-(bromomethyl)benzoate (0.347 g, 1.514 mmol) and potassium iodide (0.114 g, 0.688 mmol). The reaction mixture was stirred at the same temperature for additional 12 hr. Then, water was added to the reaction mixture, followed by extraction with ethyl acetate. The organic layer was washed with aqueous saturated ammonium chloride solution, dried with anhydrous MgSO$_4$, filtered, and concentrated in vacuo. The residue was chromatographed (Sift, 12 g cartridge; ethyl acetate/hexane=0% to 30%) to give tert-butyl (2S,6R)-4-(N-(4-(methoxycarbonyl)benzyl)-N-(pyridin-3-yl)sulfamoyl)-2,6-dimethylpiperazine-1-carboxylate as white solid (0.300 g, 42.0%).

[Step 3] methyl 4-((((3S,5R)-3,5-dimethyl-N-(pyridin-3-yl)piperazine)-1-sulfonamido)methyl)benzoate Hydrochloride

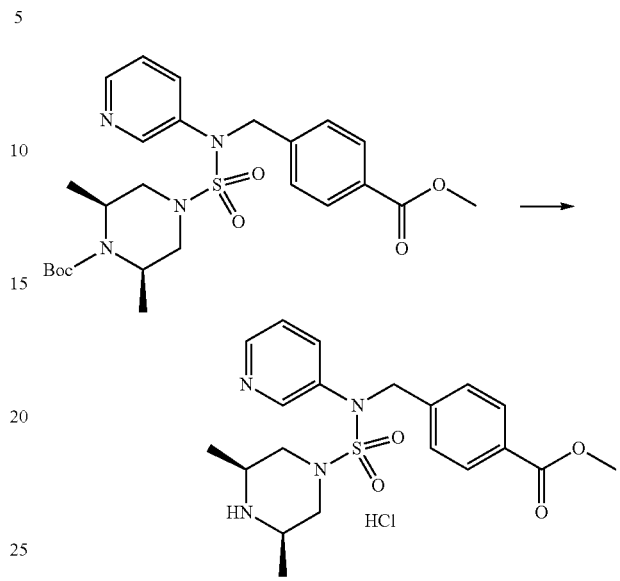

A solution of tert-butyl (2S,6R)-4-(N-(4-(methoxycarbonyl)benzyl)-N-(pyridin-3-yl)sulfamoyl)-2,6-dimethylpiperazine-1-carboxylate (0.280 g, 0.540 mmol) and hydrochloric acid (4.00 M solution in 1,4-dioxane, 0.270 mL, 1.080 mmol) in dichloromethane (20 mL) was stirred at the room temperature for 5 hr, and concentrated under the reduced pressure to remove the solvent. The crude product was used without further purification (methyl 4-((((3S,5R)-3,5-dimethyl-N-(pyridin-3-yl)piperazine)-1-sulfonamido)methyl) benzoate hydrochloride, 0.150 g, 61.1%, yellow solid).

[Step 4] methyl 4-((((3S,5R)-4-acetyl-3,5-dimethyl-N-(pyridin-3-yl)piperazine)-1-sulfonamido)methyl) benzoate

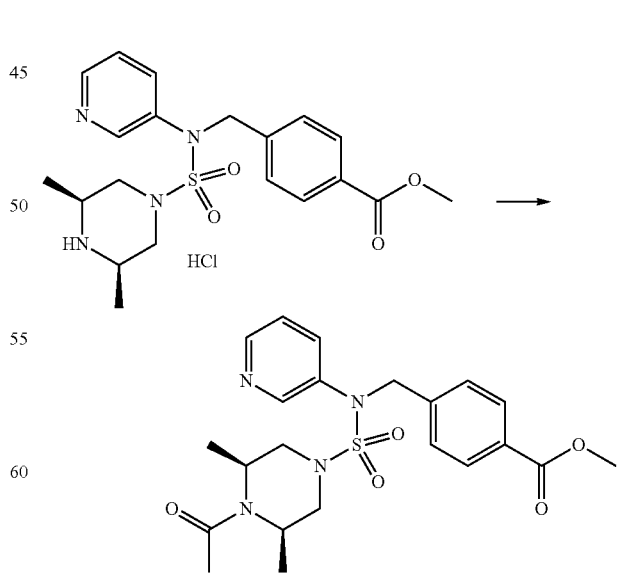

A solution of methyl 4-((((3S,5R)-3,5-dimethyl-N-(pyridin-3-yl)piperazine)-1-sulfonamido)methyl)benzoate hydrochloride (0.120 g, 0.264 mmol), triethylamine (0.032 g, 0.317 mmol) and acetic anhydride (0.037 mL, 0.396 mmol) in dichloromethane (5 mL) was stirred at the room temperature for 12 hr. Then, water was added to the reaction mixture, followed by extraction with dichloromethane. The organic layer was washed with aqueous saturated ammonium chloride solution, dried with anhydrous MgSO₄, filtered, and concentrated in vacuo. The residue was chromatographed (SiO₂, 4 g cartridge; methanol/dichloromethane=0% to 5%) to give methyl 4-((((3S,5R)-4-acetyl-3,5-dimethyl-N-(pyridin-3-yl)piperazine)-1-sulfonamido)methyl) benzoate as yellow oil (0.081 g, 66.7%).

[Step 5] (3S,5R)-4-acetyl-N-(4-(hydrazinecarbonyl)benzyl)-3,5-dimethyl-N-(pyridin-3-yl)piper azine-1-sulfonamide

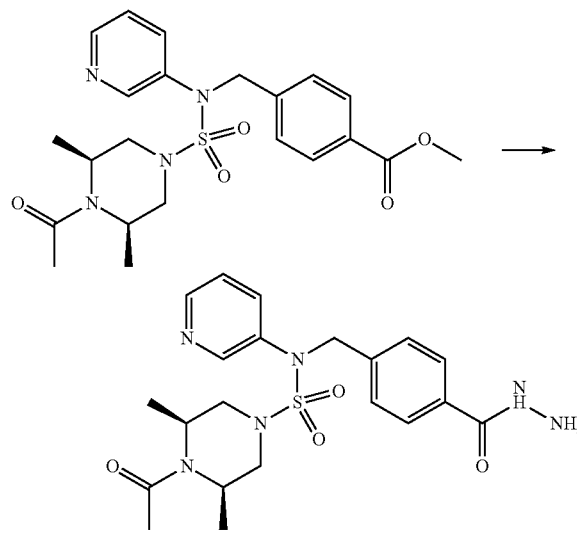

A solution of methyl 4-((((3S,5R)-4-acetyl-3,5-dimethyl-N-(pyridin-3-yl)piperazine)-1-sulfonamido)methyl) benzoate (0.081 g, 0.176 mmol) and hydrazine monohydrate (0.085 mL, 1.759 mmol) in ethanol (10 mL) was stirred at 90° C. for 12 hr. The reaction mixture was cooled down to the room temperature to terminate the reaction, and concentrated under the reduced pressure to remove the solvent. The residue was diluted with water (5 mL) and sodium bicarbonate (10 mL) and stirred. The resulting precipitates were collected by filtration, washed by water, and dried to give (3S,5R)-4-acetyl-N-(4-(hydrazinecarbonyl)benzyl)-3,5-dimethyl-N-(pyridin-3-yl)piper azine-1-sulfonamide as white solid (0.039 g, 48.1%).

[Step 6] Compound 11660

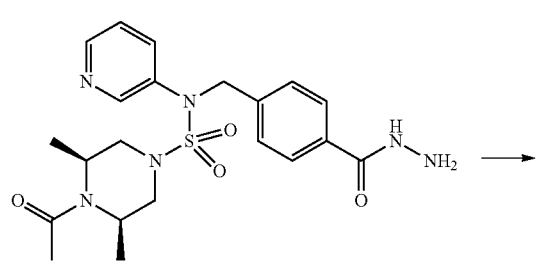

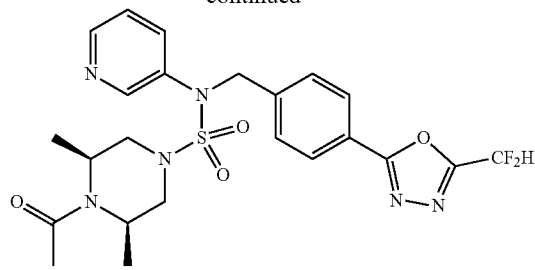

A solution of (3S,5R)-4-acetyl-N-(4-(hydrazinecarbonyl)benzyl)-3,5-dimethyl-N-(pyridin-3-yl)piper azine-1-sulfonamide (0.039 g, 0.085 mmol), triethylamine (0.043 g, 0.423 mmol) and difluoroacetic anhydride (0.044 g, 0.254 mmol) in tetrahydrofuran (10 mL) was stirred at 70° C. for 12 hr, and cooled down to the room temperature to terminate the reaction. Then, water was added to the reaction mixture, followed by extraction with dichloromethane. The organic layer was washed with aqueous saturated ammonium chloride solution, dried with anhydrous MgSO₄, filtered, and concentrated in vacuo. The residue was chromatographed (SiO₂, 4 g cartridge; ethyl acetate/hexane=0% to 60%) to give (3S,5R)-4-acetyl-N-(4-(5-(difluoromethyl)-1,3,4-oxadiazol-2-yl)benzyl)-3,5-dimethyl-N-(pyridin-3-yl)piperazine-1-sulfonamide as white solid (0.020 g, 45.4%).

¹H NMR (400 MHz, CDCl₃) δ 8.69 (brs, 1H), 8.53-8.52 (m, 1H), 8.06 (d, 2H, J=8.1 Hz), 7.79-7.77 (m, 1H), 7.46 (d, 2H, J=7.6 Hz), 7.38-7.36 (m, 1H), 7.05 (0.3H), 6.92 (s, 0.5H), 6.79 (s, 0.3H), 5.02 (s, 2H), 3.59-3.51 (m, 2H), 3.50 (s, 2H), 2.88-2.85 (m, 2H), 2.10 (s, 3H), 1.32-1.25 (m, 6H); LRMS (ES) m/z 521.3 (M⁺+1).

Example 52: Compound 11661, (3S,5R)—N-((5-(5-(difluoromethyl)-1,3,4-oxadiazol-2-yl)pyridin-2-yl)methyl)-4-ethyl-3,5-dimethyl-N-phenylpiperazine-1-sulfonamide

[Step 1] methyl 6-((((3S,5R)-4-ethyl-3,5-dimethyl-N-phenylpiperazine)-1-sulfonamido)methyl)nicotinate

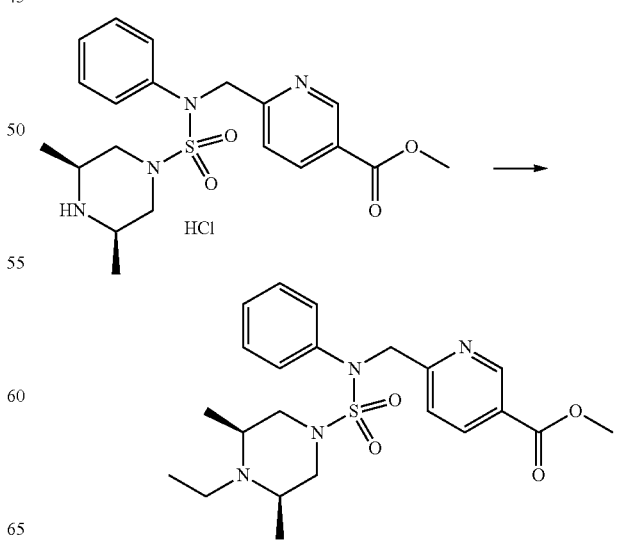

A solution of methyl 6-((((3S,5R)-3,5-dimethyl-N-phenylpiperazine)-1-sulfonamido)methyl)nicotinate hydrochloride (0.200 g, 0.440 mmol), acetaldehyde (0.039 g, 0.879 mmol) and acetic acid (0.028 mL, 0.484 mmol) in dichloromethane (5 mL) was stirred at the room temperature for 30 min, and mixed with sodium triacetoxyborohydride (0.186 g, 0.879 mmol). The reaction mixture was stirred at the same temperature for additional 12 hr. Then, water was added to the reaction mixture, followed by extraction with dichloromethane. The organic layer was washed with aqueous saturated sodium bicarbonate solution, dried with anhydrous MgSO$_4$, filtered, and concentrated in vacuo. The residue was chromatographed (SiO$_2$, 4 g cartridge; methanol/dichloromethane=0% to 5%) to give methyl 6-((((3S,5R)-4-ethyl-3,5-dimethyl-N-phenylpiperazine)-1-sulfonamido)methyl)nicotinate as yellow oil (0.110 g, 56.0%).

[Step 2] (3S,5R)-4-ethyl-N-((5-(hydrazinecarbonyl)pyridin-2-yl)methyl)-3,5-dimethyl-N-phenylpiperazine-1-sulfonamide

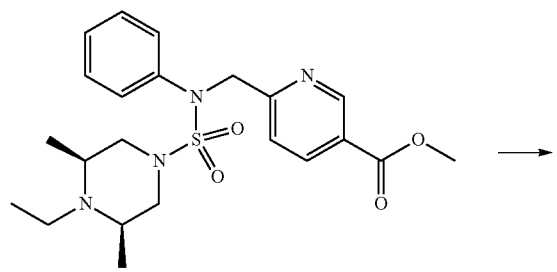

A solution of methyl 6-((((3S,5R)-4-ethyl-3,5-dimethyl-N-phenylpiperazine)-1-sulfonamido)methyl)nicotinate (0.110 g, 0.246 mmol) and hydrazine monohydrate (0.120 mL, 2.463 mmol) in ethanol (10 mL) was stirred at 90° C. for 12 hr, and cooled down to the room temperature to terminate the reaction. The reaction mixture was concentrated under the reduced pressure to remove the solvent. The residue was diluted with water (5 mL) and sodium bicarbonate (10 mL) and stirred. The resulting precipitates were collected by filtration and dried to give (3S,5R)-4-ethyl-N-((5-(hydrazinecarbonyl)pyridin-2-yl)methyl)-3,5-dimethyl-N-phenylpiperazine-1-sulfonamide as white solid (0.055 g, 50.0%).

[Step 3] Compound 11661

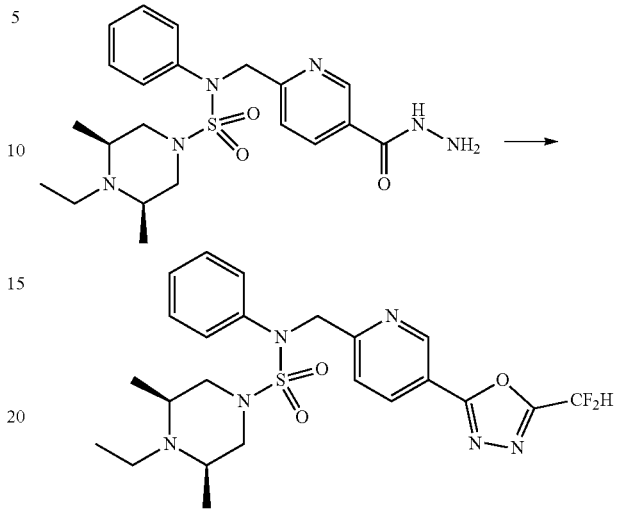

A solution of (3S,5R)-4-ethyl-N-((5-(hydrazinecarbonyl)pyridin-2-yl)methyl)-3,5-dimethyl-N-phenylpiperazine-1-sulfonamide (0.055 g, 0.123 mmol), triethylamine (0.062 g, 0.616 mmol) and difluoroacetic anhydride (0.064 g, 0.369 mmol) in tetrahydrofuran (10 mL) was stirred at 70° C. for 12 hr, and cooled down to the room temperature to terminate the reaction. Then, water was added to the reaction mixture, followed by extraction with dichloromethane. The organic layer was washed with aqueous saturated ammonium chloride solution, dried with anhydrous MgSO$_4$, filtered, and concentrated in vacuo. The residue was chromatographed (SiO$_2$, 4 g cartridge; ethyl acetate/hexane=0% to 70%) to give (3S,5R)—N-((5-(5-(difluoromethyl)-1,3,4-oxadiazol-2-yl)pyridin-2-yl)methyl)-4-ethyl-3,5-dimethyl-N-phenylpiperazine-1-sulfonamide as white solid (0.021 g, 33.7%).

$^1$H NMR (400 MHz, CDCl$_3$) δ 9.21 (s, 1H), 8.37-8.35 (m, 1H), 7.72-7.71 (m, 1 H), 7.45-7.42 (m, 2H), 7.36-7.31 (m, 2H), 7.27-7.23 (m, 1H), 7.07 (s, 0.3H), 6.94 (s, 0.5H), 6.81 (s, 0.3H), 5.13 (s, 2H), 3.55-3.53 (m, 2H), 2.97-2.86 (m, 2H), 2.60-2.46 (m, 3H), 1.62 (brs, 1H), 1.19-1.01 (m, 6H), 0.99-0.82 (m, 3H); LRMS (ES) m/z 507.1 (M$^+$+1).

Example 53: Compound 11662, (3S,5R)—N-(4-(5-(difluoromethyl)-1,3,4-oxadiazol-2-yl)benzyl)-3,4,5-trimethyl-N-(pyridin-3-yl)piperazine-1-sulfonamide

[Step 1] methyl 4-((((3S,5R)-3,4,5-trimethyl-N-(pyridin-3-yl)piperazine)-1-sulfonamido)methyl)benzoate

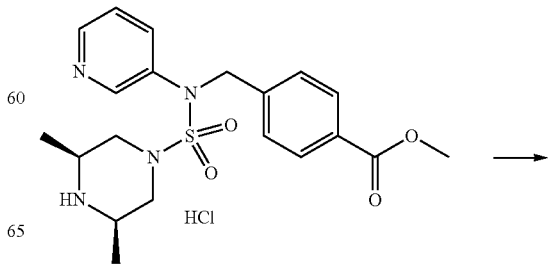

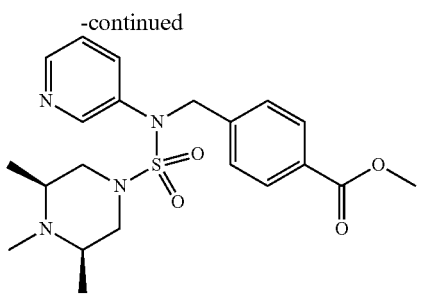

A solution of methyl 4-(((((3S,5R)-3,5-dimethyl-N-(pyridin-3-yl)piperazine)-1-sulfonamido)methyl)benzoate hydrochloride (0.120 g, 0.287 mmol), paraformaldehyde (0.017 g, 0.573 mmol), acetic acid (0.020 mL, 0.344 mmol) and sodium triacetoxyborohydride (0.122 g, 0.573 mmol) in dichloromethane (5 mL) was stirred at the room temperature for 12 hr. Then, water was added to the reaction mixture, followed by extraction with dichloromethane. The organic layer was washed with aqueous saturated sodium bicarbonate solution, dried with anhydrous MgSO$_4$, filtered, and concentrated in vacuo. The residue was chromatographed (SiO$_2$, 4 g cartridge; methanol/dichloromethane=0% to 5%) to give methyl 4-((((3S,5R)-3,4,5-trimethyl-N-(pyridin-3-yl)piperazine)-1-sulfonamido)methyl)benzoate as colorless oil (0.095 g, 76.6%).

[Step 2] (3S,5R)—N-(4-(hydrazinecarbonyl)benzyl)-3,4,5-trimethyl-N-(pyridin-3-yl)piperazine-1-sulfonamide

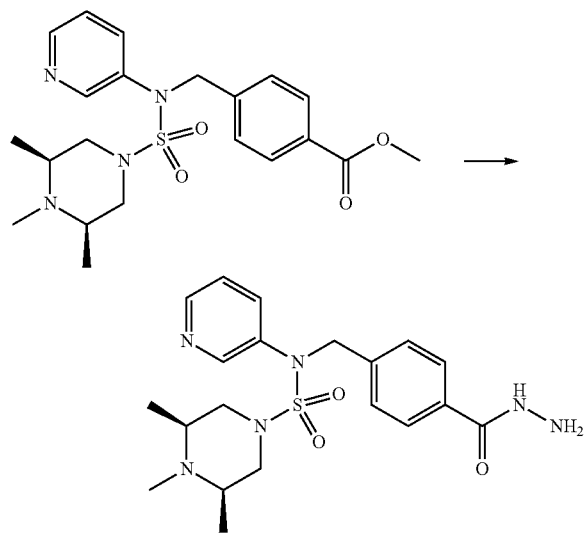

A solution of methyl 4-((((3S,5R)-3,4,5-trimethyl-N-(pyridin-3-yl)piperazine)-1-sulfonamido)methyl)benzoate (0.095 g, 0.220 mmol) and hydrazine monohydrate (0.107 mL, 2.196 mmol) in ethanol (10 mL) was stirred at 90° C. for 12 hr, and cooled down to the room temperature to terminate the reaction. The reaction mixture was concentrated under the reduced pressure to remove the solvent. The residue was diluted with water (5 mL) and sodium bicarbonate (10 mL), and stirred. The resulting precipitates were collected by filtration, washed by water, and dried to give (3S,5R)—N-(4-(hydrazinecarbonyl)benzyl)-3,4,5-trimethyl-N-(pyridin-3-yl)piperazine-1-sulfonamide as white solid (0.048 g, 50.5%).

[Step 3] Compound 11662

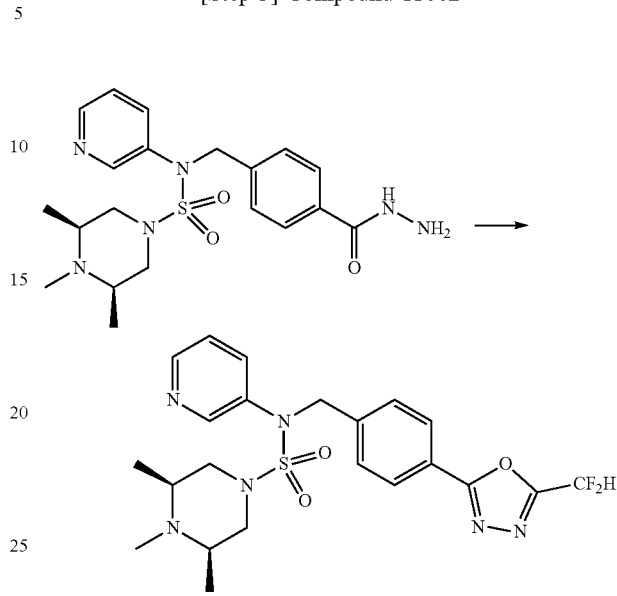

A solution of (3S,5R)—N-(4-(hydrazinecarbonyl)benzyl)-3,4,5-trimethyl-N-(pyridin-3-yl)piperazine-1-sulfonamide (0.048 g, 0.111 mmol), triethylamine (0.077 mL, 0.555 mmol) and 2,2-difluoroacetic anhydride (0.041 mL, 0.333 mmol) in tetrahydrofuran (10 mL) was stirred at 70° C. for 12 hr, and cooled down to the room temperature to terminate the reaction. Then, water was added to the reaction mixture, followed by extraction with dichloromethane. The organic layer was washed with aqueous saturated ammonium chloride solution, dried with anhydrous MgSO$_4$, filtered, and concentrated in vacuo. The residue was chromatographed (SiO$_2$, 4 g cartridge; ethyl acetate/hexane=0% to 70%) to give (3S,5R)—N-(4-(5-(difluoromethyl)-1,3,4-oxadiazol-2-yl)benzyl)-3,4,5-trimethyl-N-(pyridin-3-yl)piperazine-1-sulfonamide as white solid (0.019 g, 34.8%).

$^1$H NMR (400 MHz, CDCl$_3$) δ 8.53 (d, 1H, J=2.2 Hz), 8.51-8.50 (m, 1H), 8.06-8.03 (m, 2H), 7.66-7.63 (m, 1H), 7.44-7.42 (m, 2H), 7.30-7.26 (m, 1H), 7.05 (s, 0.2H), 6.92 (s, 0.5H), 6.79 (s, 0.2H), 4.93 (s, 2H), 3.56-3.53 (m, 2H), 2.85 (brs, 2H), 2.46-2.32 (m, 5H), 1.29-1.23 (m, 6H); LRMS (ES) m/z 493.1 (M$^+$+1).

Example 54: Compound 11670, N-(3-chloro-4-fluorophenyl)-N-((5-(5-(difluoromethyl)-1,3,4-oxadiazol-2-yl)pyridin-2-yl) methyl)-4-isopropylpiperazine-1-sulfonamide

[Step 1] tert-butyl 4-(N-(3-chloro-4-fluorophenyl)-N-((5-(methoxycarbonyl)pyridin-2-yl)methyl)sulfamoyl)piperazine-1-carboxylate

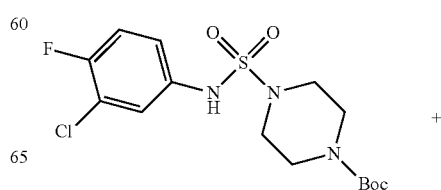

+

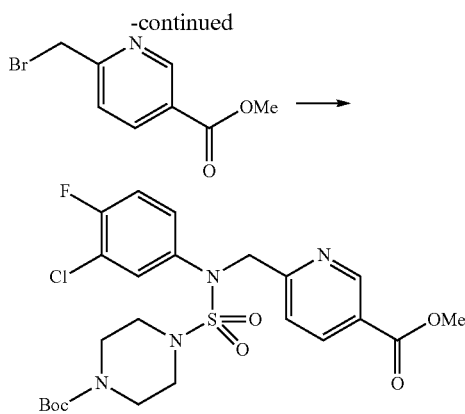

A solution of tert-butyl 4-(N-(3-chloro-4-fluorophenyl)sulfamoyl)piperazine-1-carboxylate (1.800 g, 4.570 mmol) and sodium hydride (60.00%, 0.548 g, 13.710 mmol) in N,N-dimethylformide (50 mL) was stirred at the room temperature for 10 min, and mixed with methyl 6-(bromomethyl)nicotinate (1.262 g, 5.484 mmol). The reaction mixture was stirred at 50° C. for additional 18 hr, and cooled down to the room temperature to terminate the reaction. Then, water was added to the reaction mixture, followed by extraction with ethyl acetate. The organic layer was washed with aqueous saturated sodium chloride solution, dried with anhydrous MgSO₄, filtered, and concentrated in vacuo. The residue was chromatographed (SiO₂, 40 g cartridge; ethyl acetate/hexane=0% to 80%) to give tert-butyl 4-(N-(3-chloro-4-fluorophenyl)-N-((5-(methoxycarbonyl)pyridin-2-yl)methyl)sulfamoyl)piperazine-1-carboxylate as white solid (1.140 g, 45.9%).

[Step 2] methyl 6-((N-(3-chloro-4-fluorophenyl)piperazine-1-sulfonamido)methyl)nicotinate Hydrochloride

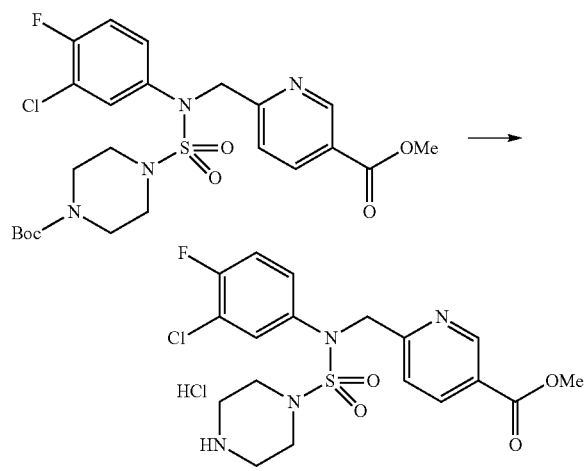

A solution of tert-butyl 4-(N-(3-chloro-4-fluorophenyl)-N-((5-(methoxycarbonyl)pyridin-2-yl)methyl)sulfamoyl)piperazine-1-carboxylate (1.140 g, 2.099 mmol) in dichloromethane (80 mL) was mixed at the room temperature with hydrochloric acid (4.00 M solution in dioxane, 2.099 mL, 8.398 mmol). The reaction mixture was stirred at the same temperature for 18 hr, and concentrated under the reduced pressure to remove the solvent. The title compound was used without further purification (methyl 6-((N-(3-chloro-4-fluorophenyl)piperazine-1-sulfonamido)methyl)nicotinate hydrochloride, 0.980 g, 97.4%, red solid).

[Step 3] methyl 6-(((N-(3-chloro-4-fluorophenyl)-4-isopropylpiperazine)-1-sulfonamido)methyl)nicotinate

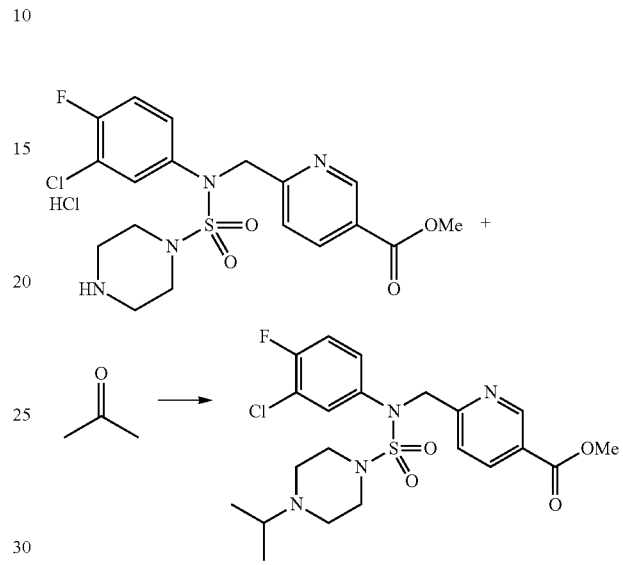

A solution of methyl 6-((N-(3-chloro-4-fluorophenyl)piperazine-1-sulfonamido)methyl)nicotinate hydrochloride (0.150 g, 0.313 mmol) and sodium triacetoxyborohydride (0.133 g, 0.626 mmol) in dichloromethane (10 mL) was mixed at the room temperature with propan-2-one (0.034 mL, 0.469 mmol). The reaction mixture was stirred at the same temperature for 18 hr. Then, water was added to the reaction mixture, followed by extraction with ethyl acetate. The organic layer was washed with aqueous saturated sodium chloride solution, dried with anhydrous MgSO₄, filtered, and concentrated in vacuo. The residue was chromatographed (SiO₂, 12 g cartridge; methanol/dichloromethane=0% to 15%) to give methyl 6-(((N-(3-chloro-4-fluorophenyl)-4-isopropylpiperazine)-1-sulfonamido)methyl)nicotinate as yellow solid (0.112 g, 73.8%).

[Step 4] N-(3-chloro-4-fluorophenyl)-N-((5-(hydrazinecarbonyl)pyridin-2-yl)methyl)-4-isopropyl piperazine-1-sulfonamide

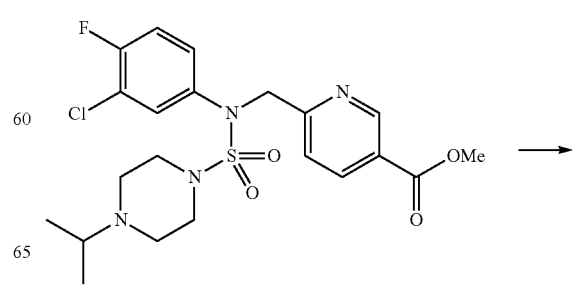

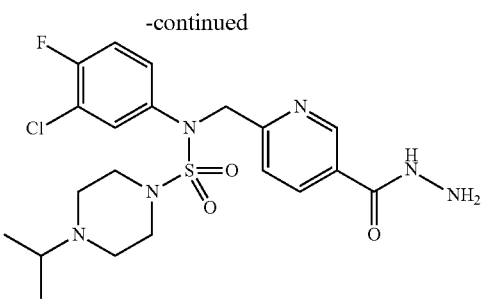

methyl 6-(((N-(3-chloro-4-fluorophenyl)-4-isopropylpiperazine)-1-sulfonamido)methyl)nicotinate (0.153 g, 0.315 mmol) and hydrazine monohydrate (0.460 mL, 9.465 mmol) were mixed at the room temperature in ethanol (8 mL)/water (2 mL), and then the mixture was stirred at 80° C. for 18 hr. The reaction mixture was cooled down to the room temperature to terminate the reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The title compound was used without further purification (N-(3-chloro-4-fluorophenyl)-N-((5-(hydrazinecarbonyl)pyridin-2-yl)methyl)-4-isopropylpiperazine-1-sulfonamide, 0.147 g, 96.1%, white solid).

[Step 5] Compound 11670

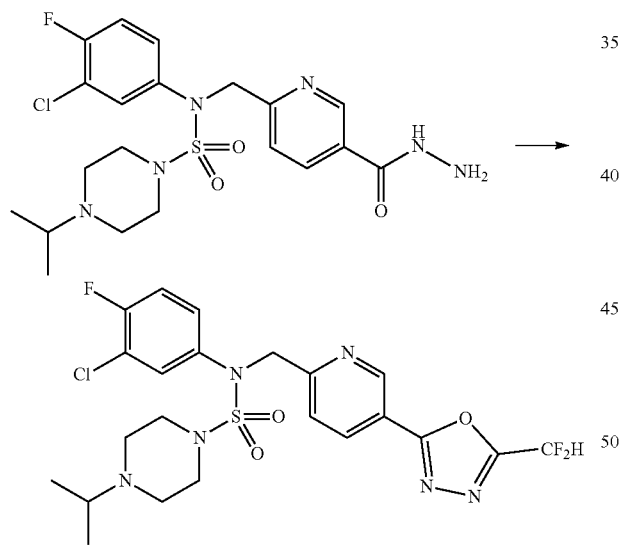

A solution of N-(3-chloro-4-fluorophenyl)-N-((5-(hydrazinecarbonyl)pyridin-2-yl)methyl)-4-isopropyl piperazine-1-sulfonamide (0.147 g, 0.303 mmol) and triethylamine (0.084 mL, 0.606 mmol) in tetrahydrofuran (15 mL) was mixed at the room temperature with 2,2-difluoroacetic anhydride (0.113 mL, 0.909 mmol), and stirred at 80° C. for 1 hr. The reaction mixture was cooled down to the room temperature to terminate the reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 12 g cartridge; methanol/dichloromethane=0% to 30%) to give N-(3-chloro-4-fluorophenyl)-N-((5-(5-(difluoromethyl)-1,3,4-oxadiazol-2-yl)pyridin-2-yl) methyl)-4-isopropylpiperazine-1-sulfonamide as colorless oil (0.085 g, 51.5%).

$^1$H NMR (400 MHz, CDCl$_3$) δ 9.24 (s, 1H), 8.37 (dd, 1H, J=8.2, 2.2 Hz), 7.62~7.60 (m, 1H), 7.55~7.52 (m, 1H), 7.35~7.31 (m, 1H), 7.11~7.06 (m, 1H), 7.05 (s, 0.25H), 6.92 (s, 0.5H), 6.79 (s, 0.25H), 5.01 (s, 2H), 3.43~3.24 (m, 4H), 2.67~2.47 (m, 4H), 1.62~1.59 (m, 2H), 1.10~0.97 (m, 5H); LRMS (ES) m/z 545.2 (M$^+$+1).

Example 55: Compound 11671, N-(3-chloro-4-fluorophenyl)-4-cyclobutyl-N-((5-(5-(difluoromethyl)-1,3,4-oxadiazol-2-yl)pyridin-2-yl)methyl)piperazine-1-sulfonamide

[Step 1] methyl 6-(((N-(3-chloro-4-fluorophenyl)-4-cyclobutylpiperazine)-1-sulfonamido)methyl)nicotinate

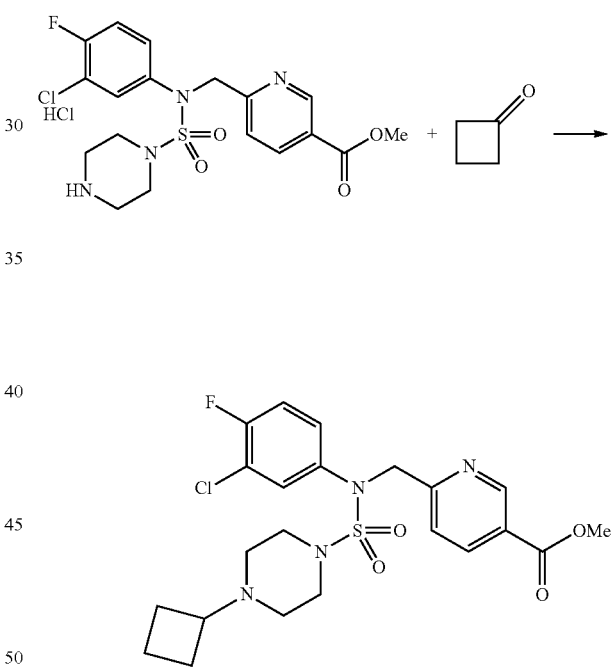

A solution of methyl 6-((N-(3-chloro-4-fluorophenyl)piperazine-1-sulfonamido)methyl)nicotinate hydrochloride (0.150 g, 0.313 mmol) and cyclobutanone (0.035 mL, 0.469 mmol) in dichloromethane (10 mL) was mixed at the room temperature with sodium triacetoxyborohydride (0.133 g, 0.626 mmol). The reaction mixture was stirred at the same temperature for 18 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 12 g cartridge; methanol/dichloromethane=0% to 15%) to give methyl 6-(((N-(3-chloro-4-fluorophenyl)-4-cyclobutylpiperazine)-1-sulfonamido)methyl)nicotinate as yellow solid (0.093 g, 59.8%).

133

[Step 2] N-(3-chloro-4-fluorophenyl)-4-cyclobutyl-N-((5-(hydrazinecarbonyl)pyridin-2-yl)methyl)piperazine-1-sulfonamide

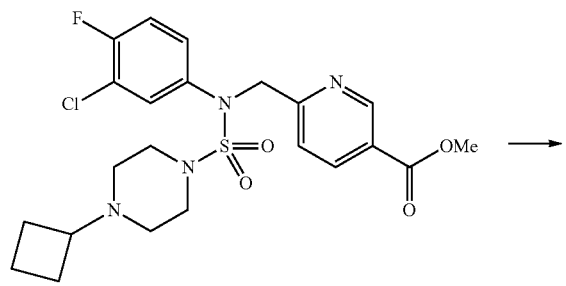

methyl 6-(((N-(3-chloro-4-fluorophenyl)-4-cyclobutylpiperazine)-1-sulfonamido)methyl)nicotinate (0.100 g, 0.201 mmol) and hydrazine monohydrate (0.293 mL, 6.036 mmol) were mixed at the room temperature in ethanol (8 mL)/water (2 mL), and then the mixture was stirred at 80° C. for 18 hr. The reaction mixture was cooled down to the room temperature to terminate the reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The crude product was used without further purification (N-(3-chloro-4-fluorophenyl)-4-cyclobutyl-N-((5-(hydrazinecarbonyl)pyridin-2-yl)methyl)piperazine-1-sulfonamide, 0.098 g, 98.0%, white solid).

[Step 3] Compound 11671

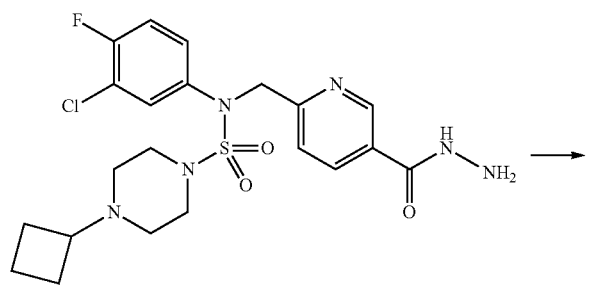

134

-continued

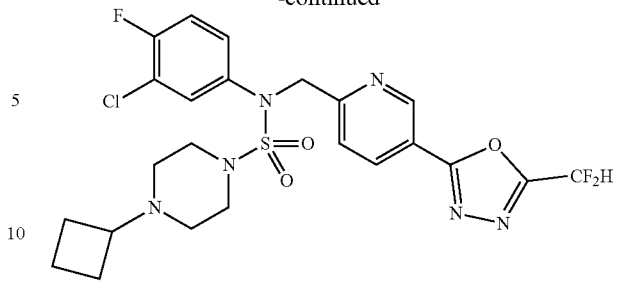

A solution of N-(3-chloro-4-fluorophenyl)-4-cyclobutyl-N-((5-(hydrazinecarbonyl)pyridin-2-yl)methyl)piperazine-1-sulfonamide (0.100 g, 0.201 mmol) and triethylamine (0.056 mL, 0.402 mmol) in tetrahydrofuran (15 mL) was mixed at the room temperature with 2,2-difluoroacetic anhydride (0.075 mL, 0.604 mmol), and stirred at 80° C. for 1 hr. The reaction mixture was cooled down to the room temperature to terminate the reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 12 g cartridge; methanol/dichloromethane=0% to 15%) to give N-(3-chloro-4-fluorophenyl)-4-cyclobutyl-N-((5-(5-(difluoromethyl)-1,3,4-oxadiazol-2-yl)pyridin-2-yl)methyl)piperazine-1-sulfonamide as white solid (0.038 g, 33.9%).

$^1$H NMR (400 MHz, CDCl$_3$) δ 9.24 (s, 1H), 8.37 (dd, 1H, J=8.2, 2.2 Hz), 7.60~7.58 (m, 1H), 7.54~7.52 (m, 1H), 7.35~7.31 (m, 1H), 7.26~7.07 (m, 1H), 7.05 (s, 0.25H), 6.92 (s, 0.5H), 6.80 (s, 0.25H), 5.00 (s, 2H), 3.50~3.15 (m, 4H), 2.78~2.75 (m, 1H), 2.53~2.04 (m, 6H), 1.93~1.59 (m, 4H); LRMS (ES) m/z 557.3 (M$^+$+1).

Example 56: Compound 11672, N-(3-chloro-4-fluorophenyl)-N-((5-(5-(difluoromethyl)-1,3,4-oxadiazol-2-yl)pyridin-2-yl) methyl)-4-(oxetan-3-yl)piperazine-1-sulfonamide

[Step 1] methyl 6-(((N-(3-chloro-4-fluorophenyl)-4-(oxetan-3-yl)piperazine)-1-sulfonamido)methyl)nicotinate

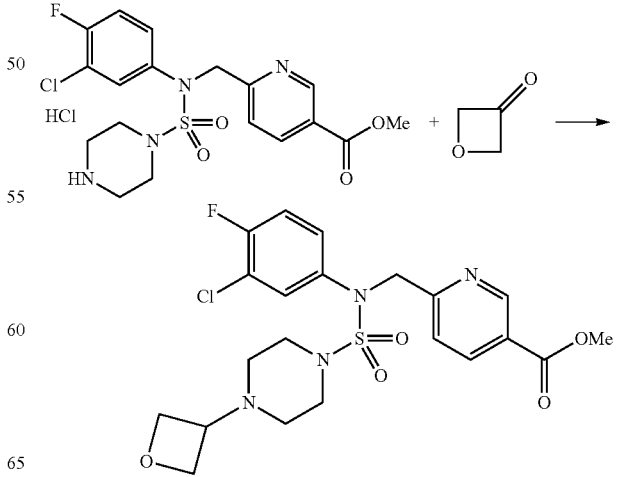

A solution of methyl 6-((N-(3-chloro-4-fluorophenyl)piperazine-1-sulfonamido)methyl)nicotinate hydrochloride (0.150 g, 0.313 mmol) and oxetan-3-one (0.030 mL, 0.469 mmol) in dichloromethane (10 mL) was mixed at the room temperature with sodium triacetoxyborohydride (0.133 g, 0.626 mmol). The reaction mixture was stirred at the same temperature for 18 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 12 g cartridge; methanol/dichloromethane=0% to 15%) to give methyl 6-(((N-(3-chloro-4-fluorophenyl)-4-(oxetan-3-yl)piperazine)-1-sulfonamido)methyl)nicotinate as yellow solid (0.154 g, 98.6%).

[Step 2] N-(3-chloro-4-fluorophenyl)-N-((5-(hydrazinecarbonyl)pyridin-2-yl)methyl)-4-(oxetan-3-yl)piperazine-1-sulfonamide

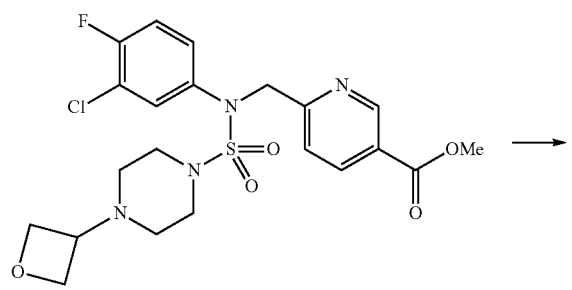

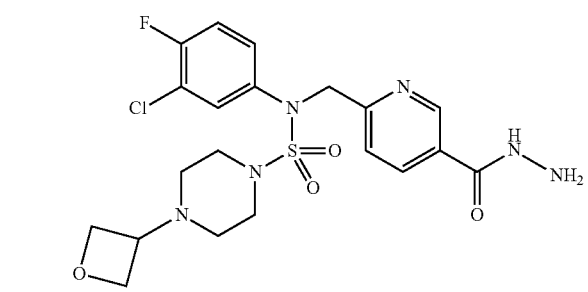

methyl 6-(((N-(3-chloro-4-fluorophenyl)-4-(oxetan-3-yl)piperazine)-1-sulfonamido)methyl)nicotinate (0.154 g, 0.309 mmol) and hydrazine monohydrate (0.450 mL, 9.259 mmol) were mixed at the room temperature in ethanol (8 mL)/water (2 mL), and then the mixture was stirred at 80° C. for 18 hr. The reaction mixture was cooled down to the room temperature to terminate the reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The title compound was used without further purification (N-(3-chloro-4-fluorophenyl)-N-((5-(hydrazinecarbonyl)pyridin-2-yl)methyl)-4-(oxetan-3-yl)piperazine-1-sulfonamide, 0.053 g, 34.4%, white solid).

[Step 3] Compound 11672

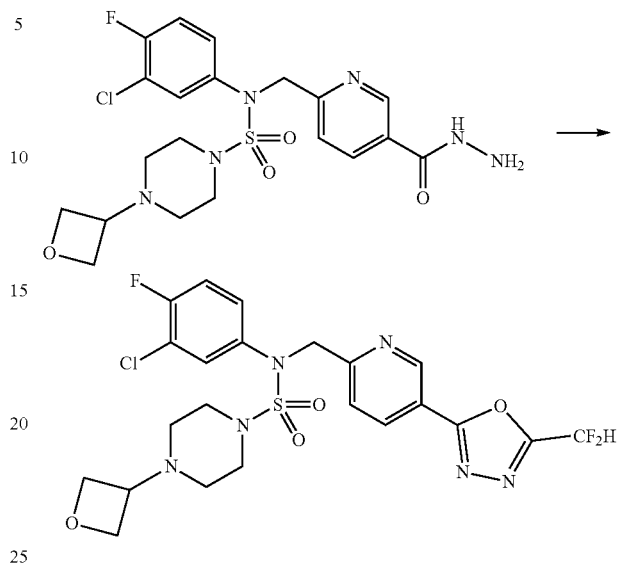

A solution of N-(3-chloro-4-fluorophenyl)-N-((5-(hydrazinecarbonyl)pyridin-2-yl)methyl)-4-(oxetan-3-yl)piperazine-1-sulfonamide (0.053 g, 0.106 mmol) and triethylamine (0.030 mL, 0.212 mmol) in tetrahydrofuran (15 mL) was mixed at the room temperature with 2,2-difluoroacetic anhydride (0.040 mL, 0.319 mmol), and stirred at 80° C. for 1 hr. The reaction mixture was cooled down to the room temperature to terminate the reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (Sift, 12 g cartridge; methanol/dichloromethane=0% to 15%) to give N-(3-chloro-4-fluorophenyl)-N-((5-(5-(difluoromethyl)-1,3,4-oxadiazol-2-yl)pyridin-2-yl) methyl)-4-(oxetan-3-yl)piperazine-1-sulfonamide as white solid (0.032 g, 53.9%).

$^1$H NMR (400 MHz, CDCl$_3$) δ 9.23~9.22 (m, 1H), 8.36 (dd, 1H, J=8.2, 2.2 Hz), 7.61~7.59 (m, 1H), 7.54~7.52 (m, 1H), 7.34~7.30 (m, 1H), 7.13~7.06 (m, 1H), 7.05 (s, 0.25H), 6.92 (s, 0.5H), 6.80 (s, 0.25H), 5.01 (s, 2H), 4.65~4.62 (m, 2H), 4.56~4.53 (m, 2H), 3.50~3.42 (m, 1H), 3.40~3.20 (m, 4H), 2.40~2.20 (m, 4H); LRMS (ES) m/z 559.2 (M$^+$+1).

Example 57: Compound 11673, N-(4-(5-(difluoromethyl)-1,3,4-oxadiazol-2-yl)benzyl)-4-isopropyl-N-phenylpiperazine-1-sulfonamide

[Step 1] methyl 4-(((4-isopropyl-N-phenylpiperazine)-1-sulfonamido)methyl)benzoate

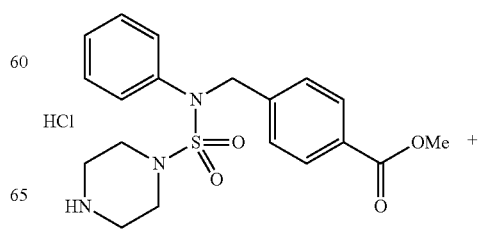

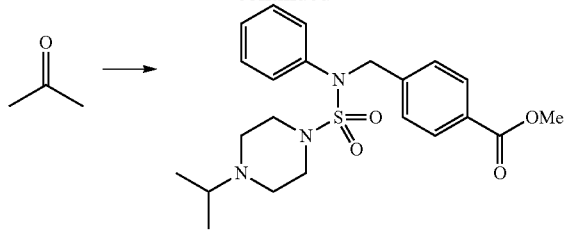

A solution of methyl 4-((N-phenylpiperazine-1-sulfonamido)methyl)benzoate hydrochloride (0.150 g, 0.352 mmol) and propan-2-one (0.039 mL, 0.528 mmol) in dichloromethane (10 mL) was mixed at the room temperature with sodium triacetoxyborohydride (0.149 g, 0.704 mmol). The reaction mixture was stirred at the same temperature for 18 hr. Then, water was added to the reaction mixture, followed by extraction with ethyl acetate. The organic layer was washed with aqueous saturated sodium chloride solution, dried with anhydrous MgSO₄, filtered, and concentrated in vacuo. The residue was chromatographed (SiO₂, 12 g cartridge; methanol/dichloromethane=0% to 15%) to give methyl 4-(((4-isopropyl-N-phenylpiperazine)-1-sulfonamido)methyl)benzoate as white solid (0.142 g, 93.4%).

[Step 2] N-(4-(hydrazinecarbonyl)benzyl)-4-isopropyl-N-phenylpiperazine-1-sulfonamide

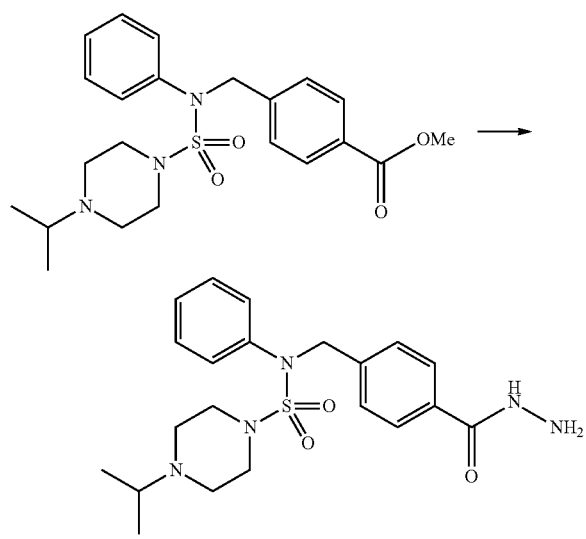

methyl 4-(((4-isopropyl-N-phenylpiperazine)-1-sulfonamido)methyl)benzoate (0.149 g, 0.345 mmol) and hydrazine monohydrate (0.503 mL, 10.358 mmol) were mixed at the room temperature in ethanol (8 mL)/water (2 mL), and then the mixture was stirred at 80° C. for 18 hr. The reaction mixture was cooled down to the room temperature to terminate the reaction. Then, water was added to the reaction mixture, followed by extraction with ethyl acetate. The organic layer was washed with aqueous saturated sodium chloride solution, dried with anhydrous MgSO₄, filtered, and concentrated in vacuo. The title compound was used without further purification (N-(4-(hydrazinecarbonyl)benzyl)-4-isopropyl-N-phenylpiperazine-1-sulfonamide, 0.135 g, 90.6%, white solid).

[Step 3] Compound 11673

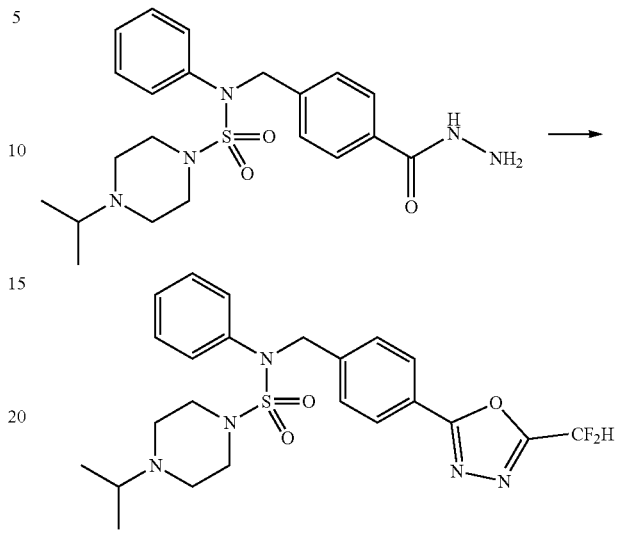

A solution of N-(4-(hydrazinecarbonyl)benzyl)-4-isopropyl-N-phenylpiperazine-1-sulfonamide (0.135 g, 0.313 mmol) and triethylamine (0.087 mL, 0.626 mmol) in tetrahydrofuran (15 mL) was mixed at the room temperature with 2,2-difluoroacetic anhydride (0.117 mL, 0.938 mmol), and stirred at 80° C. for 1 hr. The reaction mixture was cooled down to the room temperature to terminate the reaction. Then, water was added to the reaction mixture, followed by extraction with ethyl acetate. The organic layer was washed with aqueous saturated sodium chloride solution, dried with anhydrous MgSO₄, filtered, and concentrated in vacuo. The residue was chromatographed (SiO₂, 12 g cartridge; methanol/dichloromethane=0% to 15%) to give N-(4-(5-(difluoromethyl)-1,3,4-oxadiazol-2-yl)benzyl)-4-isopropyl-N-phenylpiperazine-1-sulfonamide as white solid (0.108 g, 70.2%).

¹H NMR (400 MHz, CDCl₃) δ 8.01~7.99 (m, 2H), 7.42~7.40 (m, 2H), 7.30~7.22 (m, 5H), 7.02 (s, 0.25H), 6.89 (s, 0.5H), 6.76 (s, 0.25H), 4.89 (s, 2H), 3.50~3.10 (m, 4H), 3.00~2.20 (m, 5H), 1.80~1.40 (m, 1H), 1.20~0.82 (m, 5H); LRMS (ES) m/z 492.3 (M⁺+1).

Example 58: Compound 11674, 4-cyclobutyl-N-(4-(5-(difluoromethyl)-1,3,4-oxadiazol-2-yl)benzyl)-N-phenylpiperazine-1-sulfonamide

[Step 1] methyl 4-(((4-cyclobutyl-N-phenylpiperazine)-1-sulfonamido)methyl)benzoate

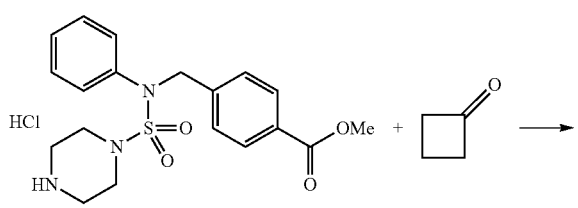

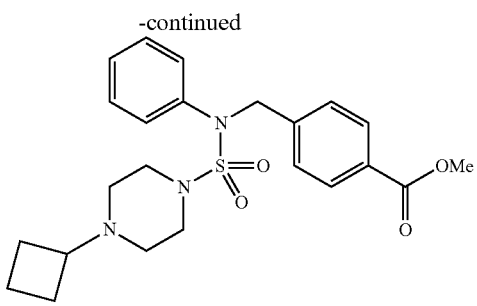

A solution of methyl 4-((N-phenylpiperazine-1-sulfonamido)methyl)benzoate hydrochloride (0.150 g, 0.352 mmol) and cyclobutanone (0.039 mL, 0.528 mmol) in dichloromethane (15 mL) was mixed at the room temperature with sodium triacetoxyborohydride (0.149 g, 0.704 mmol). The reaction mixture was stirred at the same temperature for 18 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 12 g cartridge; methanol/dichloromethane=0% to 15%) to give methyl 4-(((4-cyclobutyl-N-phenylpiperazine)-1-sulfonamido)methyl)benzoate as white solid (0.154 g, 98.6%).

[Step 2] 4-cyclobutyl-N-(4-(hydrazinecarbonyl)benzyl)-N-phenylpiperazine-1-sulfonamide

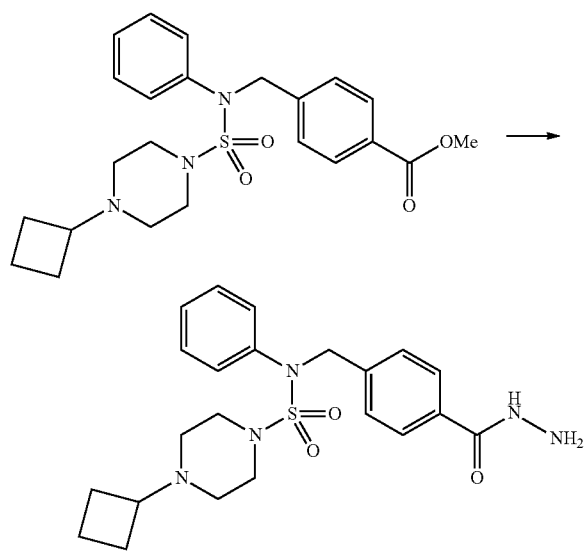

methyl 4-(((4-cyclobutyl-N-phenylpiperazine)-1-sulfonamido)methyl)benzoate (0.154 g, 0.347 mmol) and hydrazine monohydrate (0.506 mL, 10.416 mmol) were mixed at the room temperature in ethanol (8 mL)/water (2 mL), and then the mixture was stirred at 80° C. for 18 hr. The reaction mixture was cooled down to the room temperature to terminate the reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The title compound was used without further purification (4-cyclobutyl-N-(4-(hydrazinecarbonyl)benzyl)-N-phenylpiperazine-1-sulfonamide, 0.140 g, 90.9%, white solid).

[Step 3] Compound 11674

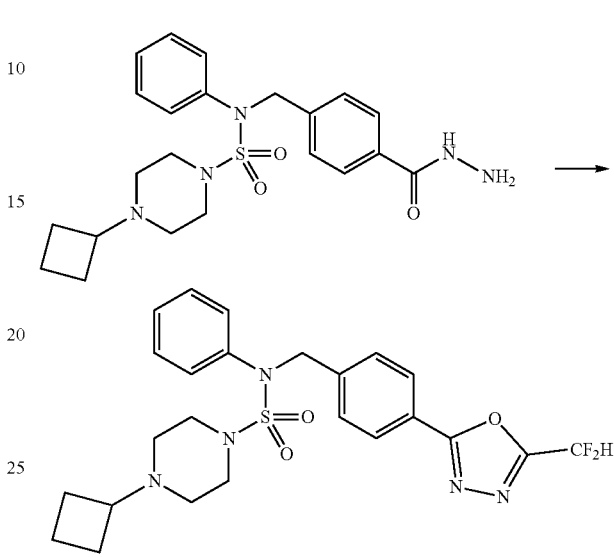

A solution of 4-cyclobutyl-N-(4-(hydrazinecarbonyl)benzyl)-N-phenylpiperazine-1-sulfonamide (0.140 g, 0.316 mmol) and triethylamine (0.088 mL, 0.631 mmol) in tetrahydrofuran (15 mL) was mixed at the room temperature with 2,2-difluoroacetic anhydride (0.118 mL, 0.947 mmol), and stirred at 80° C. for 1 hr. The reaction mixture was cooled down to the room temperature to terminate the reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 12 g cartridge; methanol/dichloromethane=0% to 15%) to give 4-cyclobutyl-N-(4-(5-(difluoromethyl)-1,3,4-oxadiazol-2-yl)benzyl)-N-phenylpiperazine-1-sulfonamide as white solid (0.085 g, 53.5%).

$^1$H NMR (400 MHz, CDCl$_3$) δ 8.01~7.99 (m, 2H), 7.41~7.39 (m, 2H), 7.32~7.23 (m, 5H), 7.02 (s, 0.25H), 6.89 (s, 0.5H), 6.76 (s, 0.25H), 4.88 (s, 2H), 3.71~3.08 (m, 4H), 2.40~2.20 (m, 3H), 2.20~2.00 (m, 3H), 2.00~1.40 (m, 5H); LRMS (ES) m/z 503.9 (M$^+$+1).

Example 59: Compound 11702, 2-((4-(((N-methyl-N-(2-(4-methylpiperazin-1-yl)ethyl)sulfamoyl)(phenyl)amino)methyl))phenyl)-5-(difluoromethyl)-1,3,4-oxadiazole

[Step 1] tert-butyl 4-(2-hydroxyethyl)piperazine-1-carboxylate

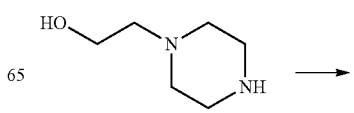

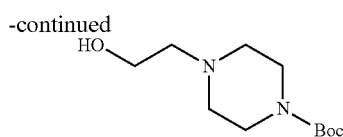

A solution of 2-(piperazin-1-yl)ethan-1-ol (0.943 mL, 7.681 mmol) and di-tert-butyl dicarbonate (1.760 g, 8.065 mmol) in tetrahydrofuran (5 mL) was stirred at the room temperature for 18 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 24 g cartridge; methanol/dichloromethane=0% to 10%) to give tert-butyl 4-(2-hydroxyethyl)piperazine-1-carboxylate as colorless oil (1.750 g, 98.9%).

[Step 2] tert-butyl 4-(2-((methylsulfonyl)oxy)ethyl)piperazine-1-carboxylate

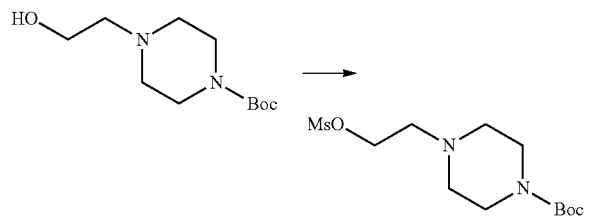

A solution of tert-butyl 4-(2-hydroxyethyl)piperazine-1-carboxylate (1.750 g, 7.598 mmol), methanesulfonyl chloride (0.706 mL, 9.118 mmol) and triethylamine (1.589 mL, 11.398 mmol) in dichloromethane (20 mL) was stirred at the room temperature for 18 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (Sift, 24 g cartridge; methanol/dichloromethane=0% to 10%) to give tert-butyl 4-(2-((methylsulfonyl)oxy)ethyl)piperazine-1-carboxylate as white solid (1.850 g, 78.9%).

[Step 3] methyl 4-((phenylamino)methyl)benzoate

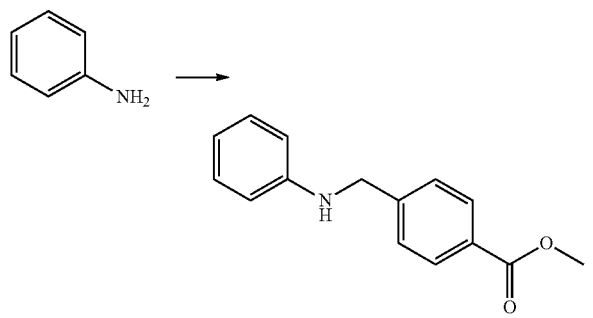

A solution of aniline (4.902 mL, 53.688 mmol), methyl 4-(bromomethyl)benzoate (13.528 g, 59.057 mmol), potassium iodide (4.456 g, 26.844 mmol) and potassium carbonate (11.130 g, 80.533 mmol) in N,N-dimethylformide (50 mL) was stirred at the room temperature for 18 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 80 g cartridge; ethyl acetate/hexane=0% to 25%) to give methyl 4-((phenylamino)methyl)benzoate as yellow liquid (7.800 g, 60.2%).

[Step 4] methyl 4-(((N-(tert-butoxycarbonyl)sulfamoyl)(phenyl)amino)methyl)benzoate

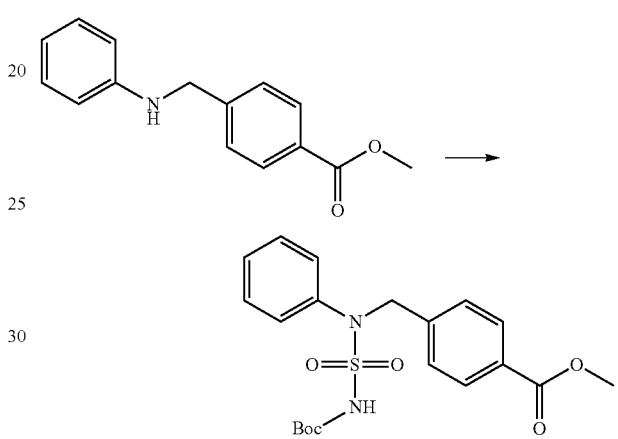

A solution of chloro sulfonylisocyanate (0.704 g, 4.973 mmol) and tert-butanol (0.456 mL, 4.766 mmol) in dichloromethane (20 mL) was stirred at 0° C. for 1 hr, and mixed with methyl 4-((phenylamino)methyl)benzoate (1.000 g, 4.144 mmol) and triethylamine (0.866 mL, 6.217 mmol). The reaction mixture was stirred at the room temperature for additional 18 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 40 g cartridge; ethyl acetate/hexane=0% to 30%) to give methyl 4-(((N-(tert-butoxycarbonyl)sulfamoyl)(phenyl)amino)methyl)benzoate as white solid (1.190 g, 68.3%).

[Step 5] methyl 4-(((N-(tert-butoxycarbonyl)-N-methylsulfamoyl)(phenyl)amino)methyl)benzoate

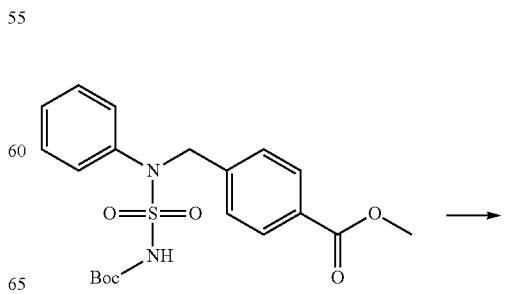

-continued

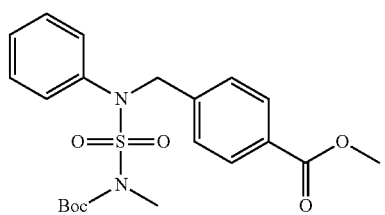

To a solution of methyl 4-(((N-(tert-butoxycarbonyl)sulfamoyl)(phenyl)amino)methyl)benzoate (1.400 g, 3.330 mmol) in N,N-dimethylformide (5 mL) was slowly added sodium hydride (60.00%, 0.200 g, 4.994 mmol) at 0° C., and the mixture was stirred for 0.5 hr. The reaction mixture was treated with iodomethane (0.311 mL, 4.994 mmol), and stirred at the room temperature for additional 3 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (Sift, 40 g cartridge; ethyl acetate/hexane=0% to 30%) to give methyl 4-(((N-(tert-butoxycarbonyl)-N-methylsulfamoyl)(phenyl)amino)methyl)benzoate as white solid (1.095 g, 75.7%).

[Step 6] methyl 4-(((N-methylsulfamoyl)(phenyl)amino)methyl)benzoate

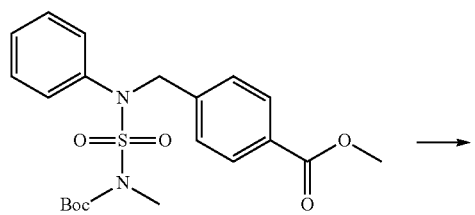

A solution of methyl 4-(((N-(tert-butoxycarbonyl)-N-methylsulfamoyl)(phenyl)amino)methyl)benzoate (1.095 g, 2.520 mmol) and hydrochloric acid (4.00 M solution 1,4-dioxane, 6.300 mL, 25.201 mmol) in 1,4-dioxane (3 mL) was stirred at the room temperature for 18 hr, and concentrated under the reduced pressure to remove the solvent. The residue was diluted with diethylether (20 mL), and stirred. The resulting precipitates were collected by filtration and dried to give methyl 4-(((N-methylsulfamoyl)(phenyl)amino)methyl)benzoate as white solid (0.711 g, 84.4%).

[Step 7] tert-butyl 4-(2-4N-(4-(methoxycarbonyl)benzyl)-N-phenylsulfamoyl)(methyl)amino)ethyl)piper azine-1-carboxylate

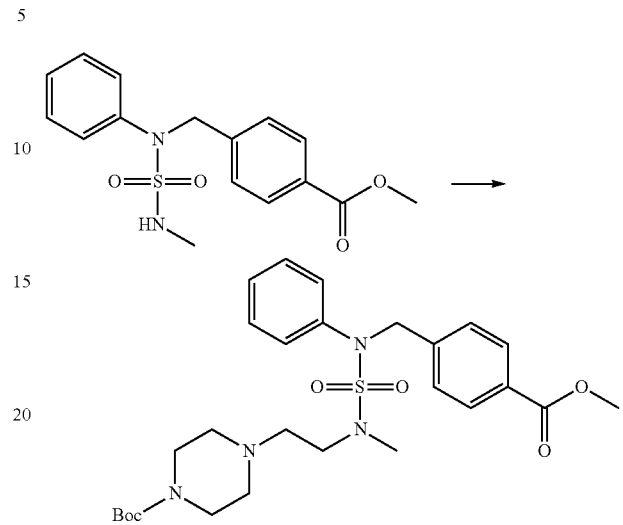

A solution of methyl 4-(((N-methylsulfamoyl)(phenyl)amino)methyl)benzoate (0.711 g, 2.126 mmol), tert-butyl 4-(2-((methylsulfonyl)oxy)ethyl)piperazine-1-carboxylate (0.787 g, 2.552 mmol) and sodium hydride (60.00%, 0.102 g, 2.552 mmol) in N,N-dimethylformide (5 mL) was stirred at the room temperature for 18 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 40 g cartridge; ethyl acetate/hexane=0% to 80%) to give tert-butyl 4-(2-4N-(4-(methoxycarbonyl)benzyl)-N-phenylsulfamoyl)(methyl)amino)ethyl)piper azine-1-carboxylate as colorless liquid (0.732 g, 62.9%).

[Step 8] methyl 4-(((N-methyl-N-(2-(piperazin-1-yl)ethyl)sulfamoyl)(phenyl)amino)methyl)benzoate Hydrochloride

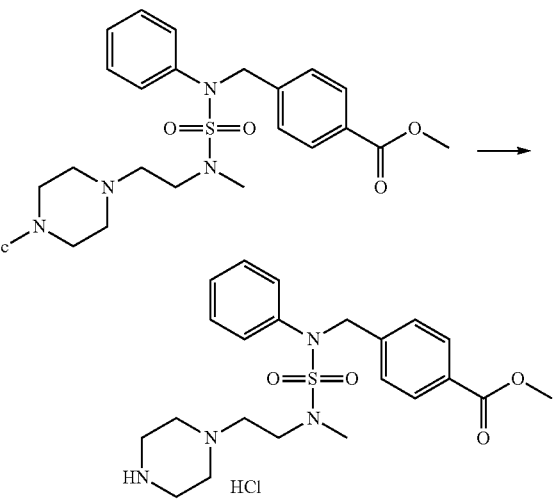

A solution of tert-butyl 4-(2-4N-(4-(methoxycarbonyl)benzyl)-N-phenylsulfamoyl)(methyl)amino)ethyl)piperazine-1-carboxylate (0.732 g, 1.338 mmol) and hydrochloric acid (4.00 M solution 1,4-dioxane, 3.345 mL, 13.381 mmol) in 1,4-dioxane (10 mL) was stirred at the room temperature for 18 hr, and concentrated under the reduced pressure to remove the solvent. The residue was diluted with diethylether (20 mL) and stirred. The resulting precipitates were collected by filtration and dried to give methyl 4-(((N-methyl-N-(2-(piperazin-1-yl)ethyl)sulfamoyl)(phenyl)amino)methyl)benzoate hydrochloride as ivory solid (0.480 g, 74.3%).

[Step 9] methyl 4-(((N-methyl-N-(2-(4-methylpiperazin-1-yl)ethyl)sulfamoyl)(phenyl)amino)methyl)benzoate

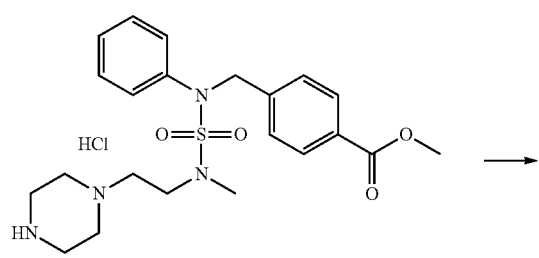

A solution of methyl 4-(((N-methyl-N-(2-(piperazin-1-yl)ethyl)sulfamoyl)(phenyl)amino)methyl)benzoate hydrochloride (0.080 g, 0.166 mmol) and paraformaldehyde (0.010 g, 0.331 mmol) in dichloromethane (5 mL) was stirred at the room temperature for 0.5 hr, and mixed with sodium triacetoxyborohydride (0.070 g, 0.331 mmol). The reaction mixture was stirred at the same temperature for additional 18 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 12 g cartridge; methanol/dichloromethane=0% to 10%) to give methyl 4-(((N-methyl-N-(2-(4-methylpiperazin-1-yl)ethyl)sulfamoyl)(phenyl)amino)methyl)benzoate as colorless oil (0.054 g, 70.8%).

[Step 10] 4-(((N-methyl-N-(2-(4-methylpiperazin-1-yl)ethyl)sulfamoyl)(phenyl)amino)methyl)benzohydrazide

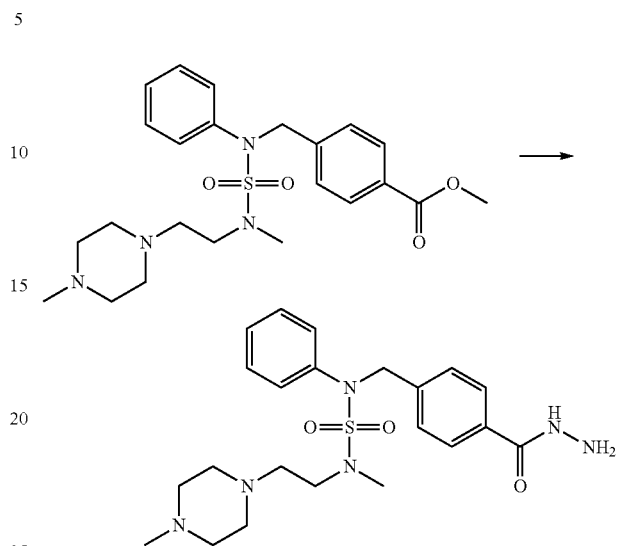

A solution of methyl 4-(((N-methyl-N-(2-(4-methylpiperazin-1-yl)ethyl)sulfamoyl)(phenyl)amino)methyl)benzoate (0.054 g, 0.117 mmol) and hydrazine monohydrate (0.057 mL, 1.172 mmol) in ethanol (3 mL) was stirred at 80° C. for 18 hr, and cooled down to the room temperature to terminate the reaction. The reaction mixture was concentrated under the reduced pressure to remove the solvent. The residue was diluted with sodium bicarbonate (5 mL) and stirred. The resulting precipitates were collected by filtration and dried to give 4-(((N-methyl-N-(2-(4-methylpiperazin-1-yl)ethyl)sulfamoyl)(phenyl)amino)methyl)benzohydrazide as white solid (0.025 g, 46.3%).

[Step 11] Compound 11702

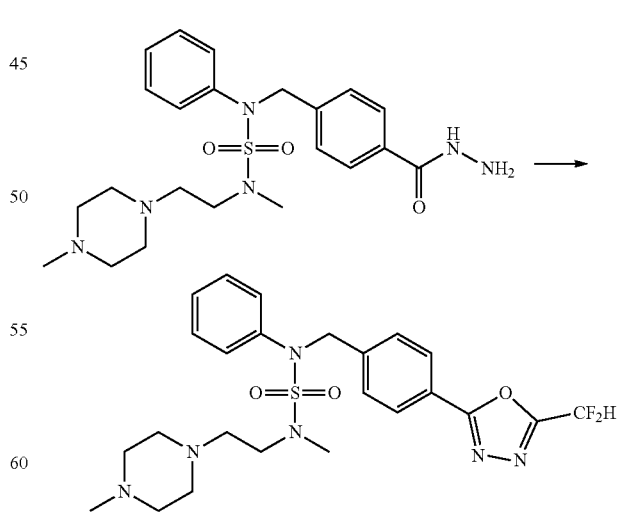

A solution of 4-(((N-methyl-N-(2-(4-methylpiperazin-1-yl)ethyl)sulfamoyl)(phenyl)amino)methyl)benzohydrazide (0.025 g, 0.054 mmol), 2,2-difluoroacetic anhydride (0.067 mL, 0.543 mmol) and triethylamine (0.038 mL, 0.271 mmol) in tetrahydrofuran (5 mL) was stirred at 80° C. for 1 hr, and cooled down to the room temperature to terminate the reaction. Then, saturated aqueous sodium bicarbonate solution was added to the reaction mixture, followed by extraction with dichloromethane. The bi-phasic mixture was passed through a plastic frit to remove the solid residue and the aqueous layer, and the organic layer collected was concentrated in vacuo. The residue was chromatographed (SiO$_2$, 4 g cartridge; methanol/dichloromethane=0% to 10%) to give 2-((4-(((N-methyl-N-(2-(4-methylpiperazin-1-yl)ethyl)sulfamoyl)(phenyl)amino)methyl))phenyl)-5-(difluoromethyl)-1,3,4-oxadiazole as colorless oil (0.023 g, 81.4%).

$^1$H NMR (400 MHz, CD$_3$OD) δ8.01 (d, 2H, J=8.4 Hz), 7.53 (d, 2H, J=8.4 Hz), 7.54~7.25 (m, 6H), 7.22 (t, 1H, J=51.5 Hz), 5.00 (s, 2H), 3.23 (t, 2H, J=6.9 Hz), 2.88 (s, 3H), 2.47~2.43 (m, 10H), 2.27 (s, 3H); LRMS (ES) m/z 521.4 (M$^+$+1)

Example 60: Compound 11704, 2-((4-(((N-methyl-N-(2-(4-(oxetan-3-yl)piperazin-1-yl)ethyl)sulfamoyl)(phenyl)amino) methyl))phenyl)-5-(difluoromethyl)-1,3,4-oxadiazole

[Step 1] methyl 4-(((N-methyl-N-(2-(4-(oxetan-3-yl)piperazin-1-yl)ethyl)sulfamoyl)(phenyl)amino)methyl)benzoate

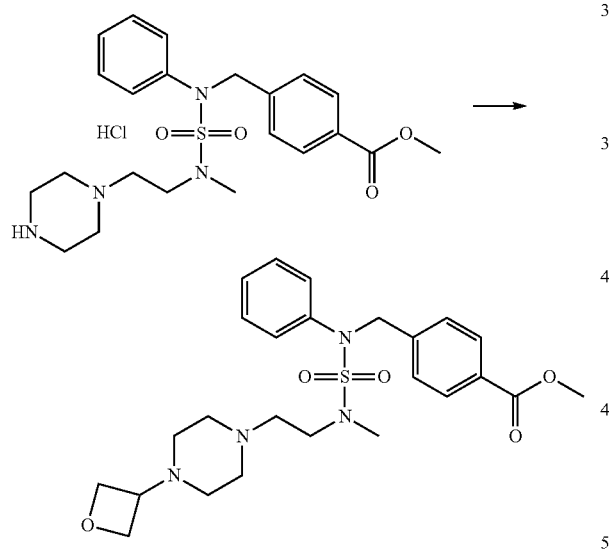

A solution of methyl 4-(((N-methyl-N-(2-(piperazin-1-yl)ethyl)sulfamoyl)(phenyl)amino)methyl)benzoate hydrochloride (0.080 g, 0.166 mmol) and oxetan-3-one (0.024 g, 0.331 mmol) in dichloromethane (5 mL) was stirred at the room temperature for 0.5 hr, and mixed with sodium triacetoxyborohydride (0.070 g, 0.331 mmol). The reaction mixture was stirred at the same temperature for additional 18 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 12 g cartridge; methanol/dichloromethane=0% to 10%) to give methyl 4-(((N-methyl-N-(2-(4-(oxetan-3-yl)piperazin-1-yl)ethyl)sulfamoyl)(phenyl)amino)methyl)benzoate as colorless liquid (0.075 g, 90.6%).

[Step 2] 4-(((N-methyl-N-(2-(4-(oxetan-3-yl)piperazin-1-yl)ethyl)sulfamoyl)(phenyl)amino)methyl)benzohydrazide

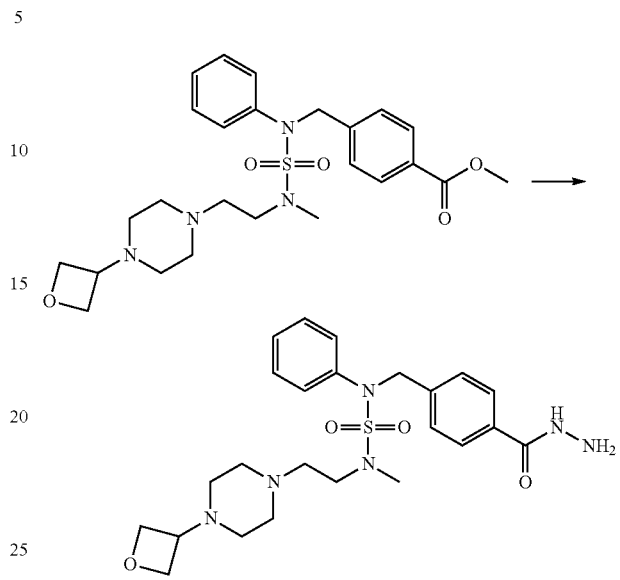

A solution of methyl 4-(((N-methyl-N-(2-(4-(oxetan-3-yl)piperazin-1-yl)ethyl)sulfamoyl)(phenyl)amino)methyl)benzoate (0.075 g, 0.150 mmol) and hydrazine monohydrate (0.073 mL, 1.500 mmol) in ethanol (3 mL) was stirred at 80° C. for 18 hr, and cooled down to the room temperature to terminate the reaction. The reaction mixture was concentrated under the reduced pressure to remove the solvent. The crude product was used without further purification (4-(((N-methyl-N-(2-(4-(oxetan-3-yl)piperazin-1-yl)ethyl)sulfamoyl)(phenyl)amino)methyl)benzohydrazide, 0.071 g, 94.2%, colorless liquid).

[Step 3] Compound 11704

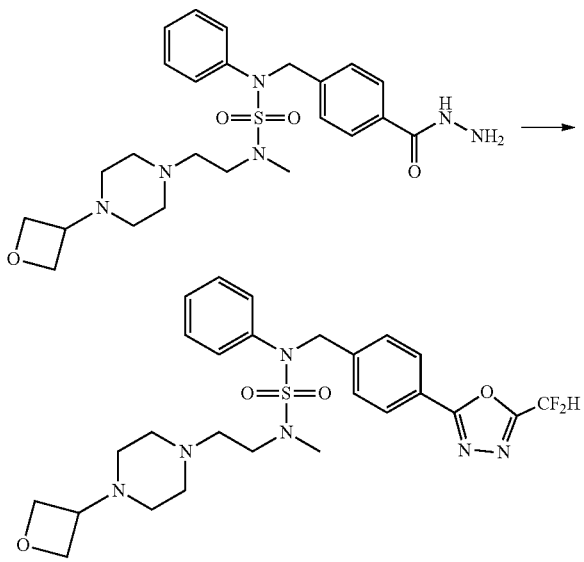

A solution of 4-(((N-methyl-N-(2-(4-(oxetan-3-yl)piperazin-1-yl)ethyl)sulfamoyl)(phenyl)amino)methyl)benzohydrazide (0.071 g, 0.141 mmol), 2,2-difluoroacetic anhydride (0.176 mL, 1.413 mmol) and triethylamine (0.098 mL, 0.706 mmol) in tetrahydrofuran (5 mL) was stirred at 80° C. for 1 hr, and cooled down to the room temperature to terminate the reaction. Then, saturated aqueous sodium bicarbonate solution was added to the reaction mixture, followed by extraction with dichloromethane. The bi-phasic mixture was passed through a plastic frit to remove the solid residue and the aqueous layer, and the organic layer collected was concentrated in vacuo. The residue was chromatographed (Sift, 4 g cartridge; methanol/dichloromethane=0% to 10%) to give 2-((4-(((N-methyl-N-(2-(4-(oxetan-3-yl)piperazin-1-yl)ethyl)sulfamoyl)(phenyl)amino) methyl))phenyl)-5-(difluoromethyl)-1,3,4-oxadiazole as yellow liquid (0.031 g, 39.0%).

$^1$H NMR (400 MHz, CD$_3$OD) δ8.01 (dt, 1H, J=8.6, 1.8 Hz), 7.53 (dt, 1H, J=2.5, 1.8 Hz), 7.41~7.32 (m, 4H), 7.29~7.25 (m, 1H), 7.22 (t, 1H, J=51.6 Hz), 4.99 (s, 2H), 4.67 (t, 2H, J=6.8 Hz), 4.57 (t, 2H, J=6.3 Hz), 3.50~3.44 (m, 1H), 3.23 (t, 2H, J=6.9 Hz), 2.87 (s, 3H), 2.52~2.45 (m, 4H), 2.47 (t, 2H, J=6.9 Hz), 2.36~2.33 (m, 4H); LRMS (ES) m/z 563.4 (M$^+$+1)

Example 61: Compound 11713, 2-((4-(((N-methyl-N-(2-(4-acetylpiperazin-1-yl)ethyl)sulfamoyl)(phenyl)amino)methyl))phenyl)-5-(difluoromethyl)-1,3,4-oxadiazole

[Step 1] methyl 4-(((N-(2-(4-acetylpiperazin-1-yl)ethyl)-N-methylsulfamoyl)(phenyl)amino)methyl)benzoate

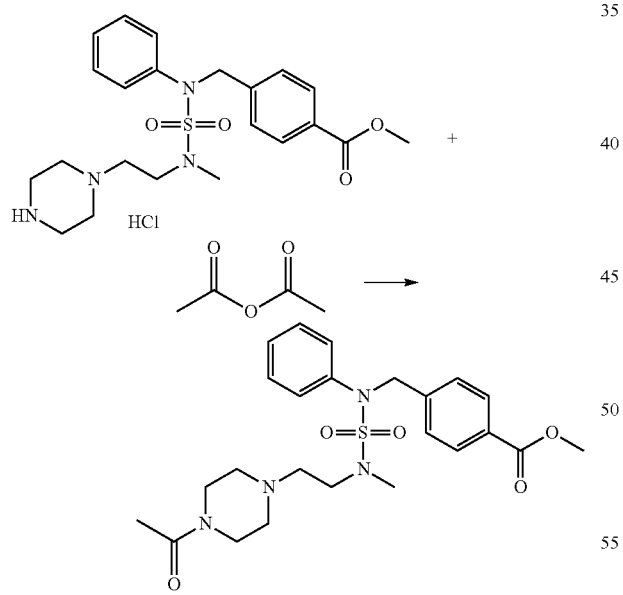

A solution of methyl 4-(((N-methyl-N-(2-(piperazin-1-yl)ethyl)sulfamoyl)(phenyl)amino)methyl)benzoate hydrochloride (0.040 g, 0.083 mmol), triethylamine (0.023 mL, 0.166 mmol) and acetic anhydride (0.017 g, 0.166 mmol) in dichloromethane (2 mL) was stirred at the room temperature for 2 hr. Then, water was added to the reaction mixture, followed by extraction with dichloromethane. The bi-phasic mixture was passed through a plastic frit to remove the solid residue and the aqueous layer, and the organic layer collected was concentrated in vacuo. The residue was chromatographed (SiO$_2$, 4 g cartridge; ethyl acetate/hexane=0% to 30%) to give methyl 4-(((N-(2-(4-acetylpiperazin-1-yl)ethyl)-N-methylsulfamoyl)(phenyl)amino)methyl)benzoate as colorless liquid (0.039 g, 96.4%).

[Step 2] 4-(((N-methyl-N-(2-(4-acetylpiperazin-1-yl)ethyl)sulfamoyl)(phenyl)amino)methyl)benzohydrazide

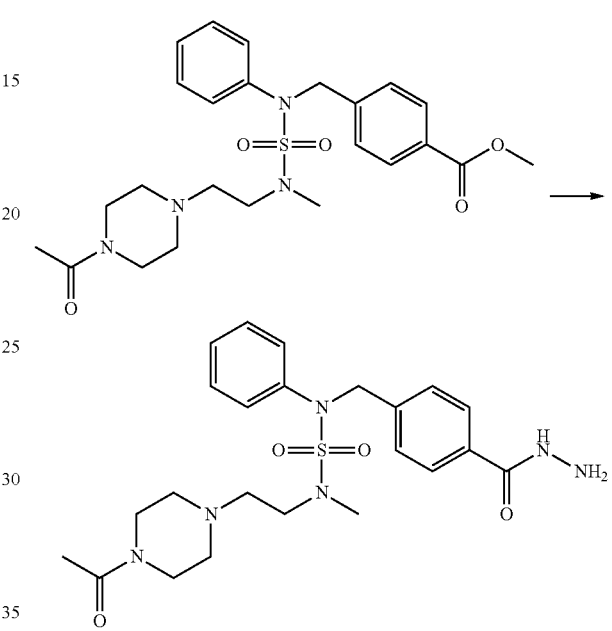

A solution of methyl 4-(((N-(2-(4-acetylpiperazin-1-yl)ethyl)-N-methylsulfamoyl)(phenyl)amino)methyl)benzoate (0.039 g, 0.080 mmol) and hydrazine monohydrate (0.039 mL, 0.798 mmol) in ethanol (2 mL) was stirred at 80° C. for 18 hr, and cooled down to the room temperature to terminate the reaction. The reaction mixture was concentrated under the reduced pressure to remove the solvent. The residue was diluted with aqueous saturated sodium bicarbonate solution (5 mL) and stirred. The resulting precipitates were collected by filtration, washed by hexane, and dried to give 4-(((N-methyl-N-(2-(4-acetylpiperazin-1-yl)ethyl)sulfamoyl)(phenyl)amino)methyl)benzohydrazide as yellow oil (0.037 g, 95.1%).

[Step 3] Compound 11713

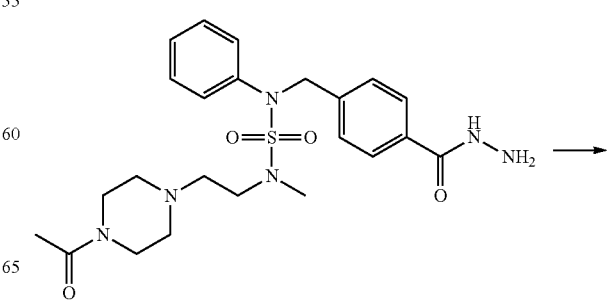

151

-continued

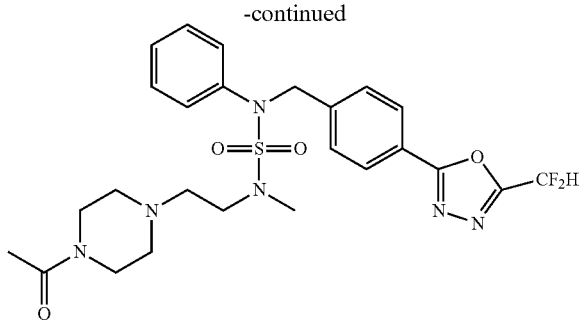

A solution of 4-(((N-methyl-N-(2-(4-acetylpiperazin-1-yl)ethyl)sulfamoyl)(phenyl)amino)methyl)benzohydrazide (0.037 g, 0.076 mmol), 2,2-difluoroacetic anhydride (0.019 mL, 0.152 mmol) and triethylamine (0.021 mL, 0.152 mmol) in tetrahydrofuran (2 mL) was stirred at 80° C. for 0.5 hr, and cooled down to the room temperature to terminate the reaction. Then, saturated aqueous sodium bicarbonate solution was added to the reaction mixture, followed by extraction with dichloromethane. The bi-phasic mixture was passed through a plastic frit to remove the solid residue and the aqueous layer, and the organic layer collected was concentrated in vacuo. The residue was chromatographed (SiO₂, 4 g cartridge; methanol/dichloromethane=0% to 5%) to give 2-((4-(((N-methyl-N-(2-(4-acetylpiperazin-1-yl)ethyl)sulfamoyl)(phenyl)amino)methyl))phenyl)-5-(difluoromethyl)-1,3,4-oxadiazole as yellow liquid (0.009 g, 21.6%).

$^1$H NMR (400 MHz, CD$_3$OD) δ8.02 (d, 2H, J=8.4 Hz), 7.53 (d, 2H, J=8.4 Hz), 7.42~7.26 (m, 5H), 7.22 (t, 1H, J=51.6 Hz), 5.01 (s, 2H), 3.55 (t, 2H, J=5.0 Hz), 3.51 (t, 2H, J=5.0 Hz), 3.26 (t, 2H, J=6.6 Hz), 2.89 (s, 3H), 2.52~2.49 (m, 4H), 2.44 (t, 2H, J=5.0 Hz), 2.09 (s, 3H); LRMS (ES) m/z 549.4 (M$^+$+1)

Example 62: Compound 11714, 2-((4-(((N-methyl-N-(2-(4-(methylsulfonyl)piperazin-1-yl)ethyl)sulfamoyl)(phenyl)amino)methyl))phenyl)-5-(difluoromethyl)-1,3,4-oxadiazole

[Step 1] methyl 4-(((N-methyl-N-(2-(4-(methylsulfonyl)piperazin-1-yl)ethyl)sulfamoyl)(phenyl)amino) methyl)benzoate

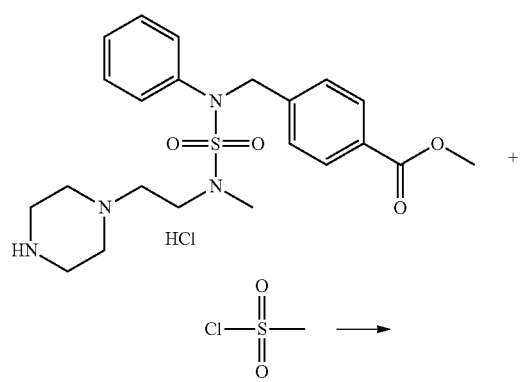

152

-continued

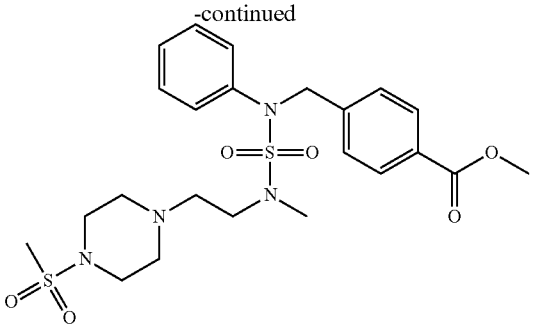

A solution of methyl 4-(((N-methyl-N-(2-(piperazin-1-yl)ethyl)sulfamoyl)(phenyl)amino)methyl)benzoate hydrochloride (0.040 g, 0.083 mmol), triethylamine (0.023 mL, 0.166 mmol) and methanesulfonyl chloride (0.013 mL, 0.166 mmol) in dichloromethane (2 mL) was stirred at the room temperature for 2 hr. Then, water was added to the reaction mixture, followed by extraction with dichloromethane. The bi-phasic mixture was passed through a plastic frit to remove the solid residue and the aqueous layer, and the organic layer collected was concentrated in vacuo. The residue was chromatographed (SiO₂, 4 g cartridge; ethyl acetate/hexane=0% to 30%) to give methyl 4-(((N-methyl-N-(2-(4-(methylsulfonyl)piperazin-1-yl)ethyl)sulfamoyl)(phenyl)amino) methyl)benzoate as yellow solid (0.043 g, 99.0%).

[Step 2] 4-(((N-methyl-N-(2-(4-(methylsulfonyl)piperazin-1-yl)ethyl)sulfamoyl)(phenyl)amino)methyl)benzohydrazide

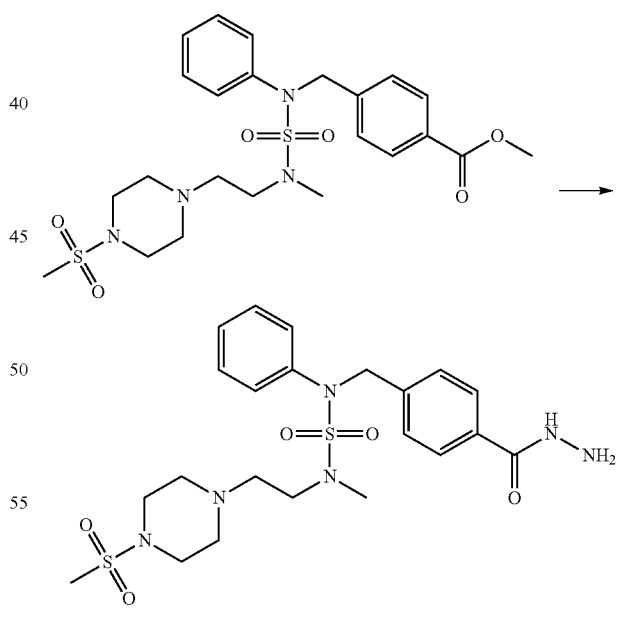

A solution of methyl 4-(((N-methyl-N-(2-(4-(methylsulfonyl)piperazin-1-yl)ethyl)sulfamoyl)(phenyl)amino) methyl)benzoate (0.043 g, 0.082 mmol) and hydrazine monohydrate (0.040 mL, 0.820 mmol) in ethanol (2 mL) was stirred at 80° C. for 18 hr, and cooled down to the room temperature to terminate the reaction. The reaction mixture was concentrated under the reduced pressure to remove the solvent. The residue was diluted with aqueous saturated sodium bicarbonate solution (5 mL) and stirred. The resulting precipitates were collected by filtration and dried to give 4-(((N-methyl-N-(2-(4-(methylsulfonyl)piperazin-1-yl)ethyl)sulfamoyl)(phenyl)amino) methyl)benzohydrazide as colorless liquid (0.039 g, 90.7%).

[Step 3] Compound 11714

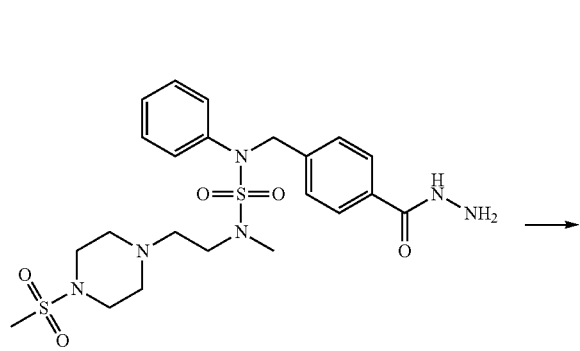

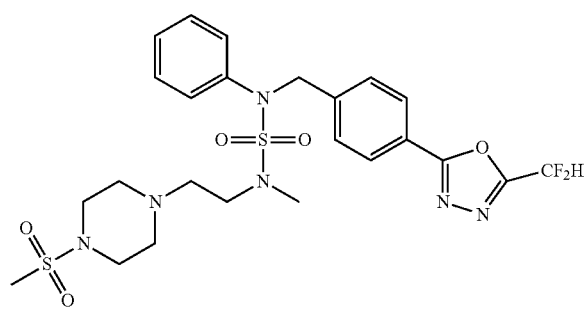

A solution of 4-(((N-methyl-N-(2-(4-(methylsulfonyl)piperazin-1-yl)ethyl)sulfamoyl)(phenyl)amino) methyl)benzohydrazide (0.039 g, 0.074 mmol), 2,2-difluoroacetic anhydride (0.018 mL, 0.149 mmol) and triethylamine (0.021 mL, 0.149 mmol) in tetrahydrofuran (2 mL) was stirred at 80° C. for 0.5 hr, and cooled down to the room temperature to terminate the reaction. Then, saturated aqueous sodium bicarbonate solution was added to the reaction mixture, followed by extraction with dichloromethane. The bi-phasic mixture was passed through a plastic frit to remove the solid residue and the aqueous layer, and the organic layer collected was concentrated in vacuo. The residue was chromatographed (SiO₂, 4 g cartridge; methanol/dichloromethane=0% to 5%) to give 2-((4-(((N-methyl-N-(2-(4-(methylsulfonyl)piperazin-1-yl)ethyl)sulfamoyl)(phenyl)amino)methyl))phenyl)-5-(difluoromethyl)-1,3,4-oxadiazole as yellow oil (0.011 g, 25.3%).

$^1$H NMR (400 MHz, CD₃OD) δ8.02 (d, 2H, J=8.5 Hz), 7.54 (d, 2H, J=8.6 Hz), 7.42~7.26 (m, 5H), 7.22 (t, 1H, J=51.7 Hz), 5.00 (s, 2H), 3.24 (t, 2H, J=6.6 Hz), 3.19~3.17 (m, 4H), 2.89 (s, 3H), 2.81 (s, 3H), 2.56~2.54 (m, 4H), 2.50 (t, 2H, J=6.6 Hz); LRMS (ES) m/z 585.3 (M⁺+1)

Example 63: Compound 11787, N-(4-(5-(difluoromethyl)-1,3,4-oxadiazol-2-yl)benzyl)-N-phenyl-2,7-diazaspiro[3.5]nonane-7-sulfonamide Hydrochloride

[Step 1] tert-butyl 7-((1H-imidazol-1-yl)sulfonyl)-2,7-diazaspiro[3.5]nonane-2-carboxylate

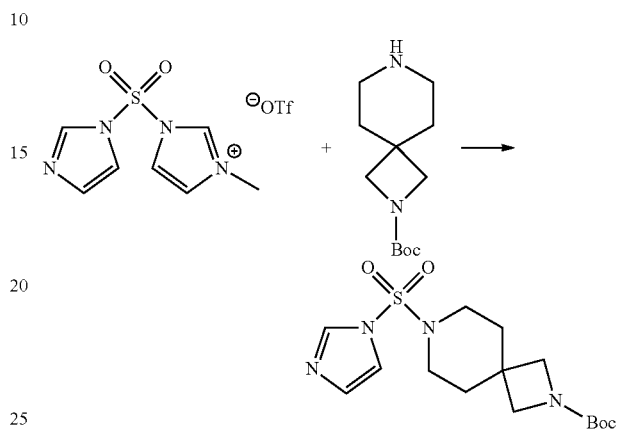

A solution of 1-((1H-imidazol-1-yl)sulfonyl)-3-methyl-1H-imidazol-3-ium trifluoromethanesulfonate (2.000 g, 5.520 mmol) and tert-butyl 2,7-diazaspiro[3.5]nonane-2-carboxylate (1.187 g, 5.244 mmol) in acetonitrile (20 mL) was stirred at the room temperature for 18 hr. Then, water was added to the reaction mixture, followed by extraction with ethyl acetate. The organic layer was washed with aqueous saturated sodium chloride solution, dried with anhydrous MgSO₄, filtered, and concentrated in vacuo. The residue was chromatographed (SiO₂, 40 g cartridge; methanol/dichloromethane=0% to 10%) to give tert-butyl 7-((1H-imidazol-1-yl)sulfonyl)-2,7-diazaspiro[3.5]nonane-2-carboxylate as white solid (0.830 g, 42.2%).

[Step 2] 1-((2-(tert-butoxycarbonyl)-2,7-diazaspiro[3.5]nonan-7-yl) sulfonyl)-3-methyl-1H-imidazol-3-ium trifluoromethanesulfonate

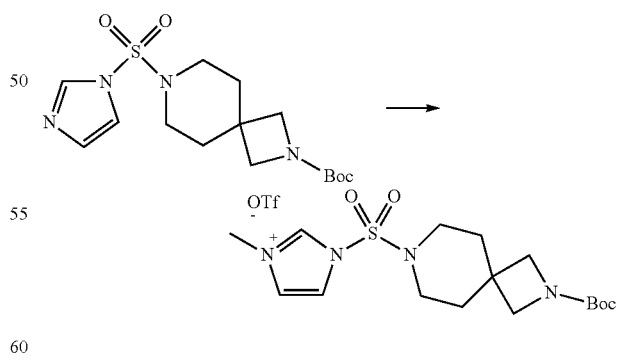

A solution of tert-butyl 7-((1H-imidazol-1-yl)sulfonyl)-2,7-diazaspiro[3.5]nonane-2-carboxylate (0.900 g, 2.525 mmol) and methyl trifluoromethanesulfonate (0.305 mL, 2.777 mmol) in dichloromethane (10 mL) was stirred at 0° C. for 3 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The precipitates were collected by filtration, washed by dichloromethane, and dried to give 1-((2-(tert-butoxycarbonyl)-2,7-diazaspiro[3.5]nonan-7-yl)sulfonyl)-3-methyl-1H-imidazol-3-ium trifluoromethanesulfonate as white solid (1.282 g, 97.5%).

[Step 3] tert-butyl 7-(N-phenylsulfamoyl)-2,7-diazaspiro[3.5]nonane-2-carboxylate

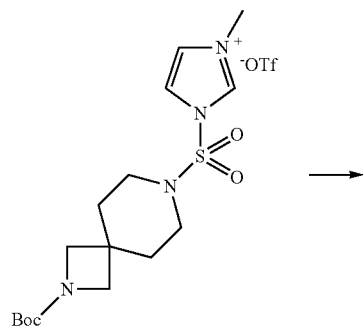

[Step 4] tert-butyl 7-(N-(4-(methoxycarbonyl)benzyl)-N-phenylsulfamoyl)-2,7-diazaspiro[3.5]nonane-2-carboxylate

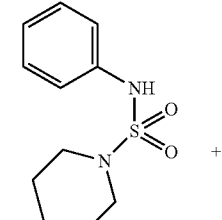

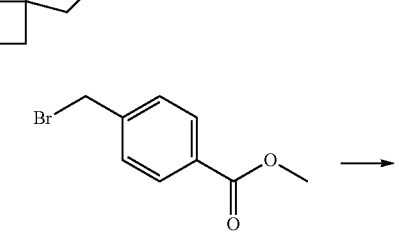

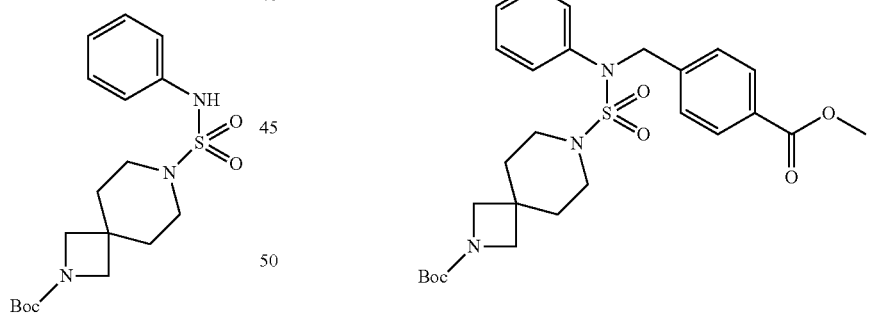

A solution of 1-((2-(tert-butoxycarbonyl)-2,7-diazaspiro[3.5]nonan-7-yl)sulfonyl)-3-methyl-1H-imidazol-3-ium trifluoromethanesulfonate (1.282 g, 2.463 mmol) and aniline (0.270 mL, 2.955 mmol) in acetonitrile (10 mL) was stirred at the room temperature for 18 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 24 g cartridge; ethyl acetate/hexane=0% to 50%) to give tert-butyl 7-(N-phenylsulfamoyl)-2,7-diazaspiro[3.5]nonane-2-carboxylate as colorless liquid (0.192 g, 20.4%).

A solution of tert-butyl 7-(N-phenylsulfamoyl)-2,7-diazaspiro[3.5]nonane-2-carboxylate (0.192 g, 0.503 mmol), methyl 4-(bromomethyl)benzoate (0.138 g, 0.604 mmol) and sodium hydride (60.00%, 0.030 g, 0.755 mmol) in N,N-dimethylformide (5 mL) was stirred at the room temperature for 18 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 4 g cartridge; ethyl acetate/hexane=0% to 30%) to give tert-butyl 7-(N-(4-(methoxycarbonyl)benzyl)-N-phenylsulfamoyl)-2,7-diazaspiro[3.5]nonane-2-carboxylate as white solid (0.151 g, 56.5%).

[Step 5] tert-butyl 7-(N-(4-(hydrazinecarbonyl)benzyl)-N-phenylsulfamoyl)-2,7-diazaspiro[3.5]nonane-2-carboxylate

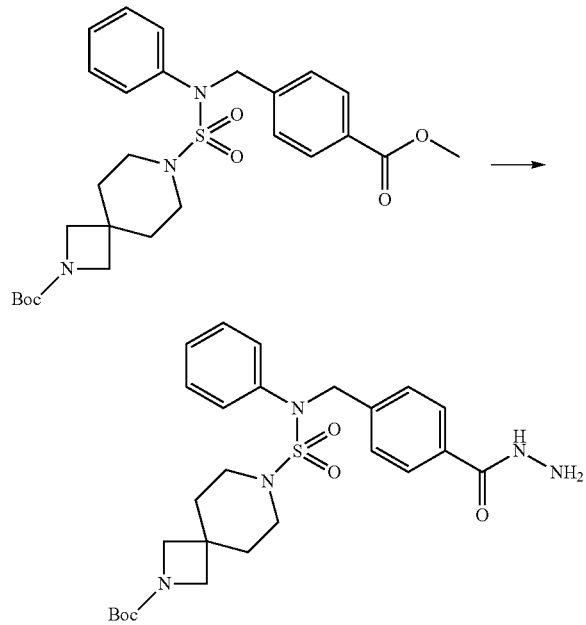

A solution of tert-butyl 7-(N-(4-(methoxycarbonyl)benzyl)-N-phenylsulfamoyl)-2,7-diazaspiro[3.5]nonane-2-carboxylate (0.075 g, 0.142 mmol) and hydrazine monohydrate (0.069 mL, 1.416 mmol) in ethanol (5 mL) was stirred at 80° C. for 18 hr, and cooled down to the room temperature to terminate the reaction. The reaction mixture was concentrated under the reduced pressure to remove the solvent. The residue was diluted with aqueous saturated sodium bicarbonate solution (5 mL) and stirred. The resulting precipitates were collected by filtration and dried to give tert-butyl 7-(N-(4-(hydrazinecarbonyl)benzyl)-N-phenylsulfamoyl)-2,7-diazaspiro[3.5]nonane-2-carboxylate as white solid (0.073 g, 97.3%).

[Step 6] tert-butyl 7-(N-(4-(5-(difluoromethyl)-1,3,4-oxadiazol-2-yl)benzyl)-N-phenylsulfamoyl)-2,7-diazaspiro[3.5]nonane-2-carboxylate

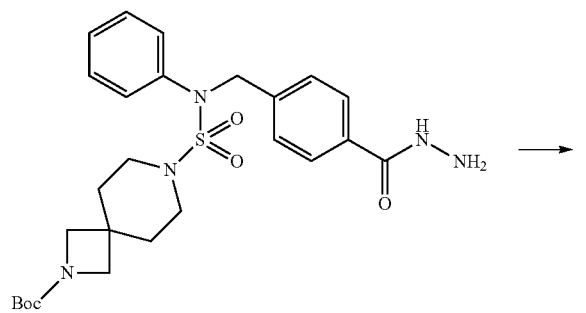

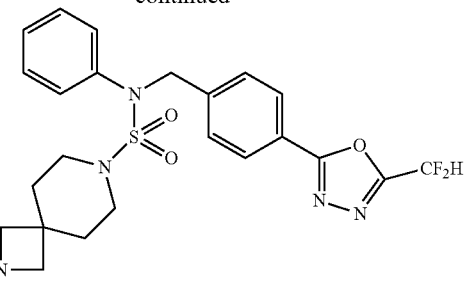

A solution of tert-butyl 7-(N-(4-(hydrazinecarbonyl)benzyl)-N-phenylsulfamoyl)-2,7-diazaspiro[3.5]nonane-2-carboxylate (0.073 g, 0.138 mmol), 2,2-difluoroacetic anhydride (0.051 mL, 0.413 mmol) and triethylamine (0.058 mL, 0.413 mmol) in tetrahydrofuran (3 mL) was stirred at 80° C. for 0.5 hr, and cooled down to the room temperature to terminate the reaction. Then, saturated aqueous sodium bicarbonate solution was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (Sift, 4 g cartridge; ethyl acetate/hexane=0% to 50%) to give tert-butyl 7-(N-(4-(5-(difluoromethyl)-1,3,4-oxadiazol-2-yl)benzyl)-N-phenylsulfamoyl)-2,7-diazaspiro[3.5]nonane-2-carboxylate as white solid (0.081 g, 99.7%).

[Step 7] Compound 11787

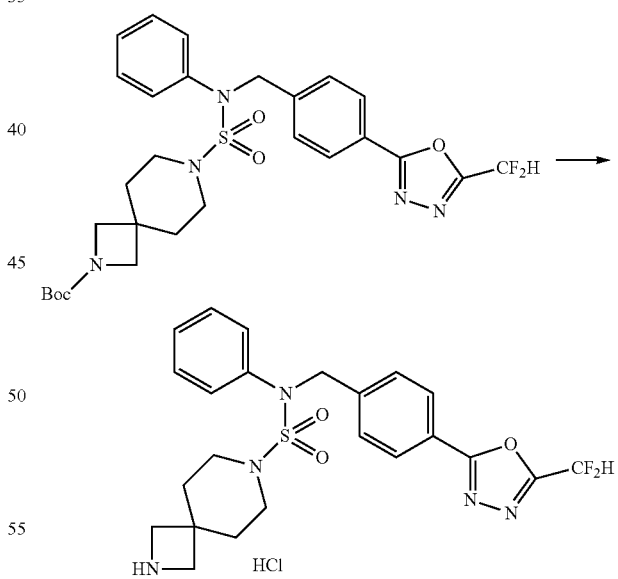

A solution of tert-butyl 7-(N-(4-(5-(difluoromethyl)-1,3,4-oxadiazol-2-yl)benzyl)-N-phenylsulfamoyl)-2,7-diazaspiro[3.5]nonane-2-carboxylate (0.081 g, 0.137 mmol) and hydrochloric acid (4.00 M solution, 0.343 mL, 1.374 mmol) in 1,4-dioxane (5 mL) was stirred at the room temperature for 2 hr, and concentrated under the reduced pressure to remove the solvent. The residue was diluted with diethylether (10 mL), and stirred. The resulting precipitates were collected by filtration and dried to give N-(4-(5-(difluoromethyl)-1,3,4-oxadiazol-2-yl)benzyl)-N-phenyl-2,7-diazaspiro[3.5]nonane-7-sulfonamide hydrochloride as yellow solid (0.067 g, 92.9%).

$^1$H NMR (400 MHz, CD$_3$OD) δ8.02 (d, 2H, J=8.1 Hz), 7.52 (d, 2H, J=8.2 Hz), 7.41~7.24 (m, 5H), 7.21 (t, 1H, J=51.6 Hz), 4.98 (s, 2H), 3.85 (s, 4H), 3.24~3.22 (m, 4H), 1.89~1.86 (m, 4H); LRMS (ES) m/z 490.3 (M$^+$+1)

Example 64: Compound 11788, N-(4-(5-(difluoromethyl)-1,3,4-oxadiazol-2-yl)benzyl)-2-(oxetan-3-yl)-N-phenyl-2,7-diazaspiro[3.5]nonane-7-sulfonamide

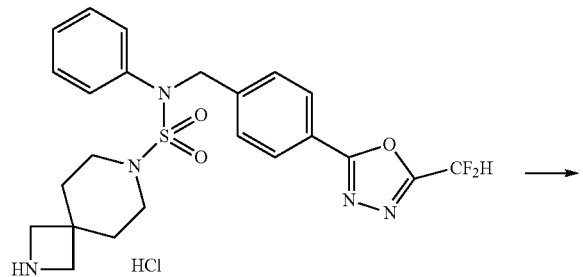

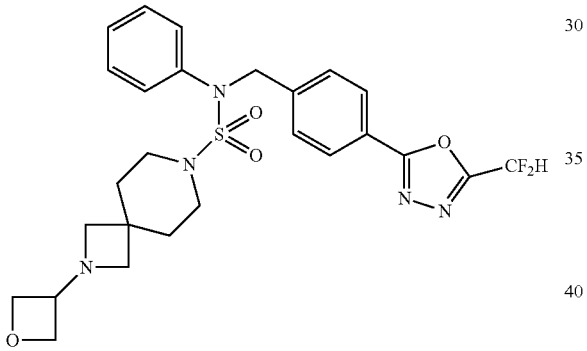

A solution of N-(4-(5-(difluoromethyl)-1,3,4-oxadiazol-2-yl)benzyl)-N-phenyl-2,7-diazaspiro[3.5]nonane-7-sulfonamide hydrochloride (0.030 g, 0.057 mmol) and oxetan-3-one (0.008 g, 0.114 mmol) in dichloromethane (3 mL) was stirred at the room temperature for 1 hr, and mixed with sodium triacetoxyborohydride (0.024 g, 0.114 mmol). The reaction mixture was stirred at the same temperature for additional 3 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (SiO$_2$, 4 g cartridge; methanol/dichloromethane=0% to 10%) to give N-(4-(5-(difluoromethyl)-1,3,4-oxadiazol-2-yl)benzyl)-2-(oxetan-3-yl)-N-phenyl-2,7-diazaspiro[3.5]nonane-7-sulfonamide as white solid (0.021 g, 67.5%).

$^1$H NMR (400 MHz, CD$_3$OD) δ8.01 (d, 2H, J=8.3 Hz), 7.52 (d, 2H, J=8.2 Hz), 7.41~7.39 (m, 2H), 7.35~7.31 (m, 2H), 7.27~7.23 (m, 1H), 7.21 (t, 1H, J=51.7 Hz), 4.99 (s, 2H), 4.74 (t, 2H, J=6.8 Hz), 4.48 (dd, 1H, J=6.8, 5.0 Hz), 3.20~3.16 (m, 8H), 1.79~1.76 (m, 4H); LRMS (ES) m/z 546.3 (M$^+$+1)

Example 65: Compound 11789, 2-cyclobutyl-N-(4-(5-(difluoromethyl)-1,3,4-oxadiazol-2-yl)benzyl)-N-phenyl-2,7-diazaspiro[3.5]nonane-7-sulfonamide

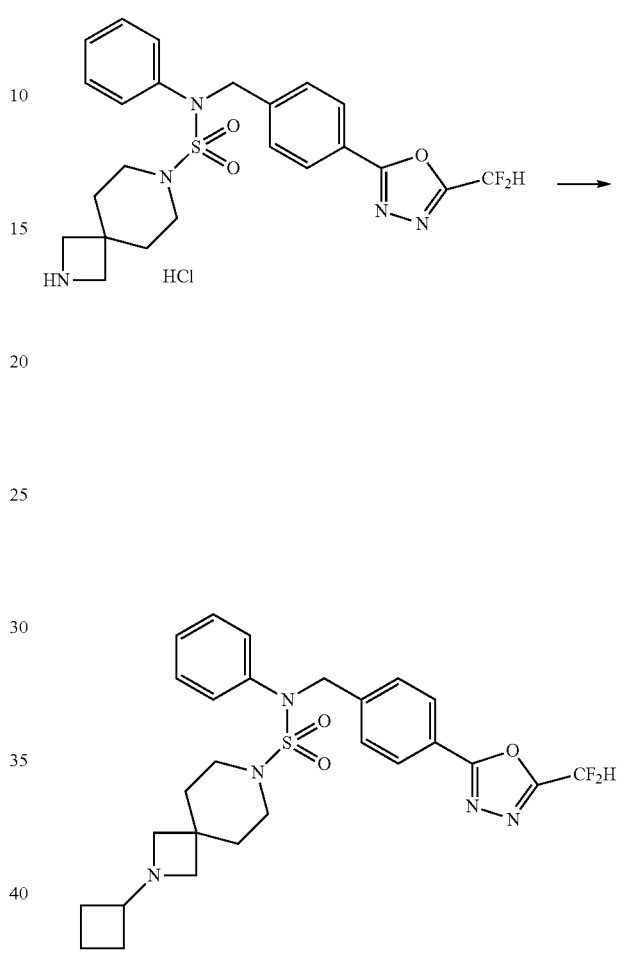

A solution of N-(4-(5-(difluoromethyl)-1,3,4-oxadiazol-2-yl)benzyl)-N-phenyl-2,7-diazaspiro[3.5]nonane-7-sulfonamide hydrochloride (0.030 g, 0.057 mmol) and cyclobutanone (0.008 g, 0.114 mmol) in dichloromethane (3 mL) was stirred at the room temperature for 1 hr, and mixed with sodium triacetoxyborohydride (0.024 g, 0.114 mmol). The reaction mixture was stirred at the same temperature for additional 3 hr. Then, water was added to the reaction mixture, followed by extraction with dichloromethane. The organic layer was washed with aqueous saturated sodium chloride solution, dried with anhydrous MgSO$_4$, filtered, and concentrated in vacuo. The residue was chromatographed (Sift, 4 g cartridge; methanol/dichloromethane=0% to 10%) to give 2-cyclobutyl-N-(4-(5-(difluoromethyl)-1,3,4-oxadiazol-2-yl)benzyl)-N-phenyl-2,7-diazaspiro[3.5]nonane-7-sulfonamide as colorless liquid (0.023 g, 74.2%).

$^1$H NMR (400 MHz, CD$_3$OD) δ8.01 (d, 2H, J=8.4 Hz), 7.51 (d, 2H, J=8.5 Hz), 7.40~7.37 (m, 2H), 7.35~7.31 (m, 2H), 7.28~7.24 (m, 1H), 7.22 (t, 1H, J=51.6 Hz), 3.61 (s, 4H), 3.22~3.19 (m, 4H), 2.24~2.16 (m, 2H), 2.10~2.01 (m, 2H), 1.91~1.83 (m, 2H), 1.82~1.79 (m, 4H); LRMS (ES) m/z 544.3 (M$^+$+1)

Example 66: Compound 11823, (R)—N-((5-(5-(difluoromethyl)-1,3,4-oxadiazol-2-yl)pyridin-2-yl)methyl)-3,4-dimethyl-N-(m-tolyl)piperazine-1-sulfonamide

[Step 1] tert-butyl (R)-4-((1H-imidazol-1-yl)sulfonyl)-2-methylpiperazine-1-carboxylate

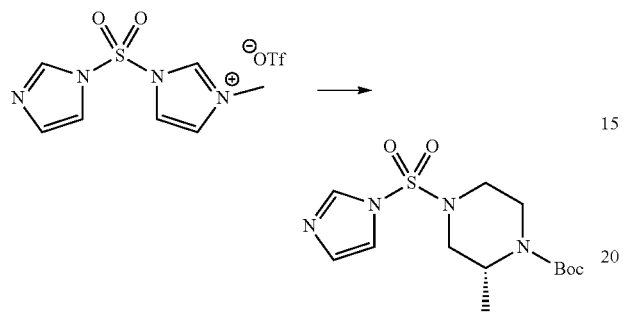

A solution of 1-((1H-imidazol-1-yl)sulfonyl)-3-methyl-1H-imidazol-3-ium trifluoromethanesulfonate (9.600 g, 26.497 mmol) and tert-butyl (R)-2-methylpiperazine-1-carboxylate (5.838 g, 29.147 mmol) in acetonitrile (100 mL) was stirred at the room temperature for 16 hr. Then, water was added to the reaction mixture, followed by extraction with ethyl acetate. The organic layer was washed with aqueous saturated ammonium chloride solution, dried with anhydrous MgSO₄, filtered, and concentrated in vacuo. The residue was chromatographed (SiO₂, 40 g cartridge; ethyl acetate/hexane=0% to 40%) to give tert-butyl (R)-4-((1H-imidazol-1-yl)sulfonyl)-2-methylpiperazine-1-carboxylate as yellow solid (4.600 g, 52.5%).

[Step 2] (R)-1-((4-(tert-butoxycarbonyl)-3-methylpiperazin-1-yl)sulfonyl)-3-methyl-1H-imidazol-3-ium trifluoromethanesulfonate

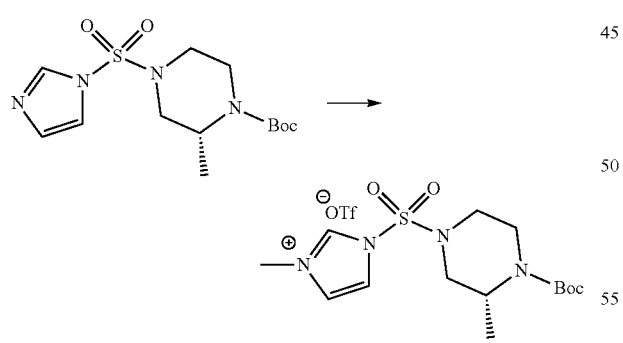

A solution of tert-butyl (R)-4-((1H-imidazol-1-yl)sulfonyl)-2-methylpiperazine-1-carboxylate (4.600 g, 13.923 mmol) and methyl trifluoromethanesulfonate (1.527 mL, 13.923 mmol) in dichloromethane (150 mL) was stirred at 0° C. for 3 hr, and concentrated under the reduced pressure to remove the solvent. The crude product was used without further purification ((R)-1-((4-(tert-butoxycarbonyl)-3-methylpiperazin-1-yl)sulfonyl)-3-methyl-1H-imidazol-3-ium trifluoromethanesulfonate, 6.700 g, 97.3%, white solid).

[Step 3] tert-butyl (R)-2-methyl-4-(N-(m-tolyl)sulfamoyl)piperazine-1-carboxylate

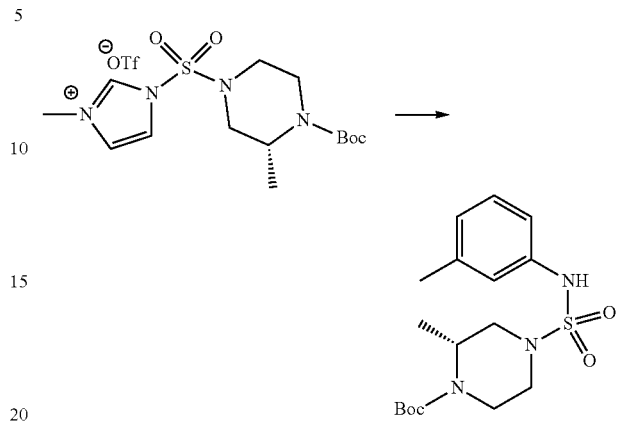

A mixture of (R)-1-((4-(tert-butoxycarbonyl)-3-methylpiperazin-1-yl)sulfonyl)-3-methyl-1H-imidazol-3-ium trifluoromethanesulfonate (3.350 g, 6.775 mmol) and m-toluidine hydrochloride (1.070 g, 7.452 mmol) in acetonitrile (100 mL), prepared at the ambient temperature, was heated at reflux for 16 hr, and cooled down to the ambient temperature. Then, water was added to the reaction mixture, followed by extraction with ethyl acetate. The organic layer was washed with aqueous saturated ammonium chloride solution, dried with anhydrous MgSO₄, filtered, and concentrated in vacuo. The residue was chromatographed (Sift, 24 g cartridge; ethyl acetate/hexane=0% to 30%) to give tert-butyl (R)-2-methyl-4-(N-(m-tolyl)sulfamoyl)piperazine-1-carboxylate as yellow solid (1.100 g, 43.9%).

[Step 4] tert-butyl (R)-4-(N-((5-(methoxycarbonyl)pyridin-2-yl)methyl)-N-(m-tolyl) sulfamoyl)-2-methyl piperazine-1-carboxylate

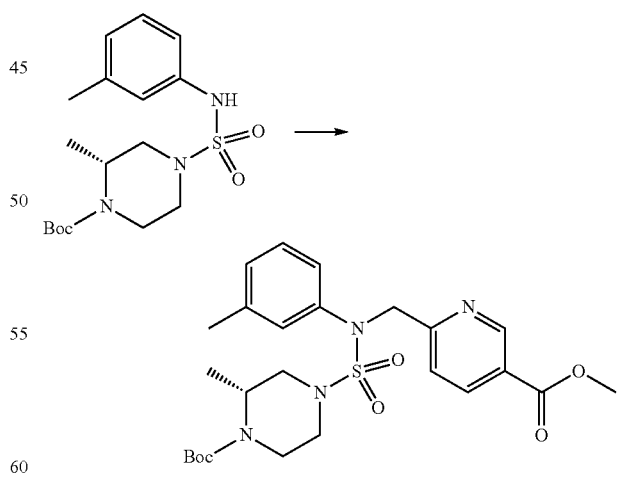

A solution of tert-butyl (R)-2-methyl-4-(N-(m-tolyl)sulfamoyl)piperazine-1-carboxylate (1.100 g, 4.082 mmol) and potassium carbonate (0.846 g, 6.123 mmol) in N,N-dimethylformide (50 mL) was stirred at the room temperature for 30 min, and mixed with methyl 6-(bromomethyl)nicotinate (1.033 g, 4.490 mmol) and potassium iodide (0.339 g, 2.041 mmol). The reaction mixture was stirred at the same temperature for additional 12 hr. Then, water was added to the reaction mixture, followed by extraction with ethyl acetate. The organic layer was washed with aqueous saturated ammonium chloride solution, dried with anhydrous MgSO$_4$, filtered, and concentrated in vacuo. The residue was chromatographed (SiO$_2$, 12 g cartridge; ethyl acetate/hexane=0% to 60%) to give tert-butyl (R)-4-(N-((5-(methoxycarbonyl)pyridin-2-yl)methyl)-N-(m-tolyl)sulfamoyl)-2-methyl piperazine-1-carboxylate as yellow solid (1.180 g, 55.7%).

[Step 5] methyl (R)-6-(((3-methyl-N-(m-tolyl)piperazine)-1-sulfonamido)methyl)nicotinate Hydrochloride

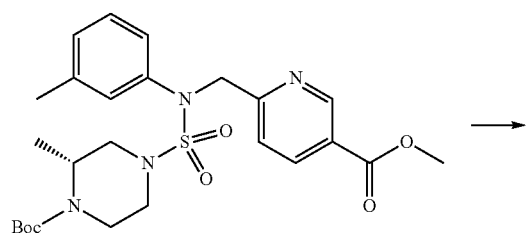

A solution of tert-butyl (R)-4-(N-((5-(methoxycarbonyl)pyridin-2-yl)methyl)-N-(m-tolyl) sulfamoyl)-2-methyl piperazine-1-carboxylate (1.100 g, 2.121 mmol) and hydrogen chloride (4.00 M solution in 1,4-dioxane, 1.060 mL, 4.242 mmol) in dichloromethane (50 mL) was stirred at the room temperature for 5 hr, and concentrated under the reduced pressure to remove the solvent. The crude product was used without further purification (methyl (R)-6-(((3-methyl-N-(m-tolyl)piperazine)-1-sulfonamido)methyl)nicotinate hydrochloride, 0.850 g, 88.1%, yellow solid).

[Step 6] methyl (R)-6-(((3,4-dimethyl-N-(m-tolyl)piperazine)-1-sulfonamido)methyl)nicotinate

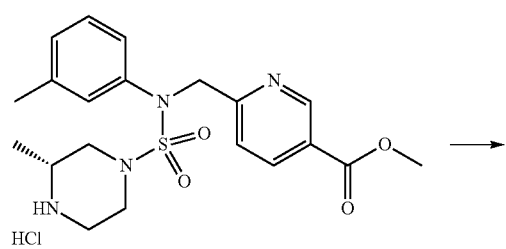

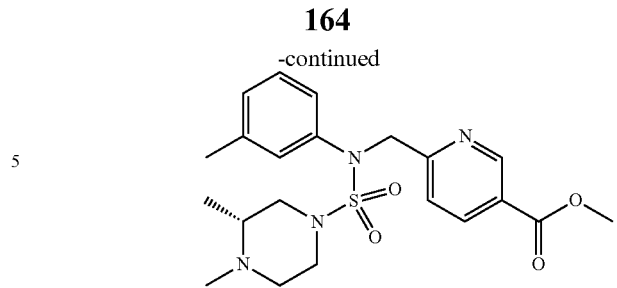

A solution of methyl (R)-6-(((3-methyl-N-(m-tolyl)piperazine)-1-sulfonamido)methyl)nicotinate hydrochloride (0.300 g, 0.659 mmol), para-formaldehyde (0.040 g, 1.319 mmol), acetic acid (0.045 mL, 0.791 mmol) and sodium triacetoxyborohydride (0.279 g, 1.319 mmol) in dichloromethane (10 mL) was stirred at the room temperature for 12 hr. Then, water was added to the reaction mixture, followed by extraction with dichloromethane. The organic layer was washed with aqueous saturated sodium bicarbonate solution, dried with anhydrous MgSO$_4$, filtered, and concentrated in vacuo. The residue was chromatographed (SiO$_2$, 4 g cartridge; methanol/dichloromethane=0% to 5%) to give methyl (R)-6-(((3,4-dimethyl-N-(m-tolyl)piperazine)-1-sulfonamido)methyl)nicotinate as yellow solid (0.120 g, 42.1%).

[Step 7] (R)—N-((5-(hydrazinecarbonyl)pyridin-2-yl)methyl)-3,4-dimethyl-N-(m-tolyl)piperazine-1-sulfonamide

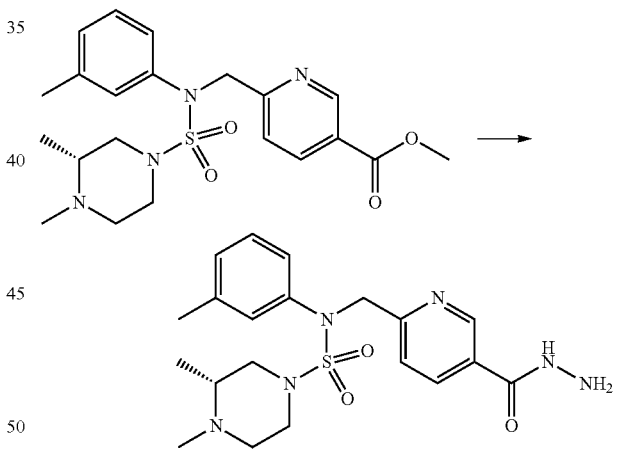

A solution of methyl (R)-6-(((3,4-dimethyl-N-(m-tolyl)piperazine)-1-sulfonamido)methyl)nicotinate (0.120 g, 0.253 mmol) and hydrazine monohydrate (0.123 mL, 2.529 mmol) in ethanol (10 mL) was stirred at 90° C. for 12 hr, and cooled down to the room temperature to terminate the reaction. The reaction mixture was concentrated under the reduced pressure to remove the solvent. Then, water was added to the concentrate, followed by extraction with dichloromethane. The organic layer was washed with aqueous saturated sodium bicarbonate solution, dried with anhydrous MgSO$_4$, filtered, and concentrated in vacuo. The title compound was used without further purification ((R)—N-((5-(hydrazinecarbonyl)pyridin-2-yl)methyl)-3,4-dimethyl-N-(m-tolyl)piperazine-1-sulfonamide, 0.100 g, 83.3%, white solid).

[Step 8] Compound 11823

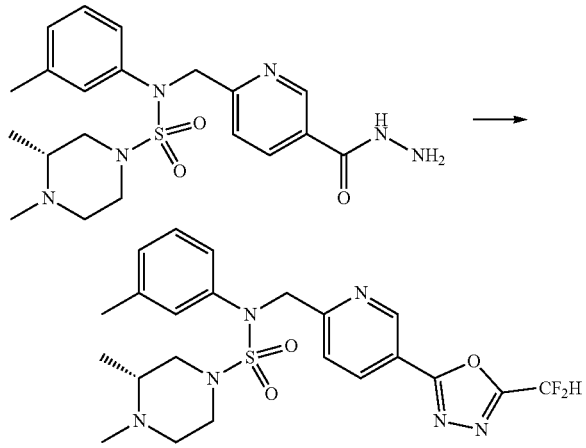

A solution of (R)—N-((5-(hydrazinecarbonyl)pyridin-2-yl)methyl)-3,4-dimethyl-N-(m-tolyl)piperazine-1-sulfonamide (0.100 g, 0.231 mmol), triethylamine (0.161 mL, 1.156 mmol) and 2,2-difluoroacetic anhydride (0.086 mL, 0.694 mmol) in tetrahydrofuran (10 mL) was stirred at 70° C. for 12 hr, and cooled down to the room temperature to terminate the reaction. Then, water was added to the reaction mixture, followed by extraction with dichloromethane. The organic layer was washed with aqueous saturated ammonium chloride solution, dried with anhydrous MgSO$_4$, filtered, and concentrated in vacuo. The residue was chromatographed (Sift, 4 g cartridge; methanol/dichloromethane=0% to 5%) to give (R)—N-((5-(5-(difluoromethyl)-1,3,4-oxadiazol-2-yl)pyridin-2-yl)methyl)-3,4-dimethyl-N-(m-tolyl)piperazine-1-sulfonamide as yellow solid (0.082 g, 72.0%).

$^1$H NMR (400 MHz, CDCl$_3$) δ 9.21 (d, 1H, J=2.1 Hz), 8.36 (d, 1H, J=8.3 Hz), 7.73 (d, 1H, J=8.2 Hz), 7.26-7.21 (m, 3H), 7.19-7.17 (m, 1.3H), 6.94 (s, 0.5H), 6.81 (s, 0.2H), 5.12 (s, 2H), 3.58-3.48 (m, 2H), 3.00-2.93 (m, 1H), 2.75-2.71 (m, 1H), 2.62-2.57 (m, 1H), 2.32 (s, 3H), 2.26 (s, 3H), 2.25-2.20 (m, 1H), 2.19-2.09 (m, 1H), 1.04 (d, 3H, J=6.3 Hz); LRMS (ES) m/z 493.3 (M$^+$+1).

Example 67: Compound 11824, (R)—N-((5-(5-(difluoromethyl)-1,3,4-oxadiazol-2-yl)pyridin-2-yl)methyl)-3-methyl-4-(oxetan-3-yl)-N-(m-tolyl)piperazine-1-sulfonamide

[Step 1] methyl (R)-6-(((3-methyl-4-(oxetan-3-yl)-N-(m-tolyl)piperazine)-1-sulfonamido)methyl)nicotinate

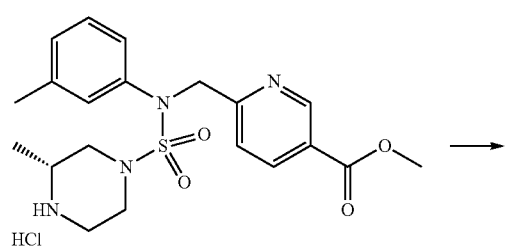

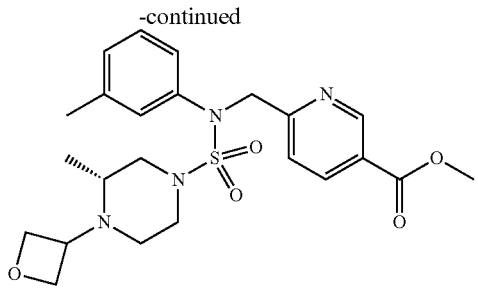

A solution of methyl (R)-6-(((3-methyl-N-(m-tolyl)piperazine)-1-sulfonamido)methyl)nicotinate hydrochloride (0.300 g, 0.659 mmol), oxetan-3-one (0.095 g, 1.319 mmol), acetic acid (0.045 mL, 0.791 mmol) and sodium triacetoxyborohydride (0.279 g, 1.319 mmol) in dichloromethane (10 mL) was stirred at the room temperature for 12 hr. Then, water was added to the reaction mixture, followed by extraction with dichloromethane. The organic layer was washed with aqueous saturated sodium bicarbonate solution, dried with anhydrous MgSO$_4$, filtered, and concentrated in vacuo. The residue was chromatographed (Sift, 4 g cartridge; methanol/dichloromethane=0% to 5%) to give methyl (R)-6-(((3-methyl-4-(oxetan-3-yl)-N-(m-tolyl)piperazine)-1-sulfonamido)methyl)nicotinate as yellow solid (0.150 g, 47.9%).

[Step 2] (R)—N-((5-(hydrazinecarbonyl)pyridin-2-yl)methyl)-3-methyl-4-(oxetan-3-yl)-N-(m-tolyl)piperazine-1-sulfonamide

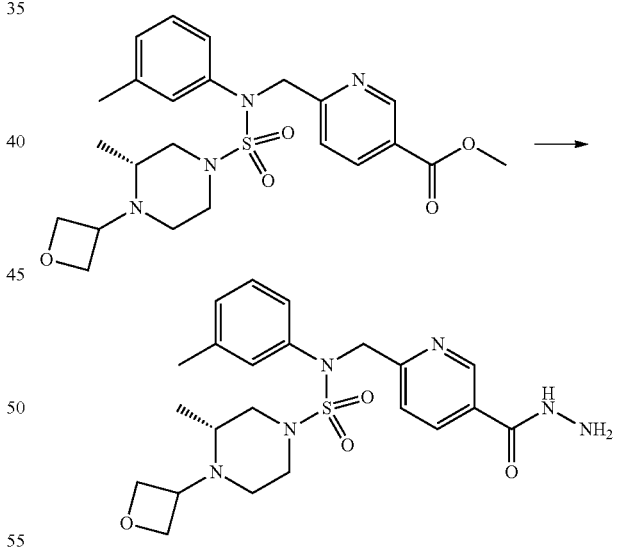

A solution of methyl (R)-6-(((3-methyl-4-(oxetan-3-yl)-N-(m-tolyl)piperazine)-1-sulfonamido)methyl)nicotinate (0.150 g, 0.316 mmol) and hydrazine monohydrate (0.154 mL, 3.161 mmol) in ethanol (10 mL) was stirred at 90° C. for 12 hr, and cooled down to the room temperature to terminate the reaction. The reaction mixture was concentrated under the reduced pressure to remove the solvent. Then, water was added to the concentrate, followed by extraction with dichloromethane. The organic layer was washed with aqueous saturated sodium bicarbonate solution, dried with anhydrous MgSO$_4$, filtered, and concentrated in vacuo. The title compound was used without further purification ((R)—N-((5-(hydrazinecarbonyl)pyridin-2-yl)methyl)-3-methyl-4-(oxetan-3-yl)-N-(m-tolyl)piperazine-1-sulfonamide, 0.100 g, 66.7%, white solid).

[Step 3] Compound 11824

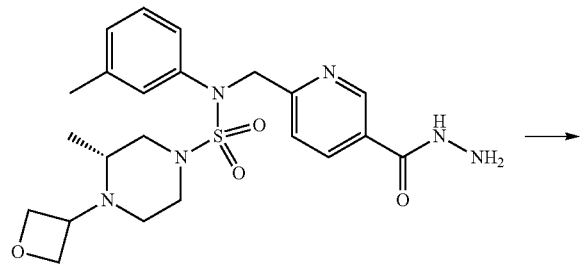

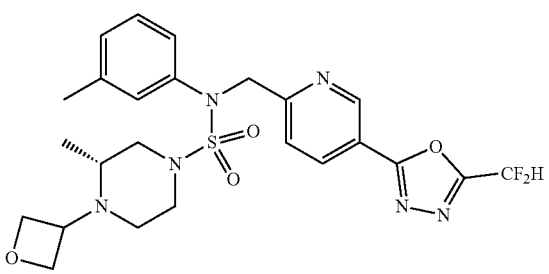

A solution of (R)—N-((5-(hydrazinecarbonyl)pyridin-2-yl)methyl)-3-methyl-4-(oxetan-3-yl)-N-(m-tolyl)piperazine-1-sulfonamide (0.100 g, 0.211 mmol), triethylamine (0.147 mL, 1.054 mmol) and 2,2-difluoroacetic anhydride (0.079 mL, 0.632 mmol) in tetrahydrofuran (10 mL) was stirred at 70° C. for 12 hr, and cooled down to the room temperature to terminate the reaction. Then, water was added to the reaction mixture, followed by extraction with dichloromethane. The organic layer was washed with aqueous saturated ammonium chloride solution, dried with anhydrous MgSO$_4$, filtered, and concentrated in vacuo. The residue was chromatographed (Sift, 4 g cartridge; ethyl acetate/hexane=0% to 80%) to give (R)—N-((5-(5-(difluoromethyl)-1,3,4-oxadiazol-2-yl)pyridin-2-yl)methyl)-3-methyl-4-(oxetan-3-yl)-N-(m-tolyl)piperazine-1-sulfonamide as yellow oil (0.073 g, 64.8%).

$^1$H NMR (400 MHz, CDCl$_3$) δ 9.23-9.21 (m, 1H), 8.37 (d, 1H, J=8.2 Hz), 7.72 (d, 1H, J=7.2 Hz), 7.28-7.26 (m, 1H), 7.22-7.21 (m, 1H), 7.08-7.06 (m, 1H), 7.05 (s, 0.2H), 6.94 (s, 0.5H), 6.81 (s, 0.3H), 5.11 (s, 2H), 4.63-4.55 (m, 4H), 3.75-3.71 (m, 1H), 3.42-3.33 (m, 2H), 3.15-3.13 (m, 1H), 2.87-2.82 (m, 1H), 2.61-2.57 (m, 1H), 2.41-2.35 (m, 1H), 2.33 (s, 3H), 2.16-2.10 (m, 1H), 0.88 (d, 3H, J=6.5 Hz); LRMS (ES) m/z 535.1 (M$^+$+1).

Example 68: Compound 11825, (R)—N-(3-chlorophenyl)-N-((5-(5-(difluoromethyl)-1,3,4-oxadiazol-2-yl)pyridin-2-yl)methyl)-3,4-dimethylpiperazine-1-sulfonamide

[Step 1] tert-butyl (R)-4-(N-(3-chlorophenyl)sulfamoyl)-2-methylpiperazine-1-carboxylate

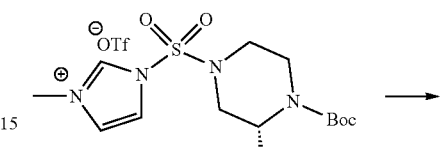

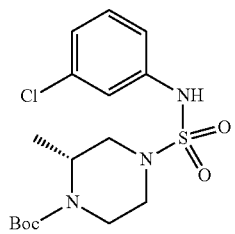

A mixture of (R)-1-((4-(tert-butoxycarbonyl)-3-methylpiperazin-1-yl)sulfonyl)-3-methyl-1H-imidazol-3-ium trifluoromethanesulfonate (3.700 g, 7.482 mmol) and 3-chloroaniline (1.050 g, 8.231 mmol) in acetonitrile (100 mL), prepared at the ambient temperature, was heated at reflux for 16 hr, and cooled down to the ambient temperature. Then, water was added to the reaction mixture, followed by extraction with ethyl acetate. The organic layer was washed with aqueous saturated ammonium chloride solution, dried with anhydrous MgSO$_4$, filtered, and concentrated in vacuo. The residue was chromatographed (SiO$_2$, 24 g cartridge; ethyl acetate/hexane=0% to 30%) to give tert-butyl (R)-4-(N-(3-chlorophenyl)sulfamoyl)-2-methylpiperazine-1-carboxylate as white solid (0.610 g, 20.9%).

[Step 2] tert-butyl (R)-4-(N-(3-chlorophenyl)-N-((5-(methoxycarbonyl)pyridin-2-yl)methyl)sulfamoyl)-2-methylpiperazine-1-carboxylate

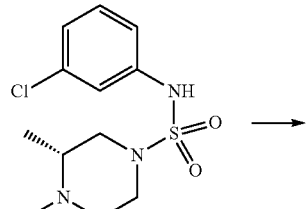

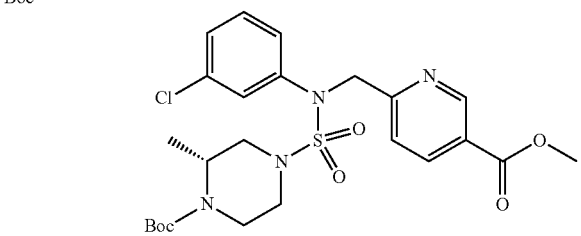

A solution of tert-butyl (R)-4-(N-(3-chlorophenyl)sulfamoyl)-2-methylpiperazine-1-carboxylate (0.610 g, 1.565 mmol) and potassium carbonate (0.324 g, 2.347 mmol) in N,N-dimethylformide (50 mL) was stirred at the room temperature for 30 min, and mixed with methyl 6-(bromomethyl)nicotinate (0.396 g, 1.721 mmol) and potassium iodide (0.130 g, 0.782 mmol). The reaction mixture was stirred at the same temperature for additional 12 hr. Then, water was added to the reaction mixture, followed by extraction with ethyl acetate. The organic layer was washed with aqueous saturated ammonium chloride solution, dried with anhydrous MgSO$_4$, filtered, and concentrated in vacuo. The residue was chromatographed (Sift, 12 g cartridge; ethyl acetate/hexane=0% to 40%) to give tert-butyl (R)-4-(N-(3-chlorophenyl)-N-((5-(methoxycarbonyl)pyridin-2-yl)methyl)sulfamoyl)-2-methylpiperazine-1-carboxylate as yellow solid (0.660 g, 78.3%).

[Step 3] methyl (R)-6-(((N-(3-chlorophenyl)-3-methylpiperazine)-1-sulfonamido)methyl)nicotinate Hydrochloride

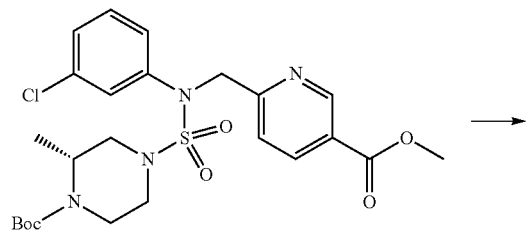

A solution of tert-butyl (R)-4-(N-(3-chlorophenyl)-N-((5-(methoxycarbonyl)pyridin-2-yl)methyl)sulfamoyl)-2-methylpiperazine-1-carboxylate (0.660 g, 1.224 mmol) and hydrogen chloride (4.00 M solution in 1,4-dioxane, 0.612 mL, 2.449 mmol) in dichloromethane (30 mL) was stirred at the room temperature for 5 hr, and concentrated under the reduced pressure to remove the solvent. The crude product was used without further purification (methyl (R)-6-(((N-(3-chlorophenyl)-3-methylpiperazine)-1-sulfonamido)methyl)nicotinate hydrochloride, 0.450 g, 77.3%, yellow solid).

[Step 4] methyl (R)-6-(((N-(3-chlorophenyl)-3,4-dimethylpiperazine)-1-sulfonamido)methyl)nicotinate

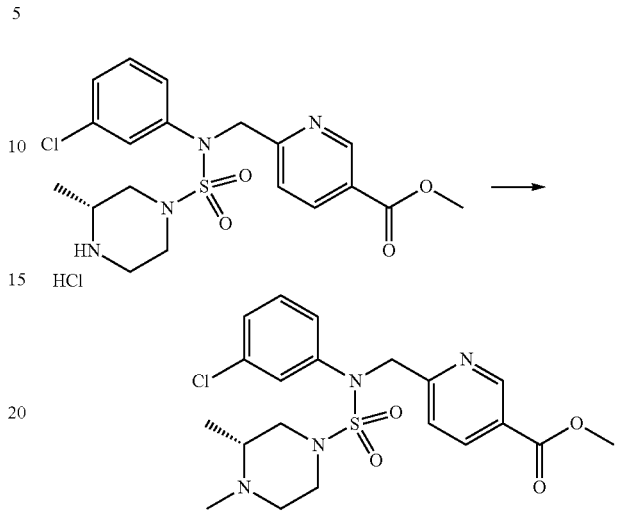

A solution of methyl (R)-6-(((N-(3-chlorophenyl)-3-methylpiperazine)-1-sulfonamido)methyl)nicotinate hydrochloride (0.210 g, 0.442 mmol), para-formaldehyde (0.027 g, 0.883 mmol), acetic acid (0.030 mL, 0.530 mmol) and sodium triacetoxyborohydride (0.187 g, 0.883 mmol) in dichloromethane (10 mL) was stirred at the room temperature for 12 hr. Then, water was added to the reaction mixture, followed by extraction with dichloromethane. The organic layer was washed with aqueous saturated sodium bicarbonate solution, dried with anhydrous MgSO$_4$, filtered, and concentrated in vacuo. The residue was chromatographed (SiO$_2$, 4 g cartridge; methanol/dichloromethane=0% to 5%) to give methyl (R)-6-(((N-(3-chlorophenyl)-3,4-dimethylpiperazine)-1-sulfonamido)methyl)nicotinate as yellow solid (0.115 g, 57.5%).

[Step 5] (R)—N-(3-chlorophenyl)-N-((5-(hydrazinecarbonyl)pyridin-2-yl)methyl)-3,4-dimethylpiperazine-1-sulfonamide

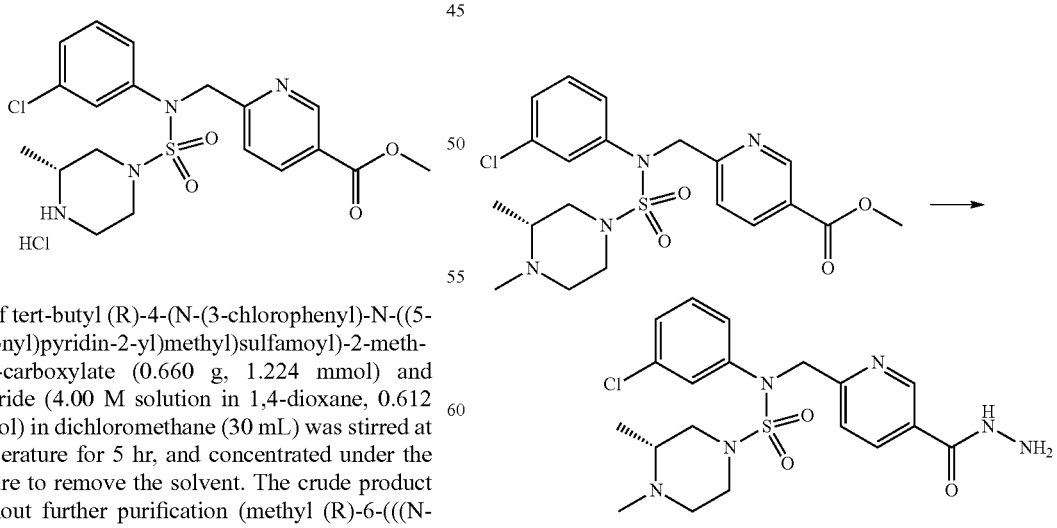

A solution of methyl (R)-6-(((N-(3-chlorophenyl)-3,4-dimethylpiperazine)-1-sulfonamido)methyl)nicotinate (0.115 g, 0.254 mmol) and hydrazine monohydrate (0.123 mL, 2.539 mmol) in ethanol (10 mL) was stirred at the room temperature for 12 hr, and concentrated under the reduced pressure to remove the solvent. Then, water was added to the concentrate, followed by extraction with dichloromethane. The organic layer was washed with aqueous saturated sodium bicarbonate solution, dried with anhydrous MgSO$_4$, filtered, and concentrated in vacuo. The title compound was used without further purification ((R)—N-(3-chlorophenyl)-N-((5-(hydrazinecarbonyl)pyridin-2-yl)methyl)-3,4-dimethyl piperazine-1-sulfonamide, 0.090 g, 78.3%, white solid).

[Step 6] Compound 11825

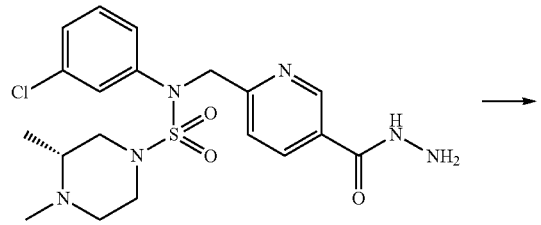

A solution of (R)—N-(3-chlorophenyl)-N-((5-(hydrazinecarbonyl)pyridin-2-yl)methyl)-3,4-dimethylpiperazine-1-sulfonamide (0.090 g, 0.199 mmol), triethylamine (0.138 mL, 0.993 mmol) and 2,2-difluoroacetic anhydride (0.074 mL, 0.596 mmol) in tetrahydrofuran (10 mL) was stirred at 70° C. for 12 hr, and cooled down to the room temperature to terminate the reaction. Then, water was added to the reaction mixture, followed by extraction with dichloromethane. The organic layer was washed with aqueous saturated ammonium chloride solution, dried with anhydrous MgSO$_4$, filtered, and concentrated in vacuo. The residue was chromatographed (SiO$_2$, 4 g cartridge; methanol/dichloromethane=0% to 5%) to give (R)—N-(3-chlorophenyl)-N-((5-(5-(difluoromethyl)-1,3,4-oxadiazol-2-yl)pyridin-2-yl)methyl)-3,4-dimethylpiperazine-1-sulfonamide as yellow solid (0.061 g, 59.8%).

$^1$H NMR (400 MHz, CDCl$_3$) δ 9.25-9.23 (m, 1H), 8.39-8.36 (m, 1H), 7.68-7.66 (m, 1H), 7.50-7.49 (m, 1H), 7.36-7.34 (m, 1H), 7.34-7.21 (m, 2H), 7.07 (s, 0.3H), 6.94 (s, 0.5H), 6.81 (s, 0.2H), 5.10 (s, 2H), 3.58-3.47 (m, 2H), 3.00-2.95 (m, 1 H), 2.76-2.72 (m, 1H), 2.63-2.58 (m, 1H), 2.27 (s, 3H), 2.24-2.19 (m, 1H), 2.10-2.09 (m, 1H), 1.04 (d, 3H, J=6.3 Hz); LRMS (ES) m/z 513.3 (M$^+$+1).

Example 69: Compound 11826, (R)—N-(3-chlorophenyl)-N-((5-(5-(difluoromethyl)-1,3,4-oxadiazol-2-yl)pyridin-2-yl)methyl)-3-methyl-4-(oxetan-3-yl)piperazine-1-sulfonamide

[Step 1] methyl (R)-6-(((N-(3-chlorophenyl)-3-methyl-4-(oxetan-3-yl)piperazine)-1-sulfonamido)methyl)nicotinate

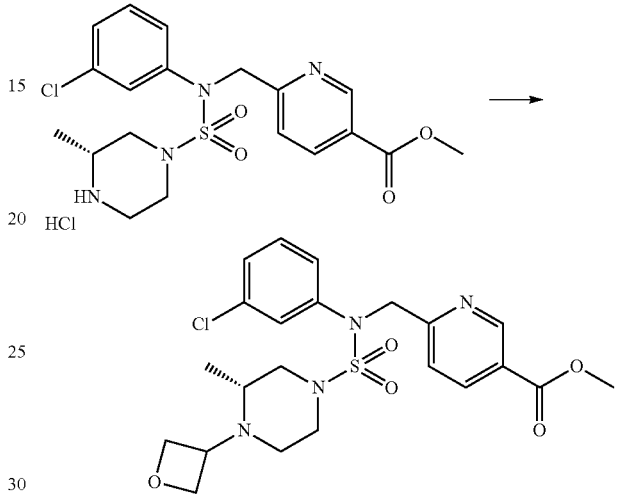

A solution of methyl (R)-6-(((N-(3-chlorophenyl)-3-methylpiperazine)-1-sulfonamido)methyl)nicotinate hydrochloride (0.200 g, 0.421 mmol), oxetan-3-one (0.061 g, 0.841 mmol) and acetic acid (0.029 mL, 0.505 mmol) in dichloromethane (10 mL) was stirred at the room temperature for 30 min, and mixed with sodium triacetoxyborohydride (0.178 g, 0.841 mmol). The reaction mixture was stirred at the same temperature for additional 12 hr. Then, water was added to the reaction mixture, followed by extraction with dichloromethane. The organic layer was washed with aqueous saturated sodium bicarbonate solution, dried with anhydrous MgSO$_4$, filtered, and concentrated in vacuo. The residue was chromatographed (SiO$_2$, 4 g cartridge; methanol/dichloromethane=0% to 5%) to give methyl (R)-6-(((N-(3-chlorophenyl)-3-methyl-4-(oxetan-3-yl)piperazine)-1-sulfonamido)methyl)nicotinate as yellow solid (0.100 g, 48.0%).

[Step 2] (R)—N-(3-chlorophenyl)-N-((5-(hydrazinecarbonyl)pyridin-2-yl)methyl)-3-methyl-4-(oxetan-3-yl)piperazine-1-sulfonamide

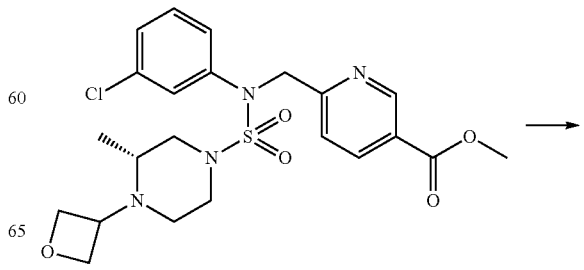

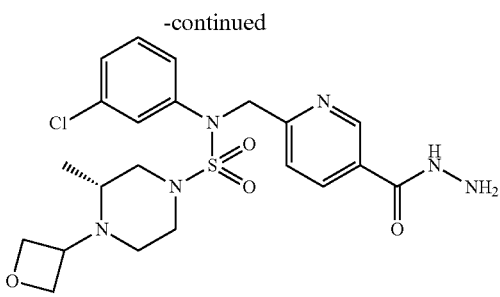

A solution of methyl (R)-6-(((N-(3-chlorophenyl)-3-methyl-4-(oxetan-3-yl)piperazine)-1-sulfonamido)methyl) nicotinate (0.100 g, 0.202 mmol) and hydrazine monohydrate (0.098 mL, 2.020 mmol) in ethanol (10 mL) was stirred at 90° C. for 12 hr, and cooled down to the room temperature to terminate the reaction. The reaction mixture was concentrated under the reduced pressure to remove the solvent. Then, water was added to the concentrate, followed by extraction with dichloromethane. The organic layer was washed with aqueous saturated sodium bicarbonate solution, dried with anhydrous MgSO₄, filtered, and concentrated in vacuo. The crude product was used without further purification ((R)—N-(3-chlorophenyl)-N-((5-(hydrazinecarbonyl)pyridin-2-yl)methyl)-3-methyl-4-(oxetan-3-yl)piperazine-1-sulfonamide, 0.085 g, 85.0%, white solid).

[Step 3] Compound 11826

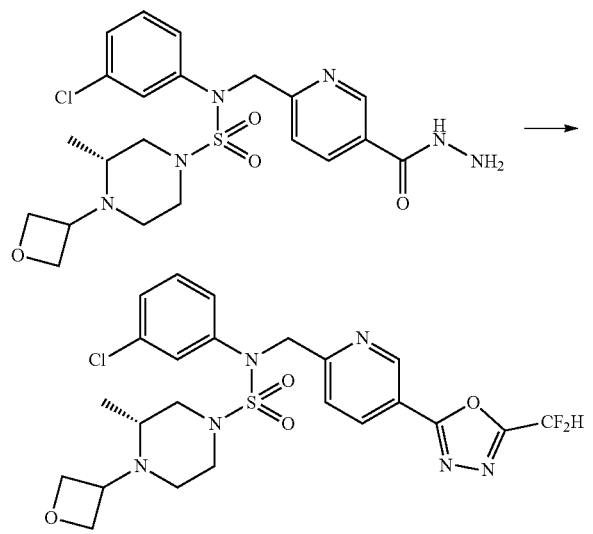

A solution of (R)—N-(3-chlorophenyl)-N-((5-(hydrazinecarbonyl)pyridin-2-yl)methyl)-3-methyl-4-(oxetan-3-yl)piperazine-1-sulfonamide (0.085 g, 0.172 mmol), triethylamine (0.120 mL, 0.859 mmol) and 2,2-difluoroacetic anhydride (0.064 mL, 0.515 mmol) in tetrahydrofuran (10 mL) was stirred at 70° C. for 12 hr, and cooled down to the room temperature to terminate the reaction. Then, water was added to the reaction mixture, followed by extraction with dichloromethane. The organic layer was washed with aqueous saturated ammonium chloride solution, dried with anhydrous MgSO₄, filtered, and concentrated in vacuo. The residue was chromatographed (SiO₂, 4 g cartridge; ethyl acetate/hexane=0% to 80%) to give (R)—N-(3-chlorophenyl)-N-((5-(5-(difluoromethyl)-1,3,4-oxadiazol-2-yl)pyridin-2-yl)methyl)-3-methyl-4-(oxetan-3-yl)piperazine-1-sulfonamide as yellow oil (0.053 g, 55.6%).

$^1$H NMR (400 MHz, CDCl₃) δ 9.26-9.23 (m, 1H), 8.39-8.36 (m, 1H), 7.65 (d, 1H, J=8.3 Hz), 7.50-7.49 (m, 1H), 7.36-7.33 (m, 1H), 7.29-7.23 (m, 2H), 7.07 (s, 0.3H), 6.94 (s, 0.5H), 6.81 (s, 0.2H), 5.09 (s, 2H), 4.64-4.55 (m, 4H), 3.75-3.71 (m, 1H), 3.40-3.33 (m, 2H), 3.17-3.15 (m, 1H), 2.88-2.83 (m, 1H), 2.62-2.58 (m, 1H), 2.39-2.38 (m, 1H), 2.15-2.10 (m, 1H), 0.87 (d, 3H, J=6.5 Hz); LRMS (ES) m/z 555.3 (M⁺+1).

Example 70: Compound 11827, (S)—N-((5-(5-(difluoromethyl)-1,3,4-oxadiazol-2-yl)pyridin-2-yl) methyl)-3,4-dimethyl-N-(m-tolyl)piperazine-1-sulfonamide

[Step 1] tert-butyl (S)-4-((1H-imidazol-1-yl)sulfonyl)-2-methylpiperazine-1-carboxylate

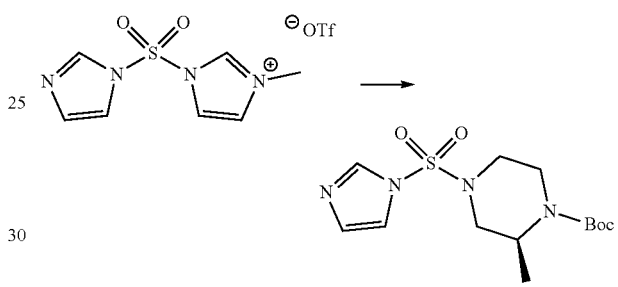

A solution of 1-((1H-imidazol-1-yl)sulfonyl)-3-methyl-1H-imidazol-3-ium trifluoromethanesulfonate (8.900 g, 24.565 mmol) and tert-butyl (S)-2-methylpiperazine-1-carboxylate (5.412 g, 27.022 mmol) in acetonitrile (5 mL) was stirred at the room temperature for 16 hr. Then, water was added to the reaction mixture, followed by extraction with ethyl acetate. The organic layer was washed with aqueous saturated ammonium chloride solution, dried with anhydrous MgSO₄, filtered, and concentrated in vacuo. The residue was chromatographed (SiO₂, 40 g cartridge; ethyl acetate/hexane=0% to 50%) to give tert-butyl (S)-4-((1H-imidazol-1-yl)sulfonyl)-2-methylpiperazine-1-carboxylate as yellow solid (5.050 g, 62.2%).

[Step 2] (S)-1-((4-(tert-butoxycarbonyl)-3-methylpiperazin-1-yl)sulfonyl)-3-methyl-1H-imidazol-3-ium trifluoromethanesulfonate

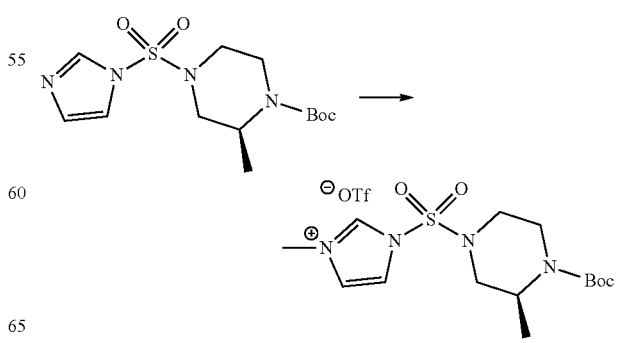

A solution of tert-butyl (S)-4-((1H-imidazol-1-yl)sulfonyl)-2-methylpiperazine-1-carboxylate (5.000 g, 15.133 mmol) and methyl trifluoromethanesulfonate (1.660 mL, 15.133 mmol) in dichloromethane (150 mL) was stirred at 0° C. for 3 hr, and concentrated under the reduced pressure to remove the solvent. The crude product was used without further purification ((S)-1-((4-(tert-butoxycarbonyl)-3-methylpiperazin-1-yl)sulfonyl)-3-methyl-1H-imidazol-3-ium trifluoromethanesulfonate, 5.800 g, 77.5%, white solid).

[Step 3] tert-butyl (S)-2-methyl-4-(N-(m-tolyl)sulfamoyl)piperazine-1-carboxylate

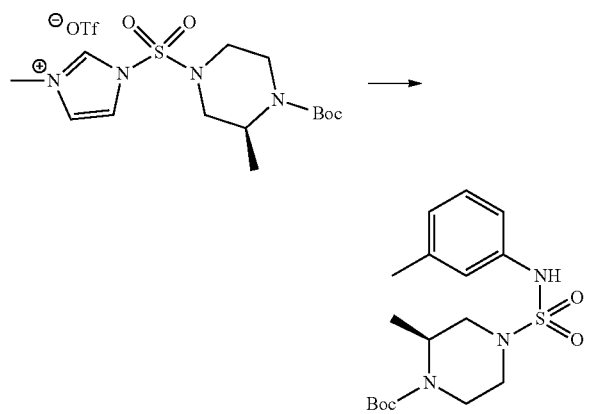

A mixture of (S)-1-((4-(tert-butoxycarbonyl)-3-methylpiperazin-1-yl)sulfonyl)-3-methyl-1H-imidazol-3-ium trifluoromethanesulfonate (4.000 g, 8.089 mmol) and m-toluidine hydrochloride (1.278 g, 8.898 mmol) in acetonitrile (100 mL), prepared at the ambient temperature, was heated at reflux for 16 hr, and cooled down to the ambient temperature. Then, water was added to the reaction mixture, followed by extraction with ethyl acetate. The organic layer was washed with aqueous saturated ammonium chloride solution, dried with anhydrous MgSO₄, filtered, and concentrated in vacuo. The residue was chromatographed (SiO₂, 24 g cartridge; ethyl acetate/hexane=0% to 30%) to give tert-butyl (S)-2-methyl-4-(N-(m-tolyl)sulfamoyl)piperazine-1-carboxylate as yellow solid (1.160 g, 38.8%).

[Step 4] tert-butyl (S)-4-(N-((5-(methoxycarbonyl)pyridin-2-yl)methyl)-N-(m-tolyl) sulfamoyl)-2-methylpiperazine-1-carboxylate

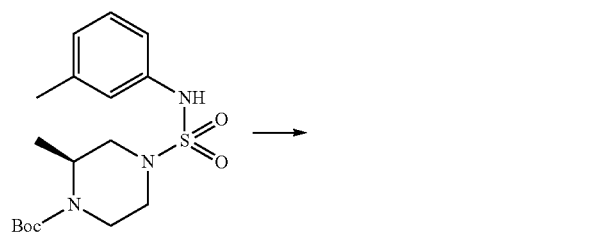

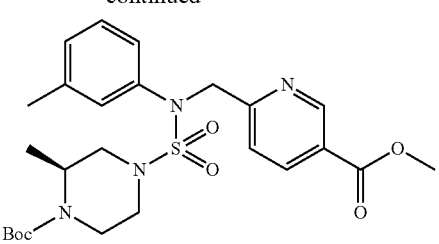

A solution of tert-butyl (S)-2-methyl-4-(N-(m-tolyl)sulfamoyl)piperazine-1-carboxylate (1.100 g, 2.977 mmol) and potassium carbonate (0.617 g, 4.466 mmol) in N,N-dimethylformide (50 mL) was stirred at the room temperature for 30 min, and mixed with methyl 6-(bromomethyl)nicotinate (0.753 g, 3.275 mmol) and potassium iodide (0.247 g, 1.489 mmol). The reaction mixture was stirred at the same temperature for additional 12 hr. Then, water was added to the reaction mixture, followed by extraction with ethyl acetate. The organic layer was washed with aqueous saturated ammonium chloride solution, dried with anhydrous MgSO₄, filtered, and concentrated in vacuo. The residue was chromatographed (SiO₂, 24 g cartridge; ethyl acetate/hexane=0% to 40%) to give tert-butyl (S)-4-(N-((5-(methoxycarbonyl)pyridin-2-yl)methyl)-N-(m-tolyl)sulfamoyl)-2-methylpiperazine-1-carboxylate as yellow solid (1.150 g, 74.5%).

[Step 5] methyl (S)-6-(((3-methyl-N-(m-tolyl)piperazine)-1-sulfonamido)methyl)nicotinate Hydrochloride

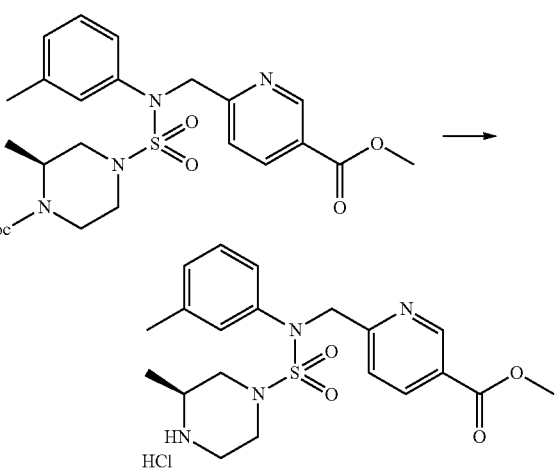

A solution of tert-butyl (S)-4-(N-((5-(methoxycarbonyl)pyridin-2-yl)methyl)-N-(m-tolyl) sulfamoyl)-2-methylpiperazine-1-carboxylate (1.100 g, 2.121 mmol) and hydrogen chloride (4.00 M solution in 1,4-dioxane, 1.060 mL, 4.242 mmol) in dichloromethane (30 mL) was stirred at the room temperature for 5 hr, and concentrated under the reduced pressure to remove the solvent. The crude product was used without further purification (methyl (S)-6-(((3-methyl-N-(m-tolyl)piperazine)-1-sulfonamido)methyl)nicotinate hydrochloride, 0.900 g, 93.3%, yellow solid).

[Step 6] methyl (S)-6-(((3,4-dimethyl-N-(m-tolyl)piperazine)-1-sulfonamido)methyl)nicotinate

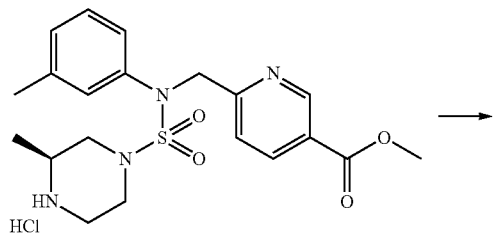

A solution of methyl (S)-6-(((3-methyl-N-(m-tolyl)piperazine)-1-sulfonamido)methyl)nicotinate hydrochloride (0.200 g, 0.440 mmol), para-formaldehyde (0.026 g, 0.879 mmol) and acetic acid (0.030 mL, 0.528 mmol) in dichloromethane (10 mL) was stirred at the room temperature for 30 min, and mixed with sodium triacetoxyborohydride (0.186 g, 0.879 mmol). The reaction mixture was stirred at the same temperature for additional 12 hr. Then, water was added to the reaction mixture, followed by extraction with dichloromethane. The organic layer was washed with aqueous saturated sodium bicarbonate solution, dried with anhydrous MgSO₄, filtered, and concentrated in vacuo. The residue was chromatographed (SiO₂, 4 g cartridge; methanol/dichloromethane=0% to 5%) to give methyl (S)-6-(((3,4-dimethyl-N-(m-tolyl)piperazine)-1-sulfonamido)methyl)nicotinate as yellow solid (0.120 g, 63.1%).

[Step 7] (S)—N-((5-(hydrazinecarbonyl)pyridin-2-yl)methyl)-3,4-dimethyl-N-(m-tolyl)piperazine-1-sulfonamide

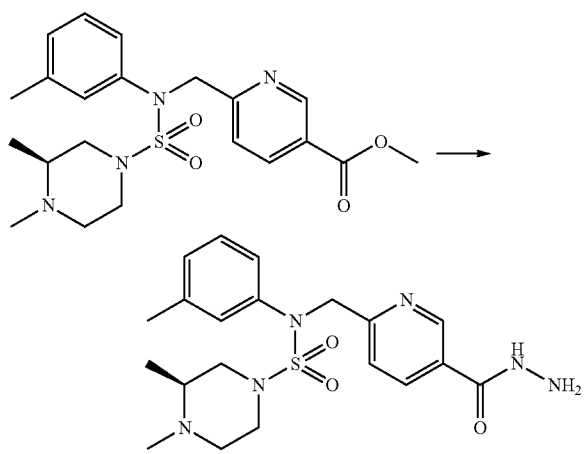

A solution of methyl (S)-6-(((3,4-dimethyl-N-(m-tolyl)piperazine)-1-sulfonamido)methyl)nicotinate (0.120 g, 0.277 mmol) and hydrazine monohydrate (0.135 mL, 2.774 mmol) in ethanol (10 mL) was stirred at 90° C. for 12 hr, and cooled down to the room temperature to terminate the reaction. The reaction mixture was concentrated under the reduced pressure to remove the solvent. Then, water was added to the concentrate, followed by extraction with dichloromethane. The organic layer was washed with aqueous saturated sodium bicarbonate solution, dried with anhydrous MgSO₄, filtered, and concentrated in vacuo. The crude product was used without further purification ((S)—N-((5-(hydrazinecarbonyl)pyridin-2-yl)methyl)-3,4-dimethyl-N-(m-tolyl)piperazine-1-sulfonamide, 0.092 g, 76.7%, white solid).

[Step 8] Compound 11827

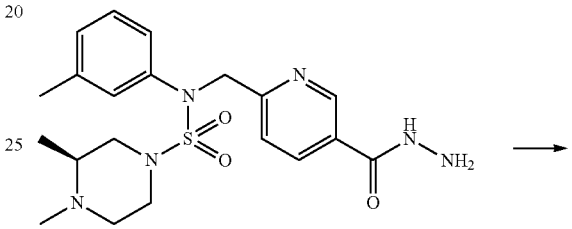

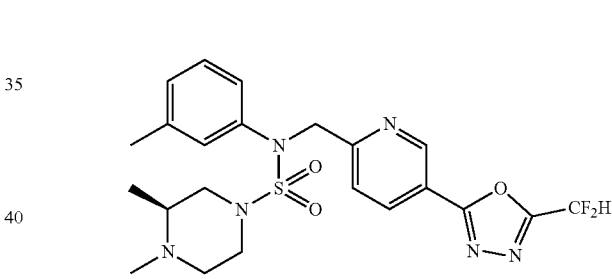

A solution of (S)—N-((5-(hydrazinecarbonyl)pyridin-2-yl)methyl)-3,4-dimethyl-N-(m-tolyl)piperazine-1-sulfonamide (0.092 g, 0.213 mmol), triethylamine (0.148 mL, 1.063 mmol) and 2,2-difluoroacetic anhydride (0.079 mL, 0.638 mmol) in tetrahydrofuran (10 mL) was stirred at the room temperature for 12 hr. Then, water was added to the reaction mixture, followed by extraction with dichloromethane. The organic layer was washed with aqueous saturated ammonium chloride solution, dried with anhydrous MgSO₄, filtered, and concentrated in vacuo. The residue was chromatographed (SiO₂, 4 g cartridge; methanol/dichloromethane=0% to 5%) to give (S)—N-((5-(5-(difluoromethyl)-1,3,4-oxadiazol-2-yl)pyridin-2-yl)methyl)-3,4-dimethyl-N-(m-tolyl)piperazine-1-sulfonamide as white solid (0.067 g, 64.0%).

$^1$H NMR (400 MHz, CDCl₃) δ 9.21-9.20 (m, 1H), 8.37-8.34 (m, 1H), 7.73 (d, 1H, J=8.2 Hz), 7.28-7.17 (m, 3H), 7.07 (s, 0.3H), 7.06-7.03 (m, 1H), 6.93 (s, 0.5H), 6.81 (s, 0.2H), 5.12 (s, 2H), 3.59-3.48 (m, 2H), 3.00-2.93 (m, 1H), 2.76-2.71 (m, 1H), 2.63-2.57 (m, 1H), 2.32 (s, 3H), 2.27 (s, 3H), 2.21-2.19 (m, 1H), 2.12-2.08 (m, 1H), 1.04 (d, 3H, J=6.3 Hz); LRMS (ES) m/z 493.3 (M⁺+1).

Example 71: Compound 11828, (S)—N-((5-(5-(difluoromethyl)-1,3,4-oxadiazol-2-yl)pyridin-2-yl)methyl)-3-methyl-4-(oxetan-3-yl)-N-(m-tolyl)piperazine-1-sulfonamide

[Step 1] methyl (S)-6-(((3-methyl-4-(oxetan-3-yl)-N-(m-tolyl)piperazine)-1-sulfonamido)methyl)nicotinate

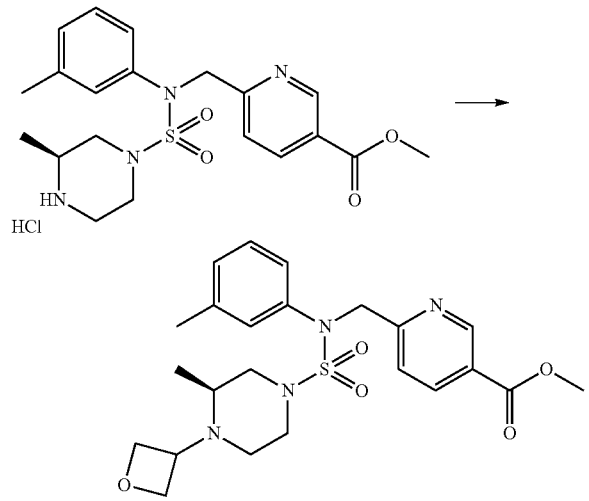

A solution of methyl (S)-6-(((3-methyl-N-(m-tolyl)piperazine)-1-sulfonamido)methyl)nicotinate hydrochloride (0.200 g, 0.440 mmol), oxetan-3-one (0.063 g, 0.879 mmol) and acetic acid (0.030 mL, 0.528 mmol) in dichloromethane (10 mL) was stirred at the room temperature for 30 min, and mixed with sodium triacetoxyborohydride (0.186 g, 0.879 mmol). The reaction mixture was stirred at the same temperature for additional 12 hr. Then, water was added to the reaction mixture, followed by extraction with dichloromethane. The organic layer was washed with aqueous saturated sodium bicarbonate solution, dried with anhydrous MgSO₄, filtered, and concentrated in vacuo. The residue was chromatographed (SiO₂, 4 g cartridge; methanol/dichloromethane=0% to 5%) to give methyl (S)-6-(((3-methyl-4-(oxetan-3-yl)-N-(m-tolyl)piperazine)-1-sulfonamido)methyl)nicotinate as yellow solid (0.130 g, 62.3%).

[Step 2] (S)—N-((5-(hydrazinecarbonyl)pyridin-2-yl)methyl)-3-methyl-4-(oxetan-3-yl)-N-(m-tolyl)piperazine-1-sulfonamide

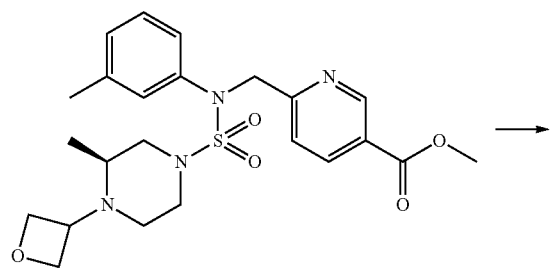

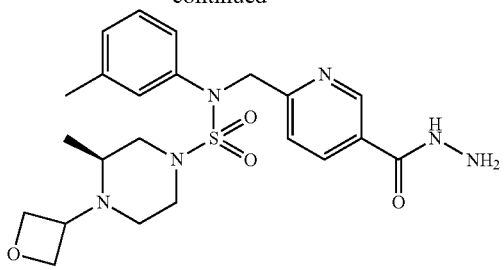

A solution of methyl (S)-6-(((3-methyl-4-(oxetan-3-yl)-N-(m-tolyl)piperazine)-1-sulfonamido)methyl)nicotinate (0.130 g, 0.274 mmol) and hydrazine monohydrate (0.133 mL, 2.739 mmol) in ethanol (10 mL) was stirred at 90° C. for 12 hr, and cooled down to the room temperature to terminate the reaction. The reaction mixture was concentrated under the reduced pressure to remove the solvent. Then, water was added to the concentrate, followed by extraction with dichloromethane. The organic layer was washed with aqueous saturated sodium bicarbonate solution, dried with anhydrous MgSO₄, filtered, and concentrated in vacuo. The crude product was used without further purification ((S)—N-((5-(hydrazinecarbonyl)pyridin-2-yl)methyl)-3-methyl-4-(oxetan-3-yl)-N-(m-tolyl)piperazine-1-sulfonamide, 0.100 g, 76.9%, white solid).

[Step 3] Compound 11828

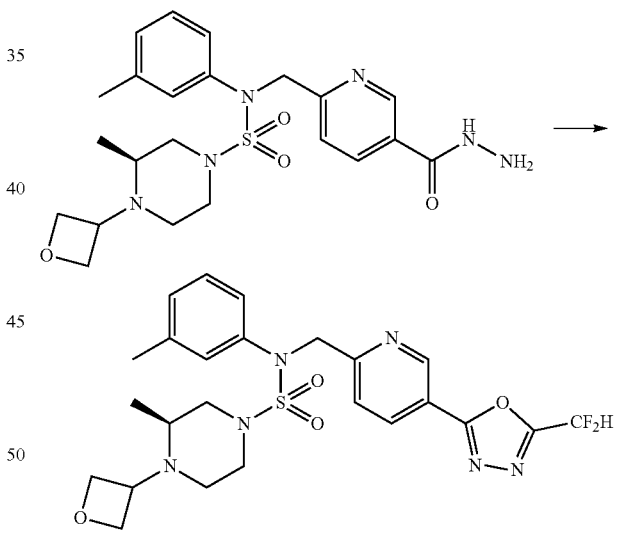

A solution of (S)—N-((5-(hydrazinecarbonyl)pyridin-2-yl)methyl)-3-methyl-4-(oxetan-3-yl)-N-(m-tolyl)piperazine-1-sulfonamide (0.100 g, 0.211 mmol), triethylamine (0.147 mL, 1.054 mmol) and 2,2-difluoroacetic anhydride (0.079 mL, 0.632 mmol) in tetrahydrofuran (10 mL) was stirred at 70° C. for 12 hr, and cooled down to the room temperature to terminate the reaction. Then, water was added to the reaction mixture, followed by extraction with dichloromethane. The organic layer was washed with aqueous saturated ammonium chloride solution, dried with anhydrous MgSO₄, filtered, and concentrated in vacuo. The residue was chromatographed (SiO₂, 4 g cartridge; ethyl acetate/hexane=0% to 80%) to give (S)—N-((5-(5-(difluoromethyl)-1,3,4-oxadiazol-2-yl)pyridin-2-yl)methyl)-3-methyl-4-(oxetan-3-yl)-N-(m-tolyl)piperazine-1-sulfonamide as yellow oil (0.079 g, 70.1%).

$^1$H NMR (400 MHz, CDCl$_3$) δ 9.22-9.20 (m, 1H), 8.37-8.35 (m, 1H), 7.71 (d, 1H, J=8.2 Hz), 7.28-7.20 (m, 3H), 7.08 (s, 0.3H), 7.07-7.05 (m, 1H), 6.94 (s, 0.5H), 6.81 (s, 0.2H), 5.11 (s, 2H), 4.65-4.56 (m, 4H), 3.74-3.71 (m, 1H), 3.39-3.33 (m, 2H), 3.15-3.13 (m, 1H), 2.87-2.82 (m, 1H), 2.61-2.58 (m, 1H), 2.49-2.35 (m, 1H), 2.33 (s, 3H), 2.15-2.10 (m, 1H), 0.87 (d, 3H, J=6.5 Hz); LRMS (ES) m/z 535.1 (M$^+$+1).

Example 72: Compound 11829, (S)—N-(3-chlorophenyl)-N-((5-(5-(difluoromethyl)-1,3,4-oxadiazol-2-yl)pyridin-2-yl)methyl)-3,4-dimethylpiperazine-1-sulfonamide

[Step 1] tert-butyl (S)-4-(N-(3-chlorophenyl)sulfamoyl)-2-methylpiperazine-1-carboxylate

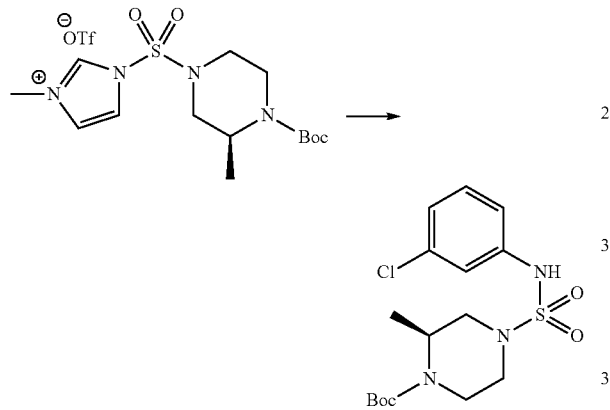

A mixture of (S)-1-((4-(tert-butoxycarbonyl)-3-methylpiperazin-1-yl)sulfonyl)-3-methyl-1H-imidazol-3-ium trifluoromethanesulfonate (3.000 g, 6.067 mmol) and 3-chloroaniline (0.851 g, 6.673 mmol) in acetonitrile (100 mL), prepared at the ambient temperature, was heated at reflux for 16 hr, and cooled down to the ambient temperature. Then, water was added to the reaction mixture, followed by extraction with ethyl acetate. The organic layer was washed with aqueous saturated ammonium chloride solution, dried with anhydrous MgSO$_4$, filtered, and concentrated in vacuo. The residue was chromatographed (SiO$_2$, 24 g cartridge; ethyl acetate/hexane=0% to 30%) to give tert-butyl (S)-4-(N-(3-chlorophenyl)sulfamoyl)-2-methylpiperazine-1-carboxylate as yellow solid (0.660 g, 27.9%).

[Step 2] tert-butyl (S)-4-(N-(3-chlorophenyl)-N-((5-(methoxycarbonyl)pyridin-2-yl)methyl)sulfamoyl)-2-methylpiperazine-1-carboxylate

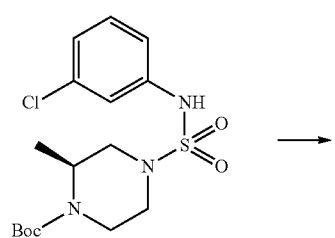

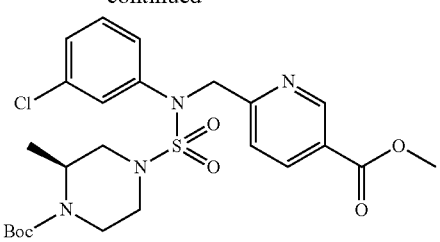

A solution of tert-butyl (S)-4-(N-(3-chlorophenyl)sulfamoyl)-2-methylpiperazine-1-carboxylate (0.660 g, 1.693 mmol) and potassium carbonate (0.351 g, 2.539 mmol) in N,N-dimethylformide (30 mL) was stirred at the room temperature for 30 min, and mixed with methyl 6-(bromomethyl)nicotinate (0.428 g, 1.862 mmol) and potassium iodide (0.140 g, 0.846 mmol). The reaction mixture was stirred at the same temperature for additional 12 hr. Then, water was added to the reaction mixture, followed by extraction with ethyl acetate. The organic layer was washed with aqueous saturated ammonium chloride solution, dried with anhydrous MgSO$_4$, filtered, and concentrated in vacuo. The residue was chromatographed (SiO$_2$, 12 g cartridge; ethyl acetate/hexane=0% to 50%) to give tert-butyl (S)-4-(N-(3-chlorophenyl)-N-((5-(methoxycarbonyl)pyridin-2-yl)methyl)sulfamoyl)-2-methylpiperazine-1-carboxylate as yellow solid (0.690 g, 75.6%).

[Step 3] methyl (S)-6-(((N-(3-chlorophenyl)-3-methylpiperazine)-1-sulfonamido)methyl)nicotinate Hydrochloride

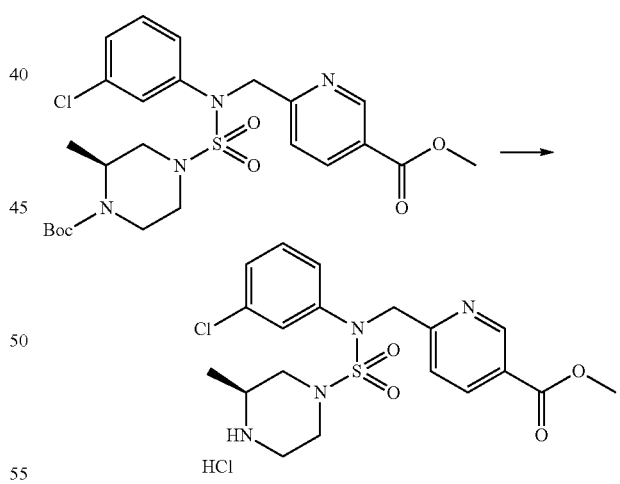

A solution of tert-butyl (S)-4-(N-(3-chlorophenyl)-N-((5-(methoxycarbonyl)pyridin-2-yl)methyl)sulfamoyl)-2-methylpiperazine-1-carboxylate (0.690 g, 1.280 mmol) and hydrogen chloride (4.00 M solution in 1,4-dioxane, 0.640 mL, 2.560 mmol) in dichloromethane (30 mL) was stirred at the room temperature for 5 hr, and concentrated under the reduced pressure to remove the solvent. The crude product was used without further purification (methyl (S)-6-(((N-(3-chlorophenyl)-3-methylpiperazine)-1-sulfonamido)methyl)nicotinate hydrochloride, 0.460 g, 75.6%, yellow solid).

183

[Step 4] methyl (S)-6-(((N-(3-chlorophenyl)-3,4-dimethylpiperazine)-1-sulfonamido)methyl)nicotinate

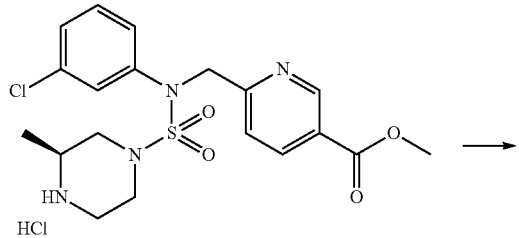

A solution of methyl (S)-6-(((N-(3-chlorophenyl)-3-methylpiperazine)-1-sulfonamido)methyl)nicotinate hydrochloride (0.200 g, 0.421 mmol), para-formaldehyde (0.025 g, 0.841 mmol) and acetic acid (0.029 mL, 0.505 mmol) in dichloromethane (10 mL) was stirred at the room temperature for 30 min, and mixed with sodium triacetoxyborohydride (0.178 g, 0.841 mmol). The reaction mixture was stirred at the same temperature for additional 12 hr. Then, water was added to the reaction mixture, followed by extraction with dichloromethane. The organic layer was washed with aqueous saturated sodium bicarbonate solution, dried with anhydrous MgSO₄, filtered, and concentrated in vacuo. The residue was chromatographed (SiO₂, 4 g cartridge; methanol/dichloromethane=0% to 5%) to give methyl (S)-6-(((N-(3-chlorophenyl)-3,4-dimethylpiperazine)-1-sulfonamido)methyl)nicotinate as yellow solid (0.140 g, 73.5%).

[Step 5] (S)—N-(3-chlorophenyl)-N-((5-(hydrazinecarbonyl)pyridin-2-yl)methyl)-3,4-dimethylpiperazine-1-sulfonamide

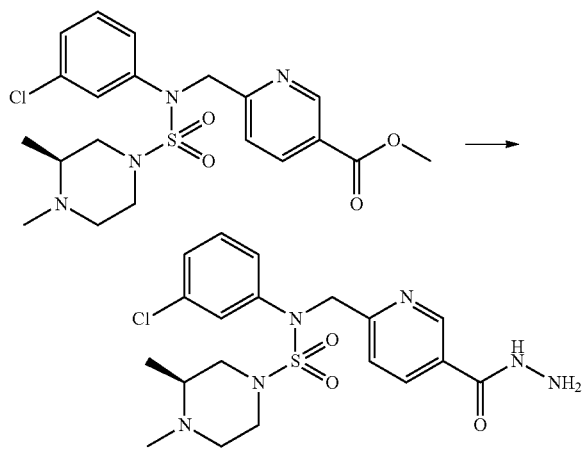

184

A solution of methyl (S)-6-(((N-(3-chlorophenyl)-3,4-dimethylpiperazine)-1-sulfonamido)methyl)nicotinate (0.140 g, 0.309 mmol) and hydrazine monohydrate (0.150 mL, 3.091 mmol) in ethanol (10 mL) was stirred at 90° C. for 12 hr, and cooled down to the room temperature to terminate the reaction. The reaction mixture was concentrated under the reduced pressure to remove the solvent. Then, water was added to the concentrate, followed by extraction with dichloromethane. The organic layer was washed with aqueous saturated sodium bicarbonate solution, dried with anhydrous MgSO₄, filtered, and concentrated in vacuo. The title compound was used without further purification ((S)—N-(3-chlorophenyl)-N-((5-(hydrazinecarbonyl)pyridin-2-yl)methyl)-3,4-dimethylpiperazine-1-sulfonamide, 0.110 g, 78.6%, white solid).

[Step 6] Compound 11829

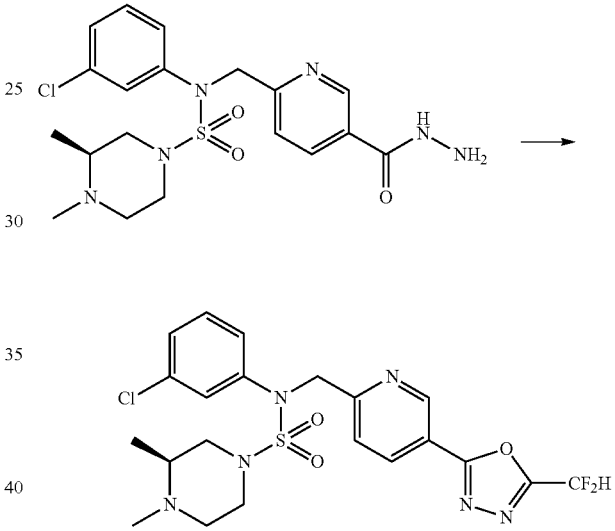

A solution of (S)—N-(3-chlorophenyl)-N-((5-(hydrazinecarbonyl)pyridin-2-yl)methyl)-3,4-dimethylpiperazine-1-sulfonamide (0.110 g, 0.243 mmol), triethylamine (0.169 mL, 1.214 mmol) and 2,2-difluoroacetic anhydride (0.091 mL, 0.729 mmol) in tetrahydrofuran (10 mL) was stirred at 70° C. for 12 hr, cooled down to the room temperature to terminate the reaction. Then, water was added to the reaction mixture, followed by extraction with dichloromethane. The organic layer was washed with aqueous saturated ammonium chloride solution, dried with anhydrous MgSO₄, filtered, and concentrated in vacuo. The residue was chromatographed (SiO₂, 4 g cartridge; methanol/dichloromethane=0% to 5%) to give (S)—N-(3-chlorophenyl)-N-((5-(5-(difluoromethyl)-1,3,4-oxadiazol-2-yl)pyridin-2-yl)methyl)-3,4-dimethylpiperazine-1-sulfonamide as yellow solid (0.085 g, 68.2%).

$^1$H NMR (400 MHz, CDCl$_3$) δ 9.25-9.23 (m, 1H), 8.39-8.36 (m, 1H), 7.67 (d, 1H, J=8.2 Hz), 7.50-7.49 (m, 1H), 7.36-7.33 (m, 1H), 7.27-7.21 (m, 2H), 7.07 (s, 0.3H), 6.94 (s, 0.5H), 6.81 (s, 0.2H), 5.10 (s, 2H), 3.58-3.48 (m, 2H), 3.02-2.95 (m, 1H), 2.77-2.73 (m, 1H), 2.64-2.58 (m, 1H), 2.27 (s, 3H), 2.24-2.19 (m, 1H), 2.18-2.09 (m, 1H), 1.04 (d, 3H, J=6.3 Hz); LRMS (ES) m/z 513.3 (M$^+$+1).

Example 73: Compound 11830, (S)—N-(3-chlorophenyl)-N-((5-(5-(difluoromethyl)-1,3,4-oxadiazol-2-yl)pyridin-2-yl)methyl)-3-methyl-4-(oxetan-3-yl)piperazine-1-sulfonamide

[Step 1] methyl (S)-6-(((N-(3-chlorophenyl)-3-methyl-4-(oxetan-3-yl)piperazine)-1-sulfonamido)methyl)nicotinate

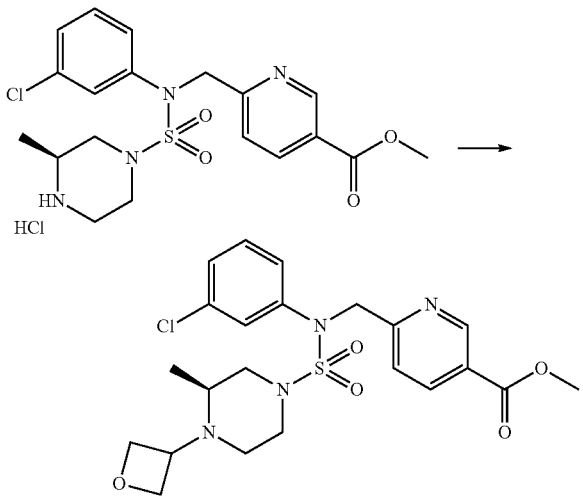

A solution of methyl (S)-6-(((N-(3-chlorophenyl)-3-methylpiperazine)-1-sulfonamido)methyl)nicotinate hydrochloride (0.200 g, 0.421 mmol), oxetan-3-one (0.059 g, 0.841 mmol) and acetic acid (0.029 mL, 0.505 mmol) in dichloromethane (10 mL) was stirred at the room temperature for 30 min, and mixed with sodium triacetoxyborohydride (0.178 g, 0.841 mmol). The reaction mixture was stirred at the same temperature for additional 12 hr. Then, water was added to the reaction mixture, followed by extraction with dichloromethane. The organic layer was washed with aqueous saturated sodium bicarbonate solution, dried with anhydrous MgSO₄, filtered, and concentrated in vacuo. The residue was chromatographed (SiO₂, 4 g cartridge; methanol/dichloromethane=0% to 5%) to give methyl (S)-6-(((N-(3-chlorophenyl)-3-methyl-4-(oxetan-3-yl)piperazine)-1-sulfonamido)methyl)nicotinate as yellow solid (0.110 g, 52.8%).

[Step 2] (S)—N-(3-chlorophenyl)-N-((5-(hydrazinecarbonyl)pyridin-2-yl)methyl)-3-methyl-4-(oxetan-3-yl)piperazine-1-sulfonamide

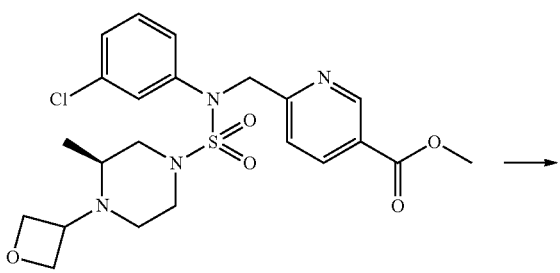

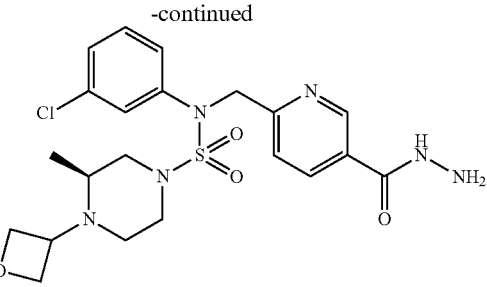

A solution of methyl (S)-6-(((N-(3-chlorophenyl)-3-methyl-4-(oxetan-3-yl)piperazine)-1-sulfonamido)methyl) nicotinate (0.110 g, 0.222 mmol) and hydrazine monohydrate (0.108 mL, 2.222 mmol) in ethanol (10 mL) was stirred at 90° C. for 12 hr, and cooled down to the room temperature to terminate the reaction. The reaction mixture was concentrated under the reduced pressure to remove the solvent. Then, water was added to the concentrate, followed by extraction with dichloromethane. The organic layer was washed with aqueous saturated sodium bicarbonate solution, dried with anhydrous MgSO₄, filtered, and concentrated in vacuo. The title compound was used without further purification (((S)—N-(3-chlorophenyl)-N-((5-(hydrazinecarbonyl)pyridin-2-yl)methyl)-3-methyl-4-(oxetan-3-yl)piperazine-1-sulfonamide, 0.083 g, 75.5%, white solid).

[Step 3] Compound 11830

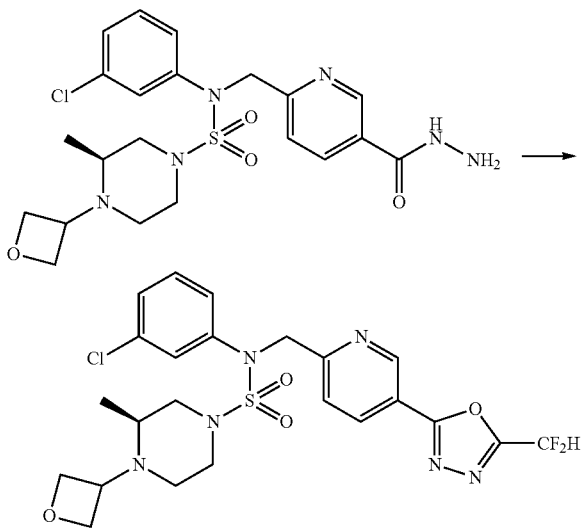

A solution of (S)—N-(3-chlorophenyl)-N-((5-(hydrazinecarbonyl)pyridin-2-yl)methyl)-3-methyl-4-(oxetan-3-yl)piperazine-1-sulfonamide (0.083 g, 0.168 mmol), triethylamine (0.117 mL, 0.838 mmol) and 2,2-difluoroacetic anhydride (0.063 mL, 0.503 mmol) in tetrahydrofuran (10 mL) was stirred at 70° C. for 12 hr, and cooled down to the room temperature to terminate the reaction. Then, water was added to the reaction mixture, followed by extraction with dichloromethane. The organic layer was washed with aqueous saturated ammonium chloride solution, dried with anhydrous MgSO₄, filtered, and concentrated in vacuo. The residue was chromatographed (SiO₂, 4 g cartridge; ethyl acetate/hexane=0% to 80%) to give (S)—N-(3-chlorophenyl)-N-((5-(5-(difluoromethyl)-1,3,4-oxadiazol-2-yl)pyridin-2-yl)methyl)-3-methyl-4-(oxetan-3-yl)piperazine-1-sulfonamide as white solid (0.059 g, 63.4%).

¹H NMR (400 MHz, CDCl₃) δ 9.26-9.24 (m, 1H), 8.39-8.36 (m, 1H), 7.66 (d, 1H, J=8.2 Hz), 7.50-7.49 (m, 1H), 7.36-7.33 (m, 1H), 7.30-7.23 (m, 2H), 7.07 (s, 0.2H), 6.95 (s, 0.5H), 6.82 (s, 0.3H), 5.09 (s, 2H), 4.65-4.56 (m, 4H), 3.75-3.71 (m, 1H), 3.40-3.34 (m, 2H), 3.15-3.14 (m, 1H), 2.88-2.83 (m, 1H), 2.62-2.59 (m, 1H), 2.40-2.38 (m, 1H), 2.15-2.10 (m, 1H), 0.87 (d, 3H, J=6.5 Hz); LRMS (ES) m/z 555.3 (M⁺+1).

Example 74: Compound 11831, N-(3-chlorophenyl)-4-cyclobutyl-N-((5-(5-(difluoromethyl)-1,3,4-oxadiazol-2-yl)pyridin-2-yl)methyl)piperazine-1-sulfonamide

[Step 1] tert-butyl 4-(N-(3-chlorophenyl)sulfamoyl)piperazine-1-carboxylate

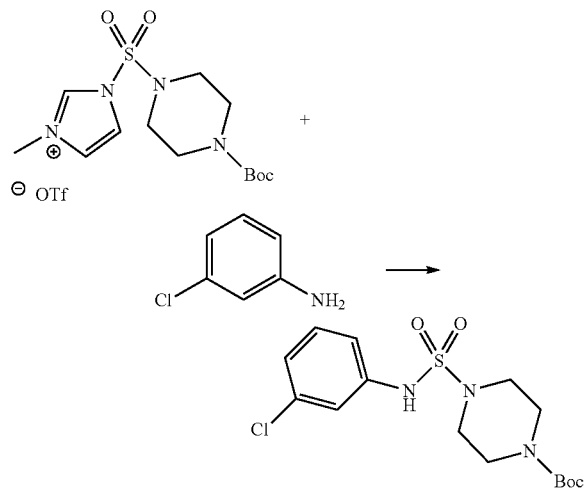

A solution of 1-((4-(tert-butoxycarbonyl)piperazin-1-yl)sulfonyl)-3-methyl-1H-imidazol-3-ium trifluoromethanesulfonate (4.750 g, 9.886 mmol) and 3-chloroaniline (1.241 mL, 11.863 mmol) in acetonitrile (50 mL) was stirred at the room temperature for 18 hr. Then, water was added to the reaction mixture, followed by extraction with ethyl acetate. The organic layer was washed with aqueous saturated sodium chloride solution, dried with anhydrous MgSO₄, filtered, and concentrated in vacuo. The residue was chromatographed (SiO₂, 40 g cartridge; ethyl acetate/hexane=0% to 80%) to give tert-butyl 4-(N-(3-chlorophenyl)sulfamoyl)piperazine-1-carboxylate as white solid (2.770 g, 74.5%).

[Step 2] tert-butyl 4-(N-(3-chlorophenyl)-N-((5-(methoxycarbonyl)pyridin-2-yl)methyl)sulfamoyl)piperazine-1-carboxylate

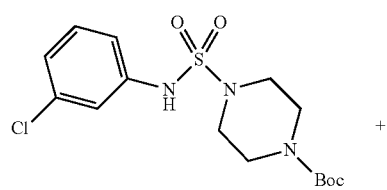

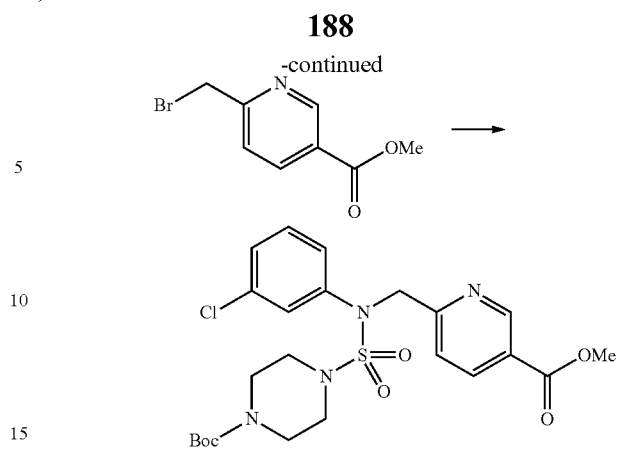

A solution of tert-butyl 4-(N-(3-chlorophenyl)sulfamoyl)piperazine-1-carboxylate (1.000 g, 2.660 mmol) and sodium hydride (60.00%, 0.213 g, 5.321 mmol) in N,N-dimethylformide (30 mL) was stirred at 0° C. for 10 min, and mixed with methyl 6-(bromomethyl)nicotinate (0.734 g, 3.193 mmol). The reaction mixture was stirred at the room temperature for additional 18 hr. Then, water was added to the reaction mixture, followed by extraction with ethyl acetate. The organic layer was washed with aqueous saturated sodium chloride solution, dried with anhydrous MgSO₄, filtered, and concentrated in vacuo. The residue was chromatographed (SiO₂, 12 g cartridge; ethyl acetate/hexane=0% to 80%) to give tert-butyl 4-(N-(3-chlorophenyl)-N-((5-(methoxycarbonyl)pyridin-2-yl)methyl)sulfamoyl)piperazine-1-carboxylate as yellow solid (1.200 g, 85.9%).

[Step 3] methyl 6-((N-(3-chlorophenyl)piperazine-1-sulfonamido)methyl)nicotinate Hydrochloride

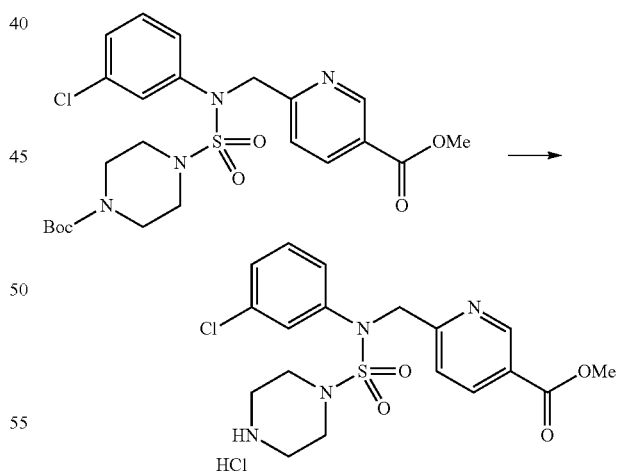

A solution of tert-butyl 4-(N-(3-chlorophenyl)-N-((5-(methoxycarbonyl)pyridin-2-yl)methyl)sulfamoyl)piperazine-1-carboxylate (1.900 g, 3.619 mmol) in dichloromethane (50 mL) was mixed at the room temperature with hydrochloric acid (4.00 M solution in dioxane, 3.619 mL, 14.476 mmol), and stirred at the same temperature for 3 hr. The reaction mixture was concentrated under the reduced pressure to remove the solvent. The title compound was used without further purification (methyl 6-((N-(3-chlorophenyl)

piperazine-1-sulfonamido)methyl)nicotinate hydrochloride, 1.200 g, 71.9%, yellow solid).

[Step 4] methyl 6-(((N-(3-chlorophenyl)-4-cyclobutylpiperazine)-1-sulfonamido)methyl)nicotinate

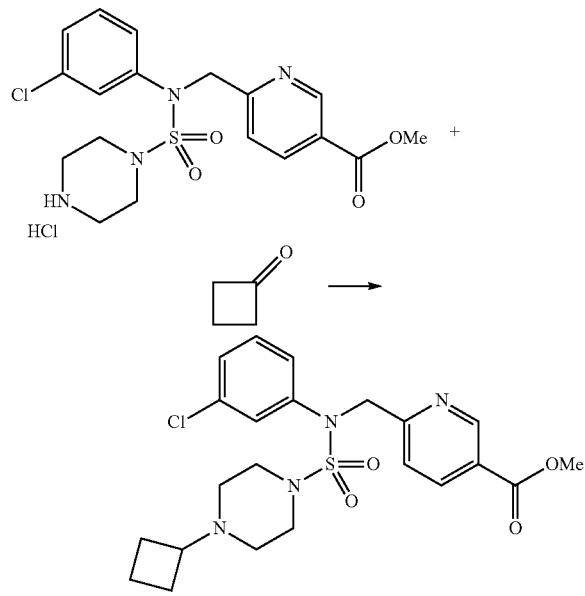

A solution of methyl 6-((N-(3-chlorophenyl)piperazine-1-sulfonamido)methyl)nicotinate hydrochloride (0.300 g, 0.650 mmol) and cyclobutanone (0.058 mL, 0.780 mmol) in dichloromethane (12 mL) was stirred at the room temperature for 10 min, and mixed with sodium triacetoxyborohydride (0.413 g, 1.951 mmol). The reaction mixture was stirred at the same temperature for additional 18 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 4 g cartridge; methanol/dichloromethane=0% to 15%) to give methyl 6-(((N-(3-chlorophenyl)-4-cyclobutylpiperazine)-1-sulfonamido)methyl)nicotinate as yellow solid (0.174 g, 55.9%).

[Step 5] N-(3-chlorophenyl)-4-cyclobutyl-N-((5-(hydrazinecarbonyl)pyridin-2-yl)methyl)piperazine-1-sulfonamide

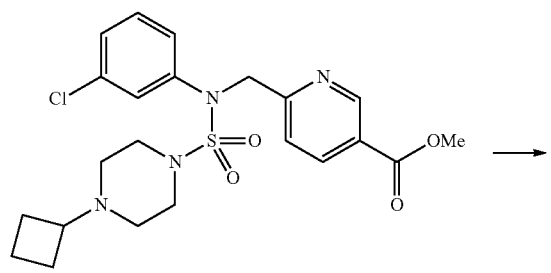

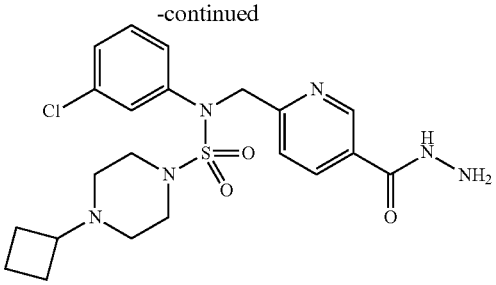

methyl 6-(((N-(3-chlorophenyl)-4-cyclobutylpiperazine)-1-sulfonamido)methyl)nicotinate (0.174 g, 0.363 mmol) and hydrazine monohydrate (0.530 mL, 10.898 mmol) were mixed at the room temperature in ethanol (10 mL), and then the mixture was stirred at 80° C. for 18 hr. The reaction mixture was cooled down to the room temperature to terminate the reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The title compound was used without further purification (N-(3-chlorophenyl)-4-cyclobutyl-N-((5-(hydrazinecarbonyl)pyridin-2-yl)methyl)piper azine-1-sulfonamide, 0.168 g, 96.5%, yellow solid).

[Step 6] Compound 11831

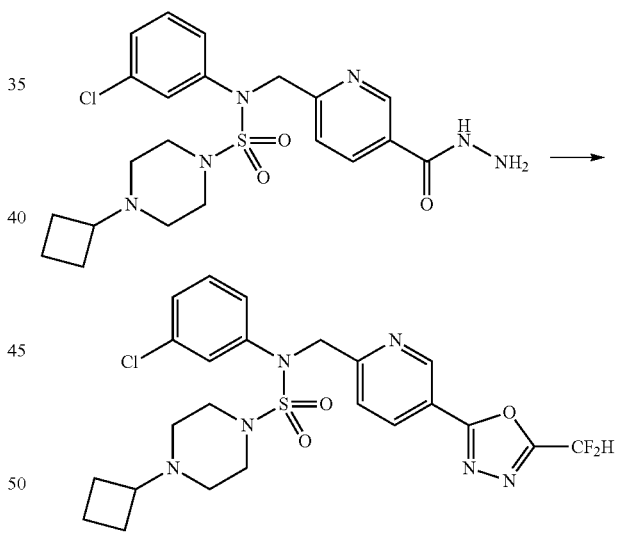

A solution of N-(3-chlorophenyl)-4-cyclobutyl-N-((5-(hydrazinecarbonyl)pyridin-2-yl)methyl)piperazine-1-sulfonamide (0.168 g, 0.351 mmol) and triethylamine (0.244 mL, 1.754 mmol) in tetrahydrofuran (15 mL) was mixed at the room temperature with 2,2-difluoroacetic anhydride (0.131 mL, 1.052 mmol), and stirred at 80° C. for 2 hr. The reaction mixture was cooled down to the room temperature to terminate the reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (Sift, 12 g cartridge; methanol/dichloromethane=0% to 15%) to give N-(3-chlorophenyl)-4-cyclobutyl- N-((5-(5-(difluoromethyl)-1,3,4-oxadiazol-2-yl)pyridin-2-yl)methyl)piperazine-1-sulfonamide as yellow solid (0.082 g, 43.4%).

$^1$H NMR (400 MHz, CD$_3$OD) δ 9.23 (d, 1H, J=1.7 Hz,), 8.36 (dd, 1H, J=8.2, 2.2 Hz), 7.66 (d, 1H, J=8.2 Hz), 7.49-7.48 (m, 1H), 7.36-7.33 (m, 1H), 7.28-7.20 (m, 2H), 7.07 (s, 0.25H), 6.94 (s, 0.5H), 6.81 (s, 0.25H), 5.09 (s, 2H), 3.32-3.28 (m, 4H), 2.83-2.70 (m, 1H), 2.34-2.30 (m, 4H), 2.05-1.99 (m, 2H), 1.88-1.84 (m, 2H), 1.73-1.63 (m, 2H); LRMS (ES) m/z 539.2 (M$^+$+1)

Example 75: Compound 11832, N-(3-chlorophenyl)-N-((5-(5-(difluoromethyl)-1,3,4-oxadiazol-2-yl)pyridin-2-yl)methyl)-4-(oxetan-3-yl)piperazine-1-sulfonamide

[Step 1] methyl 6-(((N-(3-chlorophenyl)-4-(oxetan-3-yl)piperazine)-1-sulfonamido)methyl)nicotinate

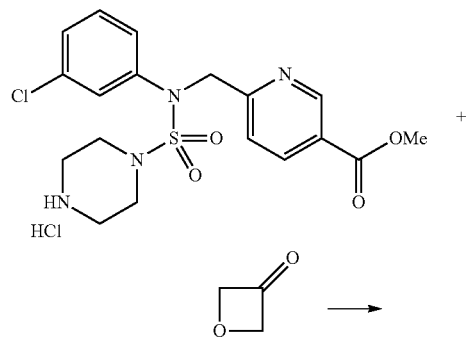

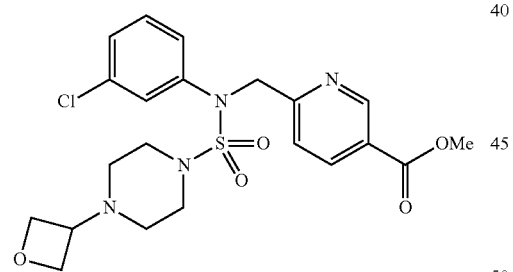

A solution of methyl 6-((N-(3-chlorophenyl)piperazine-1-sulfonamido)methyl)nicotinate hydrochloride (0.300 g, 0.650 mmol) and oxetan-3-one (0.050 mL, 0.780 mmol) in dichloromethane (15 mL) was stirred at the room temperature for 10 min, and mixed with sodium triacetoxyborohydride (0.413 g, 1.951 mmol). The reaction mixture was stirred at the same temperature for additional 18 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 4 g cartridge; methanol/dichloromethane=0% to 15%) to give methyl 6-(((N-(3-chlorophenyl)-4-(oxetan-3-yl)piperazine)-1-sulfonamido)methyl)nicotinate as yellow solid (0.211 g, 67.5%).

[Step 2] N-(3-chlorophenyl)-N-((5-(hydrazinecarbonyl)pyridin-2-yl)methyl)-4-(oxetan-3-yl)piperazine-1-sulfonamide

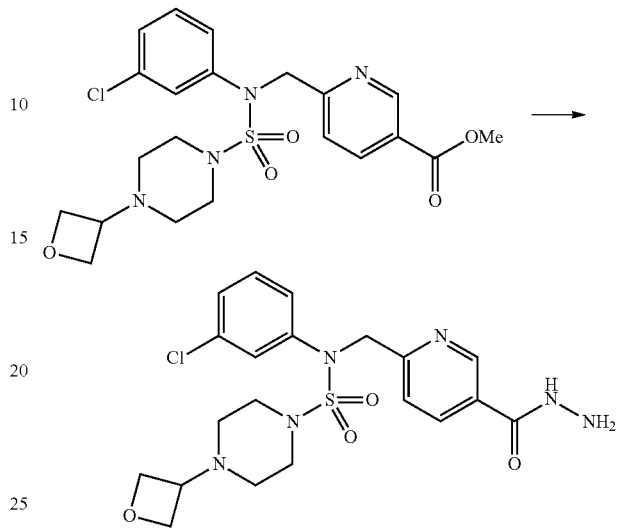

methyl 6-(((N-(3-chlorophenyl)-4-(oxetan-3-yl)piperazine)-1-sulfonamido)methyl)nicotinate (0.211 g, 0.439 mmol) and hydrazine monohydrate (0.640 mL, 13.161 mmol) were mixed at the room temperature in ethanol (10 mL), and then the mixture was stirred at 80° C. for 18 hr. The reaction mixture was cooled down to the room temperature to terminate the reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The title compound was used without further purification (N-(3-chlorophenyl)-N-((5-(hydrazinecarbonyl)pyridin-2-yl)methyl)-4-(oxetan-3-yl)piperazine-1-sulfonamide, 0.188 g, 89.1%, yellow solid).

[Step 3] Compound 11832

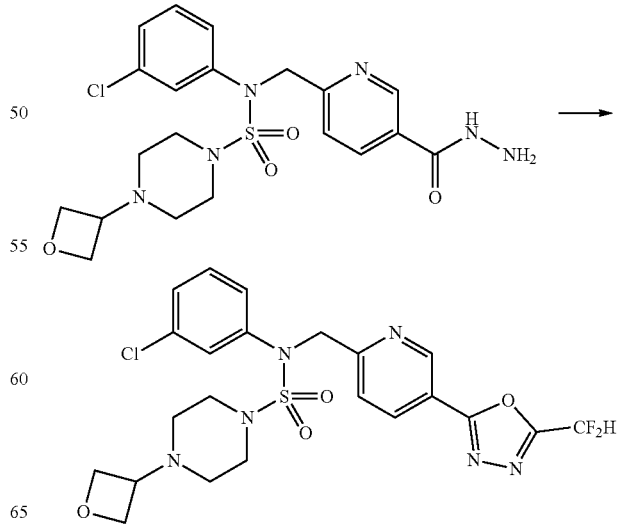

A solution of N-(3-chlorophenyl)-N-((5-(hydrazinecarbonyl)pyridin-2-yl)methyl)-4-(oxetan-3-yl)piperazine-1-sulfonamide (0.188 g, 0.391 mmol) and triethylamine (0.272 mL, 1.954 mmol) in tetrahydrofuran (15 mL) was mixed at the room temperature with 2,2-difluoroacetic anhydride (0.146 mL, 1.173 mmol), and stirred at 80° C. for 2 hr. The reaction mixture was cooled down to the room temperature to terminate the reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 4 g cartridge; methanol/dichloromethane=0% to 15%) to give N-(3-chlorophenyl)-N-((5-(5-(difluoromethyl)-1,3,4-oxadiazol-2-yl)pyridin-2-yl)methyl)-4-(oxetan-3-yl)piperazine-1-sulfonamide as yellow solid (0.094 g, 44.5%).

$^1$H NMR (400 MHz, CD$_3$OD) δ 9.23 (d, 1H, J=1.7 Hz,), 8.37 (dd, 1H, J=8.2, 2.2 Hz), 7.65 (d, 1H, J=8.2 Hz), 7.50-7.47 (m, 1H), 7.36-7.33 (m, 1H), 7.30-7.22 (m, 2H), 7.07 (s, 0.25H), 6.94 (s, 0.5H), 6.81 (s, 0.25H), 5.09 (s, 2H), 4.66-4.63 (m, 2H), 4.56-4.53 (m, 2H), 3.50-3.44 (m, 1H), 3.31-3.29 (m, 4H), 2.31-2.29 (m, 4H); LRMS (ES) m/z 541.3 (M$^+$+1).

Example 76: Compound 11833, N-((5-(5-(difluoromethyl)-1,3,4-oxadiazol-2-yl)pyridin-2-yl)methyl)-4-(oxetan-3-yl)-N-(m-tolyl)piperazine-1-sulfonamide

[Step 1] tert-butyl 4-(N-(m-tolyl)sulfamoyl)piperazine-1-carboxylate

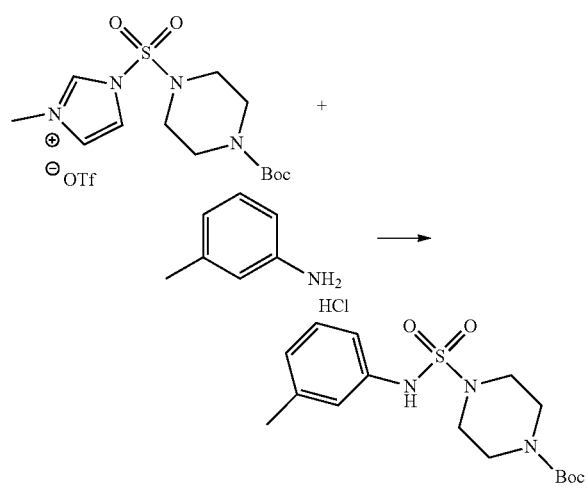

A solution of 1-((4-(tert-butoxycarbonyl)piperazin-1-yl)sulfonyl)-3-methyl-1H-imidazol-3-ium trifluoromethanesulfonate (4.750 g, 9.886 mmol) and m-toluidine hydrochloride (1.704 g, 11.863 mmol) in acetonitrile (50 mL) was stirred at the room temperature for 18 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 12 g cartridge; ethyl acetate/hexane=0% to 30%) to give tert-butyl 4-(N-(m-tolyl)sulfamoyl)piperazine-1-carboxylate as white solid (2.110 g, 60.0%).

[Step 2] tert-butyl 4-(N-((5-(methoxycarbonyl)pyridin-2-yl)methyl)-N-(m-tolyl)sulfamoyl)piperazine-1-carboxylate

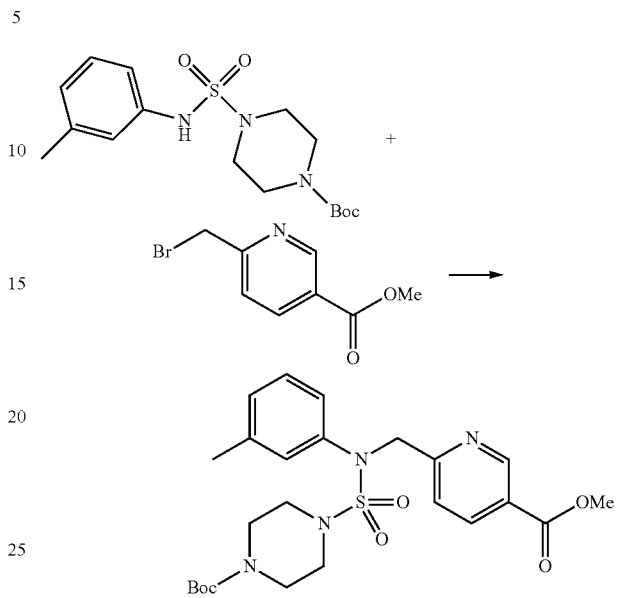

A solution of tert-butyl 4-(N-(m-tolyl)sulfamoyl)piperazine-1-carboxylate (1.000 g, 2.813 mmol) and sodium hydride (60.00%, 0.225 g, 5.627 mmol) in N,N-dimethylformide (30 mL) was stirred at 0° C. for 10 min, and mixed with methyl 6-(bromomethyl)nicotinate (0.777 g, 3.376 mmol). The reaction mixture was stirred at the room temperature for additional 18 hr. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 40 g cartridge; ethyl acetate/hexane=0% to 80%) to give tert-butyl 4-(N-((5-(methoxycarbonyl)pyridin-2-yl)methyl)-N-(m-tolyl)sulfamoyl)piperazine-1-carboxylate as yellow solid (1.170 g, 82.4%).

[Step 3] methyl 6-((N-(m-tolyl)piperazine-1-sulfonamido)methyl)nicotinate Hydrochloride

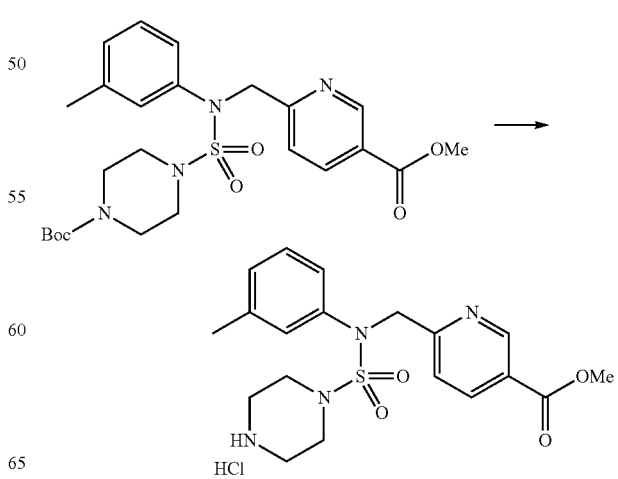

A solution of tert-butyl 4-(N-((5-(methoxycarbonyl)pyridin-2-yl)methyl)-N-(m-tolyl)sulfamoyl)piperazine-1-carboxylate (1.300 g, 2.576 mmol) in dichloromethane (50 mL) was mixed at the room temperature with hydrochloric acid (4.00 M solution in dioxane, 2.576 mL, 10.305 mmol), and stirred at the same temperature for 3 hr. The reaction mixture was concentrated under the reduced pressure to remove the solvent. The title compound was used without further purification (methyl 6-((N-(m-tolyl)piperazine-1-sulfonamido)methyl)nicotinate hydrochloride, 0.980 g, 86.3%, red solid).

[Step 4] methyl 6-(((4-(oxetan-3-yl)-N-(m-tolyl)piperazine)-1-sulfonamido)methyl)nicotinate

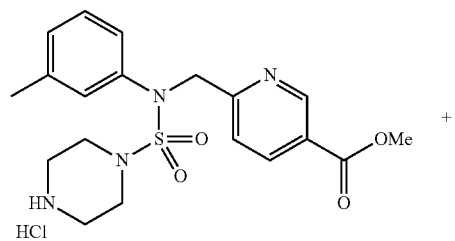

+

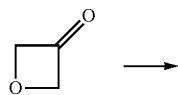

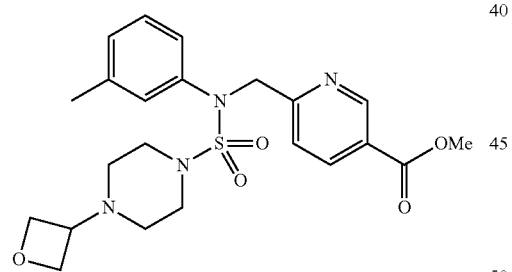

A solution of methyl 6-((N-(m-tolyl)piperazine-1-sulfonamido)methyl)nicotinate hydrochloride (0.300 g, 0.680 mmol) and oxetan-3-one (0.053 mL, 0.816 mmol) in dichloromethane (15 mL) was stirred at the room temperature for 10 min, and mixed with sodium triacetoxyborohydride (0.433 g, 2.041 mmol). The reaction mixture was stirred at the same temperature for additional 18 hr. Then, water was added to the reaction mixture, followed by extraction with ethyl acetate. The organic layer was washed with aqueous saturated sodium chloride solution, dried with anhydrous MgSO₄, filtered, and concentrated in vacuo. The residue was chromatographed (SiO₂, 4 g cartridge; methanol/dichloromethane=0% to 15%) to give methyl 6-(((4-(oxetan-3-yl)-N-(m-tolyl)piperazine)-1-sulfonamido)methyl)nicotinate as yellow solid (0.248 g, 79.1%).

[Step 5] N-((5-(hydrazinecarbonyl)pyridin-2-yl)methyl)-4-(oxetan-3-yl)-N-(m-tolyl)piperazine-1-sulfonamide

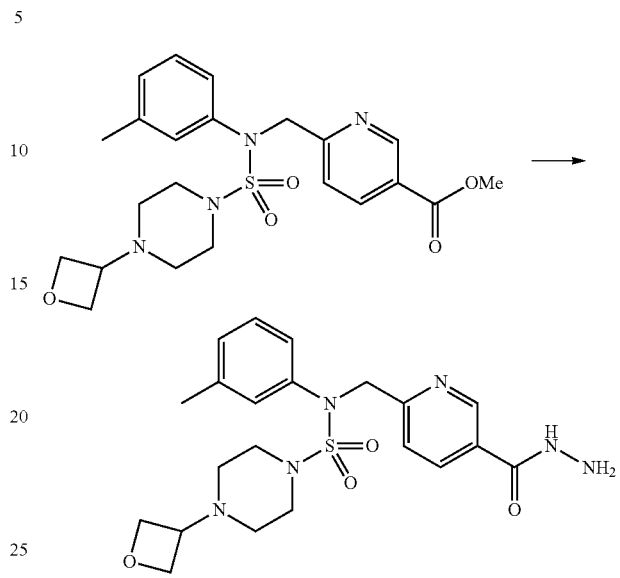

methyl 6-(((4-(oxetan-3-yl)-N-(m-tolyl)piperazine)-1-sulfonamido)methyl)nicotinate (0.248 g, 0.538 mmol) and hydrazine monohydrate (0.785 mL, 16.155 mmol) were mixed at the room temperature in ethanol (10 mL), and then the mixture was stirred at 80° C. for 18 hr. The reaction mixture was cooled down to the room temperature to terminate the reaction. Then, water was added to the reaction mixture, followed by extraction with ethyl acetate. The organic layer was washed with aqueous saturated sodium chloride solution, dried with anhydrous MgSO₄, filtered, and concentrated in vacuo. The title compound was used without further purification (N-((5-(hydrazinecarbonyl)pyridin-2-yl)methyl)-4-(oxetan-3-yl)-N-(m-tolyl)piperazine-1-sulfonamide, 0.177 g, 71.4%, yellow solid).

[Step 6] Compound 11833

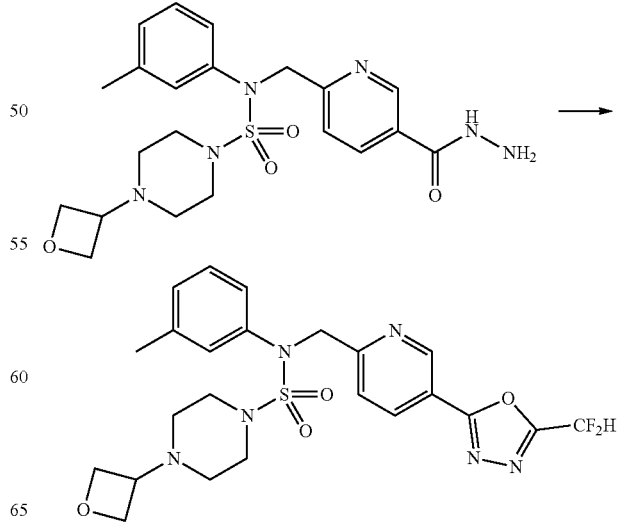

A solution of N-((5-(hydrazinecarbonyl)pyridin-2-yl)methyl)-4-(oxetan-3-yl)-N-(m-tolyl)piperazine-1-sulfonamide (0.177 g, 0.384 mmol) and triethylamine (0.268 mL, 1.922 mmol) in tetrahydrofuran (15 mL) was mixed at the room temperature with 2,2-difluoroacetic anhydride (0.143 mL, 1.153 mmol), and stirred at 80° C. for 1 hr. The reaction mixture was cooled down to the room temperature to terminate the reaction. Then, water was added to the reaction mixture, followed by extraction with ethyl acetate. The organic layer was washed with aqueous saturated sodium chloride solution, dried with anhydrous MgSO$_4$, filtered, and concentrated in vacuo. The residue was chromatographed (SiO$_2$, 4 g cartridge; methanol/dichloromethane=0% to 15%) to give N-((5-(5-(difluoromethyl)-1,3,4-oxadiazol-2-yl)pyridin-2-yl)methyl)-4-(oxetan-3-yl)-N-(m-tolyl)piperazine-1-sulfonamide as yellow solid (0.130 g, 65.0%).

$^1$H NMR (400 MHz, CD$_3$OD) δ 9.20-9.19 (m, 1H), 8.35 (dd, 1H, J=8.2, 2.2 Hz), 7.70 (d, 1H, J=8.2 Hz,), 7.26 (s, 1H), 7.24-7.18 (m, 2H), 7.06-7.05 (m, 1H), 7.03 (s, 0.25H), 6.93 (s, 0.5H), 6.81 (s, 0.25H), 5.10 (s, 2H), 4.66-4.62 (m, 2H), 4.56-4.53 (m, 2H), 3.50-3.43 (m, 1H), 3.30-3.28 (m, 4H), 2.37-2.29 (m, 7H); LRMS (ES) m/z 521.4 (M$^+$+1).

Measurement of Activity of the Compounds of the Present Invention and Analysis Protocol Experimental Example 1: HDAC Enzyme Activity Inhibition Assays (In Vitro)

In order to examine the HDAC6 selectivity of the compounds of formula I of the present invention by HDAC1 and HDAC6 enzymatic activity inhibition assays, an experiment was performed using a conventional substance as a control.

HDAC enzyme activity was measured using a HDAC Fluorimetric Drug Discovery Kit (BML-AK511, 516, Enzo Life Science). For the HDAC1 enzyme activity test, human recombinant HDAC1 (BML-SE456) was used as an enzyme source, and Fluor de Lys®-"SIRT1 (BNL-KI177) was used as a substrate. A 5-fold dilution of the compound was seeded into a 96-well plate, and then 0.3 μg of the enzyme and 10 μM of the substrate were added to each well of the plate and allowed to react at 30 for 60 minutes. Then, Fluor de Lys®-Developer II (BML-KI176) was added thereto and allowed to react for 30 minutes, after which the fluorescence value (Ex 360, Em 460) was measured using a multi-plate reader (Flexstation 3, Molecular Device). The HDAC6 enzyme was tested using human recombinant HDAC6 (382180) (Calbiochem) according to the same protocol as the HDAC1 enzyme activity test method. Based on the resulting values, each IC$_{50}$ value was calculated using GraphPad Prism4.0 program.

TABLE 2

Results of HDAC enzyme activity inhibition assays

| Ex. | Comp. | HDAC1 (nM) | HDAC6 (nM) | HDAC6 selectivity (fold) |
|---|---|---|---|---|
| 1 | 11198 | ND | 136 | 738 |
| 2 | 11199 | ND | 52 | 1911 |
| 3 | 11293 | 76012 | 66 | 1156 |
| 4 | 11294 | ND | 71 | 1411 |
| 5 | 11295 | ND | 133 | 751 |
| 6 | 11296 | ND | 157 | 636 |
| 7 | 11297 | ND | 124 | 805 |
| 8 | 11298 | ND | 75 | 1333 |
| 9 | 11299 | ND | 86 | 1169 |
| 10 | 11300 | ND | 116 | 861 |
| 11 | 11301 | ND | 28 | 3622 |
| 12 | 11302 | ND | 32 | 3174 |
| 13 | 11303 | ND | 31 | 3187 |
| 14 | 11304 | ND | 52 | 1912 |
| 15 | 11305 | ND | 38 | 2620 |
| 16 | 11306 | ND | 23 | 4363 |
| 17 | 11307 | ND | 42 | 2366 |
| 18 | 11308 | ND | 46 | 2168 |
| 19 | 11309 | 41507 | 58 | 710 |
| 20 | 11310 | ND | 76 | 1311 |
| 21 | 11311 | ND | 84 | 1188 |
| 22 | 11312 | ND | 73 | 1371 |
| 23 | 11313 | ND | 24 | 4246 |
| 24 | 11314 | ND | 33 | 3061 |
| 25 | 11315 | ND | 30 | 3367 |
| 26 | 11316 | ND | 25 | 4031 |
| 27 | 11317 | ND | 81 | 1234 |
| 28 | 11318 | ND | 43 | 2299 |
| 29 | 11319 | ND | 68 | 1464 |
| 30 | 11320 | ND | 55 | 1829 |
| 31 | 11321 | ND | 44 | 2249 |
| 32 | 11322 | ND | 66 | 1507 |
| 33 | 11363 | ND | 15 | 6863 |
| 34 | 11379 | ND | 26 | 3846 |
| 35 | 11440 | ND | 20 | 5000 |
| 36 | 11498 | 49237 | 23 | 2141 |
| 37 | 11527 | 47658 | 76 | 627 |
| 38 | 11528 | 41596 | 79 | 527 |
| 39 | 11574 | ND | 16 | 6250 |
| 40 | 11575 | ND | 48 | 2083 |
| 41 | 11640 | ND | 105 | 946 |
| 42 | 11641 | ND | 33 | 2989 |
| 43 | 11642 | ND | 348 | 287 |
| 44 | 11643 | ND | 69 | 1443 |
| 45 | 11644 | ND | 130 | 770 |
| 46 | 11651 | ND | 481 | 207 |
| 47 | 11652 | ND | 237 | 422 |
| 48 | 11653 | 52403 | 43 | 1214 |
| 49 | 11654 | 71480 | 36 | 1996 |
| 50 | 11659 | 72379 | 26 | 2753 |
| 51 | 11660 | 76482 | 63 | 1206 |
| 52 | 11661 | 115621 | 61 | 1886 |
| 53 | 11662 | 55253 | 47 | 1182 |
| 54 | 11670 | ND | 21 | 4761 |
| 55 | 11671 | ND | 27 | 3703 |
| 56 | 11672 | ND | 14 | 7142 |
| 57 | 11673 | ND | 74 | 1351 |
| 58 | 11674 | ND | 133 | 751 |
| 59 | 11702 | 50198 | 93 | 542 |
| 60 | 11704 | ND | 233 | 429 |
| 61 | 11713 | ND | 705 | 142 |
| 62 | 11714 | ND | 162 | 616 |
| 63 | 11787 | ND | 96 | 1041 |
| 64 | 11788 | ND | 178 | 561 |
| 65 | 11789 | ND | 122 | 819 |
| 66 | 11823 | ND | 48 | 2083 |
| 67 | 11824 | ND | 50 | 2000 |
| 68 | 11825 | ND | 36 | 2777 |
| 69 | 11826 | ND | 41 | 2439 |
| 70 | 11827 | ND | 52 | 1923 |
| 71 | 11828 | ND | 42 | 2380 |
| 72 | 11829 | ND | 29 | 3448 |
| 73 | 11830 | ND | 17 | 5882 |
| 74 | 11831 | ND | 36 | 2777 |
| 75 | 11832 | ND | 21 | 4761 |
| 76 | 11833 | ND | 49 | 2040 |

As can be seen in Table 2 above, the 1,3,4-oxadiazole sulfamide derivative compounds, stereoisomers thereof or pharmaceutically acceptable salts thereof according to the present invention showed about 142 to about 7142 times higher selective HDAC6 inhibitory activities in the HDAC1 and HDAC6 activity inhibition assays.

Experimental Example 2: Analysis of the Effect of HDAC6-Specific Inhibitors on Mitochondrial Axonal Transport (In Vitro)

The effect of HDAC6-specific inhibitors on mitochondrial axonal transport was analyzed. Specifically, in order to examine whether the compounds represented by formula I according to the present invention selectively inhibit HDAC6 activity to increase the acetylation of tubulin, which is a major substrate of HDAC6, thereby improving the mitochondrial axonal transport velocity reduced by amyloid-beta treatment in neuronal axons, a comparison experiment was performed using a compound that have already been developed as a control.

Hippocampal neurons from Sprague-Dawley (SD) rat embryos at embryonic day 17-18 (E17-18) were cultured in an extracellular matrix-coated dish for imaging for 7 days, and then treated with 1 M of an amyloid-beta peptides. After 24 hours, the neurons were treated with compounds for 3 hours on the 8th days in vitro and treated with MitoTracker Red CMXRos (Life Technologies, NY, USA) for the last 5 minutes to stain the mitochondria. Axonal transport of the stained mitochondria was imaged using a confocal microscope (Leica SP8; Leica Microsystems, UK) at 1-second intervals for 1 minute, and the transport velocity per second of each mitochondrion was determined using the IMARIS analysis software (BITPLANE, Zurich, Switzerland).

As a result, it was found that the 1,3,4-oxadiazole sulfamide derivative compounds, stereoisomers thereof or pharmaceutically acceptable salts according to the present invention improved the velocity of mitochondrial axonal transport.

The invention claimed is:

1. A 1,3,4-oxadiazole sulfamide compound represented by the following formula I:

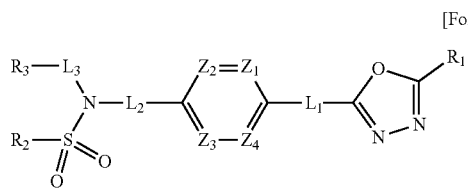

[Formula I]

wherein $L_1$, $L_2$ and $L_3$ are each independently a bond or -($C_1$-$C_2$ alkylene)-;

$Z_1$ to $Z_4$ are each independently N or $CR^Z$, wherein $R^Z$ is —H or —X;

$R_1$ is —$CX_2H$ or —$CX_3$;

$R_2$ is

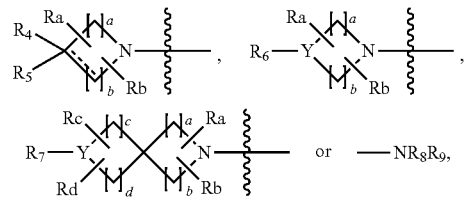

wherein Y is —N—, —O— or —S(=O)$_2$—,
a to d are each independently an integer of 1, 2 or 3,
Ra to Rd are each independently —H or -($C_1$-$C_4$ alkyl),
the dotted line is a single bond or a double bond, $R_4$ and $R_5$ are each independently -H, -X, -($C_1$-$C_4$ alkyl), -aryl or —NReRf, provided that when the dotted line is a double bond, $R_5$ is null, Re and Rf are each independently —H or -($C_1$-$C_4$ alkyl), when Y is —N—, $R_6$ and $R_7$ are each independently -H, -($C_1$-$C_4$ alkyl), -($C_1$-$C_4$ alkyl)-O—($C_1$-$C_4$ alkyl), —C(=O)-($C_1$-$C_4$ alkyl), —C(=O)—O($C_1$-$C_4$ alkyl), —C(=O)—$CF_3$, -($C_1$-$C_4$ alkyl)-C(=O)—O($C_1$-$C_4$ alkyl), —S(=O)$_2$-($C_1$-$C_4$ alkyl), -($C_3$-$C_7$ cycloalkyl), -($C_2$-$C_6$ heterocycloalkyl), -aryl, -($C_1$-$C_4$ alkyl)-aryl, -heteroaryl or amine protecting group, wherein at least one H of the -($C_1$-$C_4$ alkyl) may be substituted with —X or —OH, at least one H of the -aryl, —($C_1$-$C_4$ alkyl)-aryl or -heteroaryl may be substituted with —X, —OH or —$CF_3$, and the -($C_2$-$C_6$heterocycloalkyl) may contain an N, O or S atom in the ring, and when Y is —O— or —S(=O)$_2$—, $R_6$ and $R_7$ are null, $R_8$ and $R_9$ are each independently -H, -($C_1$-$C_4$ alkyl), -($C_3$-$C_7$ cycloalkyl), -($C_2$-$C_6$ heterocycloalkyl), -($C_1$-$C_4$ alkyl)-($C_2$-$C_6$ heterocycloalkyl), -aryl, -heteroaryl or -($C_1$-$C_4$ alkyl)-aryl, wherein at least one H of the -($C_3$-$C_7$ cycloalkyl), -($C_2$-$C_6$ heterocycloalkyl), -($C_1$-$C_4$ alkyl)-($C_2$-$C_6$ heterocycloalkyl), -aryl, -heteroaryl or -($C_1$-$C_4$ alkyl) -aryl may be substituted with -($C_1$-$C_4$ alkyl), —C(=O)-($C_1$-$C_4$ alkyl), —S(=O)$_2$-($C_1$-$C_4$ alkyl) or -($C_2$-$C_6$ heterocycloalkyl); and $R_3$ is —H, -($C_1$-$C_4$ alkyl), -($C_1$-$C_4$ alkyl) -O($C_1$-$C_4$ alkyl), -($C_1$-$C_4$ alkyl) -C(=O)—O($C_1$-$C_4$ alkyl), -($C_3$-$C_7$ cycloalkyl), -aryl, -heteroaryl or

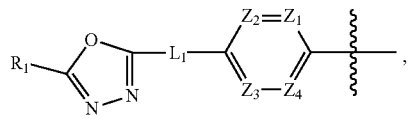

wherein at least one H of the -($C_3$-$C_7$ cycloalkyl), -aryl or -heteroaryl may be substituted with —X, —OH, -($C_1$-$C_4$ alkyl), —$CF_3$, -($C_1$-$C_4$ alkyl)-($C_2$-$C_6$ heterocycloalkyl)-($C_1$-$C_4$ alkyl), —C(=O)-($C_1$-$C_4$ alkyl), —C(=O)—O($C_1$-$C_4$ alkyl), -O($C_1$-$C_4$ alkyl), -O$CF_3$, —S(=O)$_2$-($C_1$-$C_4$ alkyl), -aryl, -heteroaryl or —$NR_{11}R_{12}$, $R_{11}$ and $R_{12}$ are each independently —H or -($C_1$-$C_4$alkyl), $R_1$, $L_1$, $Z_1$, $Z_2$, $Z_3$ and $Z_4$ are as defined above; and X is F, Cl, Br or I; and stereoisomers and pharmaceutically acceptable salts thereof.

2. The 1,3,4-oxadiazole sulfamide compound according to claim 1, wherein $L_1$ and $L_3$ are each independently a bond;

$L_2$ is -($C_1$ alkylene)-;

$Z_1$ to $Z_4$ are each independently N or $CR^Z$, wherein $R^Z$ is —H or —X;

$R_1$ is —$CX_2H$ or —$CX_3$;

$R_2$ is

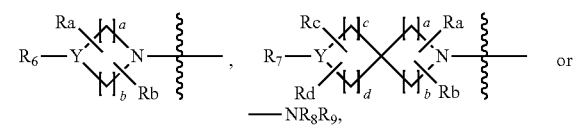

wherein Y is —N—, —O— or —S(=O)$_2$-,
a to d are each independently an integer of 1 or 2,
Ra to Rd are each independently —H or -($C_1$-$C_4$ alkyl), when Y is —N—, $R_6$ and $R_7$ are each independently -H, -($C_1$-$C_4$ alkyl), —C(=O)-($C_1$-$C_4$ alkyl), —S(=O)$_2$-($C_1$-$C_4$ alkyl), -($C_3$-$C_7$ cycloalkyl) or -($C_2$-$C_6$ heterocycloalkyl), wherein at least one H of -($C_1$-$C_4$ alkyl) may be substituted with —X or —OH, and -($C_2$-$C_6$ heterocycloalkyl) may contain an N, O or S atom in the ring, and when Y is —O— or —S(=O)$_2$—, $R_6$ and $R_7$ are null, $R_8$ and $R_9$ are each independently -H, -($C_1$-$C_4$ alkyl) or -($C_1$-$C_4$ alkyl)-($C_2$-$C_6$ heterocycloalkyl), wherein at least one H of the —($C_1$-$C_4$ alkyl)-($C_2$-$C_6$ heterocycloalkyl) may be substituted with —($C_1$-$C_4$ alkyl), —C(=O)-($C_1$-$C_4$ alkyl), —S(=O)$_2$-($C_1$-$C_4$ alkyl) or -($C_2$-$C_6$ heterocycloalkyl);

$R_3$ is -aryl or -heteroaryl, wherein at least one H of the -aryl or -heteroaryl may be substituted with —X; and X is F, Cl, Br or I.

3. The 1,3,4-oxadiazole sulfamide compound according to claim 2, wherein $L_1$ or $L_3$ are each independently a bond;

$L_2$ is -($C_1$ alkylene)-;

$Z_1$ to $Z_4$ are each independently N or CR$^Z$, wherein R$^Z$ is —H or —X;

$R_1$ is —CF$_2$H or —CF$_3$;

$R_2$ is

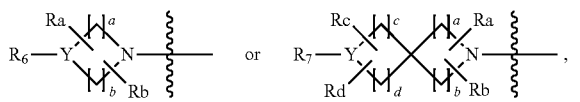

wherein Y is —N— or —S(=O)$_2$-, a to d are each independently an integer of 1 or 2, Ra to Rd are each independently —H or -($C_1$-$C_4$ alkyl), when Y is —N—, $R_6$ and $R_7$ are each independently -H, -($C_1$-$C_4$ alkyl), —C(=O)-($C_1$-$C_4$ alkyl), —S(=O)$_2$-($C_1$-$C_4$ alkyl), -($C_3$-$C_7$ cycloalkyl) or -($C_2$-$C_6$ heterocycloalkyl), wherein at least one H of the -($C_1$-$C_4$ alkyl) may be substituted with —X or —OH, and the —($C_2$-$C_6$ heterocycloalkyl) may contain an N, O or S atom in the ring, and when Y is —S(=O)$_2$—, $R_6$ and $R_7$ are null;

$R_3$ is -aryl or -heteroaryl, wherein at least one H of the -aryl or -heteroaryl may be substituted with —F; and X is F or Cl.

4. The 1,3,4-oxadiazole sulfamide compound according to claim 3, wherein $L_1$ or $L_3$ are each independently a bond;

$L_2$ is -($C_1$ alkylene)-;

$Z_1$ to $Z_4$ are each independently N or CR$^Z$, wherein R$^Z$ is —H or —X;

$R_1$ is —CF$_2$H or —CF$_3$;

$R_2$ is

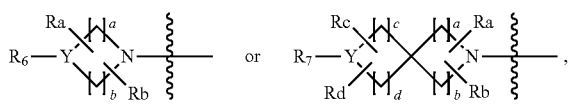

wherein Y is —N— or —S(=O)$_2$-, a and b are 2, c and d are 1,

Ra to Rd are each independently —H or -($C_1$-$C_4$ alkyl), when Y is —N—, $R_6$ and $R_7$ are each independently -H, -($C_1$-$C_4$ alkyl), —C(=O)-($C_1$-$C_4$ alkyl), —S(=O)$_2$-($C_1$-$C_4$ alkyl), -($C_3$-$C_7$ cycloalkyl) or -($C_2$-$C_6$ heterocycloalkyl), wherein at least one H of the -($C_1$-$C_4$ alkyl) may be substituted with —X or —OH, and the —($C_2$-$C_6$ heterocycloalkyl) may contain an N, O or S atom in the ring, and when Y is —S(=O)$_2$—, $R_6$ and $R_7$ are null;

$R_3$ is -aryl or -heteroaryl, wherein at least one H of the -aryl or -heteroaryl may be substituted with —F; and X is F or Cl.

5. A 1,3,4-oxadiazole sulfamide compound selected from the group consisting of the compounds set forth below, and stereoisomers and pharmaceutically acceptable salts thereof:

| Ex. | Comp. | Structure |
|---|---|---|
| 1 | 11198 | 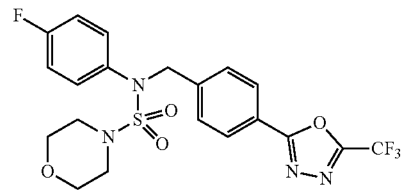 [SMILES: O=S(=O)(N1CCOCC1)N(Cc1ccc(-c2nnc(C(F)(F)F)o2)cc1)c1ccc(F)cc1] |
| 2 | 11199 | 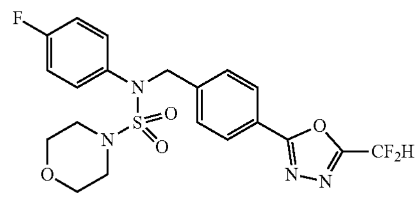 [SMILES: O=S(=O)(N1CCOCC1)N(Cc1ccc(-c2nnc(C(F)F)o2)cc1)c1ccc(F)cc1] |
| 3 | 11293 | 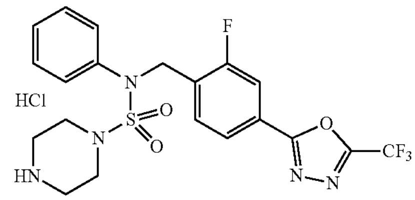 [SMILES: Cl ; O=S(=O)(N1CCNCC1)N(Cc1ccc(-c2nnc(C(F)(F)F)o2)cc1F)c1ccccc1] |
| 4 | 11294 | 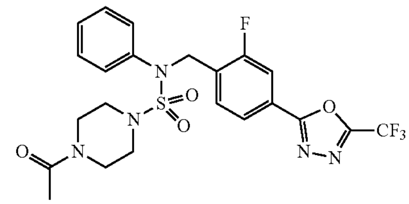 [SMILES: CC(=O)N1CCN(S(=O)(=O)N(Cc2ccc(-c3nnc(C(F)(F)F)o3)cc2F)c2ccccc2)CC1] |
| 5 | 11295 | 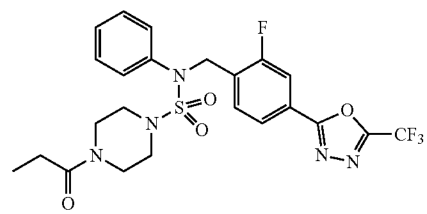 [SMILES: CCC(=O)N1CCN(S(=O)(=O)N(Cc2ccc(-c3nnc(C(F)(F)F)o3)cc2F)c2ccccc2)CC1] |
| 6 | 11296 | 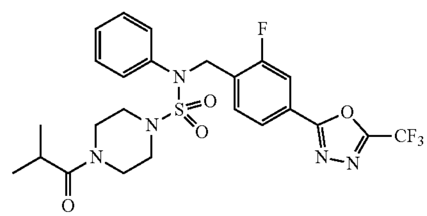 [SMILES: CC(C)C(=O)N1CCN(S(=O)(=O)N(Cc2ccc(-c3nnc(C(F)(F)F)o3)cc2F)c2ccccc2)CC1] |

| Ex. | Comp. | Structure |
|---|---|---|
| 7 | 11297 | 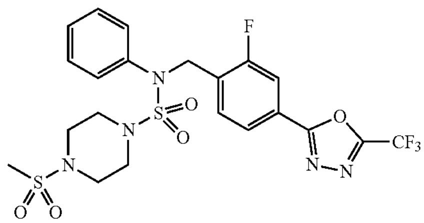 [SMILES: CS(=O)(=O)N1CCN(S(=O)(=O)N(Cc2ccc(-c3nnc(C(F)(F)F)o3)cc2F)c2ccccc2)CC1] |
| 8 | 11298 | 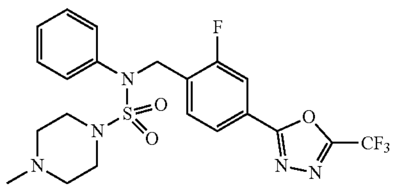 [SMILES: CN1CCN(S(=O)(=O)N(Cc2ccc(-c3nnc(C(F)(F)F)o3)cc2F)c2ccccc2)CC1] |
| 9 | 11299 | 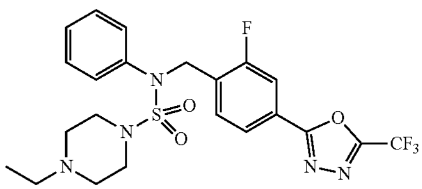 [SMILES: CCN1CCN(S(=O)(=O)N(Cc2ccc(-c3nnc(C(F)(F)F)o3)cc2F)c2ccccc2)CC1] |
| 10 | 11300 | 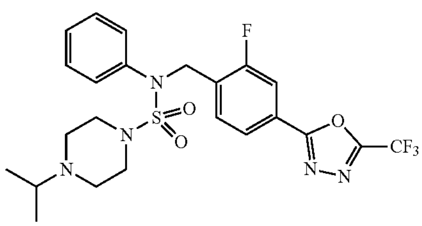 [SMILES: CC(C)N1CCN(S(=O)(=O)N(Cc2ccc(-c3nnc(C(F)(F)F)o3)cc2F)c2ccccc2)CC1] |
| 11 | 11301 | 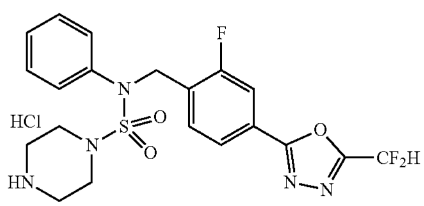 [SMILES: Cl ; O=S(=O)(N1CCNCC1)N(Cc1ccc(-c2nnc(C(F)F)o2)cc1F)c1ccccc1] |
| 12 | 11302 | 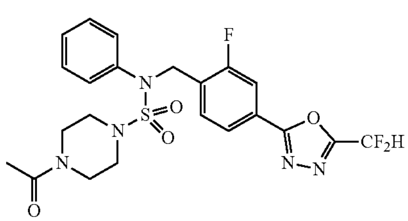 [SMILES: CC(=O)N1CCN(S(=O)(=O)N(Cc2ccc(-c3nnc(C(F)F)o3)cc2F)c2ccccc2)CC1] |
| 13 | 11303 | 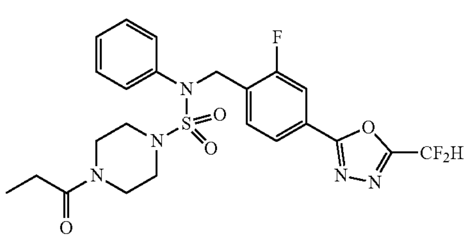 [SMILES: CCC(=O)N1CCN(S(=O)(=O)N(Cc2ccc(-c3nnc(C(F)F)o3)cc2F)c2ccccc2)CC1] |

| Ex. | Comp. | Structure |
|---|---|---|
| 14 | 11304 | 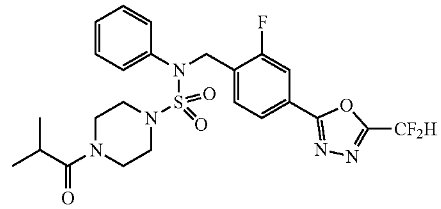 [SMILES: CC(C)C(=O)N1CCN(S(=O)(=O)N(Cc2ccc(-c3nnc(C(F)F)o3)cc2F)c2ccccc2)CC1] |
| 15 | 11305 | 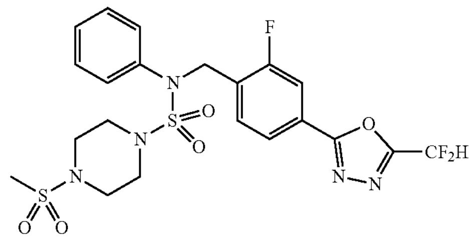 [SMILES: CS(=O)(=O)N1CCN(S(=O)(=O)N(Cc2ccc(-c3nnc(C(F)F)o3)cc2F)c2ccccc2)CC1] |
| 16 | 11306 | 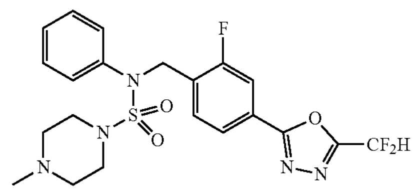 [SMILES: CN1CCN(S(=O)(=O)N(Cc2ccc(-c3nnc(C(F)F)o3)cc2F)c2ccccc2)CC1] |
| 17 | 11307 | 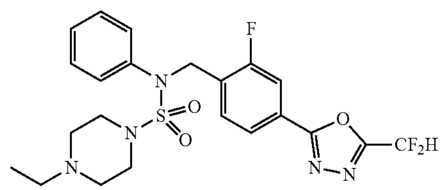 [SMILES: CCN1CCN(S(=O)(=O)N(Cc2ccc(-c3nnc(C(F)F)o3)cc2F)c2ccccc2)CC1] |
| 18 | 11308 | 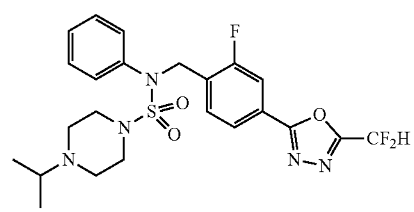 [SMILES: CC(C)N1CCN(S(=O)(=O)N(Cc2ccc(-c3nnc(C(F)F)o3)cc2F)c2ccccc2)CC1] |
| 19 | 11309 | 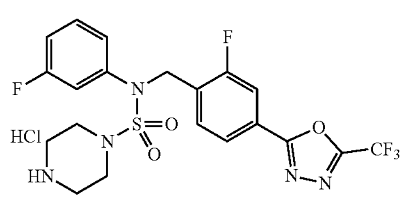 [SMILES: Cl ; O=S(=O)(N1CCNCC1)N(Cc1ccc(-c2nnc(C(F)(F)F)o2)cc1F)c1cccc(F)c1] |
| 20 | 11310 | 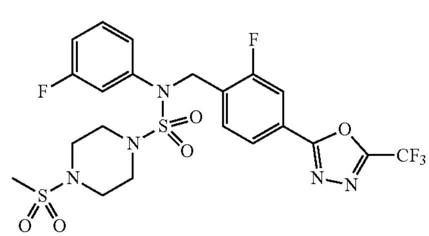 [SMILES: CS(=O)(=O)N1CCN(S(=O)(=O)N(Cc2ccc(-c3nnc(C(F)(F)F)o3)cc2F)c2cccc(F)c2)CC1] |

| Ex. | Comp. | Structure |
|---|---|---|
| 21 | 11311 | 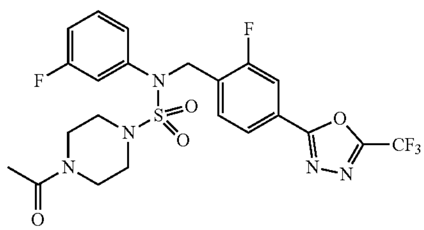 [SMILES: CC(=O)N1CCN(S(=O)(=O)N(Cc2ccc(-c3nnc(C(F)(F)F)o3)cc2F)c2cccc(F)c2)CC1] |
| 22 | 11312 | 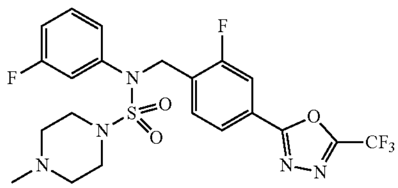 [SMILES: CN1CCN(S(=O)(=O)N(Cc2ccc(-c3nnc(C(F)(F)F)o3)cc2F)c2cccc(F)c2)CC1] |
| 23 | 11313 | 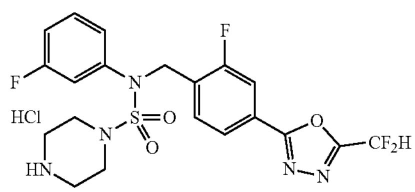 [SMILES: O=S(=O)(N1CCNCC1)N(Cc1ccc(-c2nnc(C(F)F)o2)cc1F)c1cccc(F)c1 ; Cl] |
| 24 | 11314 | 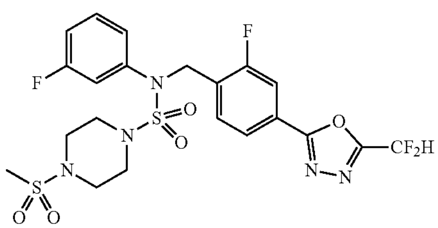 [SMILES: CS(=O)(=O)N1CCN(S(=O)(=O)N(Cc2ccc(-c3nnc(C(F)F)o3)cc2F)c2cccc(F)c2)CC1] |
| 25 | 11315 | 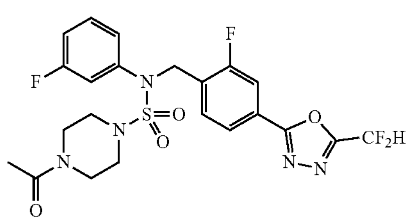 [SMILES: CC(=O)N1CCN(S(=O)(=O)N(Cc2ccc(-c3nnc(C(F)F)o3)cc2F)c2cccc(F)c2)CC1] |
| 26 | 11316 | 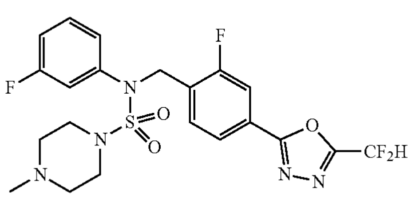 [SMILES: CN1CCN(S(=O)(=O)N(Cc2ccc(-c3nnc(C(F)F)o3)cc2F)c2cccc(F)c2)CC1] |
| 27 | 11317 | 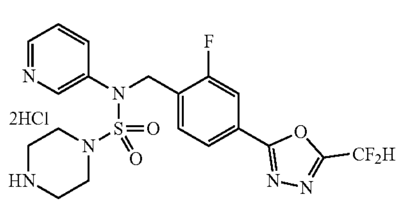 [SMILES: "2HCl" ; O=S(=O)(N1CCNCC1)N(Cc1ccc(-c2nnc(C(F)F)o2)cc1F)c1cccnc1] |
| 28 | 11318 | 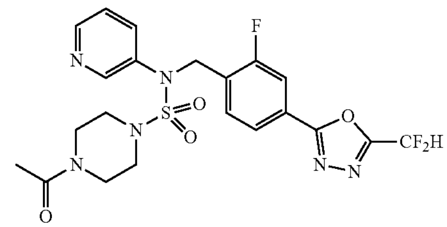 [SMILES: CC(=O)N1CCN(S(=O)(=O)N(Cc2ccc(-c3nnc(C(F)F)o3)cc2F)c2cccnc2)CC1] |
| 29 | 11319 | 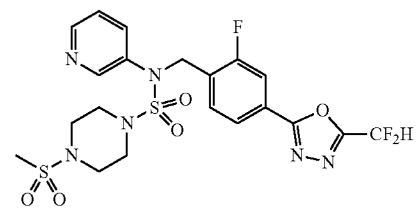 [SMILES: CS(=O)(=O)N1CCN(S(=O)(=O)N(Cc2ccc(-c3nnc(C(F)F)o3)cc2F)c2cccnc2)CC1] |
| 30 | 11320 | 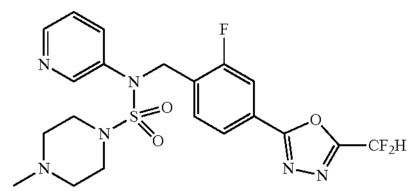 |
| 31 | 11321 | 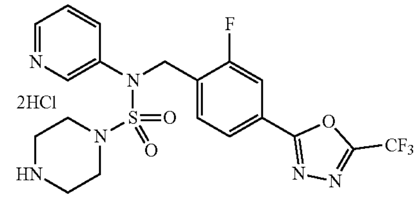 [SMILES: O=S(=O)(N1CCNCC1)N(Cc1ccc(-c2nnc(C(F)(F)F)o2)cc1F)c1cccnc1] |
| 32 | 11322 | 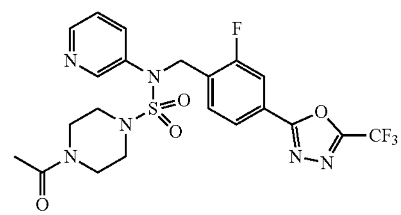 [SMILES: CC(=O)N1CCN(S(=O)(=O)N(Cc2ccc(-c3nnc(C(F)(F)F)o3)cc2F)c2cccnc2)CC1] |
| 33 | 11363 | 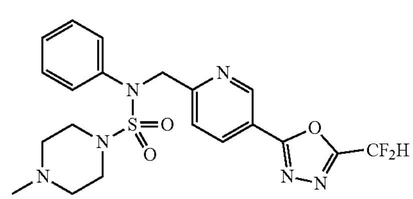 [SMILES: CN1CCN(S(=O)(=O)N(Cc2ccc(-c3nnc(C(F)F)o3)cn2)c2ccccc2)CC1] |
| 34 | 11379 | 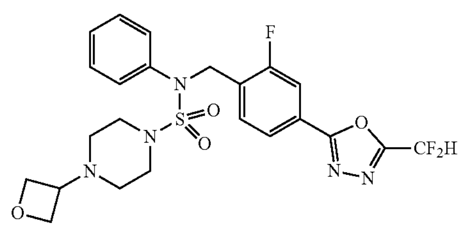 [SMILES: O=S(=O)(N1CCN(C2COC2)CC1)N(Cc1ccc(-c2nnc(C(F)F)o2)cc1F)c1ccccc1] |

| Ex. | Comp. | Structure |
|---|---|---|
| 35 | 11440 | 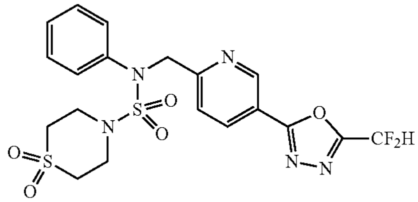 [SMILES: O=S1(=O)CCN(S(=O)(=O)N(Cc2ccc(-c3nnc(C(F)F)o3)cn2)c2ccccc2)CC1] |
| 36 | 11498 | 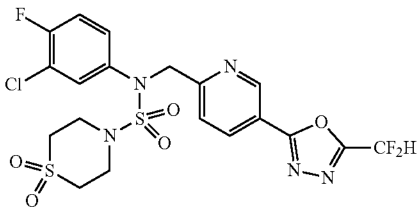 [SMILES: O=S1(=O)CCN(S(=O)(=O)N(Cc2ccc(-c3nnc(C(F)F)o3)cn2)c2ccc(F)c(Cl)c2)CC1] |
| 37 | 11527 | 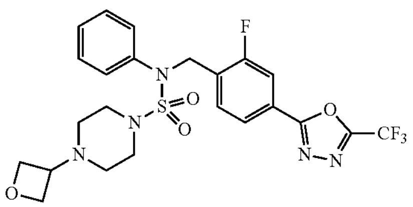 [SMILES: O=S(=O)(N1CCN(C2COC2)CC1)N(Cc1ccc(-c2nnc(C(F)(F)F)o2)cc1F)c1ccccc1] |
| 38 | 11528 | 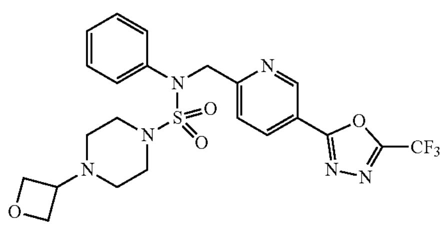 [SMILES: O=S(=O)(N1CCN(C2COC2)CC1)N(Cc1ccc(-c2nnc(C(F)(F)F)o2)cn1)c1ccccc1] |
| 39 | 11574 | 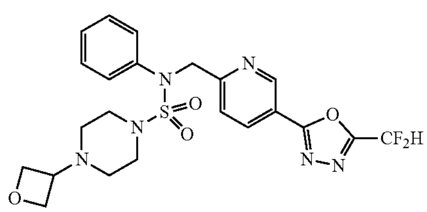 [SMILES: O=S(=O)(N1CCN(C2COC2)CC1)N(Cc1ccc(-c2nnc(C(F)F)o2)cn1)c1ccccc1] |
| 40 | 11575 | 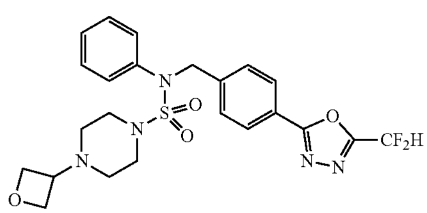 [SMILES: O=S(=O)(N1CCN(C2COC2)CC1)N(Cc1ccc(-c2nnc(C(F)F)o2)cc1)c1ccccc1] |
| 41 | 11640 | 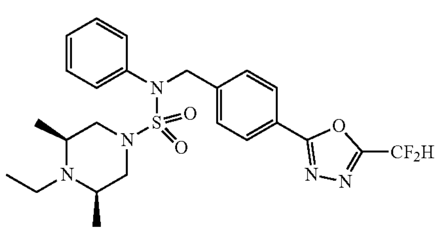 [SMILES: CCN1[C@H](C)CN(S(=O)(=O)N(Cc2ccc(-c3nnc(C(F)F)o3)cc2)c2ccccc2)C[C@@H]1C] |

| Ex. | Comp. | Structure |
|---|---|---|
| 42 | 11641 | |
| 43 | 11642 | |
| 44 | 11643 | |
| 45 | 11644 | |
| 46 | 11651 | |
| 47 | 11652 | |
| 48 | 11653 | |

| Ex. | Comp. | Structure |
|---|---|---|
| 49 | 11654 | 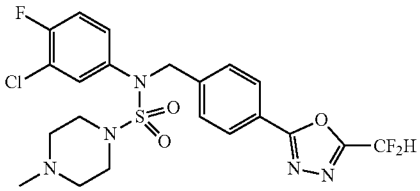 [SMILES: CN1CCN(S(=O)(=O)N(Cc2ccc(-c3nnc(C(F)F)o3)cc2)c2ccc(F)c(Cl)c2)CC1] |
| 50 | 11659 | 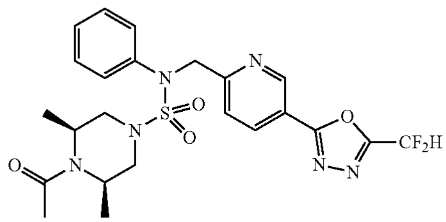 [SMILES: CC(=O)N1[C@H](C)CN(S(=O)(=O)N(Cc2ccc(-c3nnc(C(F)F)o3)cn2)c2ccccc2)C[C@@H]1C] |
| 51 | 11660 | 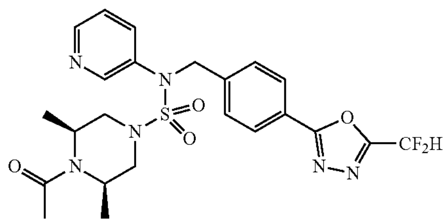 [SMILES: CC(=O)N1[C@H](C)CN(S(=O)(=O)N(Cc2ccc(-c3nnc(C(F)F)o3)cc2)c2cccnc2)C[C@@H]1C] |
| 52 | 11661 | 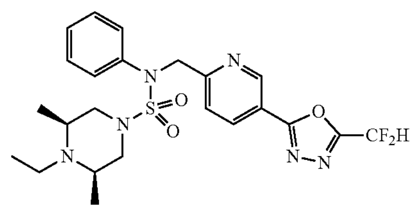 [SMILES: CCN1[C@H](C)CN(S(=O)(=O)N(Cc2ccc(-c3nnc(C(F)F)o3)cn2)c2ccccc2)C[C@@H]1C] |
| 53 | 11662 | 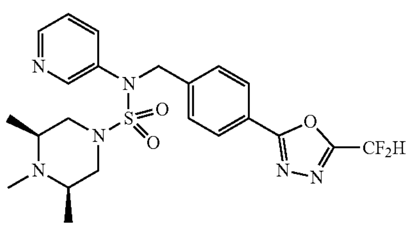 [SMILES: C[C@@H]1CN(S(=O)(=O)N(Cc2ccc(-c3nnc(C(F)F)o3)cc2)c2cccnc2)C[C@H](C)N1C] |
| 54 | 11670 | 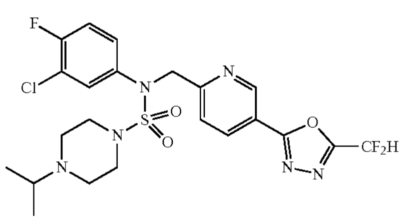 |
| 55 | 11671 | 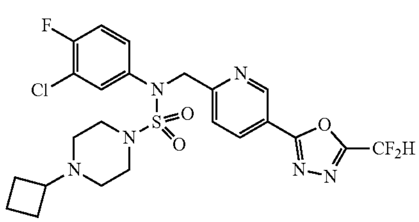 [SMILES: O=S(=O)(N1CCN(C2CCC2)CC1)N(Cc1ccc(-c2nnc(C(F)F)o2)cn1)c1ccc(F)c(Cl)c1] |
| 56 | 11672 | |
| 57 | 11673 | |
| 58 | 11674 | |
| 59 | 11702 | |
| 60 | 11704 | |

| Ex. | Comp. | Structure |
|---|---|---|
| 61 | 11713 | 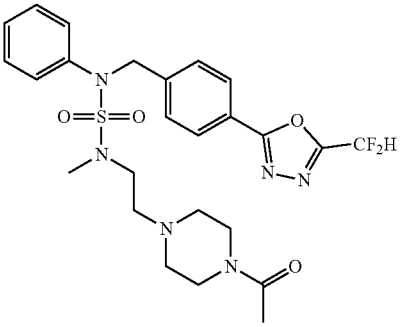 [SMILES: CC(=O)N1CCN(CCN(C)S(=O)(=O)N(Cc2ccc(-c3nnc(C(F)F)o3)cc2)c2ccccc2)CC1] |
| 62 | 11714 | 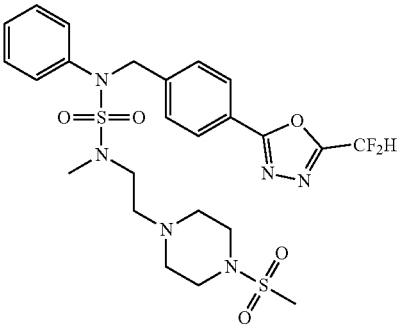 [SMILES: CN(CCN1CCN(S(C)(=O)=O)CC1)S(=O)(=O)N(Cc1ccc(-c2nnc(C(F)F)o2)cc1)c1ccccc1] |
| 63 | 11787 | 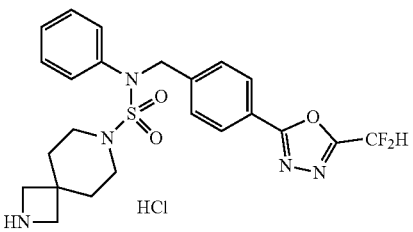 [SMILES: O=S(=O)(N1CCC2(CC1)CNC2)N(Cc1ccc(-c2nnc(C(F)F)o2)cc1)c1ccccc1 ; Cl] |
| 64 | 11788 | 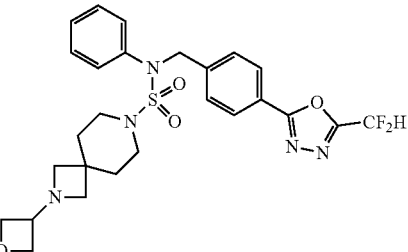 |
| 65 | 11789 | 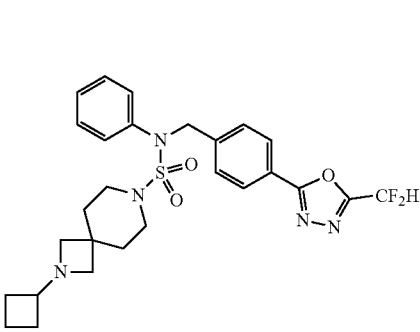 [SMILES: O=S(=O)(N1CCC2(CC1)CN(C1CCC1)C2)N(Cc1ccc(-c2nnc(C(F)F)o2)cc1)c1ccccc1] |
| Ex. | Comp. | Structure |
|---|---|---|
| 66 | 11823 | 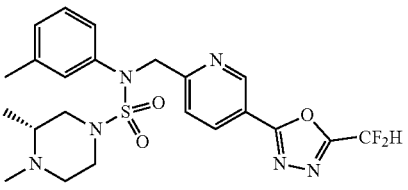 [SMILES: Cc1cccc(N(Cc2ccc(-c3nnc(C(F)F)o3)cn2)S(=O)(=O)N2CCN(C)[C@H](C)C2)c1] |
| 67 | 11824 | 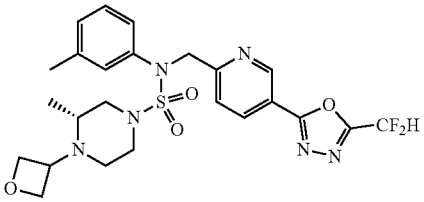 [SMILES: Cc1cccc(N(Cc2ccc(-c3nnc(C(F)F)o3)cn2)S(=O)(=O)N2CCN(C3COC3)[C@H](C)C2)c1] |
| 68 | 11825 | 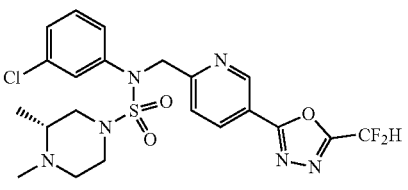 [SMILES: C[C@@H]1CN(S(=O)(=O)N(Cc2ccc(-c3nnc(C(F)F)o3)cn2)c2cccc(Cl)c2)CCN1C] |
| 69 | 11826 | 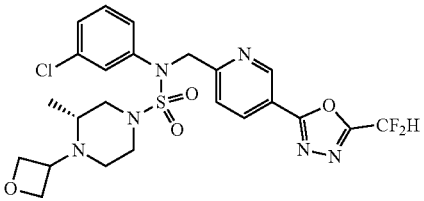 [SMILES: C[C@@H]1CN(S(=O)(=O)N(Cc2ccc(-c3nnc(C(F)F)o3)cn2)c2cccc(Cl)c2)CCN1C1COC1] |
| 70 | 11827 | 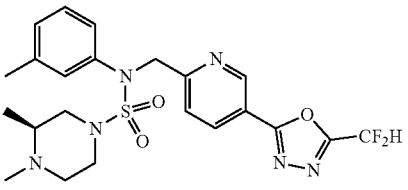 [SMILES: Cc1cccc(N(Cc2ccc(-c3nnc(C(F)F)o3)cn2)S(=O)(=O)N2CCN(C)[C@@H](C)C2)c1] |
| 71 | 11828 | 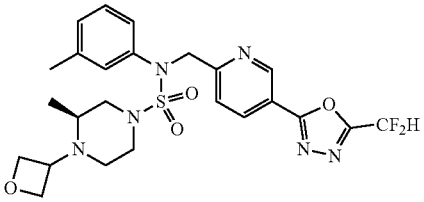 [SMILES: Cc1cccc(N(Cc2ccc(-c3nnc(C(F)F)o3)cn2)S(=O)(=O)N2CCN(C3COC3)[C@@H](C)C2)c1] |
| 72 | 11829 | 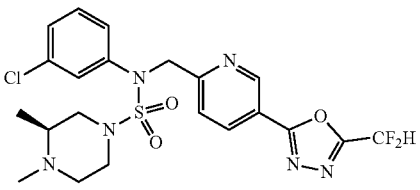 [SMILES: C[C@H]1CN(S(=O)(=O)N(Cc2ccc(-c3nnc(C(F)F)o3)cn2)c2cccc(Cl)c2)CCN1C] |

-continued

| Ex. | Comp. | Structure |
|---|---|---|
| 73 | 11830 | |
| 74 | 11831 | |
| 75 | 11832 | |
| 76 | 11833 | |

6. A 1,3,4-oxadiazole sulfamide compound according to claim 5, selected from the group consisting of the compounds set forth below:

| Ex. | Comp. | Structure |
|---|---|---|
| 11 | 11301 | |
| 12 | 11302 | |

-continued

| Ex. | Comp. | Structure |
|---|---|---|
| 13 | 11303 | 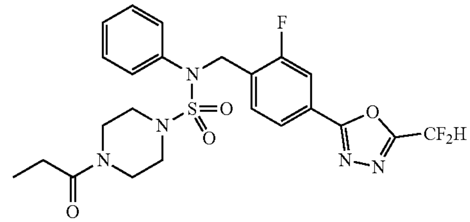 [SMILES: CCC(=O)N1CCN(S(=O)(=O)N(Cc2ccc(-c3nnc(C(F)F)o3)cc2F)c2ccccc2)CC1] |
| 15 | 11305 | 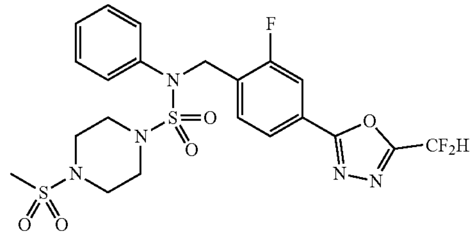 [SMILES: CS(=O)(=O)N1CCN(S(=O)(=O)N(Cc2ccc(-c3nnc(C(F)F)o3)cc2F)c2ccccc2)CC1] |
| 16 | 11306 | 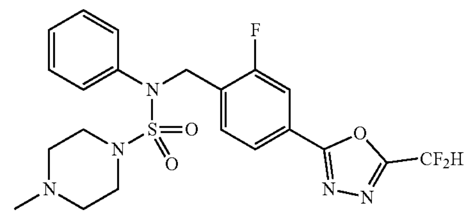 [SMILES: CN1CCN(S(=O)(=O)N(Cc2ccc(-c3nnc(C(F)F)o3)cc2F)c2ccccc2)CC1] |
| 17 | 11307 | 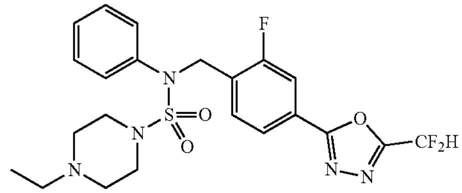 [SMILES: CCN1CCN(S(=O)(=O)N(Cc2ccc(-c3nnc(C(F)F)o3)cc2F)c2ccccc2)CC1] |
| 18 | 11308 | 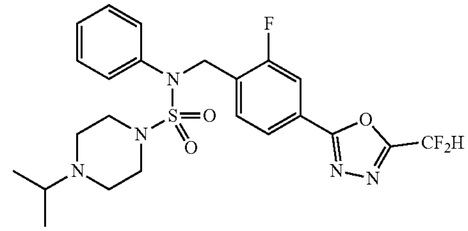 [SMILES: CC(C)N1CCN(S(=O)(=O)N(Cc2ccc(-c3nnc(C(F)F)o3)cc2F)c2ccccc2)CC1] |
| 23 | 11313 | 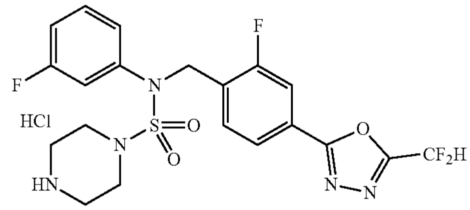 [SMILES: O=S(=O)(N1CCNCC1)N(Cc1ccc(-c2nnc(C(F)F)o2)cc1F)c1cccc(F)c1 ; Cl] |
| 24 | 11314 | 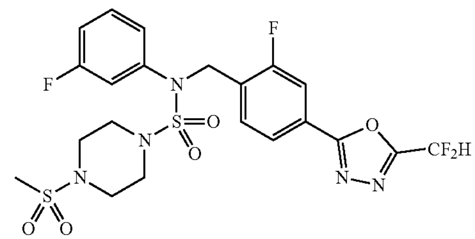 [SMILES: CS(=O)(=O)N1CCN(S(=O)(=O)N(Cc2ccc(-c3nnc(C(F)F)o3)cc2F)c2cccc(F)c2)CC1] |

-continued

| Ex. | Comp. | Structure |
|---|---|---|
| 25 | 11315 | 3-fluorophenyl-N-(2-fluoro-4-(5-(difluoromethyl)-1,3,4-oxadiazol-2-yl)benzyl)-4-acetylpiperazine-1-sulfonamide |
| 26 | 11316 | 3-fluorophenyl-N-(2-fluoro-4-(5-(difluoromethyl)-1,3,4-oxadiazol-2-yl)benzyl)-4-methylpiperazine-1-sulfonamide |
| 28 | 11318 | pyridin-3-yl-N-(2-fluoro-4-(5-(difluoromethyl)-1,3,4-oxadiazol-2-yl)benzyl)-4-acetylpiperazine-1-sulfonamide |
| 31 | 11321 | pyridin-3-yl-N-(2-fluoro-4-(5-(trifluoromethyl)-1,3,4-oxadiazol-2-yl)benzyl)piperazine-1-sulfonamide, 2HCl |
| 33 | 11363 | phenyl-N-((5-(5-(difluoromethyl)-1,3,4-oxadiazol-2-yl)pyridin-2-yl)methyl)-4-methylpiperazine-1-sulfonamide |
| 34 | 11379 | phenyl-N-(2-fluoro-4-(5-(difluoromethyl)-1,3,4-oxadiazol-2-yl)benzyl)-4-(oxetan-3-yl)piperazine-1-sulfonamide |

-continued

| Ex. | Comp. | Structure |
|---|---|---|
| 35 | 11440 | phenyl-N-((5-(5-(difluoromethyl)-1,3,4-oxadiazol-2-yl)pyridin-2-yl)methyl)thiomorpholine-1,1-dioxide-4-sulfonamide |
| 36 | 11498 | 3-chloro-4-fluorophenyl-N-((5-(5-(difluoromethyl)-1,3,4-oxadiazol-2-yl)pyridin-2-yl)methyl)thiomorpholine-1,1-dioxide-4-sulfonamide |
| 39 | 11574 | phenyl-N-((5-(5-(difluoromethyl)-1,3,4-oxadiazol-2-yl)pyridin-2-yl)methyl)-4-(oxetan-3-yl)piperazine-1-sulfonamide |
| 40 | 11575 | phenyl-N-(4-(5-(difluoromethyl)-1,3,4-oxadiazol-2-yl)benzyl)-4-(oxetan-3-yl)piperazine-1-sulfonamide |
| 42 | 11641 | phenyl-N-(4-(5-(difluoromethyl)-1,3,4-oxadiazol-2-yl)benzyl)-4-acetyl-2,6-dimethylpiperazine-1-sulfonamide |
| 48 | 11653 | 3-chloro-4-fluorophenyl-N-(4-(5-(difluoromethyl)-1,3,4-oxadiazol-2-yl)benzyl)-4-(oxetan-3-yl)piperazine-1-sulfonamide |

| Ex. | Comp. | Structure |
|---|---|---|
| 49 | 11654 | |
| 50 | 11659 | |
| 53 | 11662 | |
| 54 | 11670 | |
| 55 | 11671 | |
| 56 | 11672 | |
| 66 | 11823 | 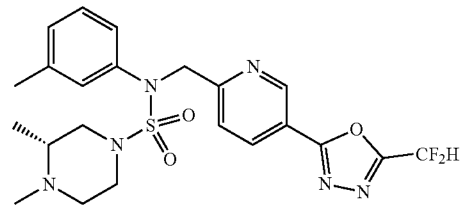 [SMILES: Cc1cccc(N(Cc2ccc(-c3nnc(C(F)F)o3)cn2)S(=O)(=O)N2CCN(C)[C@H](C)C2)c1] |
| 67 | 11824 | 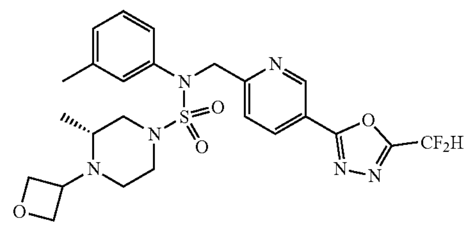 [SMILES: Cc1cccc(N(Cc2ccc(-c3nnc(C(F)F)o3)cn2)S(=O)(=O)N2CCN(C3COC3)[C@H](C)C2)c1] |
| 68 | 11825 | 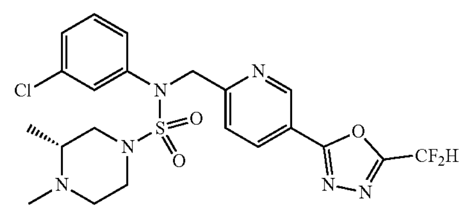 [SMILES: C[C@@H]1CN(S(=O)(=O)N(Cc2ccc(-c3nnc(C(F)F)o3)cn2)c2cccc(Cl)c2)CCN1C] |
| 69 | 11826 | 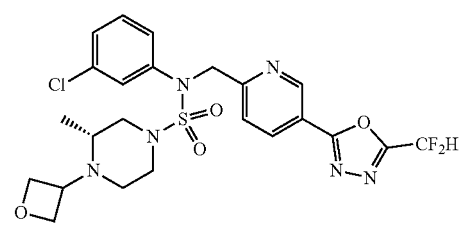 [SMILES: C[C@@H]1CN(S(=O)(=O)N(Cc2ccc(-c3nnc(C(F)F)o3)cn2)c2cccc(Cl)c2)CCN1C1COC1] |
| 70 | 11827 | 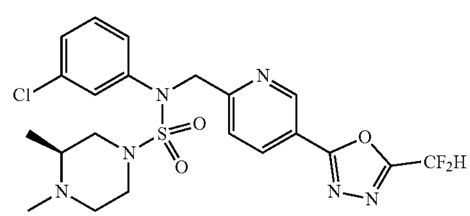 [SMILES: C[C@H]1CN(S(=O)(=O)N(Cc2ccc(-c3nnc(C(F)F)o3)cn2)c2cccc(Cl)c2)CCN1C] |
| 71 | 11828 | 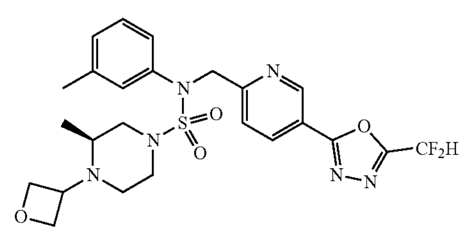 [SMILES: Cc1cccc(N(Cc2ccc(-c3nnc(C(F)F)o3)cn2)S(=O)(=O)N2CCN(C3COC3)[C@@H](C)C2)c1] |
| 72 | 11829 | 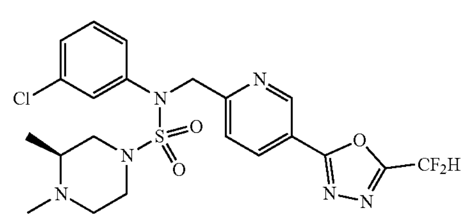 [SMILES: C[C@H]1CN(S(=O)(=O)N(Cc2ccc(-c3nnc(C(F)F)o3)cn2)c2cccc(Cl)c2)CCN1C] |

| Ex. | Comp. | Structure |
|---|---|---|
| 73 | 11830 | 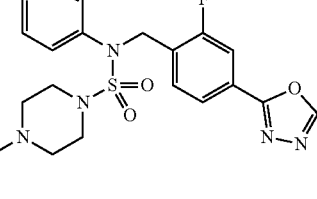 |
| 74 | 11831 | |
| 75 | 11832 | |
| 76 | 11833 | |
7. A 1,3,4-oxadiazole sulfamide compound according to claim 6, selected from the group consisting of the compounds set forth below:
| Ex. | Comp. | Structure |
|---|---|---|
| 11 | 11301 | 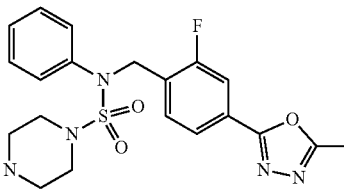 |
| 12 | 11302 | |
| Ex. | Comp. | Structure |
|---|---|---|
| 13 | 11303 | 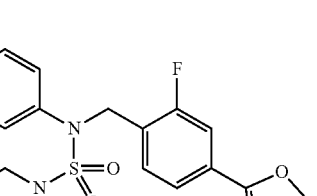 |
| 15 | 11305 | |
| 16 | 11306 | 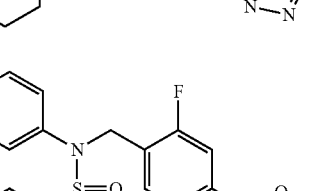 |
| 23 | 11313 | 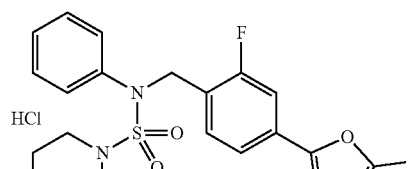 |
| 24 | 11314 | |
| 25 | 11315 | 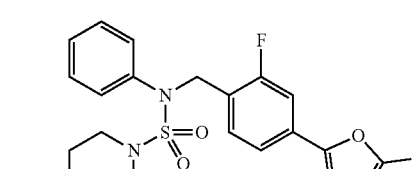 |

-continued

| Ex. | Comp. | Structure |
|---|---|---|
| 26 | 11316 | 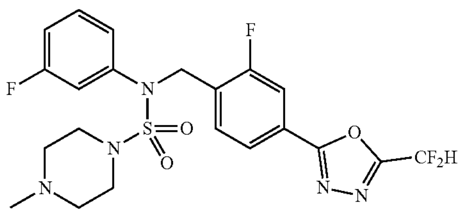 [SMILES: CN1CCN(S(=O)(=O)N(Cc2ccc(-c3nnc(C(F)F)o3)cc2F)c2cccc(F)c2)CC1] |
| 33 | 11363 | 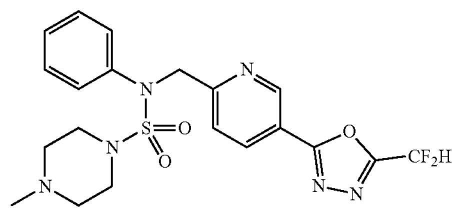 [SMILES: CN1CCN(S(=O)(=O)N(Cc2ccc(-c3nnc(C(F)F)o3)cn2)c2ccccc2)CC1] |
| 34 | 11379 | 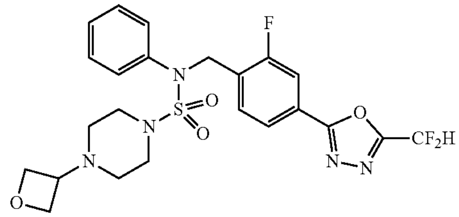 |
| 35 | 11440 | 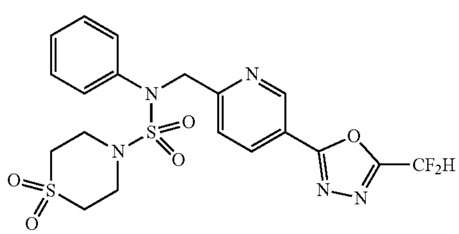 [SMILES: O=S1(=O)CCN(S(=O)(=O)N(Cc2ccc(-c3nnc(C(F)F)o3)cn2)c2ccccc2)CC1] |
| 36 | 11498 | 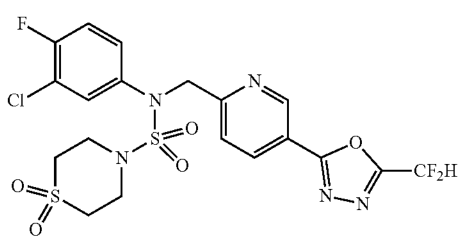 [SMILES: O=S1(=O)CCN(S(=O)(=O)N(Cc2ccc(-c3nnc(C(F)F)o3)cn2)c2ccc(F)c(Cl)c2)CC1] |
| 39 | 11574 | 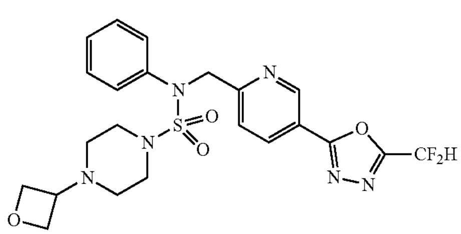 [SMILES: O=S(=O)(N1CCN(C2COC2)CC1)N(Cc1ccc(-c2nnc(C(F)F)o2)cn1)c1ccccc1] |
| 42 | 11641 | 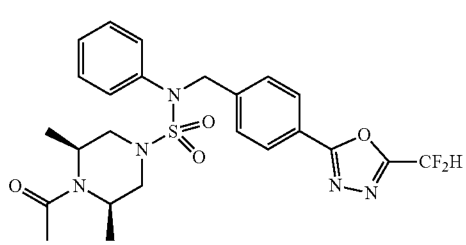 [SMILES: CC(=O)N1[C@H](C)CN(S(=O)(=O)N(Cc2ccc(-c3nnc(C(F)F)o3)cc2)c2ccccc2)C[C@@H]1C] |

-continued

| Ex. | Comp. | Structure |
|---|---|---|
| 49 | 11654 | 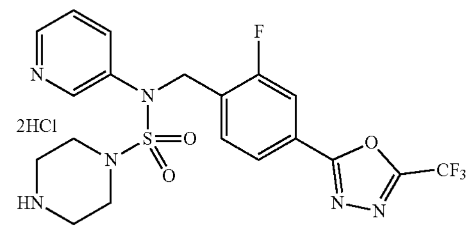 [SMILES: "2HCl" ; O=S(=O)(N1CCNCC1)N(Cc1ccc(-c2nnc(C(F)(F)F)o2)cc1F)c1cccnc1] |
| 50 | 11659 | 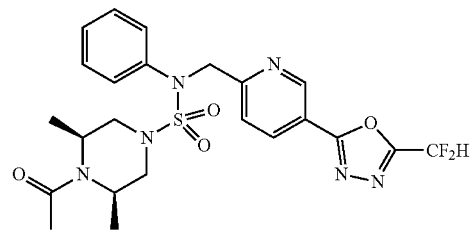 |
| 54 | 11670 | 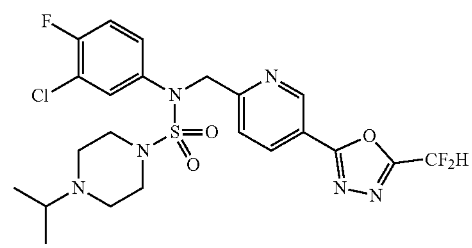 [SMILES: CC(C)N1CCN(S(=O)(=O)N(Cc2ccc(-c3nnc(C(F)F)o3)cn2)c2ccc(F)c(Cl)c2)CC1] |
| 55 | 11671 | 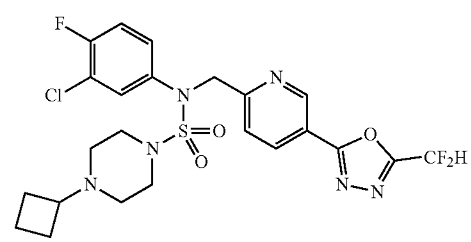 [SMILES: O=S(=O)(N1CCN(C2CCC2)CC1)N(Cc1ccc(-c2nnc(C(F)F)o2)cn1)c1ccc(F)c(Cl)c1] |
| 56 | 11672 | 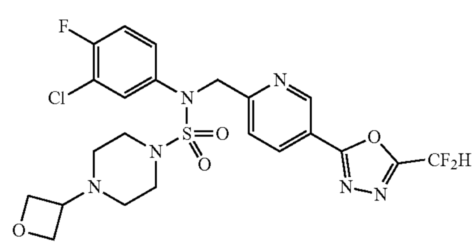 [SMILES: O=S(=O)(N1CCN(C2COC2)CC1)N(Cc1ccc(-c2nnc(C(F)F)o2)cn1)c1ccc(F)c(Cl)c1] |
| 68 | 11825 | 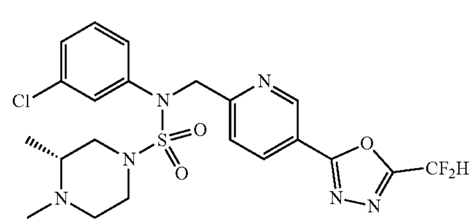 [SMILES: C[C@@H]1CN(S(=O)(=O)N(Cc2ccc(-c3nnc(C(F)F)o3)cn2)c2cccc(Cl)c2)CCN1C] |

| Ex. | Comp. | Structure |
|---|---|---|
| 72 | 11829 | *(structure)* |
| 73 | 11830 | *(structure)* |

| Ex. | Comp. | Structure |
|---|---|---|
| 74 | 11831 | *(structure)* |
| 75 | 11832 | *(structure)* |

8. A pharmaceutical composition comprising, as an active ingredient, a compound according to claim 1 and stereoisomers and pharmaceutically acceptable salts thereof.

* * * * *